(12) United States Patent
Vilanova et al.

(10) Patent No.: US 9,493,832 B2
(45) Date of Patent: Nov. 15, 2016

(54) METHODS OF DETECTING SEPSIS

(75) Inventors: David Vilanova, Caraman (FR); David H. Persing, San Martin, CA (US); Olivier Delfour, Caraman (FR); Bernard Michot, Pern (FR)

(73) Assignee: Cepheid, Sunnyvale, CA (US)

(*) Notice: Subject to any disclaimer, the term of this patent is extended or adjusted under 35 U.S.C. 154(b) by 601 days.

(21) Appl. No.: 12/698,715

(22) Filed: Feb. 2, 2010

(65) Prior Publication Data
US 2010/0227325 A1 Sep. 9, 2010

Related U.S. Application Data

(60) Provisional application No. 61/149,277, filed on Feb. 2, 2009.

(51) Int. Cl.
*C12Q 1/68* (2006.01)
*C07H 21/04* (2006.01)

(52) U.S. Cl.
CPC ....... *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 6,706,867 B1 | 3/2004 | Lorenz | |
| 6,900,016 B1 | 5/2005 | Venter et al. | |
| 7,629,444 B1 * | 12/2009 | Goldman et al. | 536/23.1 |
| 2006/0024715 A1 | 2/2006 | Liu et al. | |
| 2006/0051770 A1 | 3/2006 | Makeev et al. | |
| 2008/0026951 A1 | 1/2008 | Brown et al. | |
| 2008/0070235 A1 | 3/2008 | Russwurm et al. | |
| 2008/0193943 A1 | 8/2008 | Murray | |
| 2008/0286763 A1 | 11/2008 | Russwurm et al. | |
| 2009/0203534 A1 | 8/2009 | Hossain et al. | |
| 2012/0244530 A1 | 9/2012 | Michot et al. | |
| 2013/0084343 A1 | 4/2013 | Vilanova et al. | |
| 2013/0102488 A1 | 4/2013 | Barrie et al. | |
| 2013/0157886 A1 | 6/2013 | Michot et al. | |

FOREIGN PATENT DOCUMENTS

| | | |
|---|---|---|
| EP | 1783645 A1 | 5/2007 |
| JP | 2008-518610 | 6/2008 |
| JP | 2008-519606 | 6/2008 |
| WO | WO 9947706 A1 * | 9/1999 |
| WO | 2004087949 | 10/2004 |
| WO | 2005/098029 | 10/2005 |
| WO | 2006/048291 | 5/2006 |
| WO | 2006/069584 | 7/2006 |
| WO | 2006/137941 | 12/2006 |
| WO | 2007/054520 | 5/2007 |
| WO | 2007/073737 | 7/2007 |
| WO | 2007/109350 | 9/2007 |

(Continued)

OTHER PUBLICATIONS

Tyagi, S. and Kramer, F.R. Nature Biotechnology 14:303 (Mar. 1996).*

(Continued)

*Primary Examiner* — Diana B Johannsen
(74) *Attorney, Agent, or Firm* — McNeill Baur PLLC

(57) ABSTRACT

Methods of detecting sepsis in a sample from a patient are provided. Methods of detecting changes in expression of one or more microRNAs associated with sepsis are also provided. Compositions and kits are also provided.

11 Claims, 1 Drawing Sheet

(56) References Cited

FOREIGN PATENT DOCUMENTS

| WO | 2008/040355 | 4/2008 |
|---|---|---|
| WO | 2008/046911 | 4/2008 |
| WO | 2008/074328 | 6/2008 |
| WO | 2008147974 | 12/2008 |
| WO | 2009/079592 | 6/2009 |

OTHER PUBLICATIONS

Ahern, H. The Scientist 9(15):20 (Jul. 1995).*
Applied Biosystems, Product Bulletin, TaqMan® MicroRNA Assays. 2007.
Boyd, Everything you wanted to know about small RNA but were afraid to ask. Laboratory Investigation (2008), 88: 569-578.
Chen et al, Real-time quantification of microRNAs by stem-loop RT-PCR. Nucleic Acids Research (2005) 33(20): e179.
Dalmay, MicroRNAs and cancer, Journal of Internal Medicine (2008) 263: 366-375.
Griffiths-Jones et al, miRBase: microRNA sequences, targets and gene nomenclature, Nucleic Acids Research (2006), 34:D140-D144.
Griffiths-Jones et al, miRBase: tools for microRNA genomics, Nucleic Acids Research (2008), 36:D154-D158.
Gusev et al, MicroRNA expression profiling in cancer from a bioinformatics prospective, Expert Review of Molecular Diagnostics (2007), 7(6): 787-792.
Hammond, microRNA detection comes of age, Nature Methods (2006), (3)1: 12-13.
Liu et al, Expression profiling of microRNA using oligo DNA arrays, Science Direct (2008), Methods 44: 22-30.
Mora et al, Enzymatc microRNA detectoion in microtiter plates with DNA dendrimers, BioTechniques (2006), 41:420-424.
Mora et al, High-sensitivity detection methods for low-abundance RNA species: applicatons for functional genomics research, Expert Review of Molecular Diagnostics (2007), 7(6): 775-785.
Nelson et al, Microarray-based, high-throughput gene expression profiling of microRNAs, Nature Methods (2004). 1 (2): 1-7.
Chang et al, miR-122, a Mammalian Liver-Specific micoRNA, is Processed from hcr mRNA and May Downregulate the High Affinity Cationic Amino Acid Transporter CAT-1, RNA Biology (2004), 1(2): 106-113.
Varallyay et al, MicroRNA detection by northern blotting using locked nucleic acid probes, Nature Protocols (2008), 3(2): 190-196.
Wark et al, Multiplexed Detection Methods for Profiting MicroRNA Expression in Biological Samples, Angew. Chem. Int. Ed. (2008) 47: 644-652.
Wilkinson, A rapid and convenient method for isolation of nuclear, cytoplasmic and total cellular RNA, Nucleic Acids Research (1988), 16(22): 10934.
Zuker, Mfold web server for nucleic acid folding and hybridization prediction, Nucleic Acids Research (2003), 31 (13):3406-3415.
International Search Report and Written Opinion: PCT International application No. PCT/US2010/022885; mailed Jul. 20, 2010.
Bazzoni, F. et al; Induction and regulatory function of miR-9 in human monocytes and neutrophils exposed to proinflammatory signals; PNAS; 106: 5282-87 (2009) (published online Mar. 16, 2009).
El Gazzar, M. et al; MicroRNAs Distinguish Translational from Transcriptional Silencing During Endotoxin Tolerance; J. Biol. Chem.; 285: 20940-51 (2010) (published online Apr. 30, 2010).
GenBank Acc. No. AC116208; Rattus norvegicus clone CH230-129C14, Working Draft Sequence, 2 unordered pieces; May 13, 2003.
GenBank Acc. No. BJ069802; NIBB Mochii normalized Xenopus tailbud library Xenopus laevis cDNA clone XL054k04 5-, mRNA sequence; Sep. 29, 2003.
GenBank Acc. No. CR759927; Zebrafish DNA sequence from clone CH211-196C10 in linkage group 8, complete sequence; Jan. 29, 2005.
GenBank Acc. No. CW684880; OG_BBa0042M07.r OG_BBa Oryza glaberrima genomic clone OG_BBa0042M07 3-, genomic survey sequence; Nov. 1, 2004.
GenBank Acc. No. FC748656; CBBI4053.rev CBBI Lottia gigantea 26h,37h,61h Larvae (L) Lottia gigantea cDNA clone CBBI4053 3-, mRNA sequence; Dec. 19, 2007.
Koyama, S. et al; Innate immune response to viral infection; Cytokine; 43: 336-341 (2008).
Lim, L. et al; Mustering the micromanagers; Nature Biotech.; 25: 996-997 (2007).
Lindsay, M.; microRNAs and the immune response; Trends Immunol.; 29: 343-351 (2008).
Lodish, H. et al; Micromanagement of the immune system by microRNAs; Nature Rev. Immun.; 8: 120-130 (2008) (published online Jan. 21, 2008).
O'Connell, R. et al; Sustained expression of microRNA-155 in hematopoietic stem cells causes a myeloproliferative disorder; J. Exp. Med.; 205: 585-594 (2008).
O'Connell, R. et al; MicroRNA-155 is induced during the macrophage inflammatory response; PNAS; 104: 1604-09 (2007).
O'Neill, L.; Immunity's Early-Warning System; Scientific American; Jan. 2005, pp. 38-45.
Pauley, K. et al; MicroRNA in autoimmunity and autoimmune diseases; J. Autoimmun.; 32: 189-94 (2009).
Pedersen, I. et al; MicroRNAs in the immune response; Cytokine; 43: 391-94 (2008).
Regulus Therapeutics wins exclusive rights to modulate microRNAs, The Medical News; Dec. 2009, (3 pages).
Sonkoly, E. et al; Advances in microRNAs: implications for immunity and inflammatory diseases; J. Cell. Mol. Med.; 13: 24-38 (2009).
Taganov, K. et al; MicroRNAs and Immunity: Tiny Players in a Big Field; Immunity; 26: 133-37 (2007).
Taganov, K. et al; NF-kB-dependent induction of microRNA miR-146, an inhibitor targeted to signaling proteins of innate immune responses; PNAS; 103: 12481-86 (2008).
Tili, E. et al; Expression and function of micro RNAs in immune cells during normal or disease state; Int. J. Med. Sci.; 5: 73-79 (2008).
Tili, E. et al; Modulaton of miR-155 and miR-125b Levels following Lipopolysaccharide/TNF-(alpha) Stimulation and Their Possible Roles in Regulating the Response to Endotoxin Shock; J. Immunol.; 179: 5082-89 (2007).
Vasilescu, C. et al; MicroRNA Fingerprints Identify miR-150 as a Plasma Prognostic Marker in Patients with Sepsis; PLoS One; 4: e7405 (2009) (published online Oct. 12, 2009).
Wang, J. et al; Serum miR-146a and miR-223 as potential new biomarkers for sepsis; Biochem. Biophys. Res. Comm.; 394: 184-88 (2010) (published online Feb. 24, 2010).
Zhang, H. et al; Genome-Wide Analysis of Small RNA and Novel MicroRNA Discovery in Human Acute Lymphoblastic Leukemia Based on Extensive Sequencing Approach; PLoS One; 4: e6849 (2009).
Zhou, B. et al; miR-150, a microRNA expressed in mature B and T cells, blocks early B cell development when expressed prematurely; PNAS; 104: 7080-85 (2007).
Supplementary European Search Report issued Jun. 6, 2012, for EP Patent Application 10736571.0, 8 pages.
Icardi et al., "CD64 Index Provides Simple and Predictive Testing for Detection and Monitoring of Sepsis and Bacterial Infection in Hospital Patients," 2009, J. Clin. Microbiol., 47(12):3914-3919.
Zhernakova et al., "Detecting shared pathogenesis from the shared genetics of immune-related diseases," 2009, Nat. Rev. Genet., 10(1): 43-55.
Osuchowski et al., "Stratification is the key: inflammatory biomarkers accurately direct immunomodulatory therapy in experimental sepsis," 2009, Crit. Care Med., 37(5):1567-73.
Pritchard et al., "Blood cell origin of circulating microRNAs: a cautionary note for cancer biomarker studies," 2012, Cancer Prev. Res. (Phila.), 5(3): 492-497.

(56) References Cited

OTHER PUBLICATIONS

Kimura et al., "Diversification of transcriptional modulation: Large-scale identification and characterization of putative alternative promoters of human genes," Genome Research, 2006, 16:55-65.
Castoldi et al., "miChip: a microarray platform for expression profiling of microRNAs based on locked nucleic acid (LNA) oligonucleotide capture probes," Methods, 2007, 43(2):146-52.
Liu et al., "An oligonucleotide microchip for genome-wide microRNA profiling in human and mouse tissues," PNAS, 2004, 101(26):9740-4.
NEB Catalog (1998/1999), pp. 121, 284 (3 pages).
NCBI GEO record describing Platform GPL7766, including full miRNA_LIST table accessed from http://www.ncbi.nlm.nih.gov/geo on Jul. 10, 2013 (14 pages).
Rothstein et al., "Chronic inhibition of superoxide dismutase produces apoptotic death of spinal neurons," PNAS, 1994, 91(10):4155-9.
Speicher et al., "Karyotyping human chromosomes by combinatorial multi-fluor FISH," Nat Gen., 1996, 12(4):368-75.
File History for U.S. Appl. No. 13/658,276, filed Oct. 23, 2012.
File History for U.S. Appl. No. 13/684,874, filed Nov. 26, 2012.
File History for U.S. Appl. No. 13/359,267, filed Jan. 26, 2012.
File History for U.S. Appl. No. 13/617,789, filed Sep. 14, 2012.

\* cited by examiner

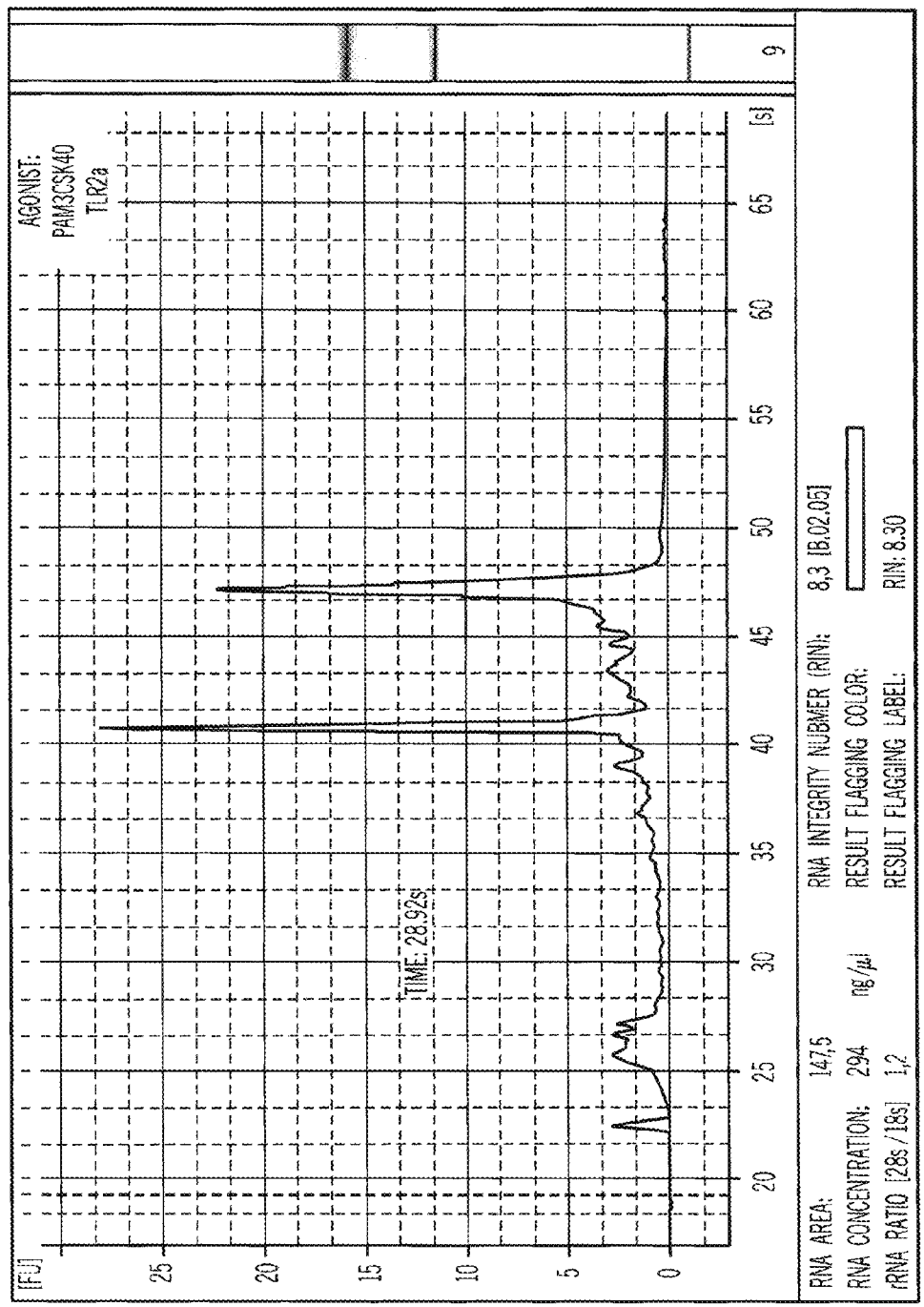

SEQUENCE LISTING

<160> NUMBER OF SEQ ID NOS: 950

<210> SEQ ID NO 1
<211> LENGTH: 29
<212> TYPE: DNA

```
<213> ORGANISM: Artificial Sequence
<220> FEATURE:
<223> OTHER INFORMATION: Synthetic probe sequence

<400> SEQUENCE: 1
ttcagaatgt taagtcccta tccttcgat                                      29

<210> SEQ ID NO 2
<211> LENGTH: 39
<212> TYPE: DNA
<213> ORGANISM: Artificial Sequence
<220> FEATURE:
<223> OTHER INFORMATION: Synthetic probe sequence

<400> SEQUENCE: 2
agagcaacag agggtttgtg taggactatg agagtggcg                           39

<210> SEQ ID NO 3
<211> LENGTH: 36
<212> TYPE: DNA
<213> ORGANISM: Artificial Sequence
<220> FEATURE:
<223> OTHER INFORMATION: Synthetic probe sequence

<400> SEQUENCE: 3
tggaaccttt agcagccaaa cagattgcac aatctc                              36

<210> SEQ ID NO 4
<211> LENGTH: 36
<212> TYPE: DNA
<213> ORGANISM: Artificial Sequence
<220> FEATURE:
<223> OTHER INFORMATION: Synthetic probe sequence

<400> SEQUENCE: 4
cccattaaga aattgcaagg ctaataaaaa tcatgc                              36

<210> SEQ ID NO 5
<211> LENGTH: 28
<212> TYPE: DNA
<213> ORGANISM: Artificial Sequence
<220> FEATURE:
<223> OTHER INFORMATION: Synthetic probe sequence

<400> SEQUENCE: 5
gcaggattct accagccagc cctcaggg                                       28

<210> SEQ ID NO 6
<211> LENGTH: 30
<212> TYPE: DNA
<213> ORGANISM: Artificial Sequence
<220> FEATURE:
<223> OTHER INFORMATION: Synthetic probe sequence

<400> SEQUENCE: 6
aattaggcag ttaatatatt gtaactaata                                     30

<210> SEQ ID NO 7
<211> LENGTH: 33
<212> TYPE: DNA
<213> ORGANISM: Artificial Sequence
<220> FEATURE:
<223> OTHER INFORMATION: Synthetic probe sequence

<400> SEQUENCE: 7
gtgcagcagc ccgcgccagc ctccgcagcc gcc                                 33
```

<210> SEQ ID NO 8
<211> LENGTH: 47
<212> TYPE: DNA
<213> ORGANISM: Artificial Sequence
<220> FEATURE:
<223> OTHER INFORMATION: Synthetic probe sequence

<400> SEQUENCE: 8
ccctacctgt cagtgtgacc atcacgagcc tcctgagacc tcctctc         47

<210> SEQ ID NO 9
<211> LENGTH: 30
<212> TYPE: DNA
<213> ORGANISM: Artificial Sequence
<220> FEATURE:
<223> OTHER INFORMATION: Synthetic probe sequence

<400> SEQUENCE: 9
ttcatacaaa cctccaacat taaattgcta                            30

<210> SEQ ID NO 10
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 10
acaaaccact aaggaaggaa gtggcataca ttctgct                    37

<210> SEQ ID NO 11
<211> LENGTH: 50
<212> TYPE: DNA
<213> ORGANISM: Artificial Sequence
<220> FEATURE:
<223> OTHER INFORMATION: Synthetic probe sequence

<400> SEQUENCE: 11
ggaaaatgtt tggcgtcaag ttcttaaaaa tgcttcctcc tcttttttcc      50

<210> SEQ ID NO 12
<211> LENGTH: 31
<212> TYPE: DNA
<213> ORGANISM: Artificial Sequence
<220> FEATURE:
<223> OTHER INFORMATION: Synthetic probe sequence

<400> SEQUENCE: 12
gacagagaga gtgagagtgc gagctcacag g                          31

<210> SEQ ID NO 13
<211> LENGTH: 39
<212> TYPE: DNA
<213> ORGANISM: Artificial Sequence
<220> FEATURE:
<223> OTHER INFORMATION: Synthetic probe sequence

<400> SEQUENCE: 13
gctctttagc acttttaccc tttgaaaata taaaatcac                  39

<210> SEQ ID NO 14
<211> LENGTH: 35
<212> TYPE: DNA
<213> ORGANISM: Artificial Sequence
<220> FEATURE:

<223> OTHER INFORMATION: Synthetic probe sequence

<400> SEQUENCE: 14
aaagactcat cagatccatt tccaaagtac agctc                          35

<210> SEQ ID NO 15
<211> LENGTH: 35
<212> TYPE: DNA
<213> ORGANISM: Artificial Sequence
<220> FEATURE:
<223> OTHER INFORMATION: Synthetic probe sequence

<400> SEQUENCE: 15
tgccagaggc tgtaattggt ctcaggtagt ctctg                          35

<210> SEQ ID NO 16
<211> LENGTH: 34
<212> TYPE: DNA
<213> ORGANISM: Artificial Sequence
<220> FEATURE:
<223> OTHER INFORMATION: Synthetic probe sequence

<400> SEQUENCE: 16
tccctgcagc tggccagcaa ttaccgcctg ccag                           34

<210> SEQ ID NO 17
<211> LENGTH: 30
<212> TYPE: DNA
<213> ORGANISM: Artificial Sequence
<220> FEATURE:
<223> OTHER INFORMATION: Synthetic probe sequence

<400> SEQUENCE: 17
aacacaagaa gaaacgcctg gtgcagagcc                                30

<210> SEQ ID NO 18
<211> LENGTH: 32
<212> TYPE: DNA
<213> ORGANISM: Artificial Sequence
<220> FEATURE:
<223> OTHER INFORMATION: Synthetic probe sequence

<400> SEQUENCE: 18
actccagcct ccgccgcctc agcttcccga gc                             32

<210> SEQ ID NO 19
<211> LENGTH: 34
<212> TYPE: DNA
<213> ORGANISM: Artificial Sequence
<220> FEATURE:
<223> OTHER INFORMATION: Synthetic probe sequence

<400> SEQUENCE: 19
ctataaaact tcgaaaagtc cctcctcctc acgt                           34

<210> SEQ ID NO 20
<211> LENGTH: 30
<212> TYPE: DNA
<213> ORGANISM: Artificial Sequence
<220> FEATURE:
<223> OTHER INFORMATION: Synthetic probe sequence

<400> SEQUENCE: 20
aaagctggca gggcttgtga gctctgcagg                                30

```
<210> SEQ ID NO 21
<211> LENGTH: 30
<212> TYPE: DNA
<213> ORGANISM: Artificial Sequence
<220> FEATURE:
<223> OTHER INFORMATION: Synthetic probe sequence

<400> SEQUENCE: 21
aaataatcaa gctgtcacat cttaaaaatc                                      30

<210> SEQ ID NO 22
<211> LENGTH: 52
<212> TYPE: DNA
<213> ORGANISM: Artificial Sequence
<220> FEATURE:
<223> OTHER INFORMATION: Synthetic probe sequence

<400> SEQUENCE: 22
acacctctgc gccccctcagg cgccctgggc ctcggcgccc cgcccgtccc ag            52

<210> SEQ ID NO 23
<211> LENGTH: 32
<212> TYPE: DNA
<213> ORGANISM: Artificial Sequence
<220> FEATURE:
<223> OTHER INFORMATION: Synthetic probe sequence

<400> SEQUENCE: 23
tttgacattc agagcactgg gcagaaatca ca                                   32

<210> SEQ ID NO 24
<211> LENGTH: 38
<212> TYPE: DNA
<213> ORGANISM: Artificial Sequence
<220> FEATURE:
<223> OTHER INFORMATION: Synthetic probe sequence

<400> SEQUENCE: 24
gcttctgatg atctattaat gcaatacatc agggtgag                             38

<210> SEQ ID NO 25
<211> LENGTH: 33
<212> TYPE: DNA
<213> ORGANISM: Artificial Sequence
<220> FEATURE:
<223> OTHER INFORMATION: Synthetic probe sequence

<400> SEQUENCE: 25
atgtcattga aaggggtat aattgtggtc tcc                                   33

<210> SEQ ID NO 26
<211> LENGTH: 29
<212> TYPE: DNA
<213> ORGANISM: Artificial Sequence
<220> FEATURE:
<223> OTHER INFORMATION: Synthetic probe sequence

<400> SEQUENCE: 26
attgatttta cattttcctg ccctgctac                                       29

<210> SEQ ID NO 27
<211> LENGTH: 32
<212> TYPE: DNA
<213> ORGANISM: Artificial Sequence
<220> FEATURE:
<223> OTHER INFORMATION: Synthetic probe sequence
```

<400> SEQUENCE: 27
agatcaaaca ggctgtgaag aagctctatg ac                32

<210> SEQ ID NO 28
<211> LENGTH: 35
<212> TYPE: DNA
<213> ORGANISM: Artificial Sequence
<220> FEATURE:
<223> OTHER INFORMATION: Synthetic probe sequence

<400> SEQUENCE: 28
cccagggtca cccaacacac tctgccttga gcctc             35

<210> SEQ ID NO 29
<211> LENGTH: 32
<212> TYPE: DNA
<213> ORGANISM: Artificial Sequence
<220> FEATURE:
<223> OTHER INFORMATION: Synthetic probe sequence

<400> SEQUENCE: 29
aaattaaatt gacactttga agcattaatc ta                32

<210> SEQ ID NO 30
<211> LENGTH: 34
<212> TYPE: DNA
<213> ORGANISM: Artificial Sequence
<220> FEATURE:
<223> OTHER INFORMATION: Synthetic probe sequence

<400> SEQUENCE: 30
caccaccaaa ccaaatgccg ctgctctcct tcca              34

<210> SEQ ID NO 31
<211> LENGTH: 33
<212> TYPE: DNA
<213> ORGANISM: Artificial Sequence
<220> FEATURE:
<223> OTHER INFORMATION: Synthetic probe sequence

<400> SEQUENCE: 31
tgcctccgcg gccgcaggta atgacctgga agg               33

<210> SEQ ID NO 32
<211> LENGTH: 34
<212> TYPE: DNA
<213> ORGANISM: Artificial Sequence
<220> FEATURE:
<223> OTHER INFORMATION: Synthetic probe sequence

<400> SEQUENCE: 32
ctcccacctc cgtgaagcta tttttaactg tgca              34

<210> SEQ ID NO 33
<211> LENGTH: 27
<212> TYPE: DNA
<213> ORGANISM: Artificial Sequence
<220> FEATURE:
<223> OTHER INFORMATION: Synthetic probe sequence

<400> SEQUENCE: 33
attggatcaa acagacgggc acaatca                      27

<210> SEQ ID NO 34
<211> LENGTH: 28

```
<212> TYPE: DNA
<213> ORGANISM: Artificial Sequence
<220> FEATURE:
<223> OTHER INFORMATION: Synthetic probe sequence

<400> SEQUENCE: 34
acaagcatca taatccccct tttgactt                                          28

<210> SEQ ID NO 35
<211> LENGTH: 34
<212> TYPE: DNA
<213> ORGANISM: Artificial Sequence
<220> FEATURE:
<223> OTHER INFORMATION: Synthetic probe sequence

<400> SEQUENCE: 35
gctctgccaa ccccaaatcc gtcaagacgc atag                                   34

<210> SEQ ID NO 36
<211> LENGTH: 33
<212> TYPE: DNA
<213> ORGANISM: Artificial Sequence
<220> FEATURE:
<223> OTHER INFORMATION: Synthetic probe sequence

<400> SEQUENCE: 36
ctgtctccat tactgcctgc caccttctcc atc                                    33

<210> SEQ ID NO 37
<211> LENGTH: 25
<212> TYPE: DNA
<213> ORGANISM: Artificial Sequence
<220> FEATURE:
<223> OTHER INFORMATION: Synthetic probe sequence

<400> SEQUENCE: 37
agataaaaaa ccacccaccc agcac                                             25

<210> SEQ ID NO 38
<211> LENGTH: 31
<212> TYPE: DNA
<213> ORGANISM: Artificial Sequence
<220> FEATURE:
<223> OTHER INFORMATION: Synthetic probe sequence

<400> SEQUENCE: 38
gctcagagcc agtgtaatcc tcctcttgtg t                                      31

<210> SEQ ID NO 39
<211> LENGTH: 31
<212> TYPE: DNA
<213> ORGANISM: Artificial Sequence
<220> FEATURE:
<223> OTHER INFORMATION: Synthetic probe sequence

<400> SEQUENCE: 39
tgccactctc atcacagggt gcaatagcat a                                      31

<210> SEQ ID NO 40
<211> LENGTH: 36
<212> TYPE: DNA
<213> ORGANISM: Artificial Sequence
<220> FEATURE:
<223> OTHER INFORMATION: Synthetic probe sequence

<400> SEQUENCE: 40
```

```
cagctagctc ttgctgcctc tgctgctcag ccttct                                    36

<210> SEQ ID NO 41
<211> LENGTH: 40
<212> TYPE: DNA
<213> ORGANISM: Artificial Sequence
<220> FEATURE:
<223> OTHER INFORMATION: Synthetic probe sequence

<400> SEQUENCE: 41
agctaacaat atattaaaac ataatatcta tttagcaggt                                40

<210> SEQ ID NO 42
<211> LENGTH: 34
<212> TYPE: DNA
<213> ORGANISM: Artificial Sequence
<220> FEATURE:
<223> OTHER INFORMATION: Synthetic probe sequence

<400> SEQUENCE: 42
ctcagcccca gctggagaat ttttcccctc atta                                      34

<210> SEQ ID NO 43
<211> LENGTH: 36
<212> TYPE: DNA
<213> ORGANISM: Artificial Sequence
<220> FEATURE:
<223> OTHER INFORMATION: Synthetic probe sequence

<400> SEQUENCE: 43
gaaagaatta cacttgacag aggcagagga aaatgc                                    36

<210> SEQ ID NO 44
<211> LENGTH: 29
<212> TYPE: DNA
<213> ORGANISM: Artificial Sequence
<220> FEATURE:
<223> OTHER INFORMATION: Synthetic probe sequence

<400> SEQUENCE: 44
cagcacagtg gagaaaagta actgtcttt                                            29

<210> SEQ ID NO 45
<211> LENGTH: 28
<212> TYPE: DNA
<213> ORGANISM: Artificial Sequence
<220> FEATURE:
<223> OTHER INFORMATION: Synthetic probe sequence

<400> SEQUENCE: 45
atgacaggat aataacatta cattaaaa                                             28

<210> SEQ ID NO 46
<211> LENGTH: 29
<212> TYPE: DNA
<213> ORGANISM: Artificial Sequence
<220> FEATURE:
<223> OTHER INFORMATION: Synthetic probe sequence

<400> SEQUENCE: 46
tacatttata gattccctct tcagccata                                            29

<210> SEQ ID NO 47
<211> LENGTH: 33
<212> TYPE: DNA
<213> ORGANISM: Artificial Sequence
```

-continued

```
<220> FEATURE:
<223> OTHER INFORMATION: Synthetic probe sequence

<400> SEQUENCE: 47
cagctatttt attcttgaca tcaatttctg aaa                                    33

<210> SEQ ID NO 48
<211> LENGTH: 33
<212> TYPE: DNA
<213> ORGANISM: Artificial Sequence
<220> FEATURE:
<223> OTHER INFORMATION: Synthetic probe sequence

<400> SEQUENCE: 48
ctgctgtttt attgtcacag ctggagccag ttc                                    33

<210> SEQ ID NO 49
<211> LENGTH: 20
<212> TYPE: DNA
<213> ORGANISM: Artificial Sequence
<220> FEATURE:
<223> OTHER INFORMATION: Synthetic probe sequence

<400> SEQUENCE: 49
tggtgccagc ttcatcgccg                                                   20

<210> SEQ ID NO 50
<211> LENGTH: 29
<212> TYPE: DNA
<213> ORGANISM: Artificial Sequence
<220> FEATURE:
<223> OTHER INFORMATION: Synthetic probe sequence

<400> SEQUENCE: 50
gccaatcaat aattctgtgc caagcaact                                         29

<210> SEQ ID NO 51
<211> LENGTH: 32
<212> TYPE: DNA
<213> ORGANISM: Artificial Sequence
<220> FEATURE:
<223> OTHER INFORMATION: Synthetic probe sequence

<400> SEQUENCE: 51
tccgttacac taattgccat gatttagtcc aa                                     32

<210> SEQ ID NO 52
<211> LENGTH: 27
<212> TYPE: DNA
<213> ORGANISM: Artificial Sequence
<220> FEATURE:
<223> OTHER INFORMATION: Synthetic probe sequence

<400> SEQUENCE: 52
ccatctttac tagatttata atttgag                                           27

<210> SEQ ID NO 53
<211> LENGTH: 28
<212> TYPE: DNA
<213> ORGANISM: Artificial Sequence
<220> FEATURE:
<223> OTHER INFORMATION: Synthetic probe sequence

<400> SEQUENCE: 53 agaggggtt gctgagccgc ctgcaaga                                           28
```

<210> SEQ ID NO 54
<211> LENGTH: 20
<212> TYPE: DNA
<213> ORGANISM: Artificial Sequence
<220> FEATURE:
<223> OTHER INFORMATION: Synthetic probe sequence

<400> SEQUENCE: 54
cccagctaca cctccacgca                                          20

<210> SEQ ID NO 55
<211> LENGTH: 46
<212> TYPE: DNA
<213> ORGANISM: Artificial Sequence
<220> FEATURE:
<223> OTHER INFORMATION: Synthetic probe sequence

<400> SEQUENCE: 55
actaaaagga gccggaggag ctggagagac gcggggccga gccggg             46

<210> SEQ ID NO 56
<211> LENGTH: 35
<212> TYPE: DNA
<213> ORGANISM: Artificial Sequence
<220> FEATURE:
<223> OTHER INFORMATION: Synthetic probe sequence

<400> SEQUENCE: 56
agccatccat ttaaatgaaa atcagcactg ataca                         35

<210> SEQ ID NO 57
<211> LENGTH: 30
<212> TYPE: DNA
<213> ORGANISM: Artificial Sequence
<220> FEATURE:
<223> OTHER INFORMATION: Synthetic probe sequence

<400> SEQUENCE: 57
ctacgtgtgt cctttctttc acatttgctg                               30

<210> SEQ ID NO 58
<211> LENGTH: 24
<212> TYPE: DNA
<213> ORGANISM: Artificial Sequence
<220> FEATURE:
<223> OTHER INFORMATION: Synthetic probe sequence

<400> SEQUENCE: 58
ctgacattta tcttcagcat ctag                                     24

<210> SEQ ID NO 59
<211> LENGTH: 35
<212> TYPE: DNA
<213> ORGANISM: Artificial Sequence
<220> FEATURE:
<223> OTHER INFORMATION: Synthetic probe sequence

<400> SEQUENCE: 59
gaattttccc ctgcacagtt aggacaggat gcatg                         35

<210> SEQ ID NO 60
<211> LENGTH: 33
<212> TYPE: DNA
<213> ORGANISM: Artificial Sequence
<220> FEATURE:
<223> OTHER INFORMATION: Synthetic probe sequence

<400> SEQUENCE: 60
cagctgccag ggagacatag aaattaaaaa caa                                    33

<210> SEQ ID NO 61
<211> LENGTH: 34
<212> TYPE: DNA
<213> ORGANISM: Artificial Sequence
<220> FEATURE:
<223> OTHER INFORMATION: Synthetic probe sequence

<400> SEQUENCE: 61
tctgttgatt gattatattt atcagtgtag aaga                                  34

<210> SEQ ID NO 62
<211> LENGTH: 32
<212> TYPE: DNA
<213> ORGANISM: Artificial Sequence
<220> FEATURE:
<223> OTHER INFORMATION: Synthetic probe sequence

<400> SEQUENCE: 62
tggtcatcaa acctcagcct ctatcccatc aa                                    32

<210> SEQ ID NO 63
<211> LENGTH: 46
<212> TYPE: DNA
<213> ORGANISM: Artificial Sequence
<220> FEATURE:
<223> OTHER INFORMATION: Synthetic probe sequence

<400> SEQUENCE: 63
gttgagagtg agcatagctt tgactctgca aactaaaagt tccagg                     46

<210> SEQ ID NO 64
<211> LENGTH: 29
<212> TYPE: DNA
<213> ORGANISM: Artificial Sequence
<220> FEATURE:
<223> OTHER INFORMATION: Synthetic probe sequence

<400> SEQUENCE: 64
gctaaatggc cccagactgt tctgctgca                                        29

<210> SEQ ID NO 65
<211> LENGTH: 33
<212> TYPE: DNA
<213> ORGANISM: Artificial Sequence
<220> FEATURE:
<223> OTHER INFORMATION: Synthetic probe sequence

<400> SEQUENCE: 65
ttcaggtttt tataaatcag gatgtcaaca aat                                   33

<210> SEQ ID NO 66
<211> LENGTH: 19
<212> TYPE: DNA
<213> ORGANISM: Artificial Sequence
<220> FEATURE:
<223> OTHER INFORMATION: Synthetic probe sequence

<400> SEQUENCE: 66
ctgccaagat acctgattt                                                   19

<210> SEQ ID NO 67

```
<211> LENGTH: 20
<212> TYPE: DNA
<213> ORGANISM: Artificial Sequence
<220> FEATURE:
<223> OTHER INFORMATION: Synthetic probe sequence

<400> SEQUENCE: 67
ccagaagatg cagaagacag                                          20

<210> SEQ ID NO 68
<211> LENGTH: 20
<212> TYPE: DNA
<213> ORGANISM: Artificial Sequence
<220> FEATURE:
<223> OTHER INFORMATION: Synthetic probe sequence

<400> SEQUENCE: 68
ctggggaaaa gggtggcacg                                          20

<210> SEQ ID NO 69
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 69
tcacaagtta gggtctcagg ga                                       22

<210> SEQ ID NO 70
<211> LENGTH: 23
<212> TYPE: DNA
<213> ORGANISM: Artificial Sequence
<220> FEATURE:
<223> OTHER INFORMATION: Synthetic probe sequence

<400> SEQUENCE: 70
tccataaagt aggaaacact aca                                      23

<210> SEQ ID NO 71
<211> LENGTH: 23
<212> TYPE: DNA
<213> ORGANISM: Artificial Sequence
<220> FEATURE:
<223> OTHER INFORMATION: Synthetic probe sequence

<400> SEQUENCE: 71
acccctatca cgattagcat taa                                      23

<210> SEQ ID NO 72
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 72
cgccaatatt tacgtgctgc ta                                       22

<210> SEQ ID NO 73
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 73
```
ggagcagcac agccaatatt gg                                                22

<210> SEQ ID NO 74
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 74
actgcctgtc tgtgcctgct gt                                                22

<210> SEQ ID NO 75
<211> LENGTH: 23
<212> TYPE: DNA
<213> ORGANISM: Artificial Sequence
<220> FEATURE:
<223> OTHER INFORMATION: Synthetic probe sequence

<400> SEQUENCE: 75
aacactgatt tcaaatggtg cta                                               23

<210> SEQ ID NO 76
<211> LENGTH: 20
<212> TYPE: DNA
<213> ORGANISM: Artificial Sequence
<220> FEATURE:
<223> OTHER INFORMATION: Synthetic probe sequence

<400> SEQUENCE: 76
ctggaggaag ggcccagagg                                                   20

<210> SEQ ID NO 77
<211> LENGTH: 23
<212> TYPE: DNA
<213> ORGANISM: Artificial Sequence
<220> FEATURE:
<223> OTHER INFORMATION: Synthetic probe sequence

<400> SEQUENCE: 77
acactcaaaa gatggcggca ctt                                               23

<210> SEQ ID NO 78
<211> LENGTH: 20
<212> TYPE: DNA
<213> ORGANISM: Artificial Sequence
<220> FEATURE:
<223> OTHER INFORMATION: Synthetic probe sequence

<400> SEQUENCE: 78
agtgccccca cagtttgagt                                                   20

<210> SEQ ID NO 79
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 79
aatgataata caacctgcta ag                                                22

<210> SEQ ID NO 80
<211> LENGTH: 22
<212> TYPE: DNA

<213> ORGANISM: Artificial Sequence
<220> FEATURE:
<223> OTHER INFORMATION: Synthetic probe sequence

<400> SEQUENCE: 80
cagaaagtgc ttccctctag ag                                    22

<210> SEQ ID NO 81
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 81
gagaaagtgc ttccctttgt ag                                    22

<210> SEQ ID NO 82
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 82
cgctctaaag ggaagcgcct tc                                    22

<210> SEQ ID NO 83
<211> LENGTH: 21
<212> TYPE: DNA
<213> ORGANISM: Artificial Sequence
<220> FEATURE:
<223> OTHER INFORMATION: Synthetic probe sequence

<400> SEQUENCE: 83
agaaagtgca tccctctgga g                                     21

<210> SEQ ID NO 84
<211> LENGTH: 23
<212> TYPE: DNA
<213> ORGANISM: Artificial Sequence
<220> FEATURE:
<223> OTHER INFORMATION: Synthetic probe sequence

<400> SEQUENCE: 84
aatcgcggtt tataccaaat gaa                                   23

<210> SEQ ID NO 85
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 85
tatccactac accccgctgc ct                                    22

<210> SEQ ID NO 86
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 86
cgcaaggtcg gttctacggg tg                                    22

<210> SEQ ID NO 87
<211> LENGTH: 78
<212> TYPE: DNA
<213> ORGANISM: Human
<220> FEATURE:
<221> NAME/KEY: misc_feature
<222> LOCATION: (1)..(78)
<223> OTHER INFORMATION: Pre-microRNA sequence

<400> SEQUENCE: 87
aagtcttaca attcagggat aggaagctat gatttacata atgaacatgg caaagagacc    60
tataaagaaa taagactt                                                 78

<210> SEQ ID NO 88
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: Pre-microRNA sequence

<400> SEQUENCE: 88
cgccactctc atagtcctac acaaaccctc tgttgctctt ctattagacc atgctaacca    60
attctgaggg ctgtgagggg taggtg                                        86

<210> SEQ ID NO 89
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: Pre-microRNA sequence

<400> SEQUENCE: 89
gttgagattg tgcaatctgt ttggctgcta aaggttccaa attatgtggg cattctgcag    60
ccccacagag tggtagaatt tcttc                                         85

<210> SEQ ID NO 90
<211> LENGTH: 67
<212> TYPE: DNA
<213> ORGANISM: Human
<220> FEATURE:
<221> NAME/KEY: misc_feature
<222> LOCATION: (1)..(67)
<223> OTHER INFORMATION: Pre-microRNA sequence

<400> SEQUENCE: 90
gcatgatttt tattagcctt gcaatttctt aatgggctcc cctgagggct ggctggtaga    60
atcctgc                                                             67

<210> SEQ ID NO 91
<211> LENGTH: 67
<212> TYPE: DNA
<213> ORGANISM: Human
<220> FEATURE:
<221> NAME/KEY: misc_feature
<222> LOCATION: (1)..(67)
<223> OTHER INFORMATION: Pre-microRNA sequence

<400> SEQUENCE: 91
gcatgatttt tattagcctt gcaatttctt aatgggctcc cctgagggct ggctggtaga    60

| atcctgc | 67 |

<210> SEQ ID NO 92
<211> LENGTH: 83
<212> TYPE: DNA
<213> ORGANISM: Human
<220> FEATURE:
<221> NAME/KEY: misc_feature
<222> LOCATION: (1)..(83)
<223> OTHER INFORMATION: Pre-microRNA sequence

<400> SEQUENCE: 92

| tattagttac aatatattaa ctgcctaatt taaaaataaa actatcttta tgaagggcaa | 60 |
| ttaaccacta agtgtaattg ata | 83 |

<210> SEQ ID NO 93
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: Pre-microRNA sequence

<400> SEQUENCE: 93

| ggcggctgcg gaggctggcg cgggctgctg cacctttaac gctttctggc gctgacaggc | 60 |
| ggcggcccag ctaaagttca cagcgcc | 87 |

<210> SEQ ID NO 94
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: Pre-microRNA sequence

<400> SEQUENCE: 94

| gagaggaggt ctcaggaggc tcgtgatggt cacactgaca ggtagggctt tcactcccat | 60 |
| cccctcttga tactcacctg ccgccccga cccctctc | 98 |

<210> SEQ ID NO 95
<211> LENGTH: 80
<212> TYPE: DNA
<213> ORGANISM: Human
<220> FEATURE:
<221> NAME/KEY: misc_feature
<222> LOCATION: (1)..(80)
<223> OTHER INFORMATION: Pre-microRNA sequence

<400> SEQUENCE: 95

| tagcaattta atgttggagg tttgtatgaa cttgaagctt atttcagttg gttgcctgga | 60 |
| accttctgca ttctttgctg | 80 |

<210> SEQ ID NO 96
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: Pre-microRNA sequence

<400> SEQUENCE: 96

| agcagaatgt atgccacttc cttccttagt ggtttgtccg ccaacattaa caggccattg | 60 |

```
ggtggatgaa gtaggtaaat tttgct                                          86
```

<210> SEQ ID NO 97
<211> LENGTH: 100
<212> TYPE: DNA
<213> ORGANISM: Human
<220> FEATURE:
<221> NAME/KEY: misc_feature
<222> LOCATION: (1)..(100)
<223> OTHER INFORMATION: Pre-microRNA sequence

<400> SEQUENCE: 97

```
ggagagctgt gtttcatgtg attagagact gtttgtgcct ctgtccatta ggaaaaaaga    60
ggaggaagca tttttaagaa cttgacgcca aacatttttcc                        100
```

<210> SEQ ID NO 98
<211> LENGTH: 66
<212> TYPE: DNA
<213> ORGANISM: Human
<220> FEATURE:
<221> NAME/KEY: misc_feature
<222> LOCATION: (1)..(66)
<223> OTHER INFORMATION: Pre-microRNA sequence

<400> SEQUENCE: 98

```
cctgtgagct cgcactctca ctctctctgt ctctgtgtca ggagtgaatg gtgtgggctc    60
ctcagg                                                               66
```

<210> SEQ ID NO 99
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: Pre-microRNA sequence

<400> SEQUENCE: 99

```
gctaaagttg cttctgccct ttgaaaatat gaaagccctt gagtgatttt atattttcaa    60
agggtaaaag tgctaaagag c                                              81
```

<210> SEQ ID NO 100
<211> LENGTH: 73
<212> TYPE: DNA
<213> ORGANISM: Human
<220> FEATURE:
<221> NAME/KEY: misc_feature
<222> LOCATION: (1)..(73)
<223> OTHER INFORMATION: Pre-microRNA sequence

<400> SEQUENCE: 100

```
tgagctgtac tttggaaatg gatctgatga gtctttttaat agaagaaaat catcattatt    60
tcccaagagc tca                                                       73
```

<210> SEQ ID NO 101
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: Pre-microRNA sequence

<400> SEQUENCE: 101

```
cagagactac ctgagaccaa ttacagcctc tggcatttgt gctgctaaat ttgtaatgag    60
ttgcaggtgt ttgtg                                                    75

<210> SEQ ID NO 102
<211> LENGTH: 74
<212> TYPE: DNA
<213> ORGANISM: Human
<220> FEATURE:
<221> NAME/KEY: misc_feature
<222> LOCATION: (1)..(74)
<223> OTHER INFORMATION: Pre-microRNA sequence

<400> SEQUENCE: 102
tctggcaggc ggtaattgct ggccagctgc agggattaca gccctgtgag ctgtgttcag    60
ggccctgtgc cagg                                                     74

<210> SEQ ID NO 103
<211> LENGTH: 77
<212> TYPE: DNA
<213> ORGANISM: Human
<220> FEATURE:
<221> NAME/KEY: misc_feature
<222> LOCATION: (1)..(77)
<223> OTHER INFORMATION: Pre-microRNA sequence

<400> SEQUENCE: 103
ggctctgcac caggcgtttc ttcttgtgtt tcctcttctc ttctggagag ggatgaagga    60
gatcctttgt gagaggc                                                  77

<210> SEQ ID NO 104
<211> LENGTH: 76
<212> TYPE: DNA
<213> ORGANISM: Human
<220> FEATURE:
<221> NAME/KEY: misc_feature
<222> LOCATION: (1)..(76)
<223> OTHER INFORMATION: Pre-microRNA sequence

<400> SEQUENCE: 104
gctcctgctc cgccgcggga gctgctccgg cggccgcagg gctcgctcgg gaagctgagg    60
cggcggaggc tggagt                                                   76

<210> SEQ ID NO 105
<211> LENGTH: 78
<212> TYPE: DNA
<213> ORGANISM: Human
<220> FEATURE:
<221> NAME/KEY: misc_feature
<222> LOCATION: (1)..(78)
<223> OTHER INFORMATION: Pre-microRNA sequence

<400> SEQUENCE: 105
tggcctgacg tgaggaggag ggacttttcg aagttttata ggaaagtttc cgctttccag    60 tcccctccc ccgtccca                                                  78

<210> SEQ ID NO 106
<211> LENGTH: 79
<212> TYPE: DNA
<213> ORGANISM: Human
<220> FEATURE:
<221> NAME/KEY: misc_feature
<222> LOCATION: (1)..(79)
<223> OTHER INFORMATION: Pre-microRNA sequence

<400> SEQUENCE: 106
```

```
gaggttggac aggcttctcc acactgagct ttacaggccc gctccctccc ctgcagagct    60
cacaagccct gccagcttt                                                 79
```

<210> SEQ ID NO 107
<211> LENGTH: 73
<212> TYPE: DNA
<213> ORGANISM: Human
<220> FEATURE:
<221> NAME/KEY: misc_feature
<222> LOCATION: (1)..(73)
<223> OTHER INFORMATION: Pre-microRNA sequence

<400> SEQUENCE: 107

```
gatttttaag atgtgacagc ttgattattt tacaaggcca aaaccctgat tcaagcctgc    60
aattttaaga atc                                                       73
```

<210> SEQ ID NO 108
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: Pre-microRNA sequence

<400> SEQUENCE: 108

```
gtgatgtgat ttctgcccag tgctctgaat gtcaaactga agaaattcag tgaaatgcgg    60
gtaaacggcg ggagtaacta tgac                                           84
```

<210> SEQ ID NO 109
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: Pre-microRNA sequence

<400> SEQUENCE: 109

```
ctcaccctga tgtattgcat taatagatca tcagaagcag ttgtcattcc agtgatatat    60
tagtgcaata catgagaatg ag                                             82
```

<210> SEQ ID NO 110
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: Pre-microRNA sequence

<400> SEQUENCE: 110

```
ggagaccaca attatacccc ctttcaatga catgtctggg gttgcagtga ctccagacaa    60
agaagctgaa atgtatgaaa gtttcc                                         86
```

<210> SEQ ID NO 111
<211> LENGTH: 79
<212> TYPE: DNA
<213> ORGANISM: Human
<220> FEATURE:
<221> NAME/KEY: misc_feature
<222> LOCATION: (1)..(79)
<223> OTHER INFORMATION: Pre-microRNA sequence -continued

<400> SEQUENCE: 111
gtagcagggc aggaaaatgt aaaatcaata aataatcagg ctgaatttta attgaatata    60
ttcctaaggc catgctgac                                                79

<210> SEQ ID NO 112
<211> LENGTH: 76
<212> TYPE: DNA
<213> ORGANISM: Human
<220> FEATURE:
<221> NAME/KEY: misc_feature
<222> LOCATION: (1)..(76)
<223> OTHER INFORMATION: Pre-microRNA sequence

<400> SEQUENCE: 112
catcaggtcg aatcagggtg ttgaccttgg ccacatcaat gtcatagagc ttcttcacag    60
cctgtttgat ctggtg                                                   76

<210> SEQ ID NO 113
<211> LENGTH: 80
<212> TYPE: DNA
<213> ORGANISM: Human
<220> FEATURE:
<221> NAME/KEY: misc_feature
<222> LOCATION: (1)..(80)
<223> OTHER INFORMATION: Pre-microRNA sequence

<400> SEQUENCE: 113
gaggctcaag gcagagtgtg ttgggtgacc ctgggtaggg cttggttggc cacttaccac    60
atggttgcca ctggggcctt                                               80

<210> SEQ ID NO 114
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: Pre-microRNA sequence

<400> SEQUENCE: 114
ctgaacaaat agcagatgtt gatgaatatt aatttgtgct tagattaatg cttcaaagtg    60
tcaatttaat ttctgtttta ctattcag                                      88

<210> SEQ ID NO 115
<211> LENGTH: 79
<212> TYPE: DNA
<213> ORGANISM: Human
<220> FEATURE:
<221> NAME/KEY: misc_feature
<222> LOCATION: (1)..(79)
<223> OTHER INFORMATION: Pre-microRNA sequence

<400> SEQUENCE: 115
tggaaggaga gcagcggcat ttggtttggt ggtgggcaga ttttctttta cgactgctaa    60
atgcctgcct ttctcccca                                                79

<210> SEQ ID NO 116
<211> LENGTH: 83
<212> TYPE: DNA
<213> ORGANISM: Human
<220> FEATURE:
<221> NAME/KEY: misc_feature
<222> LOCATION: (1)..(83)
<223> OTHER INFORMATION: Pre-microRNA sequence

<400> SEQUENCE: 116
gcctcccctt ccaggtcatt acctgcggcc gcggaggcaa cagctgccac catggcctga    60
tgagtgatct ggtgggcgac ggc    83

<210> SEQ ID NO 117
<211> LENGTH: 74
<212> TYPE: DNA
<213> ORGANISM: Human
<220> FEATURE:
<221> NAME/KEY: misc_feature
<222> LOCATION: (1)..(74)
<223> OTHER INFORMATION: Pre-microRNA sequence

<400> SEQUENCE: 117
ctcccacggc ctgaagctgc tgccaagcta tttttggttc tgcacagtta aaatagctt    60 cacggaggtg ggag    74

<210> SEQ ID NO 118
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: Pre-microRNA sequence

<400> SEQUENCE: 118
ctcattgagg gaagattgag cagaactggc attgcttgct ttcgtcaaat tgattgtgcc    60
cgtctgtttg atccaattca gtgag    85

<210> SEQ ID NO 119
<211> LENGTH: 71
<212> TYPE: DNA
<213> ORGANISM: Human
<220> FEATURE:
<221> NAME/KEY: misc_feature
<222> LOCATION: (1)..(71)
<223> OTHER INFORMATION: Pre-microRNA sequence

<400> SEQUENCE: 119
acaggctcat ccctctgaac agatgagatt agtcgatcat gtaaagtcaa aagggggatt    60
atgatgcttg t    71

<210> SEQ ID NO 120
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: Pre-microRNA sequence

<400> SEQUENCE: 120
ctatgcgtct tgacggattt ggggttggca gagcaggctg ccctgcttt ctatccccat    60 tcagtccact tatag    75

<210> SEQ ID NO 121
<211> LENGTH: 72
<212> TYPE: DNA
<213> ORGANISM: Human
<220> FEATURE:
<221> NAME/KEY: misc_feature
<222> LOCATION: (1)..(72)

<223> OTHER INFORMATION: Pre-microRNA sequence

<400> SEQUENCE: 121
gatggagaag gtggcaggca gtaatggaga cagaatttct gttaactgct gtaattaatg    60
ttatgtctca tc    72

<210> SEQ ID NO 122
<211> LENGTH: 83
<212> TYPE: DNA
<213> ORGANISM: Human
<220> FEATURE:
<221> NAME/KEY: misc_feature
<222> LOCATION: (1)..(83)
<223> OTHER INFORMATION: Pre-microRNA sequence

<400> SEQUENCE: 122
gtgctgggtg ggtggttttt tatcttcacg gatttatgga gtccttaaaa catctgttcc    60
gttctgattc ccccgctcag tac    83

<210> SEQ ID NO 123
<211> LENGTH: 77
<212> TYPE: DNA
<213> ORGANISM: Human
<220> FEATURE:
<221> NAME/KEY: misc_feature
<222> LOCATION: (1)..(77)
<223> OTHER INFORMATION: Pre-microRNA sequence

<400> SEQUENCE: 123
gttccgaggc aggctttcct cctctctgca ggggagaggc tccctcacac aagaggagga    60
ttacactggc tctgagc    77

<210> SEQ ID NO 124
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: Pre-microRNA sequence

<400> SEQUENCE: 124
aaactggaac acattcctca agggagcagg aaagcatgag aagacagtat gctattgcac    60
cctgtgatga gagtggcagt tt    82

<210> SEQ ID NO 125
<211> LENGTH: 77
<212> TYPE: DNA
<213> ORGANISM: Human
<220> FEATURE:
<221> NAME/KEY: misc_feature
<222> LOCATION: (1)..(77)
<223> OTHER INFORMATION: Pre-microRNA sequence

<400> SEQUENCE: 125
agaaggctga gcagcagagg cagcaagagc tagctgcaca tacccagcaa cagccttcca    60
cttctgatca gtcttct    77

<210> SEQ ID NO 126
<211> LENGTH: 82
<212> TYPE: DNA
<213> ORGANISM: Human
<220> FEATURE:
<221> NAME/KEY: misc_feature

```
<222> LOCATION: (1)..(82)
<223> OTHER INFORMATION: Pre-microRNA sequence

<400> SEQUENCE: 126
agcaaattta ctattgggaa taaatatttg atgcaggtga acacctgcta aatagatatt      60
atgttttaat atattgttag ct                                              82

<210> SEQ ID NO 127
<211> LENGTH: 73
<212> TYPE: DNA
<213> ORGANISM: Human
<220> FEATURE:
<221> NAME/KEY: misc_feature
<222> LOCATION: (1)..(73)
<223> OTHER INFORMATION: Pre-microRNA sequence

<400> SEQUENCE: 127
ctcagtatct tcagcttggg aaactgacct cgttaatttt aatgagggga aaaattctcc      60
agctggggct gag                                                        73

<210> SEQ ID NO 128
<211> LENGTH: 80
<212> TYPE: DNA
<213> ORGANISM: Human
<220> FEATURE:
<221> NAME/KEY: misc_feature
<222> LOCATION: (1)..(80)
<223> OTHER INFORMATION: Pre-microRNA sequence

<400> SEQUENCE: 128
gactgcaggc attttcctct gcctctgtca agtgtaattc tttcttgatg aatgacaagg      60
caggataata ggctgtggtc                                                 80

<210> SEQ ID NO 129
<211> LENGTH: 76
<212> TYPE: DNA
<213> ORGANISM: Human
<220> FEATURE:
<221> NAME/KEY: misc_feature
<222> LOCATION: (1)..(76)
<223> OTHER INFORMATION: Pre-microRNA sequence

<400> SEQUENCE: 129
aaagacagtt actttctcc actgtgctgc taccaccaat ttggtggcta ttaatagctg       60
gcagattaac ttcttt                                                     76

<210> SEQ ID NO 130
<211> LENGTH: 76
<212> TYPE: DNA
<213> ORGANISM: Human
<220> FEATURE:
<221> NAME/KEY: misc_feature
<222> LOCATION: (1)..(76)
<223> OTHER INFORMATION: Pre-microRNA sequence

<400> SEQUENCE: 130
ttttaatgta atgttattat cctgtcattt aatttagcaa tgacaagtga tgatgagatt      60
ttgatttgca ttagaa                                                     76

<210> SEQ ID NO 131
<211> LENGTH: 76
<212> TYPE: DNA
<213> ORGANISM: Human
<220> FEATURE:
```

```
<221> NAME/KEY: misc_feature
<222> LOCATION: (1)..(76)
<223> OTHER INFORMATION: Pre-microRNA sequence

<400> SEQUENCE: 131
attcaacaca gattcaggtg ctctcaacag ccatgaaaat atatggctga agagggaatc      60
tataaatgta atgaat                                                      76

<210> SEQ ID NO 132
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: Pre-microRNA sequence

<400> SEQUENCE: 132
aggtgatgtt ttcagaaatt gatgtcaaga ataaatagc tgttggcagt tacaactgtt       60
tggatgtcat tttacaaaac aattgcct                                         88

<210> SEQ ID NO 133
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: Pre-microRNA sequence

<400> SEQUENCE: 133
gagtgtgaac tggctccagc tgtgacaata aaacagcagg tggctgctgt cattagggt       60 ggcagatgag gcaggggact aacattc                                          87

<210> SEQ ID NO 134
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: Pre-microRNA sequence

<400> SEQUENCE: 134
cctggatgct gtttcattat gtagagtcag gcaaaagaca gacggatgtg tgtgtgaggc      60
ggcgatgaag ctggcaccag g                                                81

<210> SEQ ID NO 135
<211> LENGTH: 74
<212> TYPE: DNA
<213> ORGANISM: Human
<220> FEATURE:
<221> NAME/KEY: misc_feature
<222> LOCATION: (1)..(74)
<223> OTHER INFORMATION: Pre-microRNA sequence

<400> SEQUENCE: 135
gagattagcg aaagggattc tggccaaatc cctgatcaag ttgcttggca cagaattatt      60
gattggcaaa tctt                                                        74

<210> SEQ ID NO 136
<211> LENGTH: 86
<212> TYPE: DNA
<213> ORGANISM: Human
```

```
<220> FEATURE:
<221> NAME/KEY: misc_feature
<222> LOCATION: (1)..(86)
<223> OTHER INFORMATION: Pre-microRNA sequence

<400> SEQUENCE: 136
ttggactaaa tcatggcaat tagtgtaacg gaaatgttta cagcaatctc tgatggcagt        60
tctactaatg caatgattta gctcaa                                              86

<210> SEQ ID NO 137
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: Pre-microRNA sequence

<400> SEQUENCE: 137
aaatatttat gtactcaaat tataaatcta gtaaagatgg catttcacct tatactagtt        60
atttattaat aatgagagct gtattt                                              86

<210> SEQ ID NO 138
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: Pre-microRNA sequence

<400> SEQUENCE: 138 agagggtga ctgcggggct tgttgcgctg aagatttaca atgtacttct tgcaggcggc         60
tcagcaaccc cctct                                                          75

<210> SEQ ID NO 139
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: Pre-microRNA sequence

<400> SEQUENCE: 139
cagctggcct ggtgccctgg tgcgtggagg tgtagctggg ctctgaccca gctcctcaaa        60
caggttccat atggccctcc cggctg                                              86

<210> SEQ ID NO 140
<211> LENGTH: 107
<212> TYPE: DNA
<213> ORGANISM: Human
<220> FEATURE:
<221> NAME/KEY: misc_feature
<222> LOCATION: (1)..(107)
<223> OTHER INFORMATION: Pre-microRNA sequence

<400> SEQUENCE: 140
cccggctcgg ccccgcgtct ctccagctcc tccggctcct tttagtgcat aaattagtga        60
tggcatttcc cggagagcgg agcacaacac agggcgccgg gctcggg                      107

<210> SEQ ID NO 141
<211> LENGTH: 87
<212> TYPE: DNA
```

```
<213> ORGANISM: Human
<220> FEATURE:
<221> NAME/KEY: misc_feature
<222> LOCATION: (1)..(87)
<223> OTHER INFORMATION: Pre-microRNA sequence

<400> SEQUENCE: 141
gagagattgt atcagtgctg attttcattt aaatggatgg ctatgagatt ttttaaagca    60
tgccaaaaat ctgtttgtac atctctc                                        87

<210> SEQ ID NO 142
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: Pre-microRNA sequence

<400> SEQUENCE: 142
cagcaaatgt gaaagaaagg acacacgtag gtactgtcat ttaggtaatg tcatctatga    60
tcagtttttg tttcattttt tgctg                                          85

<210> SEQ ID NO 143
<211> LENGTH: 74
<212> TYPE: DNA
<213> ORGANISM: Human
<220> FEATURE:
<221> NAME/KEY: misc_feature
<222> LOCATION: (1)..(74)
<223> OTHER INFORMATION: Pre-microRNA sequence

<400> SEQUENCE: 143
ctgacattta ctttcactca tgagcacagg ggtgaccagc cccaccagtc ctagatgctg    60
aagataaatg tcag                                                      74

<210> SEQ ID NO 144
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: Pre-microRNA sequence

<400> SEQUENCE: 144
tcccctgatt tccctctgtg gaagaatgtg tgaattcaca tgcatcctgt cctaactgtg    60
caggggaaaa ttccagtcag ggga                                           84

<210> SEQ ID NO 145
<211> LENGTH: 76
<212> TYPE: DNA
<213> ORGANISM: Human
<220> FEATURE:
<221> NAME/KEY: misc_feature
<222> LOCATION: (1)..(76)
<223> OTHER INFORMATION: Pre-microRNA sequence

<400> SEQUENCE: 145
tagctgcctc agagtagaaa ataaaactca acaagatttt atcttgtttt taatttctat    60
gtctccctgg cagctg                                                    76

<210> SEQ ID NO 146
<211> LENGTH: 84
```

```
<212> TYPE: DNA
<213> ORGANISM: Human
<220> FEATURE:
<221> NAME/KEY: misc_feature
<222> LOCATION: (1)..(84)
<223> OTHER INFORMATION: Pre-microRNA sequence

<400> SEQUENCE: 146
ttaaattctt ctacactgat aaatataatc aatcaacaga gaacatgctc tgaggaatta    60
attgttgtca gttgatgtat ttaa                                          84

<210> SEQ ID NO 147
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: Pre-microRNA sequence

<400> SEQUENCE: 147
gctataatgg aaaactgatg gcttttatct ccccaacttt atgactattg atgggataga    60
ggctgaggtt tgatgaccat ttaatagc                                      88

<210> SEQ ID NO 148
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: Pre-microRNA sequence

<400> SEQUENCE: 148
cctggaactt ttagtttgca gagtcaaagc tatgctcact ctcaacaatt gtagagaggc    60
tttctggctg ggcaatctaa aaaaccggg                                     89

<210> SEQ ID NO 149
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: Pre-microRNA sequence

<400> SEQUENCE: 149
tgcagcagaa cagtctgggg ccatttagct tagggggcaaa tagttcctca tacttcaaag   60
agccctaagg acattgctgc a                                             81

<210> SEQ ID NO 150
<211> LENGTH: 80
<212> TYPE: DNA
<213> ORGANISM: Human
<220> FEATURE:
<221> NAME/KEY: misc_feature
<222> LOCATION: (1)..(80)
<223> OTHER INFORMATION: Pre-microRNA sequence

<400> SEQUENCE: 150
cttgtatttg ttgacatcct gatttataaa aacctgaaca agttcagttt caataattct    60
ttttgttcaa ggaacacaag                                               80

<210> SEQ ID NO 151
```

```
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: Pre-microRNA sequence

<400> SEQUENCE: 151
ccaggagaaa tcaggtatct tggcagtgtg accaccatga ataaacaaca actctggtgg    60
cctgtcttct gcatcttctg g                                              81

<210> SEQ ID NO 152
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: Pre-microRNA sequence

<400> SEQUENCE: 152
ccaggagaaa tcaggtatct tggcagtgtg accaccatga ataaacaaca actctggtgg    60
cctgtcttct gcatcttctg g                                              81

<210> SEQ ID NO 153
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: Pre-microRNA sequence

<400> SEQUENCE: 153
gtggggccag gcggtggtgg gcactgctgg ggtgggcaca gcagccatgc agagcgggca    60
tttgaccccg tgccacccttt ttccccag                                      88

<210> SEQ ID NO 154
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: Pre-microRNA sequence

<400> SEQUENCE: 154
accagacttt tcctagtccc tgagaccctaa acttgtgagg tattttagta acatcacaag   60
tcaggctctt gggacctagg cggagggga                                      89

<210> SEQ ID NO 155
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: Pre-microRNA sequence

<400> SEQUENCE: 155
tgcgctcctc tcagtccctg agaccctaac ttgtgatgtt taccgtttaa atccacgggt    60
taggctcttg ggagctgcga gtcgtgct                                       88
```

```
<210> SEQ ID NO 156
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: Pre-microRNA sequence

<400> SEQUENCE: 156
gacagtgcag tcacccataa agtagaaagc actactaaca gcactggagg gtgtagtgtt      60
tcctacttta tggatgagtg tactgtg                                         87

<210> SEQ ID NO 157
<211> LENGTH: 65
<212> TYPE: DNA
<213> ORGANISM: Human
<220> FEATURE:
<221> NAME/KEY: misc_feature
<222> LOCATION: (1)..(65)
<223> OTHER INFORMATION: Pre-microRNA sequence

<400> SEQUENCE: 157
ctgttaatgc taatcgtgat aggggttttt gcctccaact gactcctaca tattagcatt      60
aacag                                                                 65

<210> SEQ ID NO 158
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: Pre-microRNA sequence

<400> SEQUENCE: 158
gtcagcagtg ccttagcagc acgtaaatat tggcgttaag attctaaaat tatctccagt      60
attaactgtg ctgctgaagt aaggttgac                                       89

<210> SEQ ID NO 159
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: Pre-microRNA sequence

<400> SEQUENCE: 159
gttccactct agcagcacgt aaatattggc gtagtgaaat atatattaaa caccaatatt      60
actgtgctgc tttagtgtga c                                               81

<210> SEQ ID NO 160
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: Pre-microRNA sequence

<400> SEQUENCE: 160
agcttccctg gctctagcag cacagaaata ttggcacagg gaagcgagtc tgccaatatt      60
ggctgtgctg ctccaggcag ggtggtg                                         87
```

```
<210> SEQ ID NO 161
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: Pre-microRNA sequence

<400> SEQUENCE: 161
ggcctggctg gacagagttg tcatgtgtct gcctgtctac acttgctgtg cagaacatcc     60
gctcacctgt acagcaggca cagacaggca gtcacatgac aacccagcct               110

<210> SEQ ID NO 162
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: Pre-microRNA sequence

<400> SEQUENCE: 162
cttcaggaag ctggtttcat atggtggttt agatttaaat agtgattgtc tagcaccatt     60
tgaaatcagt gttcttgggg g                                               81

<210> SEQ ID NO 163
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: Pre-microRNA sequence

<400> SEQUENCE: 163
cttctggaag ctggtttcac atggtggctt agattttcc atctttgtat ctagcaccat      60
ttgaaatcag tgttttagga g                                               81

<210> SEQ ID NO 164
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: Pre-microRNA sequence

<400> SEQUENCE: 164
ctcatctgtc tgtttgggctg gaggcagggc ctttgtgaag gcgggtggtg ctcagatcgc    60
ctctgggccc ttcctccagc cccgaggcgg attca                                95

<210> SEQ ID NO 165
<211> LENGTH: 67
<212> TYPE: DNA
<213> ORGANISM: Human
<220> FEATURE:
<221> NAME/KEY: misc_feature
<222> LOCATION: (1)..(67)
<223> OTHER INFORMATION: Pre-microRNA sequence

<400> SEQUENCE: 165
gtggcactca aactgtgggg gcactttctg ctctctggtg aaagtgccgc catcttttga     60
gtgttac                                                               67
```

<210> SEQ ID NO 166
<211> LENGTH: 67
<212> TYPE: DNA
<213> ORGANISM: Human
<220> FEATURE:
<221> NAME/KEY: misc_feature
<222> LOCATION: (1)..(67)
<223> OTHER INFORMATION: Pre-microRNA sequence

<400> SEQUENCE: 166
gtggcactca aactgtgggg gcactttctg ctctctggtg aaagtgccgc catcttttga    60
gtgttac                                                              67

<210> SEQ ID NO 167
<211> LENGTH: 72
<212> TYPE: DNA
<213> ORGANISM: Human
<220> FEATURE:
<221> NAME/KEY: misc_feature
<222> LOCATION: (1)..(72)
<223> OTHER INFORMATION: Pre-microRNA sequence

<400> SEQUENCE: 167
actcggatgg atataataca acctgctaag tgtcctagca cttagcaggt tgtattatca    60
ttgtccgtgt ct                                                        72

<210> SEQ ID NO 168
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: Pre-microRNA sequence

<400> SEQUENCE: 168
tcccatgctg tgaccctcta gagggaagca ctttctgttg tctgaaagaa accaaagcgc    60
ttccctttgg agcgttacgg tttgaga                                        87

<210> SEQ ID NO 169
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: Pre-microRNA sequence

<400> SEQUENCE: 169
tctcaggctg tcgtcctcta gagggaagca ctttctgttg tctgaaagaa aagaaagtgc    60
ttccttttag agggttaccg tttgaga                                        87

<210> SEQ ID NO 170
<211> LENGTH: 65
<212> TYPE: DNA
<213> ORGANISM: Human
<220> FEATURE:
<221> NAME/KEY: misc_feature
<222> LOCATION: (1)..(65)
<223> OTHER INFORMATION: Pre-microRNA sequence

<400> SEQUENCE: 170
gtgaccctct agagggaagc actttctgtt gaaagaaaag aacatgcatc ctttcagagg    60
gttac                                                                    65

<210> SEQ ID NO 171
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: Pre-microRNA sequence

<400> SEQUENCE: 171
ctcaggctgt gaccctctag agggaagcac tttctgttgc ttgaaagaag agaaagcgct    60
tccttttaga ggattactct ttgag                                          85

<210> SEQ ID NO 172
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: Pre-microRNA sequence

<400> SEQUENCE: 172
tctcatgctg tgaccctaca aagggaagca ctttctcttg tccaaaggaa aagaaggcgc    60 ttcccttcccttcgg agtgttacgg tttgaga                                   87

<210> SEQ ID NO 173
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: Pre-microRNA sequence

<400> SEQUENCE: 173
ctcaagctgt gactctccag agggatgcac tttctcttat gtgaaaaaaa agaaggcgct    60 tcccttttaga gcgttacggt ttggg                                         85

<210> SEQ ID NO 174
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: Pre-microRNA sequence

<400> SEQUENCE: 174
ctcaagctgt gactctccag agggatgcac tttctcttat gtgaaaaaaa agaaggcgct    60 tcccttttaga gcgttacggt ttggg                                         85

<210> SEQ ID NO 175
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: Pre-microRNA sequence

<400> SEQUENCE: 175
catattaggt taatgcaaaa gtaatcgcgg tttgtgccag atgacgattt gaattaataa    60
attcatttgg tataaaccgc gattattttt gcatcaac                              98

<210> SEQ ID NO 176
<211> LENGTH: 74
<212> TYPE: DNA
<213> ORGANISM: Human
<220> FEATURE:
<221> NAME/KEY: misc_feature
<222> LOCATION: (1)..(74)
<223> OTHER INFORMATION: Pre-microRNA sequence

<400> SEQUENCE: 176
ccgcactctc tccattacac taccctgcct cttctccatg agaggcagcg gggtgtagtg    60
gatagagcac gggt                                                      74

<210> SEQ ID NO 177
<211> LENGTH: 70
<212> TYPE: DNA
<213> ORGANISM: Human
<220> FEATURE:
<221> NAME/KEY: misc_feature
<222> LOCATION: (1)..(70)
<223> OTHER INFORMATION: Pre-microRNA sequence

<400> SEQUENCE: 177
ggcacccacc cgtagaaccg accttgcggg gccttcgccg cacacaagct cgtgtctgtg    60
ggtccgtgtc                                                           70

<210> SEQ ID NO 178
<211> LENGTH: 22
<212> TYPE: RNA
<213> ORGANISM: Artificial Sequence
<220> FEATURE:
<223> OTHER INFORMATION: Synthetic RNA sequence

<400> SEQUENCE: 178
cgcgcgucgc uuuaucuacu gu                                             22

<210> SEQ ID NO 179
<211> LENGTH: 22
<212> TYPE: RNA
<213> ORGANISM: Artificial Sequence
<220> FEATURE:
<223> OTHER INFORMATION: Synthetic RNA sequence

<400> SEQUENCE: 179
uuaucguucg auaagucgcg uu                                             22

<210> SEQ ID NO 180
<211> LENGTH: 22
<212> TYPE: RNA
<213> ORGANISM: Artificial Sequence
<220> FEATURE:
<223> OTHER INFORMATION: Synthetic RNA sequence

<400> SEQUENCE: 180
gaaguuacua uguaggcaac cu                                             22

<210> SEQ ID NO 181
<211> LENGTH: 22
<212> TYPE: RNA
<213> ORGANISM: Artificial Sequence
<220> FEATURE:
<223> OTHER INFORMATION: Synthetic RNA sequence

```
<400> SEQUENCE: 181
cgcgggacua auuguuaccg gg                                              22

<210> SEQ ID NO 182
<211> LENGTH: 22
<212> TYPE: RNA
<213> ORGANISM: Artificial Sequence
<220> FEATURE:
<223> OTHER INFORMATION: Synthetic RNA sequence

<400> SEQUENCE: 182
ucgcgucgaa cuccgcaacc ga                                              22

<210> SEQ ID NO 183
<211> LENGTH: 22
<212> TYPE: RNA
<213> ORGANISM: Artificial Sequence
<220> FEATURE:
<223> OTHER INFORMATION: Synthetic RNA sequence

<400> SEQUENCE: 183
accgaacgcc guacccaucg gg                                              22

<210> SEQ ID NO 184
<211> LENGTH: 22
<212> TYPE: RNA
<213> ORGANISM: Artificial Sequence
<220> FEATURE:
<223> OTHER INFORMATION: Synthetic RNA sequence

<400> SEQUENCE: 184
cgaggguaac gacucucgug uc                                              22

<210> SEQ ID NO 185
<211> LENGTH: 22
<212> TYPE: RNA
<213> ORGANISM: Artificial Sequence
<220> FEATURE:
<223> OTHER INFORMATION: Synthetic RNA sequence

<400> SEQUENCE: 185
gcguaccgac gcguagacgg ac                                              22

<210> SEQ ID NO 186
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 186
ttgtaatacg actcaacagt agataaagcg acgcgcg                              37

<210> SEQ ID NO 187
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 187
ttgtaatacg actcaaacgc gacttatcga acgataa                              37

<210> SEQ ID NO 188
<211> LENGTH: 37
```

```
<212> TYPE: DNA
<213> ORGANISM: Artificial Sequence
<220> FEATURE:
<223> OTHER INFORMATION: Synthetic probe sequence

<400> SEQUENCE: 188
ttgtaatacg actcaaggtt gcctacatag taacttc                              37

<210> SEQ ID NO 189
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 189
ttgtaatacg actcacccgg taacaattag tcccgcg                              37

<210> SEQ ID NO 190
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 190
ttgtaatacg actcatcggt tgcggagttc gacgcga                              37

<210> SEQ ID NO 191
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 191
ttgtaatacg actcacccga tgggtacggc gttcggt                              37

<210> SEQ ID NO 192
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 192
ttgtaatacg actcagacac gagagtcgtt accctcg                              37

<210> SEQ ID NO 193
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 193
ttgtaatacg actcacccgg taacaattag acccgcg                              37

<210> SEQ ID NO 194
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 194
```

```
ttgtaataacg actcagtccg tctacgcgtc ggtacgc                              37
```

<210> SEQ ID NO 195
<211> LENGTH: 37
<212> TYPE: DNA
<213> ORGANISM: Artificial Sequence
<220> FEATURE:
<223> OTHER INFORMATION: Synthetic probe sequence

<400> SEQUENCE: 195

```
ttgtaataacg actcaggccg tctacgcgtc ggtacgc                              37
```

<210> SEQ ID NO 196
<211> LENGTH: 20
<212> TYPE: RNA
<213> ORGANISM: Human

<400> SEQUENCE: 196

```
cgugccaccc uuuucccag                                                   20
```

<210> SEQ ID NO 197
<211> LENGTH: 22
<212> TYPE: RNA
<213> ORGANISM: Human

<400> SEQUENCE: 197

```
ucccugagac ccuaacuugu ga                                               22
```

<210> SEQ ID NO 198
<211> LENGTH: 21
<212> TYPE: RNA
<213> ORGANISM: Human

<400> SEQUENCE: 198

```
cauaaaguag aaagcacuac u                                                21
```

<210> SEQ ID NO 199
<211> LENGTH: 23
<212> TYPE: RNA
<213> ORGANISM: Human

<400> SEQUENCE: 199

```
uuaaugcuaa ucgugauagg ggu                                              23
```

<210> SEQ ID NO 200
<211> LENGTH: 22
<212> TYPE: RNA
<213> ORGANISM: Human

<400> SEQUENCE: 200

```
uagcagcacg uaaauauugg cg                                               22
```

<210> SEQ ID NO 201
<211> LENGTH: 22
<212> TYPE: RNA
<213> ORGANISM: Human

<400> SEQUENCE: 201

```
ccaauauugg cugugcugcu cc                                               22
```

<210> SEQ ID NO 202
<211> LENGTH: 22
<212> TYPE: RNA
<213> ORGANISM: Human

```
<400> SEQUENCE: 202
acagcaggca cagacaggca gu                                              22

<210> SEQ ID NO 203
<211> LENGTH: 23
<212> TYPE: RNA
<213> ORGANISM: Human

<400> SEQUENCE: 203
uagcaccauu ugaaaucagu guu                                             23

<210> SEQ ID NO 204
<211> LENGTH: 20
<212> TYPE: RNA
<213> ORGANISM: Human

<400> SEQUENCE: 204
ccucugggcc cuuccuccag                                                 20

<210> SEQ ID NO 205
<211> LENGTH: 23
<212> TYPE: RNA
<213> ORGANISM: Human

<400> SEQUENCE: 205
aagugccgcc aucuuuugag ugu                                             23

<210> SEQ ID NO 206
<211> LENGTH: 20
<212> TYPE: RNA
<213> ORGANISM: Human

<400> SEQUENCE: 206
acucaaacug uggggggcacu                                                20

<210> SEQ ID NO 207
<211> LENGTH: 22
<212> TYPE: RNA
<213> ORGANISM: Human

<400> SEQUENCE: 207
cuuagcaggu uguauuauca uu                                              22

<210> SEQ ID NO 208
<211> LENGTH: 22
<212> TYPE: RNA
<213> ORGANISM: Human

<400> SEQUENCE: 208
cucuagaggg aagcacuuuc ug                                              22

<210> SEQ ID NO 209
<211> LENGTH: 22
<212> TYPE: RNA
<213> ORGANISM: Human

<400> SEQUENCE: 209
cuacaaaggg aagcacuuuc uc                                              22

<210> SEQ ID NO 210
<211> LENGTH: 22
<212> TYPE: RNA
```

```
<213> ORGANISM: Human

<400> SEQUENCE: 210
gaaggcgcuu cccuuuagag cg                                              22

<210> SEQ ID NO 211
<211> LENGTH: 21
<212> TYPE: RNA
<213> ORGANISM: Human

<400> SEQUENCE: 211
cuccagaggg augcacuuuc u                                               21

<210> SEQ ID NO 212
<211> LENGTH: 23
<212> TYPE: RNA
<213> ORGANISM: Human

<400> SEQUENCE: 212
uucauuuggu auaaaccgcg auu                                             23

<210> SEQ ID NO 213
<211> LENGTH: 22
<212> TYPE: RNA
<213> ORGANISM: Human

<400> SEQUENCE: 213
aggcagcggg guguagugga ua                                              22

<210> SEQ ID NO 214
<211> LENGTH: 22
<212> TYPE: RNA
<213> ORGANISM: Human

<400> SEQUENCE: 214
cacccguaga accgaccuug cg                                              22

<210> SEQ ID NO 215
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 215
cccctgcaga gctcaca                                                    17

<210> SEQ ID NO 216
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 216
aatagatatt atgtttta                                                   18

<210> SEQ ID NO 217
<211> LENGTH: 22
<212> TYPE: DNA
<213> ORGANISM: Human
```

```
<220> FEATURE:
<221> NAME/KEY: misc_feature
<222> LOCATION: (1)..(22)
<223> OTHER INFORMATION: microRNA candidate sequence

<400> SEQUENCE: 217
tagtgtaacg gaaatgttta ca                                              22

<210> SEQ ID NO 218
<211> LENGTH: 28
<212> TYPE: DNA
<213> ORGANISM: Human
<220> FEATURE:
<221> NAME/KEY: misc_feature
<222> LOCATION: (1)..(28)
<223> OTHER INFORMATION: microRNA candidate sequence

<400> SEQUENCE: 218
aaggctgagc agcagaggca gcaagagc                                        28

<210> SEQ ID NO 219
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 219
tggcctgacg tgaggagg                                                   18

<210> SEQ ID NO 220
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 220
tgggtgggtg gtttttt                                                    17

<210> SEQ ID NO 221
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 221
ttctccactg tgctgctacc                                                 20

<210> SEQ ID NO 222
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 222
agctatgctc actctcaa                                                   18
```

<210> SEQ ID NO 223
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 223
aaatcaataa ataatcag                                                     18

<210> SEQ ID NO 224
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 224
tgtgttgggt gaccctgg                                                     18

<210> SEQ ID NO 225
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 225
gcccagtgct ctgaatgtca aa                                                22

<210> SEQ ID NO 226
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 226
ctgtaattag tcagttttct gt                                                22

<210> SEQ ID NO 227
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 227
gtggactcca gcagtag                                                      17

<210> SEQ ID NO 228
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA candidate sequence

```
<400> SEQUENCE: 228
agagctctct ggctttgcct taaa                                          24

<210> SEQ ID NO 229
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 229
accctcagtc cgtattggtc tct                                           23

<210> SEQ ID NO 230
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 230
tgctgtattg tcaggtagtg a                                             21

<210> SEQ ID NO 231
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 231
agcttttggg aattcaggta g                                             21

<210> SEQ ID NO 232
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 232
tatgtatgta tgtatgt                                                  17

<210> SEQ ID NO 233
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 233
tatggaggtt ctagaccatg t                                             21

<210> SEQ ID NO 234
<211> LENGTH: 22
<212> TYPE: DNA
```

```
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 234
atcctagctt gcctgagact gt                                              22

<210> SEQ ID NO 235
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 235
tctgatcagg caaaattgca ga                                              22

<210> SEQ ID NO 236
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 236
aaaaactgtg attacttttg ca                                              22

<210> SEQ ID NO 237
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 237
gagacagtag ttcttgcctg gt                                              22

<210> SEQ ID NO 238
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 238
tctctttata tgtactggag c                                               21

<210> SEQ ID NO 239
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 239
taaaaaccgt gactacttct g                                               21
```

```
<210> SEQ ID NO 240
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 240
ataggacttt tgaaggaaga g                                         21

<210> SEQ ID NO 241
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 241
aaatgttgag atacactgaa                                           20

<210> SEQ ID NO 242
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 242
aattacagat tgtctcagag aa                                        22

<210> SEQ ID NO 243
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 243
aaaatccttt tgtttttcc ag                                         22

<210> SEQ ID NO 244
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 244
atttaactgg acatcttgca tt                                        22

<210> SEQ ID NO 245
<211> LENGTH: 24
<212> TYPE: DNA
<213> ORGANISM: Human
<220> FEATURE:
<221> NAME/KEY: misc_feature
<222> LOCATION: (1)..(24)
```

```
<223> OTHER INFORMATION: microRNA candidate sequence

<400> SEQUENCE: 245
acctggaccc agcgtagaca aaga                                              24

<210> SEQ ID NO 246
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 246
catatctacc tggacccagt g                                                 21

<210> SEQ ID NO 247
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 247
catatctacc tggacccagt gta                                               23

<210> SEQ ID NO 248
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 248
atcctagctt gcctgagact gt                                                22

<210> SEQ ID NO 249
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 249
aagagttact agaactatt                                                    19

<210> SEQ ID NO 250
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 250
gaatagtttt agtaactctt ga                                                22

<210> SEQ ID NO 251
<211> LENGTH: 22
```

```
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 251
aatttattct tggtaggttg ta                                              22

<210> SEQ ID NO 252
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 252
caacgtacta agaataaatt tc                                              22

<210> SEQ ID NO 253
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 253
agctctagaa agattgttga cca                                             23

<210> SEQ ID NO 254
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 254
attgtttagt acctataatg                                                 20

<210> SEQ ID NO 255
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 255
cggagttgta agtgttgaca a                                               21

<210> SEQ ID NO 256
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 256
```
acttacaact ctggaaaagc aga                                              23

<210> SEQ ID NO 257
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 257
agcaatactg ttacctgaaa ta                                               22

<210> SEQ ID NO 258
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 258
gaagaactgt tgcatttgcc ctg                                              23

<210> SEQ ID NO 259
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 259
tagtggtcag agggcttatg a                                                21

<210> SEQ ID NO 260
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 260
ggtgtaatgg ttagcactct gga                                              23

<210> SEQ ID NO 261
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 261
agtggtagag catttga                                                     17

<210> SEQ ID NO 262
<211> LENGTH: 18
<212> TYPE: DNA
<213> ORGANISM: Human
<220> FEATURE:
<221> NAME/KEY: misc_feature

```
<222> LOCATION: (1)..(18)
<223> OTHER INFORMATION: microRNA candidate sequence

<400> SEQUENCE: 262
gtagtgtttc ttacttta                                                 18

<210> SEQ ID NO 263
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 263
agatcgccga agcgtcgga                                                19

<210> SEQ ID NO 264
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 264
ttaaaacttt aagtgtgcct a                                             21

<210> SEQ ID NO 265
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 265
agtttctaag gatcatgtct g                                             21

<210> SEQ ID NO 266
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 266
tagtggttag tactctg                                                  17

<210> SEQ ID NO 267
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 267
agtttctaag gatcatgtct g                                             21

<210> SEQ ID NO 268
```

<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 268
accttcactg tgactctgct g                                    21

<210> SEQ ID NO 269
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA candidate sequence

<400> SEQUENCE: 269
gtttccgtag cgtagtggtt atca                                 24

<210> SEQ ID NO 270
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 270
agtccttaac aagcattgag a                                    21

<210> SEQ ID NO 271
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 271
gttaagtgct ccaaggaggt gg                                   22

<210> SEQ ID NO 272
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 272
gttgctatcg gggactac                                        18

<210> SEQ ID NO 273
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 273
gctgtgctac gtcgccctgg a                                              21

<210> SEQ ID NO 274
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 274 attttctta taggcttcta ag                                              22

<210> SEQ ID NO 275
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 275
gaatatgggt atattagttt gg                                             22

<210> SEQ ID NO 276
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 276
ggccagccac caggagggct gc                                             22

<210> SEQ ID NO 277
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 277
actaatagag gtaatagttg aa                                             22

<210> SEQ ID NO 278
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 278
taggagggaa tagtaaaagc ag                                             22

<210> SEQ ID NO 279
<211> LENGTH: 17
<212> TYPE: DNA
<213> ORGANISM: Human
<220> FEATURE:

```
<221> NAME/KEY: misc_feature
<222> LOCATION: (1)..(17)
<223> OTHER INFORMATION: microRNA candidate sequence

<400> SEQUENCE: 279
gacgtcagag ggaatcc                                                    17

<210> SEQ ID NO 280
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 280
cagaagggga gttgggagca ga                                              22

<210> SEQ ID NO 281
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA candidate sequence

<400> SEQUENCE: 281
tatgaacagt ggatagatta aagg                                            24

<210> SEQ ID NO 282
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA candidate sequence

<400> SEQUENCE: 282
atcggagaaa ctccctgcga tgag                                            24

<210> SEQ ID NO 283
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA candidate sequence

<400> SEQUENCE: 283
catcttttat ttggtaaatt atga                                            24

<210> SEQ ID NO 284
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 284
attgattgtg gcaaagtt                                                   18
```

-continued

```
<210> SEQ ID NO 285
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 285
tatattgatt gtggcaaagt t                                              21

<210> SEQ ID NO 286
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 286
atgagatact gtcggaga                                                  18

<210> SEQ ID NO 287
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 287
attgtccttg ctgtttggag ata                                            23

<210> SEQ ID NO 288
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 288
attttctgaa ctgtacat                                                  18

<210> SEQ ID NO 289
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 289
gtggattttg tttgctgt                                                  18

<210> SEQ ID NO 290
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence
```

```
<400> SEQUENCE: 290
actggcctgg gactaccggg gg                                              22

<210> SEQ ID NO 291
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 291
ttgttctttg gtctttcagc                                                 20

<210> SEQ ID NO 292
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA candidate sequence

<400> SEQUENCE: 292
cattactgat tttcttttct taga                                            24

<210> SEQ ID NO 293
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 293
aggggctggg gtttcaggtt ct                                              22

<210> SEQ ID NO 294
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 294
cagggctggg ggtttcaggt t                                               21

<210> SEQ ID NO 295
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 295
ttgtctcttg ttcctcacac ag                                              22

<210> SEQ ID NO 296
<211> LENGTH: 22
<212> TYPE: DNA
<213> ORGANISM: Human
```

```
<220> FEATURE:
<221> NAME/KEY: misc_feature
<222> LOCATION: (1)..(22)
<223> OTHER INFORMATION: microRNA candidate sequence

<400> SEQUENCE: 296
atattattag ccacttctgg at                                                  22

<210> SEQ ID NO 297
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 297
acctgaatta ccaaaagctt t                                                   21

<210> SEQ ID NO 298
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 298
tatggaaaga ctttgccact ct                                                  22

<210> SEQ ID NO 299
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 299
tatggaaaga ctttgccact ct                                                  22

<210> SEQ ID NO 300
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 300
taacgcataa tatggacatg t                                                   21

<210> SEQ ID NO 301
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 301
agactgacct tcaaccccac ag                                                  22
```

```
<210> SEQ ID NO 302
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 302
cctgcaactt tgcctgatca ga                                        22

<210> SEQ ID NO 303
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 303
tggatatgat gactgaa                                              17

<210> SEQ ID NO 304
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 304
acttgtaatg gagaacacta agc                                       23

<210> SEQ ID NO 305
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 305
attaaggaca tttgtgattg at                                        22

<210> SEQ ID NO 306
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 306
tttttgtcag tacatgttaa tg                                        22

<210> SEQ ID NO 307
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence
```

```
<400> SEQUENCE: 307
atttgctgtt aagatatggg at                                          22

<210> SEQ ID NO 308
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 308
actaccgttg gtttccgc                                               18

<210> SEQ ID NO 309
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 309
agagtttgga ttagtggg                                               18

<210> SEQ ID NO 310
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 310
aactagctct gtggatcctg ac                                          22

<210> SEQ ID NO 311
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 311
tacggataat tgtagcactt c                                           21

<210> SEQ ID NO 312
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 312
aatgttggaa tcctcgctag agc                                         23

<210> SEQ ID NO 313
<211> LENGTH: 22
<212> TYPE: DNA
```

```
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 313
tgtgggactt ctggccttga ct                                          22

<210> SEQ ID NO 314
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 314
acctgggttg tcccctctag                                             20

<210> SEQ ID NO 315
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 315
gcctggactg cctggagaaa gcg                                         23

<210> SEQ ID NO 316
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 316
gtggccgagg actttga                                                17

<210> SEQ ID NO 317
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 317
gtggccgagg actttgatt                                              19

<210> SEQ ID NO 318
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 318
gtggccgagg actttgattg                                             20
```

```
<210> SEQ ID NO 319
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 319
ttaagatttg gtgcaatat                                                  19

<210> SEQ ID NO 320
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 320
actctttaag gatagggctg aa                                              22

<210> SEQ ID NO 321
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 321 tagggaaaa gtcctgatcc gg                                               22

<210> SEQ ID NO 322
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 322
tagacaatct gtgtagagtg c                                               21

<210> SEQ ID NO 323
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 323
tgagaccagg actggatgca cca                                             23

<210> SEQ ID NO 324
<211> LENGTH: 20
<212> TYPE: DNA
<213> ORGANISM: Human
<220> FEATURE:
<221> NAME/KEY: misc_feature
<222> LOCATION: (1)..(20)
```

<223> OTHER INFORMATION: microRNA candidate sequence

<400> SEQUENCE: 324
aagtttctct gaaggtgtag                                                     20

<210> SEQ ID NO 325
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 325
agtttctctg aaggtgtag                                                      19

<210> SEQ ID NO 326
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 326
attaaggaca tttgtgatt                                                      19

<210> SEQ ID NO 327
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 327
ttgtaacatt ctggtgtgtt g                                                   21

<210> SEQ ID NO 328
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 328
ttgtaacatt ctggtgtgtt g                                                   21

<210> SEQ ID NO 329
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 329
gaattaatgg ctggctggga g                                                   21

<210> SEQ ID NO 330
<211> LENGTH: 22

```
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 330
atattggaat ccccgctaga gc                                              22

<210> SEQ ID NO 331
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 331
ggggctgtag ctcaggg                                                    17

<210> SEQ ID NO 332
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 332
ggaggaacct tggagcttcg gc                                              22

<210> SEQ ID NO 333
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 333
gcagcccagc tgaggcctct g                                               21

<210> SEQ ID NO 334
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 334
aacaacttag acacgtgact gta                                             23

<210> SEQ ID NO 335
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 335
```
ttccttaact aaagtactca ga                                        22

<210> SEQ ID NO 336
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 336
caggcagctg ttaacag                                              17

<210> SEQ ID NO 337
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 337
gaagcagcgc ctgtcgcaac tcg                                       23

<210> SEQ ID NO 338
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA candidate sequence

<400> SEQUENCE: 338
tacatggatg gaaaccttca agca                                      24

<210> SEQ ID NO 339
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 339
agacccattg aggagaaggt tc                                        22

<210> SEQ ID NO 340
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 340
caaaagtgat cgtggttttt g                                         21

<210> SEQ ID NO 341
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 341
tctctcggac aagctgtagg t                                       21

<210> SEQ ID NO 342
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 342
ctaagccagg gattgtgggt                                         20

<210> SEQ ID NO 343
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 343
cttacactct tgtccatcta ga                                      22

<210> SEQ ID NO 344
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 344
tgaacagcct ctggcaatc                                          19

<210> SEQ ID NO 345
<211> LENGTH: 29
<212> TYPE: DNA
<213> ORGANISM: Human
<220> FEATURE:
<221> NAME/KEY: misc_feature
<222> LOCATION: (1)..(29)
<223> OTHER INFORMATION: microRNA candidate sequence

<400> SEQUENCE: 345
tcacaatgct gacactcaaa ctgctgaca                               29

<210> SEQ ID NO 346
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 346
atgtagtctc ccctacctag                                         20

<210> SEQ ID NO 347

```
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 347
catgagatcc aactctgagc                                              20

<210> SEQ ID NO 348
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 348
tgagtttaga gctgtctgct                                              20

<210> SEQ ID NO 349
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 349
gacacctctg cactcaaggc gg                                           22

<210> SEQ ID NO 350
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 350
gacacctctg cactcaaggc ggc                                          23

<210> SEQ ID NO 351
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 351
gcaagaaagt gagactctgc ct                                           22

<210> SEQ ID NO 352
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 352
```
aagtttctct gaacgtgta                                                19

<210> SEQ ID NO 353
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 353
catgctagga tagaaagaat ggg                                           23

<210> SEQ ID NO 354
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 354
tatccagctt gttactatat gc                                            22

<210> SEQ ID NO 355
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 355
cctcccaaag tgctgggatt a                                             21

<210> SEQ ID NO 356
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 356
aatgatgatg caagaactga ga                                            22

<210> SEQ ID NO 357
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 357
taggagctat cagaacttag tg                                            22

<210> SEQ ID NO 358
<211> LENGTH: 22
<212> TYPE: DNA
<213> ORGANISM: Human
<220> FEATURE:

```
<221> NAME/KEY: misc_feature
<222> LOCATION: (1)..(22)
<223> OTHER INFORMATION: microRNA candidate sequence

<400> SEQUENCE: 358
gttcctgctg aactgagcca gt                                              22

<210> SEQ ID NO 359
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 359
gttcctgctg aactgagcca gt                                              22

<210> SEQ ID NO 360
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 360
ccaactaacc tctgtattcc ag                                              22

<210> SEQ ID NO 361
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA candidate sequence

<400> SEQUENCE: 361
tgttcctctg tctcccagac tctg                                            24

<210> SEQ ID NO 362
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 362
tgaggagatc gtcgaggttg gc                                              22

<210> SEQ ID NO 363
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 363
cctcccactg cagagcctgg g                                               21
```

```
<210> SEQ ID NO 364
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 364
gccgggtact ttcgtatt                                                 18

<210> SEQ ID NO 365
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 365
ttggctggtc tctgctccgc ag                                            22

<210> SEQ ID NO 366
<211> LENGTH: 26
<212> TYPE: DNA
<213> ORGANISM: Human
<220> FEATURE:
<221> NAME/KEY: misc_feature
<222> LOCATION: (1)..(26)
<223> OTHER INFORMATION: microRNA candidate sequence

<400> SEQUENCE: 366
cctcccaaag tgctgggatt acaggc                                        26

<210> SEQ ID NO 367
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA candidate sequence

<400> SEQUENCE: 367
gttggaggat gaaagta                                                  17

<210> SEQ ID NO 368
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 368
tgccttagga gaaagtttct gg                                            22

<210> SEQ ID NO 369
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence
```

```
<400> SEQUENCE: 369
gcccggagag ctgggagcca ga                                              22

<210> SEQ ID NO 370
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 370
accggatgga gctctaggga                                                 20

<210> SEQ ID NO 371
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 371
tgccttagga gaaagtttct gg                                              22

<210> SEQ ID NO 372
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA candidate sequence

<400> SEQUENCE: 372
atggatgatg atatctgagt                                                 20

<210> SEQ ID NO 373
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 373
ttccttaact aaagtactc                                                  19

<210> SEQ ID NO 374
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 374
gagccagtgg tgagacagtg ag                                              22

<210> SEQ ID NO 375
<211> LENGTH: 22
<212> TYPE: DNA
<213> ORGANISM: Human
```

```
-continued

<220> FEATURE:
<221> NAME/KEY: misc_feature
<222> LOCATION: (1)..(22)
<223> OTHER INFORMATION: microRNA candidate sequence

<400> SEQUENCE: 375
cggggctgcc ctgaacgggc cc                                          22

<210> SEQ ID NO 376
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 376
gttcgagacc agcctggcc                                              19

<210> SEQ ID NO 377
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 377
gtcgaacttg actatctag                                              19

<210> SEQ ID NO 378
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA candidate sequence

<400> SEQUENCE: 378
gtgctctgaa tgtcaaagtg aaga                                        24

<210> SEQ ID NO 379
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 379
cagttcaatg gtgttcagca ga                                          22

<210> SEQ ID NO 380
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 380
aaaagtagtt gtggtttt                                               18
```

<210> SEQ ID NO 381
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 381
aaaagtagtt gtggtttt                                                    18

<210> SEQ ID NO 382
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 382
aagggcttcc tctctgcagg ac                                               22

<210> SEQ ID NO 383
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 383 tggactttt cagatttggg gat                                               23

<210> SEQ ID NO 384
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 384
gactcactca caggattgtg ca                                               22

<210> SEQ ID NO 385
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 385
gactcactca caggattgtg ca                                               22

<210> SEQ ID NO 386
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 386
ccacttggat ctgaaggctg cc                                          22

<210> SEQ ID NO 387
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA candidate sequence

<400> SEQUENCE: 387
tgaggaggat ctgaaggatt gga                                         23

<210> SEQ ID NO 388
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 388
tcatgttgct ctgctgttgc c                                           21

<210> SEQ ID NO 389
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 389
aggagaatca cttgaaccc                                              19

<210> SEQ ID NO 390
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 390
atgaagtgtg acgtggac                                               18

<210> SEQ ID NO 391
<211> LENGTH: 26
<212> TYPE: DNA
<213> ORGANISM: Human
<220> FEATURE:
<221> NAME/KEY: misc_feature
<222> LOCATION: (1)..(26)
<223> OTHER INFORMATION: microRNA candidate sequence

<400> SEQUENCE: 391
tggacatccg caaagacctg tacgcc                                      26

<210> SEQ ID NO 392
<211> LENGTH: 22
<212> TYPE: DNA

```
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 392 gccttttaa ccgcgagcga ca                                           22

<210> SEQ ID NO 393
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA candidate sequence

<400> SEQUENCE: 393
atgaagtgtg acgtggac                                               18

<210> SEQ ID NO 394
<211> LENGTH: 28
<212> TYPE: DNA
<213> ORGANISM: Human
<220> FEATURE:
<221> NAME/KEY: misc_feature
<222> LOCATION: (1)..(28)
<223> OTHER INFORMATION: microRNA candidate sequence

<400> SEQUENCE: 394
tggacatccg caaagacctg tacgccaa                                    28

<210> SEQ ID NO 395
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA candidate sequence

<400> SEQUENCE: 395
aggactggac tcccggcagc c                                           21

<210> SEQ ID NO 396
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 396
aagggcttcc tctctgcagg ac                                          22

<210> SEQ ID NO 397
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 397
atggccagag ctcacacaga gg                                          22
```

<210> SEQ ID NO 398
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA candidate sequence

<400> SEQUENCE: 398
aaagtgctgg gattacagg                                                 19

<210> SEQ ID NO 399
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 399
gatgcctggg agttgcgatc tg                                             22

<210> SEQ ID NO 400
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: microRNA candidate sequence

<400> SEQUENCE: 400
gcaaaagaca tttccttaga attaatggct ggctgggagg cagagccaag ggccactggt    60
tcctcccagc tggtcattaa tcctcaggaa atgcctgc                            98

<210> SEQ ID NO 401
<211> LENGTH: 93
<212> TYPE: DNA
<213> ORGANISM: Human
<220> FEATURE:
<221> NAME/KEY: misc_feature
<222> LOCATION: (1)..(93)
<223> OTHER INFORMATION: microRNA candidate sequence

<400> SEQUENCE: 401
ggagttcctg tgacgcaatt agccatataa ggagctcggc cggcgcggcg gagtgtttgt    60
ttggtatcct agcaatgacg tcagagggaa tcc                                 93

<210> SEQ ID NO 402
<211> LENGTH: 93
<212> TYPE: DNA
<213> ORGANISM: Human
<220> FEATURE:
<221> NAME/KEY: misc_feature
<222> LOCATION: (1)..(93)
<223> OTHER INFORMATION: microRNA precursor sequence

<400> SEQUENCE: 402
ttggatggtt tagtgaggcc ctcggatcag cccgctgggt cagcccactg ccctggcgga    60
acgctgagaa gacagtcgaa cttgactatc tag                                 93

<210> SEQ ID NO 403

```
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: microRNA precursor sequence

<400> SEQUENCE: 403
gggggctcat taggtggaga ttggttttta atcagcacca tggcaatgat gatgcaagaa      60
ctgagatgcc acctgatccc ctgccccc                                         88

<210> SEQ ID NO 404
<211> LENGTH: 108
<212> TYPE: DNA
<213> ORGANISM: Human
<220> FEATURE:
<221> NAME/KEY: misc_feature
<222> LOCATION: (1)..(108)
<223> OTHER INFORMATION: microRNA precursor sequence

<400> SEQUENCE: 404
caaagtgctg ggattacagg cgtgagcccc cgtgcccggc ctgtgtgttt tttataaaaa      60
aagttttggc tgggcacagt ggctcacgcc tgtaatccca acactttg                  108

<210> SEQ ID NO 405
<211> LENGTH: 132
<212> TYPE: DNA
<213> ORGANISM: Human
<220> FEATURE:
<221> NAME/KEY: misc_feature
<222> LOCATION: (1)..(132)
<223> OTHER INFORMATION: microRNA precursor sequence

<400> SEQUENCE: 405
cccttcctgc cggccggccc cctcctcagg ccctccttc tcagcccag ctcccgctca       60 cccctgccac gtcaaaggag gcagaagggg agttgggagc agagagggga ccacgggctg    120
gctggtctgg gg                                                        132

<210> SEQ ID NO 406
<211> LENGTH: 125
<212> TYPE: DNA
<213> ORGANISM: Human
<220> FEATURE:
<221> NAME/KEY: misc_feature
<222> LOCATION: (1)..(125)
<223> OTHER INFORMATION: microRNA precursor sequence

<400> SEQUENCE: 406
gcctcccaaa gtgctgggat tataggcgtg agccactacg cccagcctct gaaacatttt     60
aaaaaattat ctgggttagg ccgggcgtgg tggctcacgc ctgtaattcc agcactttgg    120
gaggc                                                                125

<210> SEQ ID NO 407
<211> LENGTH: 122
<212> TYPE: DNA
<213> ORGANISM: Human
<220> FEATURE:
<221> NAME/KEY: misc_feature
<222> LOCATION: (1)..(122)
<223> OTHER INFORMATION: microRNA precursor sequence

<400> SEQUENCE: 407
gcccaggctg ctgtcaaact cctgagctca cccaggcgca atggctcatg cttgtaatcc     60
```

```
cagcactggg aggccaaggt gggcagatca cctgaggtca ggagttcgag accagcctgg    120
cc                                                                  122

<210> SEQ ID NO 408
<211> LENGTH: 67
<212> TYPE: DNA
<213> ORGANISM: Human
<220> FEATURE:
<221> NAME/KEY: misc_feature
<222> LOCATION: (1)..(67)
<223> OTHER INFORMATION: microRNA precursor sequence

<400> SEQUENCE: 408
cgggtaaagg tcgccctcaa ggtgacccgc ctactttgcg ggatgcctgg gagttgcgat    60
ctgcccg                                                             67

<210> SEQ ID NO 409
<211> LENGTH: 76
<212> TYPE: DNA
<213> ORGANISM: Human
<220> FEATURE:
<221> NAME/KEY: misc_feature
<222> LOCATION: (1)..(76)
<223> OTHER INFORMATION: microRNA precursor sequence

<400> SEQUENCE: 409
ggcttacaga attatgaaca gtggatagat taaaggcatt taatatttgt aattcataat    60
aactgtagaa atggcc                                                   76

<210> SEQ ID NO 410
<211> LENGTH: 77
<212> TYPE: DNA
<213> ORGANISM: Human
<220> FEATURE:
<221> NAME/KEY: misc_feature
<222> LOCATION: (1)..(77)
<223> OTHER INFORMATION: microRNA precursor sequence

<400> SEQUENCE: 410
gctggggttc atcggagaaa ctccctgcga tgagccacta gggtcacgga cagggaactt    60
tttgatgagc gccgagt                                                  77

<210> SEQ ID NO 411
<211> LENGTH: 83
<212> TYPE: DNA
<213> ORGANISM: Human
<220> FEATURE:
<221> NAME/KEY: misc_feature
<222> LOCATION: (1)..(83)
<223> OTHER INFORMATION: microRNA precursor sequence

<400> SEQUENCE: 411
aactttgtta atcatctttt atttggtaaa ttatgaatgg gtatacattt gtacagttcg    60
tgtatattga ttgtggcaaa gtt                                           83

<210> SEQ ID NO 412
<211> LENGTH: 83
<212> TYPE: DNA
<213> ORGANISM: Human
<220> FEATURE:
<221> NAME/KEY: misc_feature
<222> LOCATION: (1)..(83)
<223> OTHER INFORMATION: microRNA precursor sequence
```

```
<400> SEQUENCE: 412
aactttgtta atcatctttt atttggtaaa ttatgaatgg gtatacattt gtacagttcg      60
tgtatattga ttgtggcaaa gtt                                             83

<210> SEQ ID NO 413
<211> LENGTH: 83
<212> TYPE: DNA
<213> ORGANISM: Human
<220> FEATURE:
<221> NAME/KEY: misc_feature
<222> LOCATION: (1)..(83)
<223> OTHER INFORMATION: microRNA precursor sequence

<400> SEQUENCE: 413
aactttgtta atcatctttt atttggtaaa ttatgaatgg gtatacattt gtacagttcg      60
tgtatattga ttgtggcaaa gtt                                             83

<210> SEQ ID NO 414
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: microRNA precursor sequence

<400> SEQUENCE: 414
ctctctctct cagttactca caaaacatgg ctgtcttatt cagagattag caattattgt      60
aatgagatac tgtcggagag gg                                              82

<210> SEQ ID NO 415
<211> LENGTH: 80
<212> TYPE: DNA
<213> ORGANISM: Human
<220> FEATURE:
<221> NAME/KEY: misc_feature
<222> LOCATION: (1)..(80)
<223> OTHER INFORMATION: microRNA precursor sequence

<400> SEQUENCE: 415
catgtgattt ctgcccagtg ctctgaatgt caaagtgaag aaattcaatg aagcacgggt      60
aaacggcggg agtaactatg                                                 80

<210> SEQ ID NO 416
<211> LENGTH: 113
<212> TYPE: DNA
<213> ORGANISM: Human
<220> FEATURE:
<221> NAME/KEY: misc_feature
<222> LOCATION: (1)..(113)
<223> OTHER INFORMATION: microRNA precursor sequence

<400> SEQUENCE: 416
agaaaataac attgtcagac gtgtcatccc cagatacaat ggacaatatg ctattataat      60
cgtatggcat tgtccttgct gtttggagat aatactgctg actttattcc tct           113

<210> SEQ ID NO 417
<211> LENGTH: 109
<212> TYPE: DNA
<213> ORGANISM: Human
<220> FEATURE:
<221> NAME/KEY: misc_feature
<222> LOCATION: (1)..(109)
<223> OTHER INFORMATION: microRNA precursor sequence
```

<400> SEQUENCE: 417
ttatttacca gctcagaatg tggtaggagc tatcagaact tagtgatcaa gtgaagtcgt    60
agttactaat ttctgatgct cttcccctgc agaagagagc tgtgggaag               109

<210> SEQ ID NO 418
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: microRNA precursor sequence

<400> SEQUENCE: 418
gcttccagaa gtgcacgctc tagcgaggat tccaacattg ggggaattgg cccaatattg    60
gaatccccgc tagagcgtgc acctaagc                                      88

<210> SEQ ID NO 419
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: microRNA precursor sequence

<400> SEQUENCE: 419
atttaaagag aattttattt acagttattt caaatgtaga gaatgtaatt ttctgaactg    60
tacataagtg ctcaatttaa at                                            82

<210> SEQ ID NO 420
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: microRNA precursor sequence

<400> SEQUENCE: 420
tcattaattt atgcaaggta gcagccagca tattagttca caccatttgt ggattttgtt    60
tgctgtctca catgcaaggt gaaatgg                                       87

<210> SEQ ID NO 421
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: microRNA precursor sequence

<400> SEQUENCE: 421
gaggggctgt agctcagggt gtgcactgcg aggctggacc tgttgagtct gcagtggaca    60
tccatttagc ttcaggttgt c                                             81

<210> SEQ ID NO 422
<211> LENGTH: 110
<212> TYPE: DNA
<213> ORGANISM: Human
<220> FEATURE:
<221> NAME/KEY: misc_feature
<222> LOCATION: (1)..(110)

<223> OTHER INFORMATION: microRNA precursor sequence

<400> SEQUENCE: 422
ggcgtgcctg ggagttggca ctaagtacag ctgtaattag tcagtttctct gtcctgtcca    60 cacagaaaac cgtctagtta cagttgtaag ttgtgccaga cctaatcgct              110

<210> SEQ ID NO 423
<211> LENGTH: 106
<212> TYPE: DNA
<213> ORGANISM: Human
<220> FEATURE:
<221> NAME/KEY: misc_feature
<222> LOCATION: (1)..(106)
<223> OTHER INFORMATION: microRNA precursor sequence

<400> SEQUENCE: 423
ccaccaacct gtgggaaggc aggtggactc cagcagtagg taggtaacat ccaaggtagc    60
catacacagc tggtgtttgt gaatctgcac ttcccctggg caatgg                  106

<210> SEQ ID NO 424
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: microRNA precursor sequence

<400> SEQUENCE: 424
gggcttgacc cctgttcctg ctgaactgag ccagtgtaca caaaccaact gtgtttcagc    60
tcagtaggca cgggaggcag agccc                                          85

<210> SEQ ID NO 425
<211> LENGTH: 58
<212> TYPE: DNA
<213> ORGANISM: Human
<220> FEATURE:
<221> NAME/KEY: misc_feature
<222> LOCATION: (1)..(58)
<223> OTHER INFORMATION: microRNA precursor sequence

<400> SEQUENCE: 425
gctgaagctc taaggttccg cctgcgggca ggaagcggag gaaccttgga gcttcggc      58

<210> SEQ ID NO 426
<211> LENGTH: 104
<212> TYPE: DNA
<213> ORGANISM: Human
<220> FEATURE:
<221> NAME/KEY: misc_feature
<222> LOCATION: (1)..(104)
<223> OTHER INFORMATION: microRNA precursor sequence

<400> SEQUENCE: 426
atggcctctc cagtctgcag ctcccggcag cctcgggcca cactcccggg atccccaggg    60
actggcctgg gactaccggg ggtggcggcc gtggctctgg ctat                    104

<210> SEQ ID NO 427
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: microRNA precursor sequence

<400> SEQUENCE: 427 ggcttttttgc tcaagggctc gactcctgtt cctgctgaac tgagccagtg tgtaaaatga        60
gaactgatat cagctcagta ggcaccggag ggcgggtcca atcgacagcc                   110

<210> SEQ ID NO 428
<211> LENGTH: 111
<212> TYPE: DNA
<213> ORGANISM: Human
<220> FEATURE:
<221> NAME/KEY: misc_feature
<222> LOCATION: (1)..(111)
<223> OTHER INFORMATION: microRNA precursor sequence

<400> SEQUENCE: 428
ccacacctga aacacggca ggtgagcagg cgaggctggg ctgaacccgt gggtgaggag          60
tgcagcccag ctgaggcctc tgctgtctta tctgtctcct acaggcaatg g                 111

<210> SEQ ID NO 429
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: microRNA precursor sequence

<400> SEQUENCE: 429
ccacctggtt cctgtacccg ttcagacggt tctttgcaag acattcctcc cattgttcac        60
ccccaactaa cctctgtatt ccaggggc                                           88

<210> SEQ ID NO 430
<211> LENGTH: 158
<212> TYPE: DNA
<213> ORGANISM: Human
<220> FEATURE:
<221> NAME/KEY: misc_feature
<222> LOCATION: (1)..(158)
<223> OTHER INFORMATION: microRNA precursor sequence

<400> SEQUENCE: 430
tacagttctg tctaggcagt ggcttgggtt tttatcgagc aacaacttag acacgtgact        60
gtaatatgct gcaactgtgt gtactgaaaa tatgtgaaaa tggttgaatg tggactgtgt       120
atatatgtat gtaaaaattt ctgtgagatg ctgctgtc                                158

<210> SEQ ID NO 431
<211> LENGTH: 117
<212> TYPE: DNA
<213> ORGANISM: Human
<220> FEATURE:
<221> NAME/KEY: misc_feature
<222> LOCATION: (1)..(117)
<223> OTHER INFORMATION: microRNA precursor sequence

<400> SEQUENCE: 431
aggtgctcca ccgttcctgc tgtggagaag gaggcgaagt cagagagctc ttccaagctt        60
tccccaggaa gagctctctg gctttgcctt aaagctcccc agaggttttg gaggctg          117

<210> SEQ ID NO 432
<211> LENGTH: 119
<212> TYPE: DNA
<213> ORGANISM: Human
<220> FEATURE:

```
<221> NAME/KEY: misc_feature
<222> LOCATION: (1)..(119)
<223> OTHER INFORMATION: microRNA precursor sequence

<400> SEQUENCE: 432
atttctttcc ttaactaaag tactcagata tttatccaaa cattattgct atgggatttc      60
ctgcagaaag acttgaaggc gtatacagga acaatattga tgatgtagta aggtaagaa      119

<210> SEQ ID NO 433
<211> LENGTH: 109
<212> TYPE: DNA
<213> ORGANISM: Human
<220> FEATURE:
<221> NAME/KEY: misc_feature
<222> LOCATION: (1)..(109)
<223> OTHER INFORMATION: microRNA precursor sequence

<400> SEQUENCE: 433
gctgtgctgt gtgccaatgt ttcgtttgcc tcagacaggt atctcttcgt tatcagaaga      60
gttgcttcat ttcatctggg agcagaaaac agcaggcagc tgttaacag                 109

<210> SEQ ID NO 434
<211> LENGTH: 118
<212> TYPE: DNA
<213> ORGANISM: Human
<220> FEATURE:
<221> NAME/KEY: misc_feature
<222> LOCATION: (1)..(118)
<223> OTHER INFORMATION: microRNA precursor sequence

<400> SEQUENCE: 434
ttctagaacc gtaaaaaagg aagtaagtac tggtacatta cattttacac ttcatattct      60
gtggcctgtt taaagagtc accattactg attttctttt cttagatatc acctggag        118

<210> SEQ ID NO 435
<211> LENGTH: 113
<212> TYPE: DNA
<213> ORGANISM: Human
<220> FEATURE:
<221> NAME/KEY: misc_feature
<222> LOCATION: (1)..(113)
<223> OTHER INFORMATION: microRNA precursor sequence

<400> SEQUENCE: 435
gcggcggaca ccatcttctt taaaccctca gtccgtattg gtctctatgg catccataga     60
ggccattcgg ctctgaggtc ctcagtaaag aaacttagat ggtattactg tgt            113

<210> SEQ ID NO 436
<211> LENGTH: 91
<212> TYPE: DNA
<213> ORGANISM: Human
<220> FEATURE:
<221> NAME/KEY: misc_feature
<222> LOCATION: (1)..(91)
<223> OTHER INFORMATION: microRNA precursor sequence

<400> SEQUENCE: 436
ctcgtgggaa gcagcgcctg tcgcaactcg ccacttgttc tcctcacagc aggttcagga      60
gaagtggcac ctggtggagg acctgtcgcg a                                     91

<210> SEQ ID NO 437
<211> LENGTH: 117
<212> TYPE: DNA
<213> ORGANISM: Human
```

```
<220> FEATURE:
<221> NAME/KEY: misc_feature
<222> LOCATION: (1)..(117)
<223> OTHER INFORMATION: microRNA precursor sequence

<400> SEQUENCE: 437
tataaaaata ggtaatatag aaaataaaac acatactgct gtattgtcag gtagtgatag      60
gatttatcac tacctgacaa tacagtatgt gtttgtttta tatatttagg gtgtaca       117

<210> SEQ ID NO 438
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: microRNA precursor sequence

<400> SEQUENCE: 438
tggcgctgct ctgctgttcc tctgtctccc agactctggg tggatggagc aggtcggggg      60
ccaggggaca ggaaggctag ggcc                                            84

<210> SEQ ID NO 439
<211> LENGTH: 117
<212> TYPE: DNA
<213> ORGANISM: Human
<220> FEATURE:
<221> NAME/KEY: misc_feature
<222> LOCATION: (1)..(117)
<223> OTHER INFORMATION: microRNA precursor sequence

<400> SEQUENCE: 439
accctctcag gacccctcct aagggtagg caggggctgg ggtttcaggt tctcagtcag      60
aaccttggcc cctctcccca gacccccagg ctgtggtgag ggtctgagag ctggtac       117

<210> SEQ ID NO 440
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: microRNA precursor sequence

<400> SEQUENCE: 440
atctattttg tgtgagtaca gagagcatct gaatgggtac agttgttgtc tcttgttcct      60
cacacaggca ccaga                                                      75

<210> SEQ ID NO 441
<211> LENGTH: 119
<212> TYPE: DNA
<213> ORGANISM: Human
<220> FEATURE:
<221> NAME/KEY: misc_feature
<222> LOCATION: (1)..(119)
<223> OTHER INFORMATION: microRNA precursor sequence

<400> SEQUENCE: 441
ggattgacat cgctagattt cccattactg ttgctgaatc cagagagcag catgagttcc      60
tgaaatgcag ttcaatggtg ttcagcagac ggtggatgcg gaaaatcttc attttttccc    119

<210> SEQ ID NO 442
<211> LENGTH: 107
<212> TYPE: DNA
```

```
<213> ORGANISM: Human
<220> FEATURE:
<221> NAME/KEY: misc_feature
<222> LOCATION: (1)..(107)
<223> OTHER INFORMATION: microRNA precursor sequence

<400> SEQUENCE: 442
atctctgata tggaagaaat ccagaagtgg ctaataatat tgacactata acaataatgt    60
caatattatt agccacttct ggatttatga atcatgtctc aaggatt                  107

<210> SEQ ID NO 443
<211> LENGTH: 121
<212> TYPE: DNA
<213> ORGANISM: Human
<220> FEATURE:
<221> NAME/KEY: misc_feature
<222> LOCATION: (1)..(121)
<223> OTHER INFORMATION: microRNA precursor sequence

<400> SEQUENCE: 443
tggaagccta ccatttatgt cctcttgagg tacctgaatt accaaaagct ttatgtattc    60
tgaagttatt gaaataaga gcttttggga attcaggtag ttcaggagtg actttctaa     120 a                                                                   121

<210> SEQ ID NO 444
<211> LENGTH: 121
<212> TYPE: DNA
<213> ORGANISM: Human
<220> FEATURE:
<221> NAME/KEY: misc_feature
<222> LOCATION: (1)..(121)
<223> OTHER INFORMATION: microRNA precursor sequence

<400> SEQUENCE: 444
tggaagccta ccatttatgt cctcttgagg tacctgaatt accaaaagct ttatgtattc    60
tgaagttatt gaaataaga gcttttggga attcaggtag ttcaggagtg actttctaa     120 a                                                                   121

<210> SEQ ID NO 445
<211> LENGTH: 109
<212> TYPE: DNA
<213> ORGANISM: Human
<220> FEATURE:
<221> NAME/KEY: misc_feature
<222> LOCATION: (1)..(109)
<223> OTHER INFORMATION: microRNA precursor sequence

<400> SEQUENCE: 445
ccaaaagttc ttcactttaa agagtggcaa agtctttcca tatgtgtaac agacatacat    60
acatacatat ggaaagactt tgccactctt gaaagtgaag agtgtgtgt               109

<210> SEQ ID NO 446
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: microRNA precursor sequence

<400> SEQUENCE: 446
tcttcacttt caagagtggc aaagtctttc catatgtatg tatgtatgtc tgttacacat    60
atggaaagac tttgccactc tttaaagtga agaac                              95
```

<210> SEQ ID NO 447
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: microRNA precursor sequence

<400> SEQUENCE: 447
tcttcacttt caagagtggc aaagtctttc catatgtatg tatgtatgtc tgttacacat     60
atggaaagac tttgccactc tttaaagtga agaac                                95

<210> SEQ ID NO 448
<211> LENGTH: 111
<212> TYPE: DNA
<213> ORGANISM: Human
<220> FEATURE:
<221> NAME/KEY: misc_feature
<222> LOCATION: (1)..(111)
<223> OTHER INFORMATION: microRNA precursor sequence

<400> SEQUENCE: 448
ttcattctat tgagctgact ggcttgtatg gaggttctag accatgttag tgttcaagtc     60
tacatggatg gaaaccttca agcaggccaa gcaggagaca ggtggaagaa g             111

<210> SEQ ID NO 449
<211> LENGTH: 111
<212> TYPE: DNA
<213> ORGANISM: Human
<220> FEATURE:
<221> NAME/KEY: misc_feature
<222> LOCATION: (1)..(111)
<223> OTHER INFORMATION: microRNA precursor sequence

<400> SEQUENCE: 449
ttcattctat tgagctgact ggcttgtatg gaggttctag accatgttag tgttcaagtc     60
tacatggatg gaaaccttca agcaggccaa gcaggagaca ggtggaagaa g             111

<210> SEQ ID NO 450
<211> LENGTH: 118
<212> TYPE: DNA
<213> ORGANISM: Human
<220> FEATURE:
<221> NAME/KEY: misc_feature
<222> LOCATION: (1)..(118)
<223> OTHER INFORMATION: microRNA precursor sequence

<400> SEQUENCE: 450
gtctatcaag agaggaatga acagttaaat tataacatgt ccatattatg ggttagttgt     60
ggacacatac taacgcataa tatggacatg ttataattta actgttcctt tctgagag    118

<210> SEQ ID NO 451
<211> LENGTH: 101
<212> TYPE: DNA
<213> ORGANISM: Human
<220> FEATURE:
<221> NAME/KEY: misc_feature
<222> LOCATION: (1)..(101)
<223> OTHER INFORMATION: microRNA precursor sequence

<400> SEQUENCE: 451
tccctctgcc cctcacctgc tgcttggggt ttggggtgca gacattgcca gaggatgggc     60
agcagactga ccttcaaccc cacaggtatc caccacagtg g    101

<210> SEQ ID NO 452
<211> LENGTH: 96
<212> TYPE: DNA
<213> ORGANISM: Human
<220> FEATURE:
<221> NAME/KEY: misc_feature
<222> LOCATION: (1)..(96)
<223> OTHER INFORMATION: microRNA precursor sequence

<400> SEQUENCE: 452
cccaccatcc tagcttgcct gagactgtcc tggtttagc actgaaagtg cctgttccag    60
gaaaccctgc agtctccagc aaactgggac agtggg    96

<210> SEQ ID NO 453
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: microRNA precursor sequence

<400> SEQUENCE: 453
gcttctctga ggatgaaaga cccattgagg agaaggttct gctggctgag aaccttcctc    60
tccatgggtc tttcatcctc aaagaac    87

<210> SEQ ID NO 454
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: microRNA precursor sequence

<400> SEQUENCE: 454
gctctgtgat tgcctctgat caggcaaaat tgcagactgt cttcccaaat agcctgcaac    60
tttgcctgat cagaggcagt cacagagc    88

<210> SEQ ID NO 455
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: microRNA precursor sequence

<400> SEQUENCE: 455
gctctgtgat tgcctctgat caggcaaaat tgcagactgt cttcccaaat agcctgcaac    60
tttgcctgat cagaggcagt cacagagc    88

<210> SEQ ID NO 456
<211> LENGTH: 91
<212> TYPE: DNA
<213> ORGANISM: Human
<220> FEATURE:
<221> NAME/KEY: misc_feature
<222> LOCATION: (1)..(91)
<223> OTHER INFORMATION: microRNA precursor sequence

<400> SEQUENCE: 456
attctcttag gttggtgcaa aagtagttgt ggttttgcca ttcatttcag tgataaaaac    60
cgcaattact tttgcaccaa cctaatcgaa t                                    91

<210> SEQ ID NO 457
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: microRNA precursor sequence

<400> SEQUENCE: 457
tttaagaact ggatatgatg actgaaataa gctccatatc aatgagaatt tcaatgggat      60
tatgtgcagt caatgtccag taattaga                                       88

<210> SEQ ID NO 458
<211> LENGTH: 96
<212> TYPE: DNA
<213> ORGANISM: Human
<220> FEATURE:
<221> NAME/KEY: misc_feature
<222> LOCATION: (1)..(96)
<223> OTHER INFORMATION: microRNA precursor sequence

<400> SEQUENCE: 458
ttagtttggt gcaaaagtaa tcacggtttt tgctattgaa agtaatagca aaactttca      60 atagcaaaaa ctgtgattac tttgcatca atctaa                               96

<210> SEQ ID NO 459
<211> LENGTH: 96
<212> TYPE: DNA
<213> ORGANISM: Human
<220> FEATURE:
<221> NAME/KEY: misc_feature
<222> LOCATION: (1)..(96)
<223> OTHER INFORMATION: microRNA precursor sequence

<400> SEQUENCE: 459
agaaaaatgt tagggtggtg caaaagtgat cgtggttttt gcaattttt aatgacaaaa      60 accacaatta cttttgcacc aacctaacct tgtttt                              96

<210> SEQ ID NO 460
<211> LENGTH: 93
<212> TYPE: DNA
<213> ORGANISM: Human
<220> FEATURE:
<221> NAME/KEY: misc_feature
<222> LOCATION: (1)..(93)
<223> OTHER INFORMATION: microRNA precursor sequence

<400> SEQUENCE: 460
agtttccatg atagggaaac caggcaagaa atattgtctc ctcaagttgc gacgagacag      60
tagttcttgc ctggtttctc tatcatggag tct                                 93

<210> SEQ ID NO 461
<211> LENGTH: 76
<212> TYPE: DNA
<213> ORGANISM: Human
<220> FEATURE:
<221> NAME/KEY: misc_feature
<222> LOCATION: (1)..(76)
<223> OTHER INFORMATION: microRNA precursor sequence

<400> SEQUENCE: 461

```
tgtgctccag tacatataaa gagacttatt aagatgatct tttcttaata agtctcttta    60
tatgtactgg agcccg                                                   76

<210> SEQ ID NO 462
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: microRNA precursor sequence

<400> SEQUENCE: 462
tattgggtgg gtgcaaaagt aattgcggtt tttgctatta gtttcaatgg taaaaaccgt    60
gactacttct gcaccaacct agta                                          84

<210> SEQ ID NO 463
<211> LENGTH: 68
<212> TYPE: DNA
<213> ORGANISM: Human
<220> FEATURE:
<221> NAME/KEY: misc_feature
<222> LOCATION: (1)..(68)
<223> OTHER INFORMATION: microRNA precursor sequence

<400> SEQUENCE: 463
aaaataggac ttttgaagga agagtttttt ttcacatttt cacacttttc cttcaaaagt    60
catatttt                                                            68

<210> SEQ ID NO 464
<211> LENGTH: 94
<212> TYPE: DNA
<213> ORGANISM: Human
<220> FEATURE:
<221> NAME/KEY: misc_feature
<222> LOCATION: (1)..(94)
<223> OTHER INFORMATION: microRNA precursor sequence

<400> SEQUENCE: 464
agagaaagtt ttcagtgtaa ctcaacattt gaagtgtact tgcccttgga ccaagcaatt    60
cttcaaatgt tgagatacac tgaaaacttt ctct                               94

<210> SEQ ID NO 465
<211> LENGTH: 90
<212> TYPE: DNA
<213> ORGANISM: Human
<220> FEATURE:
<221> NAME/KEY: misc_feature
<222> LOCATION: (1)..(90)
<223> OTHER INFORMATION: microRNA precursor sequence

<400> SEQUENCE: 465
ggataatagg acaagacaaa ttacagattg tctcagagaa aacaaatgag ttactctctc    60
ggacaagctg taggtcctac ctaaatgtcc                                    90

<210> SEQ ID NO 466
<211> LENGTH: 90
<212> TYPE: DNA
<213> ORGANISM: Human
<220> FEATURE:
<221> NAME/KEY: misc_feature
<222> LOCATION: (1)..(90)
<223> OTHER INFORMATION: microRNA precursor sequence

<400> SEQUENCE: 466
```
ggataatagg acaagacaaa ttacagattg tctcagagaa aacaaatgag ttactctctc    60
ggacaagctg taggtcctac ctaaatgtcc                                     90

<210> SEQ ID NO 467
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: microRNA precursor sequence

<400> SEQUENCE: 467
taggttcatg caaaagtagt tgtggttttg ccattacttt caatggatgg caaaaacagc    60
aattactttt gcaccaacct a                                              81

<210> SEQ ID NO 468
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: microRNA precursor sequence

<400> SEQUENCE: 468
gagggaaagc aggccaacct cgaggatctc cccagccttg gcgttcaggt gctgaggaga    60
tcgtcgaggt tggcctgctt cccctc                                         86

<210> SEQ ID NO 469
<211> LENGTH: 92
<212> TYPE: DNA
<213> ORGANISM: Human
<220> FEATURE:
<221> NAME/KEY: misc_feature
<222> LOCATION: (1)..(92)
<223> OTHER INFORMATION: microRNA precursor sequence

<400> SEQUENCE: 469
aaggaacagg ggacacttgt aatggagaac actaagctat ggactgctat ggactgctag    60
tgctctccgt tacaagtatc ccctgttacc tt                                  92

<210> SEQ ID NO 470
<211> LENGTH: 99
<212> TYPE: DNA
<213> ORGANISM: Human
<220> FEATURE:
<221> NAME/KEY: misc_feature
<222> LOCATION: (1)..(99)
<223> OTHER INFORMATION: microRNA precursor sequence

<400> SEQUENCE: 470
gatatttgaa cctcctcccg tgaatcacaa atgtccttaa tagcaatcct taaatgccat    60
taaggacatt tgtgattgat gggaggagga tgaaatatt                           99

<210> SEQ ID NO 471
<211> LENGTH: 76
<212> TYPE: DNA
<213> ORGANISM: Human
<220> FEATURE:
<221> NAME/KEY: misc_feature
<222> LOCATION: (1)..(76)
<223> OTHER INFORMATION: microRNA precursor sequence

<400> SEQUENCE: 471
gggaaaaaaa aaaggatttg tcttgtagcc aggatattgt tttaaagaaa atccttttg     60 tttttccagg tggacc                                                    76

<210> SEQ ID NO 472
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: microRNA precursor sequence

<400> SEQUENCE: 472
agggctgcta gatttaatgg atcaaatcac aagatgccta gttaaatttg aattttaaat   60
ttaactggac atcttgcatt ttatctggta atcct                               95

<210> SEQ ID NO 473
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: microRNA precursor sequence

<400> SEQUENCE: 473
ctctgcccca tctccacctg gacccagcgt agacaaagag gtgtttctac tccatatcta   60
cctggaccca gtgtagatgg gaggag                                         86

<210> SEQ ID NO 474
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: microRNA precursor sequence

<400> SEQUENCE: 474
ctctgcccca tctccacctg gacccagcgt agacaaagag gtgtttctac tccatatcta   60
cctggaccca gtgtagatgg gaggag                                         86

<210> SEQ ID NO 475
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: microRNA precursor sequence

<400> SEQUENCE: 475
gtaggataaa tgactcatcc tagcttgcct gagactgtcc cagtttgaaa actggacctc   60
atcagtccta gacacactgg gatgtggttc accctat                             97

<210> SEQ ID NO 476
<211> LENGTH: 99
<212> TYPE: DNA
<213> ORGANISM: Human
<220> FEATURE:
<221> NAME/KEY: misc_feature
<222> LOCATION: (1)..(99)
<223> OTHER INFORMATION: microRNA precursor sequence

<400> SEQUENCE: 476
tttattgtga aatatgtcat taatatgtac tgacaaagcg tatctgtgta ataaatatgc    60
tttttgtcag tacatgttaa tggtatattt cataacaaa                          99

<210> SEQ ID NO 477
<211> LENGTH: 90
<212> TYPE: DNA
<213> ORGANISM: Human
<220> FEATURE:
<221> NAME/KEY: misc_feature
<222> LOCATION: (1)..(90)
<223> OTHER INFORMATION: microRNA precursor sequence

<400> SEQUENCE: 477
ctgttccggg catcacctcc cactgcagag cctggggagc cggacagctc ccttcccagg    60
ctctgcagtg ggaactgatg cctggaacag                                    90

<210> SEQ ID NO 478
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: microRNA precursor sequence

<400> SEQUENCE: 478
gatcattatt caggccggtc ctgcagagag gaagcccttc tgcttacagg tattggaagg    60
gcttcctctc tgcaggaccg gcctgaataa tgtaatc                            97

<210> SEQ ID NO 479
<211> LENGTH: 94
<212> TYPE: DNA
<213> ORGANISM: Human
<220> FEATURE:
<221> NAME/KEY: misc_feature
<222> LOCATION: (1)..(94)
<223> OTHER INFORMATION: microRNA precursor sequence

<400> SEQUENCE: 479
cagtttctct tccatcccat atcttaacag ctaatctagt aaattctatc ttcagaagat    60
ttgctgttaa gatatgggat ggaggagaaa tctg                               94

<210> SEQ ID NO 480
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: microRNA precursor sequence

<400> SEQUENCE: 480
tttttctccc agtcaagagt tactagaact attcaacctt cagctgtgtt gaatagtttt    60
agtaactctt gactgggaga aaag                                          84

<210> SEQ ID NO 481
<211> LENGTH: 84
<212> TYPE: DNA
<213> ORGANISM: Human
<220> FEATURE:
<221> NAME/KEY: misc_feature
<222> LOCATION: (1)..(84)

<223> OTHER INFORMATION: microRNA precursor sequence

<400> SEQUENCE: 481
tttttctccc agtcaagagt tactagaact attcaacctt cagctgtgtt gaatagtttt     60
agtaactctt gactgggaga aaag                                             84

<210> SEQ ID NO 482
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: microRNA precursor sequence

<400> SEQUENCE: 482
agctggactg agagaaattt attcttggta ggttgtacat tcctaaacat gtacaacgta     60
ctaagaataa atttctctca gtccagct                                         88

<210> SEQ ID NO 483
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: microRNA precursor sequence

<400> SEQUENCE: 483
agctggactg agagaaattt attcttggta ggttgtacat tcctaaacat gtacaacgta     60
ctaagaataa atttctctca gtccagct                                         88

<210> SEQ ID NO 484
<211> LENGTH: 91
<212> TYPE: DNA
<213> ORGANISM: Human
<220> FEATURE:
<221> NAME/KEY: misc_feature
<222> LOCATION: (1)..(91)
<223> OTHER INFORMATION: microRNA precursor sequence

<400> SEQUENCE: 484
ggttagcaca gagtgggagc tctagaaaga ttgttgacca atcatcttat tgactagacc     60
atctttctag agtataacta ttttggacac c                                     91

<210> SEQ ID NO 485
<211> LENGTH: 96
<212> TYPE: DNA
<213> ORGANISM: Human
<220> FEATURE:
<221> NAME/KEY: misc_feature
<222> LOCATION: (1)..(96)
<223> OTHER INFORMATION: microRNA precursor sequence

<400> SEQUENCE: 485
gctgcgtttg cactgcttct ccaaaaccac attataggta ctaaacaaca ttgtttagta     60
cctataatgt gctagactcc tggctgctag cgaggt                                96

<210> SEQ ID NO 486
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: microRNA precursor sequence

<400> SEQUENCE: 486
ggtatgtatc tgcttttccg gagttgtaag tgttgacaat atccagaatg acattgtctt        60
tgtcaacact tacaactctg gaaaagcaga tacatacc        98

<210> SEQ ID NO 487
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: microRNA precursor sequence

<400> SEQUENCE: 487
ggtatgtatc tgcttttccg gagttgtaag tgttgacaat atccagaatg acattgtctt        60
tgtcaacact tacaactctg gaaaagcaga tacatacc        98

<210> SEQ ID NO 488
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: microRNA precursor sequence

<400> SEQUENCE: 488
agtatgacac ctcaaagaag caatactgtt acctgaaata ggctgcgaag ataacagtat        60
ttcagataac agtattacat ctttgaagtg tcatatt        97

<210> SEQ ID NO 489
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: microRNA precursor sequence

<400> SEQUENCE: 489
aaaaaaaggg aaagaagaac tgttgcattt gccctgcact cagtttgcac agggtaaatg        60
caatagttct tctttcccctt ttttt        85

<210> SEQ ID NO 490
<211> LENGTH: 80
<212> TYPE: DNA
<213> ORGANISM: Human
<220> FEATURE:
<221> NAME/KEY: misc_feature
<222> LOCATION: (1)..(80)
<223> OTHER INFORMATION: microRNA precursor sequence

<400> SEQUENCE: 490
gttttggatt ttggactttt tcagatttgg ggatatttgc attatactta tcctaaatct        60
gaaagtccaa aacctgaaat        80

<210> SEQ ID NO 491
<211> LENGTH: 95
<212> TYPE: DNA
<213> ORGANISM: Human
<220> FEATURE:

```
<221> NAME/KEY: misc_feature
<222> LOCATION: (1)..(95)
<223> OTHER INFORMATION: microRNA precursor sequence

<400> SEQUENCE: 491
gcctcaaatt taaggaggga ctcactcaca ggattgtgca aatgcaaagt tggcttttgc    60
atgaccctgg gagtaggtgc ctccttaaat tttgc                              95

<210> SEQ ID NO 492
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: microRNA precursor sequence

<400> SEQUENCE: 492
gcctcaaatt taaggaggga ctcactcaca ggattgtgca aatgcaaagt tggcttttgc    60
atgaccctgg gagtaggtgc ctccttaaat tttgc                              95

<210> SEQ ID NO 493
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: microRNA precursor sequence

<400> SEQUENCE: 493
ctgtaggttc tgtcttgggc cacttggatc tgaaggctgc ccctttgctc tctggggtag    60
ccttcagatc ttggtgtttt gaattcttac tatag                              95

<210> SEQ ID NO 494
<211> LENGTH: 94
<212> TYPE: DNA
<213> ORGANISM: Human
<220> FEATURE:
<221> NAME/KEY: misc_feature
<222> LOCATION: (1)..(94)
<223> OTHER INFORMATION: microRNA precursor sequence

<400> SEQUENCE: 494
tgcctacagt gaatccctag tggtcagagg gcttatgata tattgtgaga gccatgtcat    60
aagccttttg gccactaggg attcaatgta tgca                               94

<210> SEQ ID NO 495
<211> LENGTH: 92
<212> TYPE: DNA
<213> ORGANISM: Human
<220> FEATURE:
<221> NAME/KEY: misc_feature
<222> LOCATION: (1)..(92)
<223> OTHER INFORMATION: microRNA precursor sequence

<400> SEQUENCE: 495
ttgaggaagg gtcaggcatg aggaggatct gaaggattgg actcaggttc gaaacctcca    60
cttcctcctc atctcctacc ctctccactc ag                                 92

<210> SEQ ID NO 496
<211> LENGTH: 118
<212> TYPE: DNA
<213> ORGANISM: Human
```

```
<220> FEATURE:
<221> NAME/KEY: misc_feature
<222> LOCATION: (1)..(118)
<223> OTHER INFORMATION: microRNA precursor sequence

<400> SEQUENCE: 496
agtatagtgg tgagtatccc cgcctgtcac gcgggagacc ggggttcgat tccccgacgg      60
ggaggccggg tactttcgta tttttaaata cagaggggag actttgttgg cgatgctt      118

<210> SEQ ID NO 497
<211> LENGTH: 99
<212> TYPE: DNA
<213> ORGANISM: Human
<220> FEATURE:
<221> NAME/KEY: misc_feature
<222> LOCATION: (1)..(99)
<223> OTHER INFORMATION: microRNA precursor sequence

<400> SEQUENCE: 497
ggcctaatgg ataaggcatt ggcctcctaa gccagggatt gtgggttcga gtcccacccg      60
gggtaaagaa aggccgaatt ttagtgttcc ttatcgggc                              99

<210> SEQ ID NO 498
<211> LENGTH: 114
<212> TYPE: DNA
<213> ORGANISM: Human
<220> FEATURE:
<221> NAME/KEY: misc_feature
<222> LOCATION: (1)..(114)
<223> OTHER INFORMATION: microRNA precursor sequence

<400> SEQUENCE: 498
gaaggcagct acacatgcgt ggcggttcca tggtgtaatg gttagcactc tggactctga      60
atccagcgat ccgagttcaa atctcggtgg aacctgcatt ggttttgtt tttt            114

<210> SEQ ID NO 499
<211> LENGTH: 92
<212> TYPE: DNA
<213> ORGANISM: Human
<220> FEATURE:
<221> NAME/KEY: misc_feature
<222> LOCATION: (1)..(92)
<223> OTHER INFORMATION: microRNA precursor sequence

<400> SEQUENCE: 499
tcagtggtag agcatttgac tgcagatcaa gaggtccccg gttcaaatcc gggtgccccc      60
tctgtgctcc ggagttacct cgttttgttg gt                                    92

<210> SEQ ID NO 500
<211> LENGTH: 61
<212> TYPE: DNA
<213> ORGANISM: Human
<220> FEATURE:
<221> NAME/KEY: misc_feature
<222> LOCATION: (1)..(61)
<223> OTHER INFORMATION: microRNA precursor sequence

<400> SEQUENCE: 500
tgtagtgttt cttactttaa atatgtaaaa tgtgtaacat gcagagcgaa aggggcagtg      60
a                                                                      61

<210> SEQ ID NO 501
<211> LENGTH: 95
<212> TYPE: DNA
```

```
<213> ORGANISM: Human
<220> FEATURE:
<221> NAME/KEY: misc_feature
<222> LOCATION: (1)..(95)
<223> OTHER INFORMATION: microRNA precursor sequence

<400> SEQUENCE: 501
aaagtcggtg ccggaggctc ccagctcaga tcgccgaagc gtcggactac cgttggtttc      60
cgcaacttcc tggattatcc tcgccaagga ctttg                                 95

<210> SEQ ID NO 502
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: microRNA precursor sequence

<400> SEQUENCE: 502
aaagtcggtg ccggaggctc ccagctcaga tcgccgaagc gtcggactac cgttggtttc      60
cgcaacttcc tggattatcc tcgccaagga ctttg                                 95

<210> SEQ ID NO 503
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: microRNA precursor sequence

<400> SEQUENCE: 503
aatcaacttc ctaggcacac ttaaagttat agctacatca gttataacta tatcagttaa      60
aactttaagt gtgcctagga agttgatt                                         88

<210> SEQ ID NO 504
<211> LENGTH: 109
<212> TYPE: DNA
<213> ORGANISM: Human
<220> FEATURE:
<221> NAME/KEY: misc_feature
<222> LOCATION: (1)..(109)
<223> OTHER INFORMATION: microRNA precursor sequence

<400> SEQUENCE: 504
acatattggt ctgttgtcag gctcagcagc atggctgact aaagacattg acatcatgac      60
attgtcatgt tgctctgctg ttgcccctgg ctctagctgg cctacttgt                 109

<210> SEQ ID NO 505
<211> LENGTH: 69
<212> TYPE: DNA
<213> ORGANISM: Human
<220> FEATURE:
<221> NAME/KEY: misc_feature
<222> LOCATION: (1)..(69)
<223> OTHER INFORMATION: microRNA precursor sequence

<400> SEQUENCE: 505
agccctgggg gtggtctcta gccaaggctc tggggtctca cccttggctg gtctctgctc      60
cgcaggcct                                                              69

<210> SEQ ID NO 506
<211> LENGTH: 120
```

```
<212> TYPE: DNA
<213> ORGANISM: Human
<220> FEATURE:
<221> NAME/KEY: misc_feature
<222> LOCATION: (1)..(120)
<223> OTHER INFORMATION: microRNA precursor sequence

<400> SEQUENCE: 506
agtggagaag gccacgattt ttttgatgtc attttgtgta agggcgcaga ctgctgcgaa      60
cagagtggtg atagcgccta ggcatagtgt gagagtttgg attagtgggt tattctctgc     120

<210> SEQ ID NO 507
<211> LENGTH: 94
<212> TYPE: DNA
<213> ORGANISM: Human
<220> FEATURE:
<221> NAME/KEY: misc_feature
<222> LOCATION: (1)..(94)
<223> OTHER INFORMATION: microRNA precursor sequence

<400> SEQUENCE: 507
atagttttag agtttctaag gatcatgtct gtgagtcagg attccagaga ccatggtcct      60
gatgggatgg agcctggaga cgtcattgag agta                                  94

<210> SEQ ID NO 508
<211> LENGTH: 115
<212> TYPE: DNA
<213> ORGANISM: Human
<220> FEATURE:
<221> NAME/KEY: misc_feature
<222> LOCATION: (1)..(115)
<223> OTHER INFORMATION: microRNA precursor sequence

<400> SEQUENCE: 508
atgatggcta tggatttggg tcagatagat ttggaagagg taaggtaaga attgaatttc      60
tcagttgaag gatgcttaca ctcttgtcca tctagacctc aattactgtt tttca          115

<210> SEQ ID NO 509
<211> LENGTH: 120
<212> TYPE: DNA
<213> ORGANISM: Human
<220> FEATURE:
<221> NAME/KEY: misc_feature
<222> LOCATION: (1)..(120)
<223> OTHER INFORMATION: microRNA precursor sequence

<400> SEQUENCE: 509
attctagatt aaatggtcaa ggaagacagt ctgtggcaaa ggcccagttc aagtttagaa      60
ctgaacagcc tctggcaatc tatcttccac aaataggcag cattttaaag gtctcagaga    120

<210> SEQ ID NO 510
<211> LENGTH: 115
<212> TYPE: DNA
<213> ORGANISM: Human
<220> FEATURE:
<221> NAME/KEY: misc_feature
<222> LOCATION: (1)..(115)
<223> OTHER INFORMATION: microRNA precursor sequence

<400> SEQUENCE: 510
cacgtcacct gatatcaggt atttactctg aactagctct gtggatcctg acagacagcc      60
tgatagacag gatccacaga gctagtccag agtaaaagac ctaaatcagc tgtgg          115

<210> SEQ ID NO 511
```

```
<211> LENGTH: 64
<212> TYPE: DNA
<213> ORGANISM: Human
<220> FEATURE:
<221> NAME/KEY: misc_feature
<222> LOCATION: (1)..(64)
<223> OTHER INFORMATION: microRNA precursor sequence

<400> SEQUENCE: 511
cagtagtggt tagtactctg aattaactta tctaaatcaa tgaaaataat agtgaacctc      60
tgct                                                                  64

<210> SEQ ID NO 512
<211> LENGTH: 101
<212> TYPE: DNA
<213> ORGANISM: Human
<220> FEATURE:
<221> NAME/KEY: misc_feature
<222> LOCATION: (1)..(101)
<223> OTHER INFORMATION: microRNA precursor sequence

<400> SEQUENCE: 512
cctgcctcgg cctcccaaag tgctgggatt acaggcagga gccccgttg ccactgctgc       60 tgctgctgcc cctgctgcca ctgtggctgg gcctggcagg g                         101

<210> SEQ ID NO 513
<211> LENGTH: 106
<212> TYPE: DNA
<213> ORGANISM: Human
<220> FEATURE:
<221> NAME/KEY: misc_feature
<222> LOCATION: (1)..(106)
<223> OTHER INFORMATION: microRNA precursor sequence

<400> SEQUENCE: 513
cggataattg tagcacttcc tggttcatac ggataattgt agcacttcct ggtttgcagg      60
gacattgcaa tacttcctgg ttcatatgga taattgtagc acttct                   106

<210> SEQ ID NO 514
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: microRNA precursor sequence

<400> SEQUENCE: 514
ctcaaacaac tcaataggaa aaaaaactaa taatctgatt taaaaacggg caaaagagag      60
tttctaagga tcatgtctga ga                                              82

<210> SEQ ID NO 515
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: microRNA precursor sequence

<400> SEQUENCE: 515
ctcggcctcc cttcatggtg ggaccagggc cagcagggaa tgtcagggcc acccctgacc      60
ttcactgtga ctctgctgca gagggtggcc tggag                                95
```

-continued

```
<210> SEQ ID NO 516
<211> LENGTH: 104
<212> TYPE: DNA
<213> ORGANISM: Human
<220> FEATURE:
<221> NAME/KEY: misc_feature
<222> LOCATION: (1)..(104)
<223> OTHER INFORMATION: microRNA precursor sequence

<400> SEQUENCE: 516
ctgtgctttg tgtgttggag gatgaaagta cggagtgatc catcggctaa gtgtcttgtc    60
acaatgctga cactcaaact gctgacagca cacgttttc acag                     104

<210> SEQ ID NO 517
<211> LENGTH: 104
<212> TYPE: DNA
<213> ORGANISM: Human
<220> FEATURE:
<221> NAME/KEY: misc_feature
<222> LOCATION: (1)..(104)
<223> OTHER INFORMATION: microRNA precursor sequence

<400> SEQUENCE: 517
ctgtgctttg tgtgttggag gatgaaagta cggagtgatc catcggctaa gtgtcttgtc    60
acaatgctga cactcaaact gctgacagca cacgttttc acag                     104

<210> SEQ ID NO 518
<211> LENGTH: 105
<212> TYPE: DNA
<213> ORGANISM: Human
<220> FEATURE:
<221> NAME/KEY: misc_feature
<222> LOCATION: (1)..(105)
<223> OTHER INFORMATION: microRNA precursor sequence

<400> SEQUENCE: 518
gaaactcggt gactccaggg actgccttag gagaaagttt ctggaagttc tgacattcca    60
gaaactttct cctaaggcag tccctgggag tcactgagtc agtcc                   105

<210> SEQ ID NO 519
<211> LENGTH: 74
<212> TYPE: DNA
<213> ORGANISM: Human
<220> FEATURE:
<221> NAME/KEY: misc_feature
<222> LOCATION: (1)..(74)
<223> OTHER INFORMATION: microRNA precursor sequence

<400> SEQUENCE: 519
gcaactcgcc tggctccctt ctctccgtct gcctcctggc cgcggggccc ggagagctgg    60
gagccagagg gtgt                                                     74

<210> SEQ ID NO 520
<211> LENGTH: 66
<212> TYPE: DNA
<213> ORGANISM: Human
<220> FEATURE:
<221> NAME/KEY: misc_feature
<222> LOCATION: (1)..(66)
<223> OTHER INFORMATION: microRNA precursor sequence

<400> SEQUENCE: 520
gcaagggttg aggagggact taacatcaat gaattcatga ggtgatgtag tctccctac    60 ctaggt                                                              66
```

<210> SEQ ID NO 521
<211> LENGTH: 80
<212> TYPE: DNA
<213> ORGANISM: Human
<220> FEATURE:
<221> NAME/KEY: misc_feature
<222> LOCATION: (1)..(80)
<223> OTHER INFORMATION: microRNA precursor sequence

<400> SEQUENCE: 521
gcccttcggt agctggtccc ttaactcagt ggtgaatggc gaccggatgg agctctaggg    60
aagcgacagc agcggcgggt                                               80

<210> SEQ ID NO 522
<211> LENGTH: 107
<212> TYPE: DNA
<213> ORGANISM: Human
<220> FEATURE:
<221> NAME/KEY: misc_feature
<222> LOCATION: (1)..(107)
<223> OTHER INFORMATION: microRNA precursor sequence

<400> SEQUENCE: 522
ggaagagggc ttaggtgcac gctctagcgg ggattccaat attgggccaa ttcccccaat    60
gttggaatcc tcgctagagc gtgcacttct ggaagctagg aacctcc                 107

<210> SEQ ID NO 523
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: microRNA precursor sequence

<400> SEQUENCE: 523
ggaagagtca agtcaaggcc agaggtccca cagcagggct ggaaagcaca cctgtgggac    60
ttctggcctt gacttgactc tttc                                          84

<210> SEQ ID NO 524
<211> LENGTH: 109
<212> TYPE: DNA
<213> ORGANISM: Human
<220> FEATURE:
<221> NAME/KEY: misc_feature
<222> LOCATION: (1)..(109)
<223> OTHER INFORMATION: microRNA precursor sequence

<400> SEQUENCE: 524
ggactgactc agtgactccc agggactgcc ttaggagaaa gtttctggaa tgtcagaact    60
tccagaaact ttctcctaag gcagtccctg gagtcaccga gtttctctt              109

<210> SEQ ID NO 525
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: microRNA precursor sequence

<400> SEQUENCE: 525
ggcacagact catccctgat caaagcctcc acccccccc caaaaaaaag atctgggcac    60
ctacttggga agctgaggca ggagaatcac ttgaaccc                           98

```
<210> SEQ ID NO 526
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: microRNA precursor sequence

<400> SEQUENCE: 526
ggcatggagt cctgtggcat ccacgaaact accttcaact ccatcatgaa gtgtgacgtg    60
gacatccgca aagacctgta cgcc                                          84

<210> SEQ ID NO 527
<211> LENGTH: 74
<212> TYPE: DNA
<213> ORGANISM: Human
<220> FEATURE:
<221> NAME/KEY: misc_feature
<222> LOCATION: (1)..(74)
<223> OTHER INFORMATION: microRNA precursor sequence

<400> SEQUENCE: 527
gggcaggagg gagtggggtg ggacccagct gttggccatg gcgacaacac ctgggttgtc    60
ccctctaggg tcca                                                     74

<210> SEQ ID NO 528
<211> LENGTH: 78
<212> TYPE: DNA
<213> ORGANISM: Human
<220> FEATURE:
<221> NAME/KEY: misc_feature
<222> LOCATION: (1)..(78)
<223> OTHER INFORMATION: microRNA precursor sequence

<400> SEQUENCE: 528
ggggctaatc gcctggactg cctggagaaa gcgaagctag tacccccttt ctccaacagt    60
ccttagtttc caggccct                                                 78

<210> SEQ ID NO 529
<211> LENGTH: 96
<212> TYPE: DNA
<213> ORGANISM: Human
<220> FEATURE:
<221> NAME/KEY: misc_feature
<222> LOCATION: (1)..(96)
<223> OTHER INFORMATION: microRNA precursor sequence

<400> SEQUENCE: 529
ggtaatctca tcagaaagat aggcagcttc caagtcccag ggcctcgtaa gcagaggcac    60
agttatggat gatgatatct gagtgatatt gtgctt                             96

<210> SEQ ID NO 530
<211> LENGTH: 57
<212> TYPE: DNA
<213> ORGANISM: Human
<220> FEATURE:
<221> NAME/KEY: misc_feature
<222> LOCATION: (1)..(57)
<223> OTHER INFORMATION: microRNA precursor sequence

<400> SEQUENCE: 530
ggttaactta caataaatga agcttttatg caggtttccg tagcgtagtg gttatca       57
```

```
<210> SEQ ID NO 531
<211> LENGTH: 120
<212> TYPE: DNA
<213> ORGANISM: Human
<220> FEATURE:
<221> NAME/KEY: misc_feature
<222> LOCATION: (1)..(120)
<223> OTHER INFORMATION: microRNA precursor sequence

<400> SEQUENCE: 531
gtaaggtgga gagattaccg tgttataaag aactttggga tattttcaa aattaacctg      60 accattcttt tgaaaccaga gtccttaaca agcattgaga tatatttctc catgaaggct    120

<210> SEQ ID NO 532
<211> LENGTH: 69
<212> TYPE: DNA
<213> ORGANISM: Human
<220> FEATURE:
<221> NAME/KEY: misc_feature
<222> LOCATION: (1)..(69)
<223> OTHER INFORMATION: microRNA precursor sequence

<400> SEQUENCE: 532
gtgagaaatg atgagggtca acattcttca taccaaagtg aagacatgag atccaactct     60
gagctcacc                                                            69

<210> SEQ ID NO 533
<211> LENGTH: 102
<212> TYPE: DNA
<213> ORGANISM: Human
<220> FEATURE:
<221> NAME/KEY: misc_feature
<222> LOCATION: (1)..(102)
<223> OTHER INFORMATION: microRNA precursor sequence

<400> SEQUENCE: 533
gtggccgagg actttgattg tacattgttc ttttttaat agtcattcca aatatcatga      60
gatgcattgt tacaggaagt cccttgccct cctaaaagcc ac                       102

<210> SEQ ID NO 534
<211> LENGTH: 120
<212> TYPE: DNA
<213> ORGANISM: Human
<220> FEATURE:
<221> NAME/KEY: misc_feature
<222> LOCATION: (1)..(120)
<223> OTHER INFORMATION: microRNA precursor sequence

<400> SEQUENCE: 534
gttgctatcg gggactacaa tggccacgtc ggtctgggtg ttaagtgctc caaggaggtg     60
gccaccgcca tccatggggc catcatcctg gccaagctct ccattgtccc cgtgcgcaga   120

<210> SEQ ID NO 535
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: microRNA precursor sequence

<400> SEQUENCE: 535
tcaaggaaaa gctgtgctac gtcgccctgg acttcgagca ggagatggcc acggcagcct    60
ccagctcctc cctgg                                                     75
```

<210> SEQ ID NO 536
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: microRNA precursor sequence

<400> SEQUENCE: 536
tccatccgta ttgaggatga ggacacctct gaactcacag agcaggctgt gagtttagag    60
ctgtctgctc taaactcagg tgga                                          84

<210> SEQ ID NO 537
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: microRNA precursor sequence

<400> SEQUENCE: 537
tctattgcta tgcctccaag ttcattaata ttttcttctc attgtaaaga ctgggggacc    60
tctttcttaa gtgatctttg tcttaagatt tggtgcaata tatcagtaga              110

<210> SEQ ID NO 538
<211> LENGTH: 64
<212> TYPE: DNA
<213> ORGANISM: Human
<220> FEATURE:
<221> NAME/KEY: misc_feature
<222> LOCATION: (1)..(64)
<223> OTHER INFORMATION: microRNA precursor sequence

<400> SEQUENCE: 538
tgtgcttgcg cataactggg gccgcctggc ctcccgcggg cggccttttt aaccgcgagc    60
gaca                                                                64

<210> SEQ ID NO 539
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: microRNA precursor sequence

<400> SEQUENCE: 539
ttccttaact aaagtactcc ctctcaaatc aaagtggtta tggttctaaa aactccgatt    60
ggagaattta caggatagga gg                                            82

<210> SEQ ID NO 540
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: microRNA precursor sequence

<400> SEQUENCE: 540
ttgggcatgg aatcctgcgg catccacaag accaccttca actccatcat gaagtgtgac    60

```
gtggacatcc gcaaagacct gtacgccaa                                      89

<210> SEQ ID NO 541
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: microRNA precursor sequence

<400> SEQUENCE: 541
ctggtggctg ggccgacgac tcggggcgcg gccgtgagcg cagaggccat ggagccggag    60
ctcgcggaca cctctgcact caaggcggcg ccctacggcc actcgcggag               110

<210> SEQ ID NO 542
<211> LENGTH: 103
<212> TYPE: DNA
<213> ORGANISM: Human
<220> FEATURE:
<221> NAME/KEY: misc_feature
<222> LOCATION: (1)..(103)
<223> OTHER INFORMATION: microRNA precursor sequence

<400> SEQUENCE: 542
gagaatttgt atattttcta tttagaagcc tatagataga atataggaaa aaaagctata    60
tttttcttat aggcttctaa gtagaaaatg tatttgcaag gat                     103

<210> SEQ ID NO 543
<211> LENGTH: 104
<212> TYPE: DNA
<213> ORGANISM: Human
<220> FEATURE:
<221> NAME/KEY: misc_feature
<222> LOCATION: (1)..(104)
<223> OTHER INFORMATION: microRNA precursor sequence

<400> SEQUENCE: 543
gatctatgac gtggagctaa ccaaactaat atacccatat tctggctagg tgatcatcag    60
aatatgggta tattagtttg gttagctcta cattgtagat ctat                    104

<210> SEQ ID NO 544
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: microRNA precursor sequence

<400> SEQUENCE: 544
gatggctttt atcattgggc cagtgacgac ccattcagcc gtatcagtga agagtgaagc    60
actgcactct ttaaggatag ggctgaatgg tttatcaccc attcagcggt               110

<210> SEQ ID NO 545
<211> LENGTH: 104
<212> TYPE: DNA
<213> ORGANISM: Human
<220> FEATURE:
<221> NAME/KEY: misc_feature
<222> LOCATION: (1)..(104)
<223> OTHER INFORMATION: microRNA precursor sequence

<400> SEQUENCE: 545
gcaccactag actccagcct gggcaagaaa gtgagactct gcctcttttt tgtttctgag    60
```
ccagagtctt gctctgttgc tcaggctgga gtgcaatggc gtga        104

<210> SEQ ID NO 546
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: microRNA precursor sequence

<400> SEQUENCE: 546
gcgcggccgc gggaggtgta acaggactgg actcccggca gccccagggc aggggcgtgg        60
ggagctggtc ctagctcagc gctcccg        87

<210> SEQ ID NO 547
<211> LENGTH: 122
<212> TYPE: DNA
<213> ORGANISM: Human
<220> FEATURE:
<221> NAME/KEY: misc_feature
<222> LOCATION: (1)..(122)
<223> OTHER INFORMATION: microRNA precursor sequence

<400> SEQUENCE: 547
ggacgtagtg gtgtagagag gcattaagaa cgcaggtggc agggccagcc accaggaggg        60
ctgcgtgcca cccgggcagc tctgctgctc actggcagtg tcacctgcgg aaactctcca       120
tc        122

<210> SEQ ID NO 548
<211> LENGTH: 140
<212> TYPE: DNA
<213> ORGANISM: Human
<220> FEATURE:
<221> NAME/KEY: misc_feature
<222> LOCATION: (1)..(140)
<223> OTHER INFORMATION: microRNA precursor sequence

<400> SEQUENCE: 548
gtagcagtgg tggtggtagc aagggggtga tgtagattct gaagagcagc ccttcctgtt        60
aggggaaaag tcctgatccg ggaacccaca gccccgttcc tgggcttctc ctctgtagcc       120
agcctcagcc gagcagctgc        140

<210> SEQ ID NO 549
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: microRNA precursor sequence

<400> SEQUENCE: 549
tcccaatacg aggcactgag ttaagtgttc tacacagata atctgttatt aatgagagaa        60
tagaatagac aatctgtgta gagtgcttaa cctggtgccc agtgttttca       110

<210> SEQ ID NO 550
<211> LENGTH: 107
<212> TYPE: DNA
<213> ORGANISM: Human
<220> FEATURE:
<221> NAME/KEY: misc_feature
<222> LOCATION: (1)..(107)

<223> OTHER INFORMATION: microRNA precursor sequence

<400> SEQUENCE: 550
tgcgttggcc tgtgggcatg gcctgagacc aggactggat gcaccactct ccctgtgatg    60
aggtgaagcc agctctggtc tgggccattt cacaggattc agaagc                   107

<210> SEQ ID NO 551
<211> LENGTH: 108
<212> TYPE: DNA
<213> ORGANISM: Human
<220> FEATURE:
<221> NAME/KEY: misc_feature
<222> LOCATION: (1)..(108)
<223> OTHER INFORMATION: microRNA precursor sequence

<400> SEQUENCE: 551
ttaaagacct taagaggcaa caaagactat actttcaggg atcatttctc tagttcaata    60
ctacagaagt ttctctgaag gtgtagcaag caccagaaac cacgagga                 108

<210> SEQ ID NO 552
<211> LENGTH: 106
<212> TYPE: DNA
<213> ORGANISM: Human
<220> FEATURE:
<221> NAME/KEY: misc_feature
<222> LOCATION: (1)..(106)
<223> OTHER INFORMATION: microRNA precursor sequence

<400> SEQUENCE: 552
ttaatatttc atcctcctcc catcaatcac aaatgtcctt aatggcattt aaggattgct    60
attaaggaca tttgtgattc acgggaggag gttcaaatat catgaa                   106

<210> SEQ ID NO 553
<211> LENGTH: 102
<212> TYPE: DNA
<213> ORGANISM: Human
<220> FEATURE:
<221> NAME/KEY: misc_feature
<222> LOCATION: (1)..(102)
<223> OTHER INFORMATION: microRNA precursor sequence

<400> SEQUENCE: 553
ttatatccag agcctgaatg aaagagccag tggtgagaca gtgagttgat tacttctcac    60
tgtttcacca ctggctcttt ggttcatgct aacaatgtat ct                       102

<210> SEQ ID NO 554
<211> LENGTH: 106
<212> TYPE: DNA
<213> ORGANISM: Human
<220> FEATURE:
<221> NAME/KEY: misc_feature
<222> LOCATION: (1)..(106)
<223> OTHER INFORMATION: microRNA precursor sequence

<400> SEQUENCE: 554
ttgtaacatc cggtgtgttg taacattcca gtgtgttgta acatttggtg ttacatgctg    60
tgttgtaaca ttctggtgtg ttgtaacatt cccggtgtgt tgtaac                   106

<210> SEQ ID NO 555
<211> LENGTH: 112
<212> TYPE: DNA
<213> ORGANISM: Human
<220> FEATURE:
<221> NAME/KEY: misc_feature
<222> LOCATION: (1)..(112)
<223> OTHER INFORMATION: microRNA precursor sequence

<400> SEQUENCE: 555
aaatacaaaa taattcgaga ataaagacta tgctttcagg gatcatttct atagttcgtt    60
actcgggaag tttctctgaa cgtgtaaagc accgaacaaa aaaaaaaaaa ac           112

<210> SEQ ID NO 556
<211> LENGTH: 108
<212> TYPE: DNA
<213> ORGANISM: Human
<220> FEATURE:
<221> NAME/KEY: misc_feature
<222> LOCATION: (1)..(108)
<223> OTHER INFORMATION: microRNA precursor sequence

<400> SEQUENCE: 556
acacattttc tttgctaagt cccttctttc tatcctagta taacttgaag aattcaaata    60
gtcatgctag gatagaaaga atgggacttg gccagggaag aagagttg               108

<210> SEQ ID NO 557
<211> LENGTH: 101
<212> TYPE: DNA
<213> ORGANISM: Human
<220> FEATURE:
<221> NAME/KEY: misc_feature
<222> LOCATION: (1)..(101)
<223> OTHER INFORMATION: microRNA precursor sequence

<400> SEQUENCE: 557
agaaattatg ccacttttaa tttcagctac tacctctatt aggatttggg agttatacta    60
atagaggtaa tagttgaaat taagagtgga tgagttctgg t                      101

<210> SEQ ID NO 558
<211> LENGTH: 108
<212> TYPE: DNA
<213> ORGANISM: Human
<220> FEATURE:
<221> NAME/KEY: misc_feature
<222> LOCATION: (1)..(108)
<223> OTHER INFORMATION: microRNA precursor sequence

<400> SEQUENCE: 558
agctgattac attattcagg ccggtcctgc agagaggaag cccttccaat acctgtaagc    60
agaagggctt cctctctgca ggaccggcct gaataatgat cctaacgc               108

<210> SEQ ID NO 559
<211> LENGTH: 108
<212> TYPE: DNA
<213> ORGANISM: Human
<220> FEATURE:
<221> NAME/KEY: misc_feature
<222> LOCATION: (1)..(108)
<223> OTHER INFORMATION: microRNA precursor sequence

<400> SEQUENCE: 559
agtaacatcc agatgtgttg taacattcca gtgtgttgta acattcctgt aacattccaa    60
tgtgttgtaa cattctggtg tgttgtaaca ttcctgtaac attctggt                108

<210> SEQ ID NO 560
<211> LENGTH: 103
<212> TYPE: DNA
<213> ORGANISM: Human
<220> FEATURE:

```
<221> NAME/KEY: misc_feature
<222> LOCATION: (1)..(103)
<223> OTHER INFORMATION: microRNA precursor sequence

<400> SEQUENCE: 560
ataccattgg gccttgcttc tttatccagc ttgttactat atgcttttta aatggggcac     60
agagtgacaa gctggttaaa gaagcaagac cccttcaaga tta                     103

<210> SEQ ID NO 561
<211> LENGTH: 108
<212> TYPE: DNA
<213> ORGANISM: Human
<220> FEATURE:
<221> NAME/KEY: misc_feature
<222> LOCATION: (1)..(108)
<223> OTHER INFORMATION: microRNA precursor sequence

<400> SEQUENCE: 561 atggggaac cacaggcagc aaatggccag agctcacaca gagggatgag tgcacttcac      60
ctgcagtgtg actcagcagg ccaacagatg ctatcaggga agagcact               108

<210> SEQ ID NO 562
<211> LENGTH: 108
<212> TYPE: DNA
<213> ORGANISM: Human
<220> FEATURE:
<221> NAME/KEY: misc_feature
<222> LOCATION: (1)..(108)
<223> OTHER INFORMATION: microRNA precursor sequence

<400> SEQUENCE: 562 atggggaac cacaggcagc aaatggccag agctcacaca gagggatgag tgcacttcac      60
ctgcagtgtg actcagcagg ccaacagatg ctatcaggga agagcact               108

<210> SEQ ID NO 563
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: microRNA precursor sequence

<400> SEQUENCE: 563
ccaaccccat cttcttaaat gtcttactgc ttttactgtt ccctcctaga gtccattctt     60
tactctagga gggaatagta aaagcagtaa gacatttagt aaaaggcttt              110

<210> SEQ ID NO 564
<211> LENGTH: 116
<212> TYPE: DNA
<213> ORGANISM: Human
<220> FEATURE:
<221> NAME/KEY: misc_feature
<222> LOCATION: (1)..(116)
<223> OTHER INFORMATION: microRNA precursor sequence

<400> SEQUENCE: 564
cccaggtaaa gggcccaggt gacccggggc tgccctgaac gggcccggct ctggtgcgct     60
tgctcagcca ggcccgctcc ccgctgcccc ctaggcttct catcgctgtc gctgtc       116

<210> SEQ ID NO 565
<211> LENGTH: 21
<212> TYPE: DNA
<213> ORGANISM: Human
```

```
-continued

<220> FEATURE:
<221> NAME/KEY: misc_feature
<222> LOCATION: (1)..(21)
<223> OTHER INFORMATION: microRNA precursor sequence

<400> SEQUENCE: 565
tacagtactg tgataactga a                                             21

<210> SEQ ID NO 566
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA precursor sequence

<400> SEQUENCE: 566
cagtggtttt accctatggt ag                                            22

<210> SEQ ID NO 567
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA precursor sequence

<400> SEQUENCE: 567
tgtagtgttt cctactttat gga                                           23

<210> SEQ ID NO 568
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA precursor sequence

<400> SEQUENCE: 568
cataaagtag aaagcactac t                                             21

<210> SEQ ID NO 569
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 569
ggtgcagtgc tgcatctctg gt                                            22

<210> SEQ ID NO 570
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA sequence

<400> SEQUENCE: 570
tacagtatag atgatgtact                                               20
```

-continued

```
<210> SEQ ID NO 571
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 571
ggatatcatc atatactgta ag                                                  22

<210> SEQ ID NO 572
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 572
tcagtgcact acagaacttt gt                                                  22

<210> SEQ ID NO 573
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 573
aaaaccgtct agttacagtt gt                                                  22

<210> SEQ ID NO 574
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 574
tagcagcaca taatggtttg tg                                                  22

<210> SEQ ID NO 575
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 575
ccagtattaa ctgtgctgct ga                                                  22

<210> SEQ ID NO 576
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence
```

-continued

```
<400> SEQUENCE: 576
ccaatattac tgtgctgctt ta                                              22

<210> SEQ ID NO 577
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 577
aggggctggc tttcctctgg tc                                              22

<210> SEQ ID NO 578
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 578
agcttccatg actcctgatg ga                                              22

<210> SEQ ID NO 579
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 579
catcagaatt catggaggct ag                                              22

<210> SEQ ID NO 580
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 580
tgtcagtttg tcaaataccc ca                                              22

<210> SEQ ID NO 581
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 581
cgtgtatttg acaagctgag tt                                              22

<210> SEQ ID NO 582
<211> LENGTH: 22
<212> TYPE: DNA
```

```
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 582
agggcttagc tgcttgtgag ca                                              22

<210> SEQ ID NO 583
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 583
tgtaaacatc cttgactgga ag                                              22

<210> SEQ ID NO 584
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 584
ctttcagtcg gatgtttaca gc                                              22

<210> SEQ ID NO 585
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 585
tccagcatca gtgattttgt tg                                              22

<210> SEQ ID NO 586
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 586
aacaatatcc tggtgctgag tg                                              22

<210> SEQ ID NO 587
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 587
cttatcagat tgtattgtaa tt                                              22
```

```
<210> SEQ ID NO 588
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 588
aaaccgttac cattactgag tt                                              22

<210> SEQ ID NO 589
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 589
tcctgtactg agctgccccg ag                                              22

<210> SEQ ID NO 590
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 590
aaaaactgag actactttg ca                                               22

<210> SEQ ID NO 591
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA sequence

<400> SEQUENCE: 591
aaaaactgta attactttt                                                  19

<210> SEQ ID NO 592
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 592
aaaagtaatt gcggtctttg gt                                              22

<210> SEQ ID NO 593
<211> LENGTH: 22
<212> TYPE: DNA
<213> ORGANISM: Human
<220> FEATURE:
<221> NAME/KEY: misc_feature
<222> LOCATION: (1)..(22)
```

<223> OTHER INFORMATION: microRNA sequence

<400> SEQUENCE: 593
caaaagtaat tgtggatttt gt                                           22

<210> SEQ ID NO 594
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 594
gctggtgcaa aagtaatggc gg                                           22

<210> SEQ ID NO 595
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 595
aagatgtgga aaaattggaa tc                                           22

<210> SEQ ID NO 596
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 596
taactggttg aacaactgaa cc                                           22

<210> SEQ ID NO 597
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 597
agacttccca tttgaaggtg gc                                           22

<210> SEQ ID NO 598
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 598
aaactctact tgtccttctg agt                                          23

<210> SEQ ID NO 599
<211> LENGTH: 22

```
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 599
tagtaccagt accttgtgtt ca                                              22

<210> SEQ ID NO 600
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 600
gactatagaa ctttccccct ca                                              22

<210> SEQ ID NO 601
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 601
gtgagtctct aagaaaagag ga                                              22

<210> SEQ ID NO 602
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 602
atgctgacat atttactaga gg                                              22

<210> SEQ ID NO 603
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 603
gttctcccaa cgtaagccca gc                                              22

<210> SEQ ID NO 604
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 604
```
atgatccagg aacctgcctc t                                             21

<210> SEQ ID NO 605
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 605
gtgggtacgg cccagtgggg gg                                            22

<210> SEQ ID NO 606
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 606
aggatgagca aagaaagtag att                                           23

<210> SEQ ID NO 607
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 607
cattattact tttggtacgc g                                             21

<210> SEQ ID NO 608
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 608
aaagttctga gacactccga ct                                            22

<210> SEQ ID NO 609
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 609
cctgttctcc attacttggc tc                                            22

<210> SEQ ID NO 610
<211> LENGTH: 22
<212> TYPE: DNA
<213> ORGANISM: Human
<220> FEATURE:
<221> NAME/KEY: misc_feature

```
<222> LOCATION: (1)..(22)
<223> OTHER INFORMATION: microRNA sequence

<400> SEQUENCE: 610
ctttcagtcg gatgtttgca gc                                        22

<210> SEQ ID NO 611
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 611
aatgacacga tcactcccgt tga                                       23

<210> SEQ ID NO 612
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 612
ttttgcaata tgttcctgaa ta                                        22

<210> SEQ ID NO 613
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 613
tagcagcggg aacagttctg cag                                       23

<210> SEQ ID NO 614
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 614
attgacactt ctgtgagtag a                                         21

<210> SEQ ID NO 615
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 615
aaaagtaatt gtggtttttgg cc                                       22

<210> SEQ ID NO 616
```

```
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 616
caaaaaccac agtttctttt gc                                              22

<210> SEQ ID NO 617
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 617
aaaagtaatt gtggttttg cc                                               22

<210> SEQ ID NO 618
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 618
ttgagaatga tgaatcatta gg                                              22

<210> SEQ ID NO 619
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 619
actcaaaacc cttcagtgac tt                                              22

<210> SEQ ID NO 620
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 620
aagcattctt tcattggttg g                                               21

<210> SEQ ID NO 621
<211> LENGTH: 26
<212> TYPE: DNA
<213> ORGANISM: Human
<220> FEATURE:
<221> NAME/KEY: misc_feature
<222> LOCATION: (1)..(26)
<223> OTHER INFORMATION: microRNA sequence

<400> SEQUENCE: 621
```
aagtagttgg tttgtatgag atggtt                                    26

<210> SEQ ID NO 622
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 622
tcgtaccgtg agtaataatg cg                                        22

<210> SEQ ID NO 623
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA sequence

<400> SEQUENCE: 623
tggccctgac tgaagaccag cagt                                      24

<210> SEQ ID NO 624
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 624
taccacaggg tagaaccacg g                                         21

<210> SEQ ID NO 625
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 625
ggattcctgg aaatactgtt ct                                        22

<210> SEQ ID NO 626
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 626
tgagaactga attccatggg tt                                        22

<210> SEQ ID NO 627
<211> LENGTH: 22
<212> TYPE: DNA
<213> ORGANISM: Human
<220> FEATURE:

```
<221> NAME/KEY: misc_feature
<222> LOCATION: (1)..(22)
<223> OTHER INFORMATION: microRNA sequence

<400> SEQUENCE: 627
cctctgaaat tcagttcttc ag                                              22

<210> SEQ ID NO 628
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 628
tgccctgtgg actcagttct gg                                              22

<210> SEQ ID NO 629
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 629
tgagaactga attccatagg ct                                              22

<210> SEQ ID NO 630
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 630
aagttctgtt atacactcag gc                                              22

<210> SEQ ID NO 631
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 631
ctggtacagg cctgggggac ag                                              22

<210> SEQ ID NO 632
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 632
actgcagtga aggcacttgt ag                                              22
```

```
<210> SEQ ID NO 633
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 633
accatcgacc gttgattgta cc                                              22

<210> SEQ ID NO 634
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 634
gctgcgcttg gatttcgtcc cc                                              22

<210> SEQ ID NO 635
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 635
cccagtgttt agactatctg ttc                                             23

<210> SEQ ID NO 636
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 636
cctattcttg gttacttgca cg                                              22

<210> SEQ ID NO 637
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 637
ctggtttcac atggtggctt ag                                              22

<210> SEQ ID NO 638
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence
```

```
<400> SEQUENCE: 638
tccgtctcag ttactttata gc                                              22

<210> SEQ ID NO 639
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 639
tcccccaggt gtgattctga ttt                                             23

<210> SEQ ID NO 640
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 640
actggactta gggtcagaag gc                                              22

<210> SEQ ID NO 641
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 641
atcgggaatg tcgtgtccgc cc                                              22

<210> SEQ ID NO 642
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 642
accctatcaa tattgtctct gc                                              22

<210> SEQ ID NO 643
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 643
atccttgcta tctgggtgct a                                               21

<210> SEQ ID NO 644
<211> LENGTH: 22
<212> TYPE: DNA
<213> ORGANISM: Human
```

```
<220> FEATURE:
<221> NAME/KEY: misc_feature
<222> LOCATION: (1)..(22)
<223> OTHER INFORMATION: microRNA sequence

<400> SEQUENCE: 644
tgtgacagat tgataactga aa                                              22

<210> SEQ ID NO 645
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 645
agtgcctgag ggagtaagag ccc                                             23

<210> SEQ ID NO 646
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 646
gcgacccact cttggtttcc a                                               21

<210> SEQ ID NO 647
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA sequence

<400> SEQUENCE: 647
ctgaagtgat gtgtaactga tcag                                            24

<210> SEQ ID NO 648
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 648
tacgtcatcg ttgtcatcgt ca                                              22

<210> SEQ ID NO 649
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 649
acttgtatgc tagctcaggt ag                                              22
```

<210> SEQ ID NO 650
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 650
aggaagccct ggagggctg gag                                    23

<210> SEQ ID NO 651
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 651
tgaggtagta gattgtatag tt                                    22

<210> SEQ ID NO 652
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 652
tgaggtagta gtttgtacag tt                                    22

<210> SEQ ID NO 653
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 653
agcagcattg tacagggcta tga                                   23

<210> SEQ ID NO 654
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 654
agcttcttta cagtgctgcc ttg                                   23

<210> SEQ ID NO 655
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 655
agcagcattg tacagggcta tca					23

<210> SEQ ID NO 656
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 656
taggacacat ggtctacttc t					21

<210> SEQ ID NO 657
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 657
acggtgctgg atgtggcctt t					21

<210> SEQ ID NO 658
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 658
tacgtagata tatatgtatt tt					22

<210> SEQ ID NO 659
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 659
tagtactgtg catatcatct at					22

<210> SEQ ID NO 660
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 660
ttctggaatt ctgtgtgagg ga					22

<210> SEQ ID NO 661
<211> LENGTH: 21
<212> TYPE: DNA

```
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 661
tgagatgaag cactgtagct c                                              21

<210> SEQ ID NO 662
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 662
tctcccaacc cttgtaccag tg                                             22

<210> SEQ ID NO 663
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 663
ctcctacata ttagcattaa ca                                             22

<210> SEQ ID NO 664
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 664
aacattcaac gctgtcggtg agt                                            23

<210> SEQ ID NO 665
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 665
aacattcatt gctgtcggtg ggt                                            23

<210> SEQ ID NO 666
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 666
caaagaattc tccttttggg ct                                             22
```

<210> SEQ ID NO 667
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 667
taggtagttt cctgttgttg gg                                              22

<210> SEQ ID NO 668
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA sequence

<400> SEQUENCE: 668
cctcctgccc tccttgctgt                                                 20

<210> SEQ ID NO 669
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 669
tagcttatca gactgatgtt ga                                              22

<210> SEQ ID NO 670
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 670
agagttgagt ctggacgtcc cg                                              22

<210> SEQ ID NO 671
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 671
acctggcata caatgtagat tt                                              22

<210> SEQ ID NO 672
<211> LENGTH: 21
<212> TYPE: DNA
<213> ORGANISM: Human
<220> FEATURE:
<221> NAME/KEY: misc_feature
<222> LOCATION: (1)..(21)

```
<223> OTHER INFORMATION: microRNA sequence

<400> SEQUENCE: 672
actggacttg gagtcagaag g                                              21

<210> SEQ ID NO 673
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 673
agctcggtct gaggcccctc agt                                            23

<210> SEQ ID NO 674
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 674
atgcacctgg gcaaggattc tg                                             22

<210> SEQ ID NO 675
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 675
aatgcacctg ggcaaggatt ca                                             22

<210> SEQ ID NO 676
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 676
catgccttga gtgtaggacc gt                                             22

<210> SEQ ID NO 677
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 677
aaaagtactt gcggattttg ct                                             22

<210> SEQ ID NO 678
<211> LENGTH: 22
```

```
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 678
gatgagctca ttgtaatatg ag                                           22

<210> SEQ ID NO 679
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 679
tcttgtgttc tctagatcag t                                            21

<210> SEQ ID NO 680
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 680
ttatggtttg cctgggactg ag                                           22

<210> SEQ ID NO 681
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 681
taattttatg tataagctag t                                            21

<210> SEQ ID NO 682
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 682
agtcattgga gggtttgagc ag                                           22

<210> SEQ ID NO 683
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 683
```
tgggtttacg ttgggagaac t                                              21

<210> SEQ ID NO 684
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 684
tattgcactt gtcccggcct gt                                             22

<210> SEQ ID NO 685
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 685
cacccggctg tgtgcacatg tgc                                            23

<210> SEQ ID NO 686
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 686
tcttctctgt tttggccatg tg                                             22

<210> SEQ ID NO 687
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 687
aaattattgt acatcggatg ag                                             22

<210> SEQ ID NO 688
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 688
cggatgagca aagaaagtgg tt                                             22

<210> SEQ ID NO 689
<211> LENGTH: 21
<212> TYPE: DNA
<213> ORGANISM: Human
<220> FEATURE:
<221> NAME/KEY: misc_feature

```
<222> LOCATION: (1)..(21)
<223> OTHER INFORMATION: microRNA sequence

<400> SEQUENCE: 689
agtgaatgat gggttctgac c                                            21

<210> SEQ ID NO 690
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 690
tctgggcaac aaagtgagac ct                                           22

<210> SEQ ID NO 691
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 691
actctttccc tgttgcacta c                                            21

<210> SEQ ID NO 692
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 692
aaccatcgac cgttgagtgg ac                                           22

<210> SEQ ID NO 693
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 693
gcccaaaggt gaattttttg gg                                           22

<210> SEQ ID NO 694
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 694
taaggtgcat ctagtgcaga tag                                          23

<210> SEQ ID NO 695
```

```
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 695
taaggtgcat ctagtgcagt tag                                              23

<210> SEQ ID NO 696
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 696
tgatatgttt gatattgggt t                                                21

<210> SEQ ID NO 697
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 697
actgtagtat gggcacttcc ag                                               22

<210> SEQ ID NO 698
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 698
tgcctactga gctgaaacac ag                                               22

<210> SEQ ID NO 699
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 699
cactagattg tgagctcctg ga                                               22

<210> SEQ ID NO 700
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 700
```
ctgggagagg gttgtttact cc                                            22

<210> SEQ ID NO 701
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 701
aattgcacgg tatccatctg ta                                            22

<210> SEQ ID NO 702
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 702
ttttgcgatg tgttcctaat at                                            22

<210> SEQ ID NO 703
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 703
aaaactgtaa ttacttttgt ac                                            22

<210> SEQ ID NO 704
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 704
ccaaaactgc agttactttt gc                                            22

<210> SEQ ID NO 705
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 705
ttacagttgt tcaaccagtt act                                           23

<210> SEQ ID NO 706
<211> LENGTH: 24
<212> TYPE: DNA
<213> ORGANISM: Human
<220> FEATURE:

```
<221> NAME/KEY: misc_feature
<222> LOCATION: (1)..(24)
<223> OTHER INFORMATION: microRNA sequence

<400> SEQUENCE: 706
actggctagg gaaaatgatt ggat                                              24

<210> SEQ ID NO 707
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 707
caaagtgctg ttcgtgcagg tag                                               23

<210> SEQ ID NO 708
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: precursor sequence

<400> SEQUENCE: 708
tgccctggct cagttatcac agtgctgatg ctgtctattc taaaggtaca gtactgtgat      60
aactgaagga tggca                                                        75

<210> SEQ ID NO 709
<211> LENGTH: 79
<212> TYPE: DNA
<213> ORGANISM: Human
<220> FEATURE:
<221> NAME/KEY: misc_feature
<222> LOCATION: (1)..(79)
<223> OTHER INFORMATION: precursor sequence

<400> SEQUENCE: 709
actgtccttt ttcggttatc atggtaccga tgctgtatat ctgaaaggta cagtactgtg      60
ataactgaag aatggtggt                                                    79

<210> SEQ ID NO 710
<211> LENGTH: 100
<212> TYPE: DNA
<213> ORGANISM: Human
<220> FEATURE:
<221> NAME/KEY: misc_feature
<222> LOCATION: (1)..(100)
<223> OTHER INFORMATION: precursor sequence

<400> SEQUENCE: 710
tgtgtctctc tctgtgtcct gccagtggtt ttaccctatg gtaggttacg tcatgctgtt      60
ctaccacagg gtagaaccac ggacaggata ccggggcacc                           100

<210> SEQ ID NO 711
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: precursor sequence
```

```
<400> SEQUENCE: 711
gacagtgcag tcacccataa agtagaaagc actactaaca gcactggagg gtgtagtgtt    60
tcctacttta tggatgagtg tactgtg                                       87

<210> SEQ ID NO 712
<211> LENGTH: 106
<212> TYPE: DNA
<213> ORGANISM: Human
<220> FEATURE:
<221> NAME/KEY: misc_feature
<222> LOCATION: (1)..(106)
<223> OTHER INFORMATION: precursor sequence

<400> SEQUENCE: 712
gcgcagcgcc ctgtctccca gcctgaggtg cagtgctgca tctctggtca gttgggagtc    60
tgagatgaag cactgtagct caggaagaga gaagttgttc tgcagc                  106

<210> SEQ ID NO 713
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: precursor sequence

<400> SEQUENCE: 713
tggggccctg gctgggatat catcatatac tgtaagtttg cgatgagaca ctacagtata    60
gatgatgtac tagtccgggc accccc                                        86

<210> SEQ ID NO 714
<211> LENGTH: 68
<212> TYPE: DNA
<213> ORGANISM: Human
<220> FEATURE:
<221> NAME/KEY: misc_feature
<222> LOCATION: (1)..(68)
<223> OTHER INFORMATION: precursor sequence

<400> SEQUENCE: 714
gaggcaaagt tctgagacac tccgactctg agtatgatag aagtcagtgc actacagaac    60
tttgtctc                                                            68

<210> SEQ ID NO 715
<211> LENGTH: 61
<212> TYPE: DNA
<213> ORGANISM: Human
<220> FEATURE:
<221> NAME/KEY: misc_feature
<222> LOCATION: (1)..(61)
<223> OTHER INFORMATION: precursor sequence

<400> SEQUENCE: 715
acagctgtaa ttagtcagtt ttctgtcctg tccacacaga aaccgtcta gttacagttg    60 t                                                                   61

<210> SEQ ID NO 716
<211> LENGTH: 83
<212> TYPE: DNA
<213> ORGANISM: Human
<220> FEATURE:
<221> NAME/KEY: misc_feature
<222> LOCATION: (1)..(83)
```

<223> OTHER INFORMATION: precursor sequence

<400> SEQUENCE: 716
ccttggagta aagtagcagc acataatggt ttgtggattt tgaaaaggtg caggccatat    60
tgtgctgcct caaaaataca agg    83

<210> SEQ ID NO 717
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 717
gtcagcagtg ccttagcagc acgtaaatat tggcgttaag attctaaaat tatctccagt    60
attaactgtg ctgctgaagt aaggttgac    89

<210> SEQ ID NO 718
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: precursor sequence

<400> SEQUENCE: 718
gttccactct agcagcacgt aaatattggc gtagtgaaat atatattaaa caccaatatt    60
actgtgctgc tttagtgtga c    81

<210> SEQ ID NO 719
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: precursor sequence

<400> SEQUENCE: 719 aggggggcgag ggattggaga gaaaggcagt tcctgatggt ccctccca ggggctggct    60 ttcctctggt ccttccctcc ca    82

<210> SEQ ID NO 720
<211> LENGTH: 100
<212> TYPE: DNA
<213> ORGANISM: Human
<220> FEATURE:
<221> NAME/KEY: misc_feature
<222> LOCATION: (1)..(100)
<223> OTHER INFORMATION: precursor sequence

<400> SEQUENCE: 720
actgtcatcc cactgcttcc agcttccatg actcctgatg gaggaatcac atgaattcat    60
cagaattcat ggaggctaga agcagtatga ggatcattta    100

<210> SEQ ID NO 721
<211> LENGTH: 110
<212> TYPE: DNA
<213> ORGANISM: Human
<220> FEATURE:
<221> NAME/KEY: misc_feature

```
<222> LOCATION: (1)..(110)
<223> OTHER INFORMATION: precursor sequence

<400> SEQUENCE: 721
cctggcctcc tgcagtgcca cgctccgtgt atttgacaag ctgagttgga cactccatgt    60
ggtagagtgt cagtttgtca ataccccaa gtgcggcaca tgcttaccag                110

<210> SEQ ID NO 722
<211> LENGTH: 78
<212> TYPE: DNA
<213> ORGANISM: Human
<220> FEATURE:
<221> NAME/KEY: misc_feature
<222> LOCATION: (1)..(78)
<223> OTHER INFORMATION: precursor sequence

<400> SEQUENCE: 722
ctgaggagca gggcttagct gcttgtgagc agggtccaca ccaagtcgtg ttcacagtgg    60
ctaagttccg cccccag                                                    78

<210> SEQ ID NO 723
<211> LENGTH: 92
<212> TYPE: DNA
<213> ORGANISM: Human
<220> FEATURE:
<221> NAME/KEY: misc_feature
<222> LOCATION: (1)..(92)
<223> OTHER INFORMATION: precursor sequence

<400> SEQUENCE: 723
gggcagtctt tgctactgta aacatccttg actggaagct gtaaggtgtt cagaggagct    60
ttcagtcgga tgtttacagc ggcaggctgc ca                                   92

<210> SEQ ID NO 724
<211> LENGTH: 67
<212> TYPE: DNA
<213> ORGANISM: Human
<220> FEATURE:
<221> NAME/KEY: misc_feature
<222> LOCATION: (1)..(67)
<223> OTHER INFORMATION: precursor sequence

<400> SEQUENCE: 724
tctccaacaa tatcctggtg ctgagtgatg actcaggcga ctccagcatc agtgattttg    60
ttgaaga                                                               67

<210> SEQ ID NO 725
<211> LENGTH: 72
<212> TYPE: DNA
<213> ORGANISM: Human
<220> FEATURE:
<221> NAME/KEY: misc_feature
<222> LOCATION: (1)..(72)
<223> OTHER INFORMATION: precursor sequence

<400> SEQUENCE: 725
tacatcggcc attataatac aacctgataa gtgttatagc acttatcaga ttgtattgta    60
attgtctgtg ta                                                         72

<210> SEQ ID NO 726
<211> LENGTH: 72
<212> TYPE: DNA
<213> ORGANISM: Human
<220> FEATURE:
```

```
<221> NAME/KEY: misc_feature
<222> LOCATION: (1)..(72)
<223> OTHER INFORMATION: precursor sequence

<400> SEQUENCE: 726
cttgggaatg gcaaggaaac cgttaccatt actgagttta gtaatggtaa tggttctctt      60
gctataccca ga                                                         72

<210> SEQ ID NO 727
<211> LENGTH: 68
<212> TYPE: DNA
<213> ORGANISM: Human
<220> FEATURE:
<221> NAME/KEY: misc_feature
<222> LOCATION: (1)..(68)
<223> OTHER INFORMATION: precursor sequence

<400> SEQUENCE: 727
gcatcctgta ctgagctgcc ccgaggccct tcatgctgcc cagctcgggg cagctcagta      60
caggatac                                                              68

<210> SEQ ID NO 728
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: precursor sequence

<400> SEQUENCE: 728
ttattaggtt ggtacaaaag caatcgcggt ttttgctatt acttttaaag gcaaaaactg      60
agactacttt tgcaccaacc tgatagaa                                        88

<210> SEQ ID NO 729
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 729
attaggttgg tgcaaaagta atcacagttt ttgacattac tttcaaagac aaaaactgta      60
attacttttg gaccaaccta atag                                            84

<210> SEQ ID NO 730
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: precursor sequence

<400> SEQUENCE: 730
taataactat taggttggtg cgaacataat tgcagttttt atcattactt ttaatggcaa      60
aaactgtaat tactttgca ccaacctaat attttagt                              98

<210> SEQ ID NO 731
<211> LENGTH: 87
<212> TYPE: DNA
<213> ORGANISM: Human
```

```
<220> FEATURE:
<221> NAME/KEY: misc_feature
<222> LOCATION: (1)..(87)
<223> OTHER INFORMATION: precursor sequence

<400> SEQUENCE: 731
attaggttgg tgcaaaccta attgcaattt ttgcagtttt tttaagtaat tgcaaaaact      60
gtaattactt ttgcaccaac ctaatac                                          87

<210> SEQ ID NO 732
<211> LENGTH: 105
<212> TYPE: DNA
<213> ORGANISM: Human
<220> FEATURE:
<221> NAME/KEY: misc_feature
<222> LOCATION: (1)..(105)
<223> OTHER INFORMATION: precursor sequence

<400> SEQUENCE: 732
gagttctaac gtattaggtt ggtgcaaaag taatagtggt ttttgccatt aaaagtaatg      60
acaaaaactg taattacttt tggaacaata ttaatagaat ttcag                    105

<210> SEQ ID NO 733
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: precursor sequence

<400> SEQUENCE: 733
tattaggttg ctgcaaaagt aatcatgttt ttttccattg taagtaatgg gaaaaactgt      60
aattactttt gtaccaacct aatagc                                           86

<210> SEQ ID NO 734
<211> LENGTH: 112
<212> TYPE: DNA
<213> ORGANISM: Human
<220> FEATURE:
<221> NAME/KEY: misc_feature
<222> LOCATION: (1)..(112)
<223> OTHER INFORMATION: precursor sequence

<400> SEQUENCE: 734
gggcagccag tgaatagtta gctggtgcaa aagtaattgc ggtctttggt attactttca      60
gtggcaaaaa ctgcattact tttgcaccag cctactagaa cgctgagttc ag            112

<210> SEQ ID NO 735
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: precursor sequence

<400> SEQUENCE: 735
aggttggtgc aaaagtaatt gtggattttg tcgttaaaaa tagcaaaacc cgcaattact      60
tttgcaccaa cctaa                                                       75

<210> SEQ ID NO 736
<211> LENGTH: 100
<212> TYPE: DNA
```

```
<213> ORGANISM: Human
<220> FEATURE:
<221> NAME/KEY: misc_feature
<222> LOCATION: (1)..(100)
<223> OTHER INFORMATION: precursor sequence

<400> SEQUENCE: 736
atattaggct ggtgcaaaag taatggcggt ttttgccatt acttttcatt tttaccatta      60
aaagtaatgg caaaaagcat gattactttt tcaccaacct                          100

<210> SEQ ID NO 737
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: precursor sequence

<400> SEQUENCE: 737
tacaatccaa cgaggattct aatttctcca cgtctttggt aataaggttt ggcaaagatg      60
tggaaaaatt ggaatcctca ttcgattggt tataacca                            98

<210> SEQ ID NO 738
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: precursor sequence

<400> SEQUENCE: 738
atctgtgctc tttgattaca gttgttcaac cagttactaa tctaactaat tgtaactggt      60
tgaacaactg aacccaaagg gtgcaaagta gaaacatt                            98

<210> SEQ ID NO 739
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 739
catcataagg agcctagact tcccatttga aggtggccat ttcctaccac cttcaaatgg      60
taagtccagg ctccttctga ttcaataaat gaggagc                             97

<210> SEQ ID NO 740
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: precursor sequence

<400> SEQUENCE: 740
ctcttgttca cagccaaact ctacttgtcc ttctgagtgt aattacgtac atgcagtagc      60
tcaggagaca agcaggttta ccctgtggat gagtctga                            98

<210> SEQ ID NO 741
<211> LENGTH: 97
```

<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 741
aatgctgttt caaggtagta ccagtacctt gtgttcagtg gaaccaaggt aaacacaagg    60
tattggtatt accttgagat agcattacac ctaagtg                            97

<210> SEQ ID NO 742
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: precursor sequence

<400> SEQUENCE: 742
agggtagagg gatgagggggg aaagttctat agtcctgtaa ttagatctca ggactataga    60
actttccccc tcatccctct gccct                                         85

<210> SEQ ID NO 743
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 743
tacttattac tggtagtgag tctctaagaa aagaggaggt ggttgttttc ctcctcttt     60 ctttgagact cactaccaat aataagaaat actacta                            97

<210> SEQ ID NO 744
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: precursor sequence

<400> SEQUENCE: 744
atagctgttg tgtcacttcc tcatgctgac atatttacta gagggtaaaa ttaataacct    60
tctagtaaga gtggcagtcg aagggaaggg ctcat                              95

<210> SEQ ID NO 745
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 745
tccctttccc aggggagggg ctgggtttac gttgggagaa cttttacggt gaaccaggag    60
gttctcccaa cgtaagccca gcccctcccc tctgcct                            97

<210> SEQ ID NO 746

```
<211> LENGTH: 96
<212> TYPE: DNA
<213> ORGANISM: Human
<220> FEATURE:
<221> NAME/KEY: misc_feature
<222> LOCATION: (1)..(96)
<223> OTHER INFORMATION: precursor sequence

<400> SEQUENCE: 746
gtgaccctgg gcaagttcct gaagatcaga cacatcagat cccttatctg taaaatgggc    60
atgatccagg aacctgcctc tacggttgcc ttgggg                              96

<210> SEQ ID NO 747
<211> LENGTH: 90
<212> TYPE: DNA
<213> ORGANISM: Human
<220> FEATURE:
<221> NAME/KEY: misc_feature
<222> LOCATION: (1)..(90)
<223> OTHER INFORMATION: precursor sequence

<400> SEQUENCE: 747
gtgggtacgg cccagtgggg gggagaggga cacgccctgg gctctgccca gggtgcagcc    60
ggactgactg agcccctgtg ccgccccag                                      90

<210> SEQ ID NO 748
<211> LENGTH: 113
<212> TYPE: DNA
<213> ORGANISM: Human
<220> FEATURE:
<221> NAME/KEY: misc_feature
<222> LOCATION: (1)..(113)
<223> OTHER INFORMATION: precursor sequence

<400> SEQUENCE: 748
attggaaatc ctttgagttg cttctcaagg atgagcaaag aaagtagatt ttttagattc    60
taaagaaact atcttctttg ctcatccttg agaagcaact ccttatccat taa          113

<210> SEQ ID NO 749
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: precursor sequence

<400> SEQUENCE: 749
cgctggcgac gggacattat tactttggt acgcgctgtg acacttcaaa ctcgtaccgt     60
gagtaataat gcgccgtcca cggca                                          85

<210> SEQ ID NO 750
<211> LENGTH: 68
<212> TYPE: DNA
<213> ORGANISM: Human
<220> FEATURE:
<221> NAME/KEY: misc_feature
<222> LOCATION: (1)..(68)
<223> OTHER INFORMATION: precursor sequence

<400> SEQUENCE: 750
gaggcaaagt tctgagacac tccgactctg agtatgatag aagtcagtgc actacagaac    60
tttgtctc                                                             68
```

```
<210> SEQ ID NO 751
<211> LENGTH: 77
<212> TYPE: DNA
<213> ORGANISM: Human
<220> FEATURE:
<221> NAME/KEY: misc_feature
<222> LOCATION: (1)..(77)
<223> OTHER INFORMATION: precursor sequence

<400> SEQUENCE: 751
ccgggaccca gttcaagtaa ttcaggatag gttgtgtgct gtccagcctg ttctccatta    60
cttggctcgg ggaccgg                                                   77

<210> SEQ ID NO 752
<211> LENGTH: 71
<212> TYPE: DNA
<213> ORGANISM: Human
<220> FEATURE:
<221> NAME/KEY: misc_feature
<222> LOCATION: (1)..(71)
<223> OTHER INFORMATION: precursor sequence

<400> SEQUENCE: 752
gcgactgtaa acatcctcga ctggaagctg tgaagccaca gatgggcttt cagtcggatg    60
tttgcagctg c                                                         71

<210> SEQ ID NO 753
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: precursor sequence

<400> SEQUENCE: 753
gaaagcgctt tggaatgaca cgatcactcc cgttgagtgg gcacccgaga agccatcggg    60
aatgtcgtgt ccgcccagtg ctctttc                                        87

<210> SEQ ID NO 754
<211> LENGTH: 78
<212> TYPE: DNA
<213> ORGANISM: Human
<220> FEATURE:
<221> NAME/KEY: misc_feature
<222> LOCATION: (1)..(78)
<223> OTHER INFORMATION: precursor sequence

<400> SEQUENCE: 754
gcagaattat ttttgcaata tgttcctgaa tatgtaatat aagtgtattg ggatcatttt    60
gcatccatag ttttgtat                                                  78

<210> SEQ ID NO 755
<211> LENGTH: 71
<212> TYPE: DNA
<213> ORGANISM: Human
<220> FEATURE:
<221> NAME/KEY: misc_feature
<222> LOCATION: (1)..(71)
<223> OTHER INFORMATION: precursor sequence

<400> SEQUENCE: 755
tgccctagca gcgggaacag ttctgcagtg agcgatcggt gctctggggt attgtttccg    60
ctgccagggt a                                                         71
```

```
<210> SEQ ID NO 756
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: precursor sequence

<400> SEQUENCE: 756
aacatgttgt ctgtggtacc ctactctgga gagtgacaat catgtataat taaatttgat    60
tgacacttct gtgagtagag taacgcatga cacgtacg                            98

<210> SEQ ID NO 757
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: precursor sequence

<400> SEQUENCE: 757
gttgtctgtg gtaccctact ctggagagtg acaatcatgt ataactaaat ttgattgaca    60
cttctgtgag tagagtaacg catgacac                                       88

<210> SEQ ID NO 758
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: precursor sequence

<400> SEQUENCE: 758
gttgtctgtg gtaccctact ctggagagtg acaatcatgt ataactaaat ttgattgaca    60
cttctgtgag tagagtaacg catgacac                                       88

<210> SEQ ID NO 759
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 759
cagactatat atttaggttg gcgcaaaagt aattgtggtt ttggcctttta ttttcaatgg   60 caagaacctc agttgctttt gtgccaacct aatactt                             97

<210> SEQ ID NO 760
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 760
aaacaagtta tattaggttg gtgcaaaagt aattgtggtt tttgcctgta aaagtaatgg   60
caaaaaccac agtttctttt gcaccagact aataaag                             97
```

```
<210> SEQ ID NO 761
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 761
gagagggaag atttaggttg gtgcaaaagt aattgtggtt tttgccattg aaagtaatgg    60
caaaaaccac agtttctttt gcaccaacct aataaaa                            97

<210> SEQ ID NO 762
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 762
ataaaatttc caattggaac ctaatgattc atcagactca gatatttaag ttaacagtat    60
ttgagaatga tgaatcatta ggttccggtc agaaatt                            97

<210> SEQ ID NO 763
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 763
ttaggtaatt cctccactca aaacccttca gtgacttcca tgacatgaaa taggaagtca    60
ttggagggtt tgagcagagg aatgacctgt tttaaaa                            97

<210> SEQ ID NO 764
<211> LENGTH: 91
<212> TYPE: DNA
<213> ORGANISM: Human
<220> FEATURE:
<221> NAME/KEY: misc_feature
<222> LOCATION: (1)..(91)
<223> OTHER INFORMATION: precursor sequence

<400> SEQUENCE: 764
ggctggaaag gaagaagcat tctttcattg gttggtgtgt attgccttgt caaccaataa    60
gaggatgcca tttatccttt tctgactagc t                                  91

<210> SEQ ID NO 765
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: precursor sequence

<400> SEQUENCE: 765
atcttattcc gagcattcca gtaacttttt tgtgtatgta cttagctgta ctataagtag    60
```
ttggtttgta tgagatggtt aaaaa                                              85

<210> SEQ ID NO 766
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: precursor sequence

<400> SEQUENCE: 766
atcttattcc gagcattcca gtaacttttt tgtgtatgta cttagctgta ctataagtag       60
ttggtttgta tgagatggtt aaaaa                                              85

<210> SEQ ID NO 767
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: precursor sequence

<400> SEQUENCE: 767
atcttattcc gagcattcca gtaacttttt tgtgtatgta cttagctgta ctataagtag       60
ttggtttgta tgagatggtt aaaaa                                              85

<210> SEQ ID NO 768
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: precursor sequence

<400> SEQUENCE: 768
atcttattcc gagcattcca gtaacttttt tgtgtatgta cttagctgta ctataagtag       60
ttggtttgta tgagatggtt aaaaa                                              85

<210> SEQ ID NO 769
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: precursor sequence

<400> SEQUENCE: 769
cgctggcgac gggacattat tactttggt acgcgctgtg acacttcaaa ctcgtaccgt        60
gagtaataat gcgccgtcca cggca                                              85

<210> SEQ ID NO 770
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: precursor sequence

<400> SEQUENCE: 770
ggtagaattc cagtggccct gactgaagac cagcagttgt actgtggctg ttggtttcaa       60
gcagaggcct aaaggactgt cttcctg                                             87

<210> SEQ ID NO 771
<211> LENGTH: 100
<212> TYPE: DNA
<213> ORGANISM: Human
<220> FEATURE:
<221> NAME/KEY: misc_feature
<222> LOCATION: (1)..(100)
<223> OTHER INFORMATION: precursor sequence

<400> SEQUENCE: 771
tgtgtctctc tctgtgtcct gccagtggtt ttaccctatg gtaggttacg tcatgctgtt      60
ctaccacagg gtagaaccac ggacaggata ccggggcacc                            100

<210> SEQ ID NO 772
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: precursor sequence

<400> SEQUENCE: 772
caccttgtcc tcacggtcca gttttcccag gaatccctta gatgctaaga tggggattcc      60
tggaaatact gttcttgagg tcatggtt                                         88

<210> SEQ ID NO 773
<211> LENGTH: 99
<212> TYPE: DNA
<213> ORGANISM: Human
<220> FEATURE:
<221> NAME/KEY: misc_feature
<222> LOCATION: (1)..(99)
<223> OTHER INFORMATION: precursor sequence

<400> SEQUENCE: 773
ccgatgtgta tcctcagctt tgagaactga attccatggg ttgtgtcagt gtcagacctc      60
tgaaattcag ttcttcagct gggatatctc tgtcatcgt                             99

<210> SEQ ID NO 774
<211> LENGTH: 73
<212> TYPE: DNA
<213> ORGANISM: Human
<220> FEATURE:
<221> NAME/KEY: misc_feature
<222> LOCATION: (1)..(73)
<223> OTHER INFORMATION: precursor sequence

<400> SEQUENCE: 774
cctggcactg agaactgaat tccataggct gtgagctcta gcaatgccct gtggactcag      60
ttctggtgcc cgg                                                         73

<210> SEQ ID NO 775
<211> LENGTH: 99
<212> TYPE: DNA
<213> ORGANISM: Human
<220> FEATURE:
<221> NAME/KEY: misc_feature
<222> LOCATION: (1)..(99)
<223> OTHER INFORMATION: precursor sequence

<400> SEQUENCE: 775

```
caagcacgat tagcatttga ggtgaagttc tgttatacac tcaggctgtg gctctctgaa    60
agtcagtgca tcacagaact ttgtctcgaa agctttcta                           99
```

<210> SEQ ID NO 776
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 776

```
ctccccatgg ccctgtctcc caaccctttgt accagtgctg ggctcagacc ctggtacagg   60
cctgggggac agggacctgg ggac                                           84
```

<210> SEQ ID NO 777
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 777

```
gtcagaataa tgtcaaagtg cttacagtgc aggtagtgat atgtgcatct actgcagtga   60
aggcacttgt agcattatgg tgac                                           84
```

<210> SEQ ID NO 778
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: precursor sequence

<400> SEQUENCE: 778

```
tgagttttga ggttgcttca gtgaacattc aacgctgtcg gtgagtttgg aattaaaatc   60
aaaaccatcg accgttgatt gtaccctatg gctaaccatc atctactcca              110
```

<210> SEQ ID NO 779
<211> LENGTH: 92
<212> TYPE: DNA
<213> ORGANISM: Human
<220> FEATURE:
<221> NAME/KEY: misc_feature
<222> LOCATION: (1)..(92)
<223> OTHER INFORMATION: precursor sequence

<400> SEQUENCE: 779

```
cggctggaca gcgggcaacg gaatcccaaa agcagctgtt gtctccagag cattccagct   60
gcgcttggat ttcgtcccct gctctcctgc ct                                  92
```

<210> SEQ ID NO 780
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: precursor sequence

<400> SEQUENCE: 780
ccagaggaca cctccactcc gtctacccag tgtttagact atctgttcag gactcccaaa    60
ttgtacagta gtctgcacat tggttaggct gggctgggtt agaccctcgg              110

<210> SEQ ID NO 781
<211> LENGTH: 77
<212> TYPE: DNA
<213> ORGANISM: Human
<220> FEATURE:
<221> NAME/KEY: misc_feature
<222> LOCATION: (1)..(77)
<223> OTHER INFORMATION: precursor sequence

<400> SEQUENCE: 781
gtggcctcgt tcaagtaatc caggataggc tgtgcaggtc ccaatgggcc tattcttggt    60
tacttgcacg gggacgc                                                  77

<210> SEQ ID NO 782
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: precursor sequence

<400> SEQUENCE: 782
cttctggaag ctggtttcac atggtggctt agattttcc atctttgtat ctagcaccat    60
ttgaaatcag tgttttagga g                                             81

<210> SEQ ID NO 783
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: precursor sequence

<400> SEQUENCE: 783
ttgtacctgg tgtgattata aagcaatgag actgattgtc atatgtcgtt tgtgggatcc    60
gtctcagtta ctttatagcc atacctggta tctta                              95

<210> SEQ ID NO 784
<211> LENGTH: 72
<212> TYPE: DNA
<213> ORGANISM: Human
<220> FEATURE:
<221> NAME/KEY: misc_feature
<222> LOCATION: (1)..(72)
<223> OTHER INFORMATION: precursor sequence

<400> SEQUENCE: 784
ggagcttatc agaatctcca ggggtacttt ataatttcaa aaagtccccc aggtgtgatt    60
ctgatttgct tc                                                       72

<210> SEQ ID NO 785
<211> LENGTH: 90
<212> TYPE: DNA
<213> ORGANISM: Human
<220> FEATURE:
<221> NAME/KEY: misc_feature
<222> LOCATION: (1)..(90)
<223> OTHER INFORMATION: precursor sequence

<400> SEQUENCE: 785
gagagaagca ctggacttag ggtcagaagg cctgagtctc tctgctgcag atgggctctc    60
tgtccctgag ccaagctttg tcctccctgg    90

<210> SEQ ID NO 786
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: precursor sequence

<400> SEQUENCE: 786
gaaagcgctt tggaatgaca cgatcactcc cgttgagtgg gcacccgaga agccatcggg    60
aatgtcgtgt ccgcccagtg ctctttc    87

<210> SEQ ID NO 787
<211> LENGTH: 115
<212> TYPE: DNA
<213> ORGANISM: Human
<220> FEATURE:
<221> NAME/KEY: misc_feature
<222> LOCATION: (1)..(115)
<223> OTHER INFORMATION: precursor sequence

<400> SEQUENCE: 787
tctgtttatc accagatcct agaaccctat caatattgtc tctgctgtgt aaatagttct    60
gagtagtgca atattgctta tagggttttg gtgtttggaa agaacaatgg gcagg    115

<210> SEQ ID NO 788
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: precursor sequence

<400> SEQUENCE: 788
tgctcccccT ctctaatcct tgctatctgg gtgctagtgc tggctcaatg caatgcacct    60
gggcaaggat tcagagaggg ggagct    86

<210> SEQ ID NO 789
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 789
cagatctcag acatctcggg gatcatcatg tcacgagata ccagtgtgca cttgtgacag    60
attgataact gaaaggtctg ggagccactc atcttca    97

<210> SEQ ID NO 790
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 790
tgatgctttg ctggctggtg cagtgcctga gggagtaaga gccctgttgt tgtaagatag      60
tgtcttactc cctcaggcac atctccaaca agtctct                              97

<210> SEQ ID NO 791
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 791
tgatgctttg ctggctggtg cagtgcctga gggagtaaga gccctgttgt tgtcagatag      60
tgtcttactc cctcaggcac atctccagcg agtctct                              97

<210> SEQ ID NO 792
<211> LENGTH: 96
<212> TYPE: DNA
<213> ORGANISM: Human
<220> FEATURE:
<221> NAME/KEY: misc_feature
<222> LOCATION: (1)..(96)
<223> OTHER INFORMATION: precursor sequence

<400> SEQUENCE: 792
ggggactgcc gggtgaccct ggaaatccag agtgggtggg gccagtctga ccgtttctag      60
gcgacccact cttggtttcc agggttgccc tggaaa                               96

<210> SEQ ID NO 793
<211> LENGTH: 99
<212> TYPE: DNA
<213> ORGANISM: Human
<220> FEATURE:
<221> NAME/KEY: misc_feature
<222> LOCATION: (1)..(99)
<223> OTHER INFORMATION: precursor sequence

<400> SEQUENCE: 793
tttagcggtt tctccctgaa gtgatgtgta actgatcagg atctactcat gtcgtctttg      60
gtaaagttat gtcgcttgtc agggtgagga gagttttttg                           99

<210> SEQ ID NO 794
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 794
gcttgatgat gctgctgatg ctggcggtga tcccgatggt gtgagctgga aatggggtgc      60
tacgtcatcg ttgtcatcgt catcatcatc atccgag                              97

<210> SEQ ID NO 795
<211> LENGTH: 97
<212> TYPE: DNA
<213> ORGANISM: Human
<220> FEATURE:
<221> NAME/KEY: misc_feature
<222> LOCATION: (1)..(97)

```
<223> OTHER INFORMATION: precursor sequence

<400> SEQUENCE: 795
accaagtgat attcattgtc tacctgagct agaatacaag tagttggcgt cttcagagac      60
acttgtatgc tagctcaggt agatattgaa tgaaaaa                              97

<210> SEQ ID NO 796
<211> LENGTH: 118
<212> TYPE: DNA
<213> ORGANISM: Human
<220> FEATURE:
<221> NAME/KEY: misc_feature
<222> LOCATION: (1)..(118)
<223> OTHER INFORMATION: precursor sequence

<400> SEQUENCE: 796
gcaggtgaac tggcaggcca ggaagaggag gaagccctgg aggggctgga ggtgatggat      60
gttttcctcc ggttctcagg gctccacctc tttcgggccg tagagccagg gctggtgc      118

<210> SEQ ID NO 797
<211> LENGTH: 87
<212> TYPE: DNA
<213> ORGANISM: Human
<220> FEATURE:
<221> NAME/KEY: misc_feature
<222> LOCATION: (1)..(87)
<223> OTHER INFORMATION: precursor sequence

<400> SEQUENCE: 797
tcagagtgag gtagtagatt gtatagttgt ggggtagtga ttttaccctg ttcaggagat      60
aactatacaa tctattgcct tccctga                                         87

<210> SEQ ID NO 798
<211> LENGTH: 83
<212> TYPE: DNA
<213> ORGANISM: Human
<220> FEATURE:
<221> NAME/KEY: misc_feature
<222> LOCATION: (1)..(83)
<223> OTHER INFORMATION: precursor sequence

<400> SEQUENCE: 798
tgtgggatga ggtagtagat tgtatagttt tagggtcata ccccatcttg gagataacta      60
tacagtctac tgtctttccc acg                                             83

<210> SEQ ID NO 799
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 799
aggctgaggt agtagtttgt acagtttgag ggtctatgat accacccggt acaggagata      60
actgtacagg ccactgcctt gcca                                            84

<210> SEQ ID NO 800
<211> LENGTH: 78
<212> TYPE: DNA
<213> ORGANISM: Human
<220> FEATURE:
<221> NAME/KEY: misc_feature
```

```
<222> LOCATION: (1)..(78)
<223> OTHER INFORMATION: precursor sequence

<400> SEQUENCE: 800
tactgccctc ggcttcttta cagtgctgcc ttgttgcata tggatcaagc agcattgtac    60
agggctatga aggcattg                                                  78

<210> SEQ ID NO 801
<211> LENGTH: 78
<212> TYPE: DNA
<213> ORGANISM: Human
<220> FEATURE:
<221> NAME/KEY: misc_feature
<222> LOCATION: (1)..(78)
<223> OTHER INFORMATION: precursor sequence

<400> SEQUENCE: 801
ttgtgctttc agcttcttta cagtgctgcc ttgtagcatt caggtcaagc agcattgtac    60
agggctatga aagaacca                                                  78

<210> SEQ ID NO 802
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: precursor sequence

<400> SEQUENCE: 802
ctctctgctt tcagcttctt tacagtgttg ccttgtggca tggagttcaa gcagcattgt    60
acagggctat caaagcacag a                                              81

<210> SEQ ID NO 803
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: precursor sequence

<400> SEQUENCE: 803
acttcctggt atttgaagat gcggttgacc atggtgtgta cgctttattt gtgacgtagg    60
acacatggtc tacttcttct caatatca                                       88

<210> SEQ ID NO 804
<211> LENGTH: 113
<212> TYPE: DNA
<213> ORGANISM: Human
<220> FEATURE:
<221> NAME/KEY: misc_feature
<222> LOCATION: (1)..(113)
<223> OTHER INFORMATION: precursor sequence

<400> SEQUENCE: 804
ctgtcccgct ggcctggcag gtgacggtgc tggatgtggc ctttttgcct tttctaaagg    60
ccacattttc cagcccattc aaccttccag agccctctga agtggccaca ggc           113

<210> SEQ ID NO 805
<211> LENGTH: 78
<212> TYPE: DNA
<213> ORGANISM: Human
<220> FEATURE:
```

```
<221> NAME/KEY: misc_feature
<222> LOCATION: (1)..(78)
<223> OTHER INFORMATION: precursor sequence

<400> SEQUENCE: 805
acctcccaaa tatatatata tatgtacgta tgtgtatata aatgtacg tagatatata      60 tgtatttttg gtgggttt                                                  78

<210> SEQ ID NO 806
<211> LENGTH: 81
<212> TYPE: DNA
<213> ORGANISM: Human
<220> FEATURE:
<221> NAME/KEY: misc_feature
<222> LOCATION: (1)..(81)
<223> OTHER INFORMATION: precursor sequence

<400> SEQUENCE: 806
atttgctcat agatgatatg catagtactc ccagaactca ttaagttggt agtactgtgc    60
atatcatcta tgagcgaata g                                              81

<210> SEQ ID NO 807
<211> LENGTH: 83
<212> TYPE: DNA
<213> ORGANISM: Human
<220> FEATURE:
<221> NAME/KEY: misc_feature
<222> LOCATION: (1)..(83)
<223> OTHER INFORMATION: precursor sequence

<400> SEQUENCE: 807
cctcatggca gtgttctgga atcctacgtg agggacaatc attcagaccc acgtagcagt    60
gttctggaat tctgtgtgag gga                                            83

<210> SEQ ID NO 808
<211> LENGTH: 106
<212> TYPE: DNA
<213> ORGANISM: Human
<220> FEATURE:
<221> NAME/KEY: misc_feature
<222> LOCATION: (1)..(106)
<223> OTHER INFORMATION: precursor sequence

<400> SEQUENCE: 808
gcgcagcgcc ctgtctccca gcctgaggtg cagtgctgca tctctggtca gttgggagtc    60
tgagatgaag cactgtagct caggaagaga gaagttgttc tgcagc                  106

<210> SEQ ID NO 809
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 809
ctccccatgg ccctgtctcc caaccttgt accagtgctg ggctcagacc ctggtacagg    60
cctgggggac agggacctgg ggac                                           84

<210> SEQ ID NO 810
<211> LENGTH: 65
<212> TYPE: DNA
<213> ORGANISM: Human
```

```
<220> FEATURE:
<221> NAME/KEY: misc_feature
<222> LOCATION: (1)..(65)
<223> OTHER INFORMATION: precursor sequence

<400> SEQUENCE: 810
ctgttaatgc taatcgtgat aggggttttt gcctccaact gactcctaca tattagcatt    60
aacag                                                                65

<210> SEQ ID NO 811
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: precursor sequence

<400> SEQUENCE: 811
tgagttttga ggttgcttca gtgaacattc aacgctgtcg gtgagtttgg aattaaaatc    60
aaaaccatcg accgttgatt gtaccctatg gctaaccatc atctactcca              110

<210> SEQ ID NO 812
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: precursor sequence

<400> SEQUENCE: 812
agaagggcta tcaggccagc cttcagagga ctccaaggaa cattcaacgc tgtcggtgag    60
tttgggattt gaaaaaacca ctgaccgttg actgtacctt ggggtcctta              110

<210> SEQ ID NO 813
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: precursor sequence

<400> SEQUENCE: 813
cctgtgcaga gattattttt taaaaggtca caatcaacat tcattgctgt cggtgggttg    60
aactgtgtgg acaagctcac tgaacaatga atgcaactgt ggccccgctt              110

<210> SEQ ID NO 814
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 814
ctgatggctg cactcaacat tcattgctgt cggtgggttt gagtctgaat caactcactg    60
atcaatgaat gcaaactgcg gaccaaaca                                      89

<210> SEQ ID NO 815
<211> LENGTH: 86
<212> TYPE: DNA
```

<213> ORGANISM: Human
<220> FEATURE:
<221> NAME/KEY: misc_feature
<222> LOCATION: (1)..(86)
<223> OTHER INFORMATION: precursor sequence

<400> SEQUENCE: 815
tgcttgtaac tttccaaaga attctccttt tgggctttct ggttttattt taagcccaaa    60
ggtgaatttt ttgggaagtt tgagct    86

<210> SEQ ID NO 816
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 816
actggtcggt gatttaggta gtttcctgtt gttgggatcc acctttctct cgacagcacg    60
acactgcctt cattacttca gttg    84

<210> SEQ ID NO 817
<211> LENGTH: 52
<212> TYPE: DNA
<213> ORGANISM: Human
<220> FEATURE:
<221> NAME/KEY: misc_feature
<222> LOCATION: (1)..(52)
<223> OTHER INFORMATION: precursor sequence

<400> SEQUENCE: 817
gcagcaagga aggcaggggt cctaaggtgt gtcctcctgc cctccttgct gt    52

<210> SEQ ID NO 818
<211> LENGTH: 72
<212> TYPE: DNA
<213> ORGANISM: Human
<220> FEATURE:
<221> NAME/KEY: misc_feature
<222> LOCATION: (1)..(72)
<223> OTHER INFORMATION: precursor sequence

<400> SEQUENCE: 818
tgtcgggtag cttatcagac tgatgttgac tgttgaatct catggcaaca ccagtcgatg    60
ggctgtctga ca    72

<210> SEQ ID NO 819
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: precursor sequence

<400> SEQUENCE: 819
ccgccccggg ccgcggctcc tgattgtcca aacgcaattc tcgagtctat ggctccggcc    60
gagagttgag tctggacgtc ccgagccgcc gcccccaaac ctcgagcggg    110

<210> SEQ ID NO 820
<211> LENGTH: 110
<212> TYPE: DNA
<213> ORGANISM: Human

```
<220> FEATURE:
<221> NAME/KEY: misc_feature
<222> LOCATION: (1)..(110)
<223> OTHER INFORMATION: precursor sequence

<400> SEQUENCE: 820
tgaacatcca ggtctggggc atgaacctgg catacaatgt agatttctgt gttcgttagg    60
caacagctac attgtctgct gggtttcagg ctacctggaa acatgttctc              110

<210> SEQ ID NO 821
<211> LENGTH: 66
<212> TYPE: DNA
<213> ORGANISM: Human
<220> FEATURE:
<221> NAME/KEY: misc_feature
<222> LOCATION: (1)..(66)
<223> OTHER INFORMATION: precursor sequence

<400> SEQUENCE: 821
agggctcctg actccaggtc ctgtgtgtta cctagaaata gcactggact tggagtcaga    60
aggcct                                                              66

<210> SEQ ID NO 822
<211> LENGTH: 94
<212> TYPE: DNA
<213> ORGANISM: Human
<220> FEATURE:
<221> NAME/KEY: misc_feature
<222> LOCATION: (1)..(94)
<223> OTHER INFORMATION: precursor sequence

<400> SEQUENCE: 822
ataaaggaag ttaggctgag gggcagagag cgagactttt ctattttcca aaagctcggt    60
ctgaggcccc tcagtcttgc ttcctaaccc gcgc                               94

<210> SEQ ID NO 823
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 823
gctccccctc tctaatcctt gctacctggg tgagagtgct gtctgaatgc aatgcacctg    60
ggcaaggatt ctgagagcga gagc                                          84

<210> SEQ ID NO 824
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: precursor sequence

<400> SEQUENCE: 824 tgctcccct ctctaatcct tgctatctgg gtgctagtgc tggctcaatg caatgcacct     60
gggcaaggat tcagagaggg ggagct                                        86

<210> SEQ ID NO 825
<211> LENGTH: 91
<212> TYPE: DNA
```

```
<213> ORGANISM: Human
<220> FEATURE:
<221> NAME/KEY: misc_feature
<222> LOCATION: (1)..(91)
<223> OTHER INFORMATION: precursor sequence

<400> SEQUENCE: 825
cgacttgctt tctctcctcc atgccttgag tgtaggaccg ttggcatctt aattaccctc      60
ccacacccaa ggcttgcaaa aaagcgagcc t                                    91

<210> SEQ ID NO 826
<211> LENGTH: 116
<212> TYPE: DNA
<213> ORGANISM: Human
<220> FEATURE:
<221> NAME/KEY: misc_feature
<222> LOCATION: (1)..(116)
<223> OTHER INFORMATION: precursor sequence

<400> SEQUENCE: 826
cttttctcaa gtattgctgt taggttggtg caaaagtact tgcggatttt gctttacttt      60
taatggcaaa aaccgcaatt attttttgctt caacctaata tgatgcaaaa ttggct       116

<210> SEQ ID NO 827
<211> LENGTH: 95
<212> TYPE: DNA
<213> ORGANISM: Human
<220> FEATURE:
<221> NAME/KEY: misc_feature
<222> LOCATION: (1)..(95)
<223> OTHER INFORMATION: precursor sequence

<400> SEQUENCE: 827
gatagtaata agaaagatga gctcattgta atatgagctt catttataca tttcatatta      60
ccattagctc atcttttta ttactacctt caaca                                 95

<210> SEQ ID NO 828
<211> LENGTH: 96
<212> TYPE: DNA
<213> ORGANISM: Human
<220> FEATURE:
<221> NAME/KEY: misc_feature
<222> LOCATION: (1)..(96)
<223> OTHER INFORMATION: precursor sequence

<400> SEQUENCE: 828
gttatgtgaa ggtattcttg tgttctctag atcagtgctt ttagaaaatt tgtgtgatct      60
aaagaacaca aagaataccct acacagaacc acctgc                              96

<210> SEQ ID NO 829
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 829
tagggtgacc agccattatg gtttgcctgg gactgaggaa tttgctggga tatgtcagtt      60
ccaggccaac caggctggtt ggtctccctg aagcaac                              97

<210> SEQ ID NO 830
<211> LENGTH: 97
```

```
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 830
tagccagtca gaaatgagct tattcataaa agtgcagtat ggtgaagtca atctgtaatt     60
ttatgtataa gctagtctct gattgaaaca tgcagca                             97

<210> SEQ ID NO 831
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 831
ttaggtaatt cctccactca aaacccttca gtgacttcca tgacatgaaa taggaagtca     60
ttggagggtt tgagcagagg aatgacctgt tttaaaa                             97

<210> SEQ ID NO 832
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 832 tcccttccc aggggagggg ctgggtttac gttgggagaa cttttacggt gaaccaggag      60
gttctcccaa cgtaagccca gcccctcccc tctgcct                             97

<210> SEQ ID NO 833
<211> LENGTH: 78
<212> TYPE: DNA
<213> ORGANISM: Human
<220> FEATURE:
<221> NAME/KEY: misc_feature
<222> LOCATION: (1)..(78)
<223> OTHER INFORMATION: precursor sequence

<400> SEQUENCE: 833
ctttctacac aggttgggat cggttgcaat gctgtgtttc tgtatggtat tgcacttgtc     60
ccggcctgtt gagtttgg                                                  78

<210> SEQ ID NO 834
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: precursor sequence

<400> SEQUENCE: 834
tcatccctgg gtggggattt gttgcattac ttgtgttcta tataaagtat tgcacttgtc     60
ccggcctgtg gaaga                                                     75

<210> SEQ ID NO 835
```

```
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 835
cccggctgtg tggacatgtg cccagggccc gggacagcgc cacggaagag gacgcacccg    60
gctgtgtgca catgtgccca gggcccggg                                      89

<210> SEQ ID NO 836
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 836
cccggctgtg tgcacatgtg cccagggccc gggacagcgc cacggaagag gacgcacccg    60
gctgtgtgca catgtgccca gggcccggg                                      89

<210> SEQ ID NO 837
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 837
cccggctgtg tgcacatgtg cccagggccc gggacagcgc cacggaagag gacgcacccg    60
gctgtgtgca catgtgccca gggcccggg                                      89

<210> SEQ ID NO 838
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: precursor sequence

<400> SEQUENCE: 838
attaggagag tatcttctct gttttggcca tgtgtgtact cacagcccct cacacatggc    60
cgaaacagag aagttacttt cctaat                                         86

<210> SEQ ID NO 839
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: precursor sequence

<400> SEQUENCE: 839
gttccagaca catctcatct gatatacaat attttcttaa attgtataaa gagaaattat    60
tgtacatcgg atgagctgtg tctgggat                                       88
```

```
<210> SEQ ID NO 840
<211> LENGTH: 63
<212> TYPE: DNA
<213> ORGANISM: Human
<220> FEATURE:
<221> NAME/KEY: misc_feature
<222> LOCATION: (1)..(63)
<223> OTHER INFORMATION: precursor sequence

<400> SEQUENCE: 840
tacggatgag caaagaaagt ggtttcttaa aatggaatct actctttgtg aagatgctgt    60
gaa                                                                  63

<210> SEQ ID NO 841
<211> LENGTH: 67
<212> TYPE: DNA
<213> ORGANISM: Human
<220> FEATURE:
<221> NAME/KEY: misc_feature
<222> LOCATION: (1)..(67)
<223> OTHER INFORMATION: precursor sequence

<400> SEQUENCE: 841
tcttacggat gagcaaagaa agtggtttgc gcctcaagaa accactttct tgctcatcc     60 ataagga                                                              67

<210> SEQ ID NO 842
<211> LENGTH: 117
<212> TYPE: DNA
<213> ORGANISM: Human
<220> FEATURE:
<221> NAME/KEY: misc_feature
<222> LOCATION: (1)..(117)
<223> OTHER INFORMATION: precursor sequence

<400> SEQUENCE: 842
gccctgggct tgtgcttggg gagtgaatga tgggttctga ccccccatgca cccctgtggg    60 ccccctggcat cactggcccc atccttcacc cctgccaacc acgcttgccc tgtgcct     117

<210> SEQ ID NO 843
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 843
tgtagagata ggatctcact ttgttgccca ggctggtctc aaactcctgg tctgggcaac    60
aaagtgagac cttatctcta caag                                           84

<210> SEQ ID NO 844
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: precursor sequence

<400> SEQUENCE: 844
tttgggaggc cgaggctggt gcatcacttg agcccagcaa tttgagacca atctgggcaa    60
caaagtgaga cctccgtctc tacaaaga                                       88
```

<210> SEQ ID NO 845
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: precursor sequence

<400> SEQUENCE: 845
ggcctgcccg acactctttc cctgttgcac tactataggc cgctgggaag cagtgcaatg   60
atgaaagggc atcggtcagg tc                                           82

<210> SEQ ID NO 846
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: precursor sequence

<400> SEQUENCE: 846
cggaaaattt gccaagggtt tgggggaaca ttcaacctgt cggtgagttt gggcagctca   60
ggcaaaccat cgaccgttga gtggaccctg aggcctggaa ttgccatcct              110

<210> SEQ ID NO 847
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: precursor sequence

<400> SEQUENCE: 847
tgcttgtaac tttccaaaga attctccttt tgggctttct ggttttattt taagcccaaa   60
ggtgaatttt ttgggaagtt tgagct                                       86

<210> SEQ ID NO 848
<211> LENGTH: 71
<212> TYPE: DNA
<213> ORGANISM: Human
<220> FEATURE:
<221> NAME/KEY: misc_feature
<222> LOCATION: (1)..(71)
<223> OTHER INFORMATION: precursor sequence

<400> SEQUENCE: 848
tgttctaagg tgcatctagt gcagatagtg aagtagatta gcatctactg ccctaagtgc   60
tccttctggc a                                                       71

<210> SEQ ID NO 849
<211> LENGTH: 71
<212> TYPE: DNA
<213> ORGANISM: Human
<220> FEATURE:
<221> NAME/KEY: misc_feature
<222> LOCATION: (1)..(71)
<223> OTHER INFORMATION: precursor sequence

<400> SEQUENCE: 849
tgtgttaagg tgcatctagt gcagttagtg aagcagctta gaatctactg ccctaaatgc   60
cccttctggc a                                                       71

<210> SEQ ID NO 850
<211> LENGTH: 79
<212> TYPE: DNA
<213> ORGANISM: Human
<220> FEATURE:
<221> NAME/KEY: misc_feature
<222> LOCATION: (1)..(79)
<223> OTHER INFORMATION: precursor sequence

<400> SEQUENCE: 850
tgcttctgtg tgatatgttt gatattgggt tgtttaatta ggaaccaact aaatgtcaaa    60
catattctta cagcagcag                                                 79

<210> SEQ ID NO 851
<211> LENGTH: 69
<212> TYPE: DNA
<213> ORGANISM: Human
<220> FEATURE:
<221> NAME/KEY: misc_feature
<222> LOCATION: (1)..(69)
<223> OTHER INFORMATION: precursor sequence

<400> SEQUENCE: 851
agtaccaaag tgctcatagt gcaggtagtt ttggcatgac tctactgtag tatgggcact    60
tccagtact                                                            69

<210> SEQ ID NO 852
<211> LENGTH: 73
<212> TYPE: DNA
<213> ORGANISM: Human
<220> FEATURE:
<221> NAME/KEY: misc_feature
<222> LOCATION: (1)..(73)
<223> OTHER INFORMATION: precursor sequence

<400> SEQUENCE: 852
ctctgcctcc cgtgcctact gagctgaaac acagttggtt tgtgtacact ggctcagttc    60
agcaggaaca ggg                                                       73

<210> SEQ ID NO 853
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: precursor sequence

<400> SEQUENCE: 853
ggtccttgcc ctcaaggagc tcacagtcta ttgagttacc tttctgactt tcccactaga    60
ttgtgagctc ctggagggca ggcact                                         86

<210> SEQ ID NO 854
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 854
accatgctgt agtgtgtgta aacatcctac actctcagct gtgagctcaa ggtggctggg    60

```
agagggttgt ttactccttc tgccatgga                                       89

<210> SEQ ID NO 855
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: precursor sequence

<400> SEQUENCE: 855
tgttgtcggg tggatcacga tgcaattttg atgagtatca taggagaaaa attgcacggt    60
atccatctgt aaacc                                                      75

<210> SEQ ID NO 856
<211> LENGTH: 91
<212> TYPE: DNA
<213> ORGANISM: Human
<220> FEATURE:
<221> NAME/KEY: misc_feature
<222> LOCATION: (1)..(91)
<223> OTHER INFORMATION: precursor sequence

<400> SEQUENCE: 856
aaacgatact aaactgtttt tgcgatgtgt tcctaatatg cactataaat atattgggaa    60
cattttgcat gtatagtttt gtatcaatat a                                    91

<210> SEQ ID NO 857
<211> LENGTH: 100
<212> TYPE: DNA
<213> ORGANISM: Human
<220> FEATURE:
<221> NAME/KEY: misc_feature
<222> LOCATION: (1)..(100)
<223> OTHER INFORMATION: precursor sequence

<400> SEQUENCE: 857
ccaaagaaag atgctaaact attttttgcga tgtgttccta atatgtaata taatgtatt    60 ggggacattt tgcattcata gttttgtatc aataatatgg                          100

<210> SEQ ID NO 858
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 858
agttattaga ttagtgcaaa agtaattgca gtttttgcat tacgttctat ggcaaaactg    60
taattacttt tgtaccaaca taatacttc                                       89

<210> SEQ ID NO 859
<211> LENGTH: 114
<212> TYPE: DNA
<213> ORGANISM: Human
<220> FEATURE:
<221> NAME/KEY: misc_feature
<222> LOCATION: (1)..(114)
<223> OTHER INFORMATION: precursor sequence

<400> SEQUENCE: 859
tggtgaaaat gtgttgattg taatggttcc tattctgatc aataaacatg gtttgagcct    60
```
agttacaatg atctaaaatt cacggtccaa aactgcagtt acttttgcac caac    114

<210> SEQ ID NO 860
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: precursor sequence

<400> SEQUENCE: 860
atctgtgctc tttgattaca gttgttcaac cagttactaa tctaactaat tgtaactggt    60
tgaacaactg aacccaaagg gtgcaaagta gaaacatt    98

<210> SEQ ID NO 861
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: precursor sequence

<400> SEQUENCE: 861
gaacattgaa actggctagg gaaaatgatt ggatagaaac tattattcta ttcatttatc    60
cccagcctac aaaatgaaaa aa    82

<210> SEQ ID NO 862
<211> LENGTH: 80
<212> TYPE: DNA
<213> ORGANISM: Human
<220> FEATURE:
<221> NAME/KEY: misc_feature
<222> LOCATION: (1)..(80)
<223> OTHER INFORMATION: precursor sequence

<400> SEQUENCE: 862
ctgggggctc caaagtgctg ttcgtgcagg tagtgtgatt acccaaccta ctgctgagct    60
agcacttccc gagccccgg    80

<210> SEQ ID NO 863
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 863
ctgtaattag tcagttttct gt    22

<210> SEQ ID NO 864
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA sequence

<400> SEQUENCE: 864
taatggtaat ggttctcttg    20

```
<210> SEQ ID NO 865
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 865
taatgattca tcagactcag a                                          21

<210> SEQ ID NO 866
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 866
ttagtagttt tactatgatg agg                                        23

<210> SEQ ID NO 867
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 867
acctgagcta gaatacaagt agt                                        23

<210> SEQ ID NO 868
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 868
aggaccttcc ctgaaccaag ga                                         22

<210> SEQ ID NO 869
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 869
gaaagcccat gtttgtattg ga                                         22

<210> SEQ ID NO 870
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence
```

<400> SEQUENCE: 870
tctgtcattt ctttaggcca ata                                         23

<210> SEQ ID NO 871
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 871
ccctgaacga ggggtctgga g                                           21

<210> SEQ ID NO 872
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 872
caaaaactgc attactttg ca                                           22

<210> SEQ ID NO 873
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 873
agacacattt ggagagggaa c                                           21

<210> SEQ ID NO 874
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 874
tatatatata tatgtacgta tg                                          22

<210> SEQ ID NO 875
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA sequence

<400> SEQUENCE: 875
gttggtgcaa aagtaattg                                              19

<210> SEQ ID NO 876
<211> LENGTH: 17
<212> TYPE: DNA

```
-continued

<213> ORGANISM: Human
<220> FEATURE:
<221> NAME/KEY: misc_feature
<222> LOCATION: (1)..(17)
<223> OTHER INFORMATION: microRNA sequence

<400> SEQUENCE: 876
gttggtgcaa aagtaat                                                    17

<210> SEQ ID NO 877
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA sequence

<400> SEQUENCE: 877
aaactggaat tacttttg                                                   18

<210> SEQ ID NO 878
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 878
agtggttctc ttgtggctca ag                                              22

<210> SEQ ID NO 879
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA sequence

<400> SEQUENCE: 879
ctgggcctct gctccccag                                                  19

<210> SEQ ID NO 880
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA sequence

<400> SEQUENCE: 880
tctcactttg ttgcccag                                                   18

<210> SEQ ID NO 881
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA sequence

<400> SEQUENCE: 881
tgtgggttat tgttaagt                                                   18
```

<210> SEQ ID NO 882
<211> LENGTH: 24
<212> TYPE: DNA
<213> ORGANISM: Human
<220> FEATURE:
<221> NAME/KEY: misc_feature
<222> LOCATION: (1)..(24)
<223> OTHER INFORMATION: microRNA sequence

<400> SEQUENCE: 882
agcgcgggct gagcgctgcc agtc                                          24

<210> SEQ ID NO 883
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 883
gtagattttc cttctatggt t                                             21

<210> SEQ ID NO 884
<211> LENGTH: 23
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 884
ctcattaaat gtttgttgaa tga                                           23

<210> SEQ ID NO 885
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA sequence

<400> SEQUENCE: 885
caaaagcaat cgcggttttt gc                                            22

<210> SEQ ID NO 886
<211> LENGTH: 17
<212> TYPE: DNA
<213> ORGANISM: Human
<220> FEATURE:
<221> NAME/KEY: misc_feature
<222> LOCATION: (1)..(17)
<223> OTHER INFORMATION: microRNA sequence

<400> SEQUENCE: 886
gttggtgcaa aagtaat                                                  17

<210> SEQ ID NO 887
<211> LENGTH: 26
<212> TYPE: DNA
<213> ORGANISM: Human
<220> FEATURE:
<221> NAME/KEY: misc_feature
<222> LOCATION: (1)..(26)

```
<223> OTHER INFORMATION: microRNA sequence

<400> SEQUENCE: 887
acatgtgccc agggcccggg acagcg                                              26

<210> SEQ ID NO 888
<211> LENGTH: 26
<212> TYPE: DNA
<213> ORGANISM: Human
<220> FEATURE:
<221> NAME/KEY: misc_feature
<222> LOCATION: (1)..(26)
<223> OTHER INFORMATION: microRNA sequence

<400> SEQUENCE: 888
acatgtgccc agggcccggg acagcg                                              26

<210> SEQ ID NO 889
<211> LENGTH: 26
<212> TYPE: DNA
<213> ORGANISM: Human
<220> FEATURE:
<221> NAME/KEY: misc_feature
<222> LOCATION: (1)..(26)
<223> OTHER INFORMATION: microRNA sequence

<400> SEQUENCE: 889
acatgtgccc agggcccggg acagcg                                              26

<210> SEQ ID NO 890
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA sequence

<400> SEQUENCE: 890
gggggggggg gggggggg                                                       18

<210> SEQ ID NO 891
<211> LENGTH: 19
<212> TYPE: DNA
<213> ORGANISM: Human
<220> FEATURE:
<221> NAME/KEY: misc_feature
<222> LOCATION: (1)..(19)
<223> OTHER INFORMATION: microRNA sequence

<400> SEQUENCE: 891
aggagaattg cttgaaccc                                                      19

<210> SEQ ID NO 892
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 892
tcgaccggac ctcgaccggc t                                                   21

<210> SEQ ID NO 893
<211> LENGTH: 23
```

```
<212> TYPE: DNA
<213> ORGANISM: Human
<220> FEATURE:
<221> NAME/KEY: misc_feature
<222> LOCATION: (1)..(23)
<223> OTHER INFORMATION: microRNA sequence

<400> SEQUENCE: 893
gtcatttttg tgatgttgca gct                                           23

<210> SEQ ID NO 894
<211> LENGTH: 20
<212> TYPE: DNA
<213> ORGANISM: Human
<220> FEATURE:
<221> NAME/KEY: misc_feature
<222> LOCATION: (1)..(20)
<223> OTHER INFORMATION: microRNA sequence

<400> SEQUENCE: 894
ctcactgaac aatgaatgca                                               20

<210> SEQ ID NO 895
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 895
caaaaactgc aattactttt g                                             21

<210> SEQ ID NO 896
<211> LENGTH: 21
<212> TYPE: DNA
<213> ORGANISM: Human
<220> FEATURE:
<221> NAME/KEY: misc_feature
<222> LOCATION: (1)..(21)
<223> OTHER INFORMATION: microRNA sequence

<400> SEQUENCE: 896
caaaaaccgc aattactttt g                                             21

<210> SEQ ID NO 897
<211> LENGTH: 18
<212> TYPE: DNA
<213> ORGANISM: Human
<220> FEATURE:
<221> NAME/KEY: misc_feature
<222> LOCATION: (1)..(18)
<223> OTHER INFORMATION: microRNA sequence

<400> SEQUENCE: 897
caaaaactgc agttactt                                                 18

<210> SEQ ID NO 898
<211> LENGTH: 61
<212> TYPE: DNA
<213> ORGANISM: Human
<220> FEATURE:
<221> NAME/KEY: misc_feature
<222> LOCATION: (1)..(61)
<223> OTHER INFORMATION: precursor sequence

<400> SEQUENCE: 898
```

```
acagctgtaa ttagtcagtt ttctgtcctg tccacacaga aaaccgtcta gttacagttg     60
t                                                                    61

<210> SEQ ID NO 899
<211> LENGTH: 72
<212> TYPE: DNA
<213> ORGANISM: Human
<220> FEATURE:
<221> NAME/KEY: misc_feature
<222> LOCATION: (1)..(72)
<223> OTHER INFORMATION: precursor sequence

<400> SEQUENCE: 899
cttgggaatg gcaaggaaac cgttaccatt actgagttta gtaatggtaa tggttctctt     60
gctataccca ga                                                        72

<210> SEQ ID NO 900
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 900
ataaaatttc caattggaac ctaatgattc atcagactca gatatttaag ttaacagtat     60
ttgagaatga tgaatcatta ggttccggtc agaaatt                             97

<210> SEQ ID NO 901
<211> LENGTH: 96
<212> TYPE: DNA
<213> ORGANISM: Human
<220> FEATURE:
<221> NAME/KEY: misc_feature
<222> LOCATION: (1)..(96)
<223> OTHER INFORMATION: precursor sequence

<400> SEQUENCE: 901
tgtatccttg gttttagta gttttactat gatgaggtgt gccatccacc ccatcatagt      60
aaactactga aaatcaaaga tacaagtgcc tgacca                              96

<210> SEQ ID NO 902
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 902
accaagtgat attcattgtc tacctgagct agaatacaag tagttggcgt cttcagagac     60
acttgtatgc tagctcaggt agatattgaa tgaaaaa                             97

<210> SEQ ID NO 903
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 903
```

```
taccgaccct cgatttggtt caggaccttc cctgaaccaa ggaagagtca cagtctcttc    60
cttggttcag ggagggtccc caacaatgtc ctcatgg                             97

<210> SEQ ID NO 904
<211> LENGTH: 120
<212> TYPE: DNA
<213> ORGANISM: Human
<220> FEATURE:
<221> NAME/KEY: misc_feature
<222> LOCATION: (1)..(120)
<223> OTHER INFORMATION: precursor sequence

<400> SEQUENCE: 904
attttgatat ataagccagt ttaatgtttt ctatacagac cctggctttt cttaaatttt    60
atatattgga aagcccatgt ttgtattgga aactgctggt ttctttcata ctgaaaatct   120

<210> SEQ ID NO 905
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: precursor sequence

<400> SEQUENCE: 905
atcattcaga aatggtatac aggaaaatga cctatgaatt gacagacaat atagctgagt    60
ttgtctgtca tttctttagg ccaatattct gtatgactgt gctacttcaa              110

<210> SEQ ID NO 906
<211> LENGTH: 98
<212> TYPE: DNA
<213> ORGANISM: Human
<220> FEATURE:
<221> NAME/KEY: misc_feature
<222> LOCATION: (1)..(98)
<223> OTHER INFORMATION: precursor sequence

<400> SEQUENCE: 906
acccaaaccc taggtctgct gactcctagt ccagggctcg tgatggctgg tgggccctga    60
acgaggggtc tggaggcctg ggtttgaata tcgacagc                            98

<210> SEQ ID NO 907
<211> LENGTH: 112
<212> TYPE: DNA
<213> ORGANISM: Human
<220> FEATURE:
<221> NAME/KEY: misc_feature
<222> LOCATION: (1)..(112)
<223> OTHER INFORMATION: precursor sequence

<400> SEQUENCE: 907
gggcagccag tgaatagtta gctggtgcaa aagtaattgc ggtctttggt attactttca    60
gtggcaaaaa ctgcattact tttgcaccag cctactagaa cgctgagttc ag           112

<210> SEQ ID NO 908
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence
```

<400> SEQUENCE: 908
atctgagttg ggagggtccc tctccaaatg tgtcttgggg tgggggatca agacacattt    60
ggagagggaa cctcccaact cggcctctgc catcatt                             97

<210> SEQ ID NO 909
<211> LENGTH: 78
<212> TYPE: DNA
<213> ORGANISM: Human
<220> FEATURE:
<221> NAME/KEY: misc_feature
<222> LOCATION: (1)..(78)
<223> OTHER INFORMATION: precursor sequence

<400> SEQUENCE: 909
acctcccaaa tatatatata tatgtacgta tgtgtatata aatgtatacg tagatatata    60
tgtatttttg gtgggttt                                                  78

<210> SEQ ID NO 910
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 910
tgcagggagg tattaagttg gtgcaaaagt aattgtgatt tttgccatta aaagtaacga    60
caaaactggc aattactttt gcaccaaacc tggtatt                             97

<210> SEQ ID NO 911
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 911
attaggttgg tgcaaaagta atcacagttt ttgacattac tttcaaagac aaaaactgta    60
attacttttg gaccaaccta atag                                           84

<210> SEQ ID NO 912
<211> LENGTH: 102
<212> TYPE: DNA
<213> ORGANISM: Human
<220> FEATURE:
<221> NAME/KEY: misc_feature
<222> LOCATION: (1)..(102)
<223> OTHER INFORMATION: precursor sequence

<400> SEQUENCE: 912
tctgtccatt aggtgggtgc aaaagtaatc gcggtttttg tcattacttt taatggtaaa    60
aactggaatt acttttgcac tgacctaata ttaagccaga ta                      102

<210> SEQ ID NO 913
<211> LENGTH: 97
<212> TYPE: DNA
<213> ORGANISM: Human
<220> FEATURE:
<221> NAME/KEY: misc_feature
<222> LOCATION: (1)..(97)
<223> OTHER INFORMATION: precursor sequence

<400> SEQUENCE: 913
tacttactct acgtgtgtgt cactcgatga ccactgtgaa gacagtaaaa tgtacagtgg    60
ttctcttgtg gctcaagcgt aatgtagagt actggtc                             97

<210> SEQ ID NO 914
<211> LENGTH: 82
<212> TYPE: DNA
<213> ORGANISM: Human
<220> FEATURE:
<221> NAME/KEY: misc_feature
<222> LOCATION: (1)..(82)
<223> OTHER INFORMATION: precursor sequence

<400> SEQUENCE: 914
tgtgggcagg gccctgggga gctgaggctc tgggggtggc cggggctgac cctgggcctc    60
tgctccccag tgtctgaccg cg                                             82

<210> SEQ ID NO 915
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 915
tgtagagata ggatctcact ttgttgccca ggctggtctc aaactcctgg tctgggcaac    60
aaagtgagac cttatctcta caag                                           84

<210> SEQ ID NO 916
<211> LENGTH: 75
<212> TYPE: DNA
<213> ORGANISM: Human
<220> FEATURE:
<221> NAME/KEY: misc_feature
<222> LOCATION: (1)..(75)
<223> OTHER INFORMATION: precursor sequence

<400> SEQUENCE: 916
agttggtccg agtgttgtgg gttattgtta agttgattta acattgtctc cccccacaac    60
cgcgcttgac tagct                                                     75

<210> SEQ ID NO 917
<211> LENGTH: 93
<212> TYPE: DNA
<213> ORGANISM: Human
<220> FEATURE:
<221> NAME/KEY: misc_feature
<222> LOCATION: (1)..(93)
<223> OTHER INFORMATION: precursor sequence

<400> SEQUENCE: 917
gtgcttcctg cgggctgagc gcgggctgag cgctgccagt cagcgctcac attaaggctg    60
acagcgccct gcctggctcg gccggcgaag ctc                                 93

<210> SEQ ID NO 918
<211> LENGTH: 80
<212> TYPE: DNA
<213> ORGANISM: Human
<220> FEATURE:
<221> NAME/KEY: misc_feature
<222> LOCATION: (1)..(80)

<223> OTHER INFORMATION: precursor sequence

<400> SEQUENCE: 918

```
ggtatttaaa aggtagattt tccttctatg gttacgtgtt tgatggttaa tcatagagga    60
aaatccacgt tttcagtatc                                                80
```

<210> SEQ ID NO 919
<211> LENGTH: 85
<212> TYPE: DNA
<213> ORGANISM: Human
<220> FEATURE:
<221> NAME/KEY: misc_feature
<222> LOCATION: (1)..(85)
<223> OTHER INFORMATION: precursor sequence

<400> SEQUENCE: 919

```
gcacattgta ggcctcatta aatgtttgtt gaatgaaaaa atgaatcatc aacagacatt    60
aattgggcgc ctgctctgtg atctc                                          85
```

<210> SEQ ID NO 920
<211> LENGTH: 88
<212> TYPE: DNA
<213> ORGANISM: Human
<220> FEATURE:
<221> NAME/KEY: misc_feature
<222> LOCATION: (1)..(88)
<223> OTHER INFORMATION: precursor sequence

<400> SEQUENCE: 920

```
ttattaggtt ggtacaaaag caatcgcggt ttttgctatt acttttaaag gcaaaaactg    60
agactacttt tgcaccaacc tgatagaa                                       88
```

<210> SEQ ID NO 921
<211> LENGTH: 105
<212> TYPE: DNA
<213> ORGANISM: Human
<220> FEATURE:
<221> NAME/KEY: misc_feature
<222> LOCATION: (1)..(105)
<223> OTHER INFORMATION: precursor sequence

<400> SEQUENCE: 921

```
gagttctaac gtattaggtt ggtgcaaaag taatagtggt ttttgccatt aaaagtaatg    60
acaaaaactg taattacttt tggaacaata ttaatagaat ttcag                   105
```

<210> SEQ ID NO 922
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 922

```
cccggctgtg tggacatgtg cccagggccc gggacagcgc cacggaagag gacgcacccg    60
gctgtgtgca catgtgccca gggcccggg                                      89
```

<210> SEQ ID NO 923
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 923
cccggctgtg tgcacatgtg cccagggccc gggacagcgc cacggaagag gacgcacccg    60
gctgtgtgca catgtgccca gggcccggg                                     89

<210> SEQ ID NO 924
<211> LENGTH: 89
<212> TYPE: DNA
<213> ORGANISM: Human
<220> FEATURE:
<221> NAME/KEY: misc_feature
<222> LOCATION: (1)..(89)
<223> OTHER INFORMATION: precursor sequence

<400> SEQUENCE: 924
cccggctgtg tgcacatgtg cccagggccc gggacagcgc cacggaagag gacgcacccg    60
gctgtgtgca catgtgccca gggcccggg                                     89

<210> SEQ ID NO 925
<211> LENGTH: 84
<212> TYPE: DNA
<213> ORGANISM: Human
<220> FEATURE:
<221> NAME/KEY: misc_feature
<222> LOCATION: (1)..(84)
<223> OTHER INFORMATION: precursor sequence

<400> SEQUENCE: 925
gtgagtgtgg ggtggctggg gggggggggg ggggggccggg gacggcttgg gcctgcctag    60
tcggcctgac cacccacccc acag                                          84

<210> SEQ ID NO 926
<211> LENGTH: 103
<212> TYPE: DNA
<213> ORGANISM: Human
<220> FEATURE:
<221> NAME/KEY: misc_feature
<222> LOCATION: (1)..(103)
<223> OTHER INFORMATION: precursor sequence

<400> SEQUENCE: 926
tgaggcagga gaattgcttg aacccgggtg gtggaggttg cagtgagcca agattgcgcc    60
actgcactcc agcctgggcg acaaagcaag actctttctt gga                    103

<210> SEQ ID NO 927
<211> LENGTH: 149
<212> TYPE: DNA
<213> ORGANISM: Human
<220> FEATURE:
<221> NAME/KEY: misc_feature
<222> LOCATION: (1)..(149)
<223> OTHER INFORMATION: precursor sequence

<400> SEQUENCE: 927
catcaagacc cagctgagtc actgtcactg cctaccaatc tcgaccggac ctcgaccggc    60
tcgtctgtgt tgccaatcga ctcggcgtgg cgtcggtcgt ggtagatagg cggtcatgca   120
tacgaatttt cagctcttgt tctggtgac                                    149

<210> SEQ ID NO 928
<211> LENGTH: 87
<212> TYPE: DNA

<213> ORGANISM: Human
<220> FEATURE:
<221> NAME/KEY: misc_feature
<222> LOCATION: (1)..(87)
<223> OTHER INFORMATION: precursor sequence

<400> SEQUENCE: 928

```
agcggtggcc agtgtcattt ttgtgatgtt gcagctagta atatgagccc agttgcatag      60
tcacaaaagt gatcattgga aactgtg                                          87
```

<210> SEQ ID NO 929
<211> LENGTH: 110
<212> TYPE: DNA
<213> ORGANISM: Human
<220> FEATURE:
<221> NAME/KEY: misc_feature
<222> LOCATION: (1)..(110)
<223> OTHER INFORMATION: precursor sequence

<400> SEQUENCE: 929

```
cctgtgcaga gattattttt taaaaggtca caatcaacat tcattgctgt cggtgggttg      60
aactgtgtgg acaagctcac tgaacaatga atgcaactgt ggccccgctt                110
```

<210> SEQ ID NO 930
<211> LENGTH: 118
<212> TYPE: DNA
<213> ORGANISM: Human
<220> FEATURE:
<221> NAME/KEY: misc_feature
<222> LOCATION: (1)..(118)
<223> OTHER INFORMATION: precursor sequence

<400> SEQUENCE: 930

```
tctgattctg catgtattag gttggtgcaa aagtaatcgc ggttttttgtc attgaaagta     60 atagcaaaaa ctgcaattac ttttgcacca acctaaaagt agtcactgtc ttcagata       118
```

<210> SEQ ID NO 931
<211> LENGTH: 111
<212> TYPE: DNA
<213> ORGANISM: Human
<220> FEATURE:
<221> NAME/KEY: misc_feature
<222> LOCATION: (1)..(111)
<223> OTHER INFORMATION: precursor sequence

<400> SEQUENCE: 931

```
gctattaggt tggtgcaaaa gtaatcgcgg tttttgtcat tactttaatt actttacgtt     60
tcattaatga caaaaaccgc aattacttttt gcaccaacct aatacttgct a             111
```

<210> SEQ ID NO 932
<211> LENGTH: 86
<212> TYPE: DNA
<213> ORGANISM: Human
<220> FEATURE:
<221> NAME/KEY: misc_feature
<222> LOCATION: (1)..(86)
<223> OTHER INFORMATION: precursor sequence

<400> SEQUENCE: 932

```
tattaggttg gtgcaaaagt atttgcgggt tttgtcgtag aaagtaatgg caaaaactgc     60
agttacttgt gcaccaacca aatgct                                          86
```

<210> SEQ ID NO 933
<211> LENGTH: 15

```
<212> TYPE: DNA
<213> ORGANISM: Artificial Sequence
<220> FEATURE:
<223> OTHER INFORMATION: Synthetic oligonucleotide

<400> SEQUENCE: 933
ttgtaatacg actca                                                        15

<210> SEQ ID NO 934
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 934
acagtagata aagcgacgcg cg                                                22

<210> SEQ ID NO 935
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 935
aacgcgactt atcgaacgat aa                                                22

<210> SEQ ID NO 936
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 936
aggttgccta catagtaact tc                                                22

<210> SEQ ID NO 937
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 937
cccggtaaca attagtcccg cg                                                22

<210> SEQ ID NO 938
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 938
tcggttgcgg agttcgacgc ga                                                22

<210> SEQ ID NO 939
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 939
```
cccgatgggt acggcgttcg gt                                                22

<210> SEQ ID NO 940
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 940
gacacgagag tcgttaccct cg                                                22

<210> SEQ ID NO 941
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 941
cccggtaaca attagacccg cg                                                22

<210> SEQ ID NO 942
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 942
gtccgtctac gcgtcggtac gc                                                22

<210> SEQ ID NO 943
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 943
ggccgtctac gcgtcggtac gc                                                22

<210> SEQ ID NO 944
<211> LENGTH: 22
<212> TYPE: RNA
<213> ORGANISM: Artificial Sequence
<220> FEATURE:
<223> OTHER INFORMATION: Synthetic RNA sequence

<400> SEQUENCE: 944
cgcgauaaac gccggaugga cc                                                22

<210> SEQ ID NO 945
<211> LENGTH: 22
<212> TYPE: RNA
<213> ORGANISM: Artificial Sequence
<220> FEATURE:
<223> OTHER INFORMATION: Synthetic RNA sequence

<400> SEQUENCE: 945
ucgagcgacu cccguaauuu aa                                                22

<210> SEQ ID NO 946
<211> LENGTH: 22
<212> TYPE: DNA
<213> ORGANISM: Artificial Sequence

```
<220> FEATURE:
<223> OTHER INFORMATION: Synthetic probe sequence

<400> SEQUENCE: 946
ggtccatccg gcgtttatcg cg                                              22

<210> SEQ ID NO 947
<211> LENGTH: 22
<212> TYPE: DNA
<213> ORGANISM: Artificial Sequence
<220> FEATURE:
<223> OTHER INFORMATION: Synthetic probe sequence

<400> SEQUENCE: 947
ttaaattacg ggagtcgctc ga                                              22

<210> SEQ ID NO 948
<211> LENGTH: 113
<212> TYPE: DNA
<213> ORGANISM: Human
<220> FEATURE:
<221> NAME/KEY: misc_feature
<222> LOCATION: (1)..(113)
<223> OTHER INFORMATION: Pre-microRNA sequence

<400> SEQUENCE: 948
ctgggacggg cggggcgccg aggcccaggg cgcctgaggg gcgcagaggt gtcagcgtgc      60
aaccgccgcc ccccagcgtt cccgccacca ccgccaccac cctcaaagcc cgg            113

<210> SEQ ID NO 949
<211> LENGTH: 104
<212> TYPE: DNA
<213> ORGANISM: Human
<220> FEATURE:
<221> NAME/KEY: misc_feature
<222> LOCATION: (1)..(104)
<223> OTHER INFORMATION: microRNA precursor sequence

<400> SEQUENCE: 949
tggatgattt ggagtagcaa agcagcaatt gttctttggt ctttcagcca tgacctgacc      60
ttctgtctgt gagaccaaag aactactttg cttggccacc atct                      104

<210> SEQ ID NO 950
<211> LENGTH: 22
<212> TYPE: DNA
<213> ORGANISM: Human
<220> FEATURE:
<221> NAME/KEY: misc_feature
<222> LOCATION: (1)..(22)
<223> OTHER INFORMATION: microRNA candidate sequence

<400> SEQUENCE: 950
atggccagag ctcacacaga gg                                              22
```

US 9,493,832 B2

METHODS OF DETECTING SEPSIS

This application claims priority to U.S. Provisional Application No. 61/149,277, filed Feb. 2, 2009, which is incorporated by reference herein in its entirety for any purpose.

1. BACKGROUND

Sepsis is the presence in the blood or other tissues of pathogenic microorganisms or their toxins combined with the host's inflammatory response, known as systemic inflammatory response syndrome ("SIRS") caused by the infection. The immune response is mediated by a class of proteins called toll-like receptors ("TLR") that recognize structurally-conserved molecules broadly shared by microorganisms but which are distinguishable from host molecules.

Once microorganisms have breached barriers such as the skin or intestinal tract, the body's TLRs recognize them and stimulate an immune response. Thus, in addition to symptoms caused by the microbial infection itself, sepsis is also characterized by symptoms of acute inflammation brought on by the host's immune response. These latter symptoms may include fever and elevated white blood cell count, or low white blood cell count and low body temperature. SIRS is characterized by hemodynamic compromise and resultant metabolic dysregulation, and may be accompanied by symptoms such as high heart rate, high respiratory rate and elevated body temperature. The immunological response also causes widespread activation of acute phase proteins, affecting the complement system and the coagulation pathways, which then cause damage to the vasculature and organs. Various neuroendocrine counter-regulatory systems are then activated as well, often compounding the problem.

Sepsis is often treated in the intensive care unit with intravenous fluids and antibiotics and/or antiviral compounds. However sepsis progresses quickly, and so even with immediate and aggressive treatment, severe sepsis can lead to organ failure and death. Severe sepsis is estimated to cause 215,000 deaths per year in the United States, more than acute myocardial infarction, stroke or pneumonia, which is likely due to late diagnosis or misdiagnosis of sepsis.

Thus, there is a need for early molecular markers in detecting sepsis.

2. SUMMARY

Methods for detecting the presence of sepsis in a subject are provided. In some embodiments, a method comprises detecting a level of at least one target RNA in a sample from the subject. In some embodiments, the at least one target RNA (1) is capable of specifically hybridizing to a nucleic acid having a sequence selected from SEQ ID NOs: 1 to 86; or (ii) comprises a sequence that is complementary to at least 15 contiguous nucleotides of a sequence selected from SEQ ID NOs: 1 to 86; or (iii) comprises at least 15 contiguous nucleotides of a sequence selected from SEQ ID NOs: 196 to 399, 950, 565 to 707, and 863 to 897. In some embodiments, a method comprises comparing the level of the at least one target RNA in the sample to a normal level of the at least one target RNA. In some embodiments, a level of at least one target RNA in the sample that is greater than a normal level of the at least one target RNA indicates the presence of sepsis in the subject.

Methods for facilitating the detection of sepsis in a subject are also provided. In some embodiments, the method comprises detecting a level of at least one target RNA in a sample from the subject. In some embodiments, the at least one target RNA (i) is capable of specifically hybridizing to a nucleic acid having a sequence selected from SEQ ID NOs: 1 to 86; or (ii) comprises a sequence that is complementary to at least 15 contiguous nucleotides of a sequence selected from SEQ ID NOs: 1 to 86; or (iii) comprises at least 15 contiguous nucleotides of a sequence selected from SEQ ID NOs: 196 to 399, 950, 565 to 707, and 863 to 897. In some embodiments, a method comprises communicating the results of the detection to a medical practitioner for the purpose of determining whether the subject has sepsis.

In some embodiments, detecting a level of at least one target RNA in a sample comprises hybridizing nucleic acids of the sample with at least one polynucleotide that is complementary to a target RNA in the sample or to a complement thereof. In some embodiments, a method further comprises detecting at least one complex comprising a polynucleotide hybridized to at least one nucleic acid selected from the target RNA, a DNA amplicon of the target RNA, and a complement of the target RNA.

In some embodiments, a method for detecting the presence of sepsis in a subject comprises obtaining a sample from the subject and providing the sample to a laboratory for detection of the level of at least one target RNA in the sample. In some embodiments, the at least one target RNA: (i) is capable of specifically hybridizing to a nucleic acid having a sequence selected from SEQ ID. NOs: 1 to 86; or (ii) comprises a sequence that is complementary to at least 15 contiguous nucleotides of a sequence selected from SEQ ID NOs: 1 to 86; or (iii) comprises at least 15 contiguous nucleotides of a sequence selected from SEQ ID NOs: 196 to 399, 950, 565 to 707, and 863 to 897. In some embodiments, the method comprises receiving from the laboratory a communication indicating the level of at least one target RNA in the sample. In some embodiments, a level of at least one target RNA that is greater than a normal level of the at least one target RNA indicates the presence of sepsis.

In some embodiments, a method comprises detecting levels of at least two, at least three, at least five, or at least ten target RNAs. In some embodiments, detection of a level of at least one target RNA that is greater than a normal level of the at least one target RNA indicates the presence of sepsis. In some embodiments, detection of levels of at least two target RNAs that are greater than normal levels of the at least two target RNAs indicates the presence of sepsis. In some embodiments, detection of levels of at least three target RNAs that are greater than normal levels of the at least two target RNAs indicates the presence of sepsis. In some embodiments, detection of levels of at least five target RNAs that are greater than normal levels of the at least two target RNAs indicates the presence of sepsis.

In some embodiments, a method comprises detecting a level of at least one target RNA that (i) does not specifically hybridize to a nucleic acid having a sequence selected from SEQ ID NOs: 1 to 86; and (ii) does not comprise a sequence that is complementary to at least 15 contiguous nucleotides of a sequence selected from SEQ ID NOs: 1 to 86; and (iii) does not comprise at least 15 contiguous nucleotides of a sequence selected from SEQ ID NOs: 196 to 399, 950, 565 to 707, and 863 to 897.

In some embodiments, a synthetic polynucleotide is provided. In some embodiments, a synthetic polynucleotide comprises a first region, wherein the first region comprises a sequence of at least 8, at least 9, at least 10, at least 11, at least 12, at least 13, at least 14, at least 15, at least 16, at least 17, or at least 18 contiguous nucleotides that is identical or complementary to a sequence of at least 8 contiguous nucleotides of one of SEQ ID NOs: 1 to 67, 215 to 399, and 950. In some embodiments, the first region is identical or complementary to a region of a target RNA. In some embodiments, a synthetic polynucleotide comprises a second region that is not identical or complementary to a region of the target RNA. In some embodiments, a synthetic polynucleotide comprises a detectable label. In some embodiments, a synthetic polynucleotide comprises a FRET label.

In some embodiments, a composition is provided. In some embodiments, a composition comprises a plurality of synthetic polynucleotides. In some embodiments, a kit is provided. In some embodiments, a kit comprises a synthetic polynucleotide. In some embodiments, a kit comprises a composition. In some embodiments, a kit comprises at least one polymerase and/or dNTPs.

Further embodiments and details of the inventions are described below

3. BRIEF DESCRIPTION OF THE FIGURES

FIG. 1 shows an electropherogram obtained on an Agilent Bioanalyser 2100 to assess the quality of total RNA purified as described in Example 1 from human monocyte cell line THP-1 after stimulation for 8 h with an agonist, Pam3CSK4.

4. DETAILED DESCRIPTION

4.1. Detecting Sepsis
4.1.1. General Methods

Methods detecting sepsis by measuring levels of microRNA species are provided. In some embodiments, elevated levels of microRNA species are indicative of sepsis. In some embodiments, reduced levels of microRNA species are indicative of sepsis. In some embodiments, the method comprises detecting an above-normal level of at least one target RNA that is capable of specifically hybridizing to a sequence selected from SEQ ID NOs: 1 to 86. In some embodiments, the method comprises detecting an above-normal level of at least one target RNA that comprises at least 15, at least 16, at least 17, at least 18, at least 19, at least 20, at least 21, at least 22, at least 23, or at least 24 contiguous nucleotides of a sequence selected from SEQ ID NO.: 196 to 399, 950, 565 to 707, and 863 to 897. In some embodiments, the method comprises detecting an above-normal level of at least one target RNA that comprises a sequence that is complementary to at least 15, at least 16, at least 17, at least 18, at least 19, at least 20, at least 21, at least 22, at least 23, or at least 24 contiguous nucleotides of a sequence selected from SEQ ID NO.:1 to 86. In some embodiments, the target RNA, in its mature form, comprises fewer than 30 nucleotides. The target RNA, in some embodiments, is a microRNA.

In the present disclosure, "a sequence selected from" encompasses both "one sequence selected from" and "one or more sequences selected from." Thus, when "a sequence selected from" is used, it is to be understood that one, or more than one of the listed sequences may be chosen.

Detection of a level of target RNA that is greater than a normal level of target RNA indicates the presence of sepsis in the patient from whom the sample is taken sample. In some embodiments, the detecting is done quantitatively. In other embodiments, the detecting is done qualitatively. In some embodiments, detecting a target RNA comprises forming a complex comprising a polynucleotide and a nucleic acid selected from a target RNA, a DNA amplicon of a target RNA, and a complement of a target RNA. In some embodiments, the level of the complex is then detected and compared to a normal level of the same complex. The level of the complex, in some embodiments, correlates with the level of the target RNA in the sample.

"Sepsis" is an infection accompanied by an acute inflammatory reaction (systemic inflammatory response syndrome) with systemic manifestations associated with release of endogenous mediators of inflammation into the bloodstream. If left untreated, sepsis can become severe sepsis, which is often accompanied by the failure of at least one organ or septic shock, which is severe sepsis accompanied by organ hypoperfusion and hypotension that are poorly responsive to initial fluid resuscitation. The systemic inflammatory response is mediated by toll-like receptors ("TLRs").

"Toll-like receptors" or "TLRs" are a class of proteins in vertebrates and invertebrates that recognize particular structurally conserved molecules on microorganisms that are distinguishable from host molecules, and which mediate immune cell responses. TLRs are located either on the surface of cells or in cellular compartments and are classified by the types of molecules they recognize and that stimulate them, as shown in Table 1.

TABLE 1

| Receptor | Ligand(s) | Microorganism | TLR Location |
|---|---|---|---|
| TLR1 | Multiple triacyl lipopeptides | Bacteria | Cell surface |
| TLR2 (TLR2a, TLR2b) | Multiple glycolipids Multiple lipopeptides Multiple lipoproteins Lipoteichoic acid Peptidoglycan Pam3CSK4 | Bacteria Bacteria Bacteria Bacteria (Gram positive) bacteria Bacteria | Cell surface |
| TLR3 | Double-stranded RNA, polyI:C | Viruses | Cell compartment |
| TLR4 (TLR4a, TLR4b) | Lipopolysaccharide | Gram-negative bacteria | Cell surface |
| TLR5 | Flagellin | Bacteria | Cell surface |
| TLR7 | Single-stranded RNA | Virus | Cell compartment |
| TLR9 | Unmethylated CpG DNA | Bacteria, viral | Cell compartment |

Stimulation of various TLRs results in over-expression of one or more target RNAs, as shown in Table 2. In some embodiments, one or more target RNAs is over-expressed as a result of stimulation of a subset of TLRs that recognize bacteria (e.g., TLR1, TLR2, TLR4 or TLR5). In some embodiments, one or more target RNAs is over-expressed as a result of stimulation of a subset of TLRs that recognize viruses (e.g. TLR3 or TLR7). In some embodiments, one or more target RNAs is over-expressed as a result of stimulation of a subset of TLRs that recognize molecules common to both bacteria and viruses (TLR9). In some embodiments, one or more target RNAs is over-expressed as a result of stimulation of a subset of TLRs that recognize gram-negative bacteria (e.g., TLR4a and TLR4b). In some embodiments, one or more target RNAs is over-expressed as a result of stimulation of a subset of TLRs that recognize both gram-negative and gram-positive bacteria (e.g., TLR2a, TLR2b and TLR5). In some embodiments, one or more target RNAs is over-expressed as a result of stimulation of a subset of TLRs that recognize gram-positive bacteria, gram-negative bacteria and mycobacteria (e.g., TLR2a).

Table 2, below, lists 86 hybridization probes that have been found to be complimentary to, and to hybridize with, target RNAs in human monocytes stimulated with various toll-like receptor agonists (ligands). These target RNAs can be detected at elevated levels in stimulated THP-1 cells as demonstrated in Example 1. Sixty-seven of the probes are complementary to, and hybridize with, novel target RNA species that are expressed in human cells. The other nineteen probes are complementary to, and hybridize with, publicly known microRNAs that have been submitted by others to miRBase (microrna.sanger.ac.uk/; see Griffiths-Jones S. et al. (2007) *Nucl. Acids Res.* 36:154-158): hsa-miR-1227, hsa-miR-125b, hsa-miR-125 b, hsa-miR-142-3p, hsa-miR-155, hsa-miR-16, hsa-miR-195*, hsa-miR-214, hsa-miR-29b, hsa-miR-326, hsa-miR-371-3p, hsa-miR-371-5p, hsa-miR-374b*, hsa-miR-520c-5p, hsa-miR-526a, hsa-miR-518d-5p, hsa-miR-524-5p, hsa-miR-525-3p, hsa-miR-525-5p, hsa-miR-579, hsa-miR-885-3p and hsa-miR-99b). However, to the knowledge of the inventors, these known microRNAs have not been disclosed to have utility for detection of sepsis. The sequences of those microRNAs are shown in Table 4. Certain candidate microRNAs that may hybridize to certain probes listed in Table 2 are shown in Table 11.

Table 12, below, lists microRNAs that are present at elevated levels in a sepsis patient sample. Some pairs of microRNAs listed in Table 12 have the same sequences. In such instances, the precursor gene for that microRNA sequence is located at multiple locations in the genome, so the sequence may be from any of those genes. When a precursor gene for a particular microRNA sequence is present at multiple locations in the genome, multiple candidate names are shown (based on each of the precursor genes), with the same ranking and same sequence. One or more of those candidates may be upregulated in the sepsis patient sample. Some of the microRNAs listed in Table 12 are isomirs of one another. When multiple isomirs are listed in Table 12, one or more than one of the isomirs may be present at elevated levels in a sample from a patient with sepsis.

Table 14 lists microRNAs from miRBase that are present at elevated levels in a sepsis patient sample.

Table 16 lists microRNA star forms that are present at elevated levels in a sepsis patient sample. While the mature microRNAs for the listed star forms have been identified and are submitted into miRBase, none of the star forms in Table 16 have, to the inventors' knowledge, been previously identified or submitted to miRBase.

In some embodiments, a method comprises detecting multiple isomirs with a single probe. Detection of an elevated level of one or multiple isomirs is considered to be indicative of sepsis. When multiple microRNAs having the same sequence but are expressed from different genes, one or more of the genes may be upregulated in a sepsis patient. Detection of a microRNA expressed from any one of the genes is considered to be indicative of sepsis.

For convenience of reference herein, and not by way of limitation, some "target RNA" species are denominated "microRNAs" in the tables set forth herein and Example 1. In some embodiments, the target RNA is a single mature microRNA capable of specifically hybridizing to a hybridization probe set forth in Table 2. In some embodiments, a target RNA is a single mature microRNA that comprises a sequence that is complementary to at least 15 contiguous nucleotides of a sequence selected from SEQ ID NO.:1 to 86. In some embodiments, a target RNA is a single mature microRNA that comprises at least 15 contiguous nucleotides of a sequence selected from SEQ ID NOs: 196 to 399, 950, 565 to 707, and 863 to 897. In some embodiments, target RNA may include a plurality of target RNAs, all of which are capable of specifically hybridizing to a single complementary probe sequence (for example, when two or more target microRNAs are isomirs). In some embodiments, the so-denominated "microRNA" is one or more RNA species capable of specifically hybridizing to the respective hybridization probe, such that one or more target RNAs do not meet canonical definitions for mature microRNAs. In some embodiments, a target RNA is an mRNA. In some embodiments, the "target RNA" is a piwi-interacting RNA (piRNA), i.e., a small RNA expressed in animal cells that is distinct in size (26-31 nt) from microRNA and that forms distinct complexes with Piwi proteins that are involved in transcriptional gene silencing.

Mature human microRNAs are typically composed of 17-27 contiguous ribonucleotides, and often are 21 or 22 nucleotides in length. The sequences of some target microRNAs that can be detected in accordance with the present disclosure can be found within the pre-microRNA sequences shown in Tables 3, 13, 15, and 17 (SEQ ID NOs: 87 to 177, 948, 400 to 564, 949, 708 to 862, and 898 to 932). The sequences of some publicly known microRNAs are shown in Tables 4 and 14. Further, in some embodiments, a microRNA comprises at least 10, at least 11, at least 12, at least 13, at least 14, at least 15, at least 16, at least 17, at least 18, at least 19, at least 20, at least 21, at least 22, at least 23, at least 24, at least 25, or at least 26 contiguous nucleotides of a sequence in Table 11, 12, or 16 (SEQ ID NOs: 215 to 399, 950, and 863 to 897).

While not intending to be bound by theory, mammalian microRNAs mature as described herein. A gene coding for a microRNA is transcribed, leading to production of a microRNA precursor known as the "pri-microRNA" or "pri-miRNA." The pri-miRNA can be part of a polycistronic RNA comprising multiple pri-miRNAs. In some circumstances, the pri-miRNA forms a hairpin with a stem and loop, which may comprise mismatched bases. The hairpin structure of the pri-miRNA is recognized by Drosha, which is an RNase III endonuclease protein. Drosha can recognize terminal loops in the pri-miRNA and cleave approximately two helical turns into the stem to produce a 60-70 nucleotide precursor known as the "pre-microRNA" or "pre-miRNA." Drosha can cleave the pri-miRNA with a staggered cut typical of RNase III endonucleases yielding a pre-miRNA stem loop with a 5' phosphate and an approximately 2-nucleotide 3' overhang. Approximately one helical turn of the stem (about 10 nucleotides) extending beyond the Drosha cleavage site can be essential for efficient processing. The pre-miRNA is subsequently actively transported from the nucleus to the cytoplasm by Ran-GTP and the export receptor Exportin-5.

The pre-miRNA can be recognized by Dicer, another RNase III endonuclease. In some circumstances, Dicer recognizes the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and an approximately 2-nucleotide 3' overhang. The resulting siRNA-like duplex, which may comprise mismatches, comprises the mature microRNA and a similar-sized fragment known as the microRNA*. The microRNA and microRNA* may be derived from opposing arms of the pri-miRNA and pre-miRNA. The mature microRNA is then loaded into the RNA-induced silencing complex ("RISC"), a ribonucleoprotein complex. In some cases, the microRNA* also has gene silencing or other activity.

TABLE 2

| Probe | Probe Sequence (5' to 3' without linker) | Probe SEQ ID NO. | Gram+, Myco-bacteria, Gram- TLR2a | gram+, gram- TLR2b | Gram- TLR4b | Gram- TLR4a | gram+, gram- TLR5 |
|---|---|---|---|---|---|---|---|
| 10096-L3-1 | TTCAGAATGTTAAGTCCCTATCCTTCGAT | 1 | | | | | |
| 10118-L4-1 | AGAGCAACAGAGGGTTTGTGTAGGACTATGAGAGTGGCG | 2 | | | | | |
| 10179-L4-1 | TGGAACCTTTAGCAGCCAAACAGATTGCACAATCTC | 3 | | | | | |
| 10201-L4-1 | CCCATTAAGAAATTGCAAGGCTAATAAAAATCATGC | 4 | | | | | |
| 10201-R4-1 | GCAGGATTCTACCAGCCAGCCCTCAGGG | 5 | | | | | |
| 10225-L3-1 | AATTAGGCAGTTAATATATTGTAACTAATA | 6 | | | 11 | | |
| 10231-L3-1 | GTGCAGCAGCCCGCGCCAGCCTCCGCAGCCGCC | 7 | | | | | |
| 10562_A-L4-1 | CCCTACCTGTCAGTGTGACCATCACGAGCCTCCTGAGACCTCCTCTC | 8 | 17 | | | | |
| 10630-L3-1 | TTCATACAAACCTCCAACATTAAATTGCTA | 9 | | | | | |
| 11556-L4-1 | ACAAACCACTAAGGAAGGAAGTGGCATACATTCTGCT | 10 | | | | | |
| 11744-R4-1 | GGAAAATGTTTGGCGTCAAGTTCTTAAAAATGCTTCCTCCTCTTTTTTCC | 11 | 4.31 | | 13 | | |
| 12381-L4-1 | GACAGAGAGAGTGAGAGTGCGAGCTCACAGG | 12 | 5.00 | | | | |
| 12428-R4-1 | GCTCTTTAGCACTTTTACCCTTTGAAAATATAAAATCAC | 13 | 7 | | 5 | | |
| 12432-L4-1 | AAAGACTCATCAGATCCATTTCCAAAGTACAGCTC | 14 | 15 | | | | |
| 12473-L4-1 | TGCCAGAGGCTGTAATTGGTCTCAGGTAGTCTCTG | 15 | 6 | | 6 | | |
| 3817-L2-2 | TCCCTGCAGCTGGCCAGCAATTACCGCCTGCCAG | 16 | | | | | |
| 3923-L3-1 | AACACAAGAAGAAACGCCTGGTGCAGAGCC | 17 | | | 11 | | |
| 3953-R3-2 | ACTCCAGCCTCCGCCGCCTCAGCTTCCCGAGC | 18 | | | | | |
| 3995-L2-2 | CTATAAAACTTCGAAAAGTCCCTCCTCCTCACGT | 19 | | | 7 | | |
| 4214-R4-1 | AAAGCTGGCAGGGCTTGTGAGCTCTGCAGG | 20 | | | 12 | | |
| 4256-L1-1 | AAATAATCAAGCTGTCACATCTTAAAAATC | 21 | | | 14 | | |
| 4315_I-L4-1 | ACACCTCTGCGCCCCTCAGGCGCCCTGGGCCTCGGCGCCCCGCCCGTCCCAG | 22 | 1.91 | | | | |
| 4440-L3-2 | TTTGACATTCAGAGCACTGGGCAGAAATCACA | 23 | | 2 | | | |
| 448-L4-1 | GCTTCTGATGATCTATTAATGCAATACATCAGGGTGAG | 24 | | | | | |
| 4483-L3-1 | ATGTCATTGAAAGGGGTATAATTGTGGTCTCC | 25 | | | | | |
| 4504-L3-1 | ATTGATTTTACATTTTCCTGCCCTGCTAC | 26 | | | | | |
| 4972-R3-2 | AGATCAAACAGGCTGTGAAGAAGCTCTATGAC | 27 | | | 8 | | |
| 5230-L4-1 | CCCAGGGTCACCCAACACACTCTGCCTTGAGCCTC | 28 | | | | | |
| 5316-R3-1 | AAATTAAATTGACACTTTGAAGCATTAATCTA | 29 | | | 56 | | |
| 5342-L3-1 | CACCACCAAACCAAATGCCGCTGCTCTCCTTCCA | 30 | | | | | 4.30 |
| 5491-L3-2 | TGCCTCCGCGGCCGCAGGTAATGACCTGGAAGG | 31 | | | | | |
| 5598-R2-2 | CTCCCACCTCCGTGAAGCTATTTTAACTGTGCA | 32 | | | | | |
| 5619-R3-1 | ATTGGATCAAACAGACGGGCACAATCA | 33 | | | 35 | | |
| 5749-R3-1 | ACAAGCATCATAATCCCCCTTTTGACTT | 34 | 5.60 | | 7 | 21 | |

TABLE 2-continued

| Name | Sequence | SEQ ID NO | | | | |
|---|---|---|---|---|---|---|
| 5956-L3-1 | GCTCTGCCAACCCCAAATCCGTCAAGACGCATAG | 35 | | | 5 | |
| 6087-L4-1 | CTGTCTCCATTACTGCCTGCCACCTTCTCCATC | 36 | | | | |
| 6192-L3-1 | AGATAAAAAACCACCCACCCAGCAC | 37 | | | | |
| 6395-R1-2 | GCTCAGAGCCAGTGTAATCCTCCTCTTGTGT | 38 | | | | 8 |
| 6428-R1-1 | TGCCACTCTCATCACAGGGTGCAATAGCATA | 39 | | 14 | | |
| 6433-L4-1 | CAGCTAGCTCTTGCTGCCTCTGCTGCTCAGCCTTCT | 40 | | | | |
| 6511-R4-1 | AGCTAACAATATATTAAAACATAATATCTATTTAGCAGGT | 41 | | | | |
| 6647-R2-1 | CTCAGCCCCAGCTGGAGAATTTTTCCCCTCATTA | 42 | | | | |
| 6693-L3-2 | GAAAGAATTACACTTGACAGAGGCAGAGGAAAATGC | 43 | | | | |
| 6998-L2-1 | CAGCACAGTGGAGAAAAGTAACTGTCTTT | 44 | | | | |
| 7094-L3-1 | ATGACAGGATAATAACATTACATTAAAA | 45 | | | 44 | |
| 7158-R3-1 | TACATTTATAGATTCCCTCTTCAGCCATA | 46 | | | 8 | |
| 7271-L2-1 | CAGCTATTTATTCTTGACATCAATTTCTGAAA | 47 | | 13 | | |
| 7411-L3-2 | CTGCTGTTTTATTGTCACAGCTGGAGCCAGTTC | 48 | | 18 | | |
| 7824-R3-1 | TGGTGCCAGCTTCATCGCCG | 49 | | | 13 | |
| 7828-R1-1 | GCCAATCAATAATTCTGTGCCAAGCAACT | 50 | | | | |
| 7997-L1-1 | TCCGTTACACTAATTGCCATGATTTAGTCCAA | 51 | | | | |
| 8012-L3-1 | CCATCTTTACTAGATTTATAATTTGAG | 52 | | | | 39 |
| 8016-R3-1 | AGAGGGGGTTGCTGAGCCGCCTGCAAGA | 53 | | | | |
| 8075-L3-1 | CCCAGCTACACCTCCACGCA | 54 | | | | |
| 8433_D-L4-1 | ACTAAAAGGAGCCGGAGGAGCTGGAGAGACGCGGGGCCGAGCCGGG | 55 | | | | |
| 8468-L3-2 | AGCCATCCATTTAAATGAAAATCAGCACTGATACA | 56 | | 18 | 13 | 31 |
| 8505-L3-1 | CTACGTGTGTCCTTTCTTTCACATTTGCTG | 57 | | 41 | | |
| 9229-R3-1 | CTGACATTTATCTTCAGCATCTAG | 58 | | 16 | 43 | |
| 9369-R3-2 | GAATTTTCCCCTGCACAGTTAGGACAGGATGCATG | 59 | 5 | | | |
| 9391-R3-1 | CAGCTGCCAGGGAGACATAGAAATTAAAAACAA | 60 | | | | 3 |
| 9576-L3-2 | TCTGTTGATTGATTATATTTATCAGTGTAGAAGA | 61 | | | | |
| 9638-R3-1 | TGGTCATCAAACCTCAGCCTCTATCCCATCAA | 62 | 6 | | | |
| 9654-L4-1 | GTTGAGAGTGAGCATAGCTTTGACTCTGCAAACTAAAAGTTCCAGG | 63 | 28 | | | |
| 9688-L2-1 | GCTAAATGGCCCCAGACTGTTCTGCTGCA | 64 | 13 | | | |
| 9840-L3-2 | TTCAGGTTTTTATAAATCAGGATGTCAACAAAT | 65 | | | | 3 |
| 9850-L3-1 | CTGCCAAGATACCTGATTT | 66 | | | | |
| 9850-R3-1 | CCAGAAGATGCAGAAGACAG | 67 | | 12 | | 12 |
| miR-1227 | CTGGGGAAAAGGGTGGCACG | 68 | | | | |
| miR-125b | TCACAAGTTAGGGTCTCAGGGA | 69 | | | 5 | |
| miR-142-3p | TCCATAAAGTAGGAAACACTACA | 70 | | | | |
| miR-155 | ACCCCTATCACGATTAGCATTAA | 71 | 1 | 2.50 | 1.42 | 1.33 |
| miR-16 | CGCCAATATTTACGTGCTGCTA | 72 | | | | |

TABLE 2-continued

| | | | | | |
|---|---|---|---|---|---|
| miR-195* | GGAGCAGCACAGCCAATATTGG | 73 | | 780 | 93 107 |
| miR-214 | ACTGCCTGTCTGTGCCTGCTGT | 74 | 2352 | 1910 | |
| miR-29b | AACACTGATTTCAAATGGTGCTA | 75 | | | |
| miR-326 | CTGGAGGAAGGGCCCAGAGG | 76 | | 8 | 44 181 |
| miR-371-3p | ACACTCAAAAGATGGCGGCACTT | 77 | | | |
| miR-371-5p | AGTGCCCCCACAGTTTGAGT | 78 | 4 | | |
| miR-374b* | AATGATAATACAACCTGCTAAG | 79 | | 621 | |
| miR-520c-5p miR-526a miR-518d-5p | CAGAAAGTGCTTCCCTCTAGAG | 80 | | | |
| miR-524-5p | GAGAAAGTGCTTCCCTTTGTAG | 81 | | | |
| miR-525-3p | CGCTCTAAAGGGAAGCGCCTTC | 82 | | | |
| miR-525-5p | AGAAAGTGCATCCCTCTGGAG | 83 | | | |
| miR-579 | AATCGCGGTTTATACCAAATGAA | 84 | | | 1.29 |
| miR-885-3p | TATCCACTACACCCCGCTGCCT | 85 | | | |
| miR-99b | CGCAAGGTCGGTTCTACGGGTG | 86 | 5 | 8 | 5 |

| | Bacterial and Viral | Viral infection | |
|---|---|---|---|
| Probe | Infection Unmethylated CpG (bacterial, Viral) TLR9 | Viral nucleic acid TLR3 | Viral nucleic acid TLR7 |
| 10096-L3-1 | | 12.00 | |
| 10118-L4-1 | | | |
| 10179-L4-1 | | 14.00 | |
| 10201-L4-1 | | 12.00 | |
| 10201-R4-1 | | 5.00 | |
| 10225-L3-1 | | | |
| 10231-L3-1 | | | 2.70 |
| 10562_A-L4-1 | | | |
| 10630-L3-1 | 22.00 | | |
| 11556-L4-1 | | 7.00 | |
| 11744-R4-1 | | | |
| 12381-L4-1 | | | |
| 12428-R4-1 | | | |
| 12432-L4-1 | | | |
| 12473-L4-1 | | | |
| 3817-L2-2 | | | 3.00 |
| 3923-L3-1 | | | |
| 3953-R3-2 | 1.77 | | |
| 3995-L2-2 | | | |
| 4214-R4-1 | | | |
| 4256-L1-1 | | | |
| 4315_I-L4-1 | | | |
| 4440-L3-2 | | | |
| 448-L4-1 | | 7.00 | |
| 4483-L3-1 | | 14.00 | |
| 4504-L3-1 | | 8.00 | |
| 4972-R3-2 | | | |
| 5230-L4-1 | | | 7.00 |
| 5316-R3-1 | | | |
| 5342-L3-1 | 2.70 | | |
| 5491-L3-2 | | 7.00 | 12.00 |
| 5598-R2-2 | | | 2.30 |
| 5619-R3-1 | | | |
| 5749-R3-1 | | | |
| 5956-L3-1 | | | 11.00 |
| 6087-L4-1 | 5.00 | | 1.00 |
| 6192-L3-1 | | | 8.00 |
| 6395-R1-2 | | | |
| 6428-R1-1 | | | |
| 6433-L4-1 | | | |
| 6511-R4-1 | | 5.00 | |
| 6647-R2-1 | | | 1.70 |
| 6693-L3-2 | | 4.60 | |

TABLE 2-continued

| Candidate | | | |
|---|---|---|---|
| 6998-L2-1 | | 9.00 | |
| 7094-L3-1 | | | |
| 7158-R3-1 | | | |
| 7271-L2-1 | | | |
| 7411-L3-2 | | | |
| 7824-R3-1 | | | |
| 7828-R1-1 | 73.00 | | |
| 7997-L1-1 | 238.00 | | |
| 8012-L3-1 | | | |
| 8016-R3-1 | | | 13.00 |
| 8075-L3-1 | | | 5.00 |
| 8433_D-L4-1 | | 7.40 | |
| 8468-L3-2 | | | |
| 8505-L3-1 | | | |
| 9229-R3-1 | | | |
| 9369-R3-2 | | | |
| 9391-R3-1 | 5.00 | | 3.00 |
| 9576-L3-2 | | | 10.00 |
| 9638-R3-1 | | | |
| 9654-L4-1 | | 14.00 | |
| 9688-L2-1 | | | |
| 9840-L3-2 | | | 3.00 |
| 9850-L3-1 | | | 11.00 |
| 9850-R3-1 | | | |
| miR-1227 | | 7.00 | |
| miR-125b | | | |
| miR-142-3p | 1.87 | | |
| miR-155 | | 0.90 | |
| miR-16 | 2.39 | | |
| miR-195* | | | |
| miR-214 | | | |
| miR-29b | 2.02 | | |
| miR-326 | | | |
| miR-371-3p | | | 11.00 |
| miR-371-5p | | | |
| miR-374b* | | | |
| miR-520c-5p | | | 9.00 |
| miR-526a | | | |
| miR-518d-5p | | | |
| miR-524-5p | | | 34.00 |
| miR-525-3p | | | 14.00 |
| miR-525-5p | | | 9.00 |
| miR-579 | | | |
| miR-885-3p | | | 3.80 |
| miR-99b | | | |

TABLE 3

| Pre-microRNA Candidate | Chromosomal location | Pre-microRNA sequences | Pre-micro RNA SEQ ID NO. |
|---|---|---|---|
| 10096-L3-1 | 5q14.3 | AAGTCTTACAATTCAGGGATAGGAAGCTATGATTTACATAATGAACATGGCAAAGAGACCTATAAAGAAATAAGACTT | 87 |
| 10118-L4-1 | 9q33.3 | CGCCACTCTCATAGTCCTACACAAACCCTCTGTTGCTCTTCTATTAGACCATGCTAACCAATTCTGAGGGCTGTGAGGGGTAGGTG | 88 |
| 10179-L4-1 | 3q13.31 | GTTGAGATTGTGCAATCTGTTTGGCTGCTAAAGGTTCCAAATTATGTGGGCATTCTGCAGCCCCACAGAGTGGTAGAATTTCTTC | 89 |
| 10201-L4-1 | 6p12.2 | GCATGATTTTTATTAGCCTTGCAATTTCTTAATGGGCTCCCCTGAGGGCTGGCTGGTAGAATCCTGC | 90 |
| 10201-R4-1 | 6p12.2 | GCATGATTTTTATTAGCCTTGCAATTTCTTAATGGCTCCCCTGAGGGCTGGCTGGTAGAATCCTGC | 91 |
| 10225-L3-1 | 10q26.13 | TATTAGTTACAATATATTAACTGCCTAATTTAAAAATAAAACTATCTTTATGAAGGGCAATTAACCACTAAGTGTAATTGATA | 92 |
| 10231-L3-1 | 9p11.2 | GGCGGCTGCGGAGGCTGGCGCGGGCTGCTGCACCTTTAACGCTTTCTGGCGCTGACAGGCGGCGGCCCAGCTAAAGTTCACAGCGCC | 93 |
| 10562_A-L4-1 | 8p12 | GAGAGGAGGTCTCAGGAGGCTCGTGATGGTCACACTGACAGGTAGGGCTTTCACTCCCATCCCCTCTTGATACTCACCTGCCGCCCCCGACCCCTCTC | 94 |
| 10630-L3-1 | 1p35.3 | TAGCAATTTAATGTTGGAGGTTTGTATGAACTTGAAGCTTATTTCAGTTGGTTGCCTGGAACCTTCTGCATTCTTTGCTG | 95 |

TABLE 3-continued

| Pre-microRNA Candidate | Chromosomal location | Pre-microRNA sequences | Pre-micro RNA SEQ ID NO. |
|---|---|---|---|
| 11556-L4-1 | 10q23.32 | AGCAGAATGTATGCCACTTCCTTCCTTAGTGGTTTGTCCGCCAACATTAACAGGCCATTGGGTGGATGAAGTAGGTAAATTTTGCT | 96 |
| 11744-R4-1 | 1q32.2 | GGAGAGCTGTGTTTCATGTGATTAGAGACTGTTTGTGCCTCTGTCCATTAGGAAAAAGAGGAGGAAGCATTTTTAAGAACTTGACGCCAAACATTTTCC | 97 |
| 12381-L4-1 | 6p21.33 | CCTGTGAGCTCGCACTCTCACTCTCTCTGTCTCTGTGTCAGGAGTGAATGGTGTGGGCTCCTCAGG | 98 |
| 12428-R4-1 | 8p12 | GCTAAAGTTGCTTCTGCCCTTTGAAAATATGAAAGCCCTTGAGTGATTTTATATTTTCAAAGGGTAAAAGTGCTAAAGAGC | 99 |
| 12432-L4-1 | 8p12 | TGAGCTGTACTTTGGAAATGGATCTGATGAGTCTTTTAATAGAAGAAAATCATCATTATTTCCCAAGAGCTCA | 100 |
| 12473-L4-1 | 9p21.3 | CAGAGACTACCTGAGACCAATTACAGCCTCTGGCATTTGTGCTGCTAAATTTGTAATGAGTTGCAGGTGTTTGTG | 101 |
| 3817-L2-2 | 2q13 | TCTGGCAGGCGGTAATTGCTGGCCAGCTGCAGGGATTACAGCCCTGTGAGCTGTGTTCAGGGCCCTGTGCCAGG | 102 |
| 3923-L3-1 | 19p12 | GGCTCTGCACCAGGCGTTTCTTCTTGTGTTTCCTCTTCTCTTCTGGAGAGGGATGAAGGAGATCCTTTGTGAGAGGC | 103 |
| 3953-R3-2 | 9q33.3 | GCTCCTGCTCCGCCGCGGGAGCTGCTCCGGCGGCCGCAGGGCTCGCTCGGGAAGCTGAGGCGGCGGAGGCTGGAGT | 104 |
| 3995-L2-2 | 7p21.1 | TGGCCTGACGTGAGGAGGAGGGACTTTTCGAAGTTTTATAGGAAAGTTTCCGCTTTCCAGTCCCCCTCCCCCGTCCCA | 105 |
| 4214-R4-1 | 8p12 | GAGGTTGGACAGGCTTCTCCACACTGAGCTTTACAGGCCCGCTCCCTCCCCTGCAGAGCTCACAAGCCCTGCCAGCTTT | 106 |
| 4256-L1-1 | 2p22.1 | GATTTTTAAGATGTGACAGCTTGATTATTTTACAAGGCCAAAACCCTGATTCAAGCCTGCAATTTTAAGAATC | 107 |
| 4315_I-L4-1 | 1q22 | CTGGGACGGGCGGGGCGCCGAGGCCCAGGGCGCCTGAGGGGCGCAGAGGTGTCAGCGTGCAACCGCCGCCCCCCAGCGTTCCCGCCACCACCGCCACCACCCTCAAAGCCCGG | 948 |
| 4440-L3-2 | 7q11.22 | GTGATGTGATTTCTGCCCAGTGCTCTGAATGTCAAACTGAAGAAATTCAGTGAAATGCGGGTAAACGGCGGGAGTAACTATGAC | 108 |
| 448-L4-1 | 8q21.12 | CTCACCCTGATGTATTGCATTAATAGATCATCAGAAGCAGTTGTCATTCCAGTGATATATTAGTGCAATACATGAGAATGAG | 109 |
| 4483-L3-1 | 16q12.1 | GGAGACCACAATTATACCCCCTTTCAATGACATGTCTGGGGTTGCAGTGACTCCAGACAAAGAAGCTGAAATGTATGAAAGTTTCC | 110 |
| 4504-L3-1 | 13q14.3 | GTAGCAGGGCAGGAAAATGTAAAATCAATAAATAATCAGGCTGAATTTTAATTGAATATATTCCTAAGGCCATGCTGAC | 111 |
| 4972-R3-2 | 3p26.3 | CATCAGGTCGAATCAGGGTGTTGACCTTGGCCACATCAATGTCATAGAGCTTCTTCACAGCCTGTTTGATCTGGTG | 112 |
| 5230-L4-1 | 9q33.2 | GAGGCTCAAGGCAGAGTGTGTTGGGTGACCCTGGGTAGGGCTTGGTTGGCCACTTACCACATGGTTGCCACTGGGGCCTT | 113 |
| 5316-R3-1 | 13q14.3 | CTGAACAAATAGCAGATGTTGATGAATATTAATTTGTGCTTAGATTAATGCTTCAAAGTGTCAATTTAATTTCTGTTTTACTATTCAG | 114 |
| 5342-L3-1 | 8p21.2 | TGGAAGGAGAGCAGCGGCATTTGGTTTGGTGGTGGGCAGATTTTCTTTTACGACTGCTAAATGCCTGCCTTTCTCCCCA | 115 |
| 5491-L3-2 | 6p21.33 | GCCTCCCCTTCCAGGTCATTACCTGCGGCCGCGGAGGCAACAGCTGCCACCATGGCCTGATGAGTGATCTGGTGGGCGACGG | 116 |
| 5598-R2-2 | 11q13.2 | CTCCCACGGCCTGAAGCTGCTGCCAAGCTATTTTGGTTCTGCACAGTTAAAAATAGCTTCACGGAGGTGGGAG | 117 |
| 5619-R3-1 | 15q25.3 | CTCATTGAGGGAAGATTGAGCAGAACTGGCATTGCTTGCTTTCGTCAAATTGATTGTGCCCGTCTGTTTGATCCAATTCAGTGAG | 118 |
| 5749-R3-1 | 18q23 | ACAGGCTCATCCCTCTGAACAGATGAGATTAGTCGATCATGTAAAGTCAAAAGGGGATTATGATGCTTGT | 119 |
| 5956-L3-1 | 1q41 | CTATGCGTCTTGACGGATTTGGGGTTGGCAGAGCAGGCTGCCCCTGCTTTCTATCCCCATTCAGTCCACTTATAG | 120 |

TABLE 3-continued

| Pre-microRNA Candidate | Chromosomal location | Pre-microRNA sequences | Pre-microRNA SEQ ID NO. |
|---|---|---|---|
| 6087-L4-1 | 9q33.1 | GATGGAGAAGGTGGCAGGCAGTAATGGAGACAGAATTTCTGTTAACTGCTGTAATTAATGTTATGTCTCATC | 121 |
| 6192-L3-1 | 11q25 | GTGCTGGGTGGGTGGTTTTTTATCTTCACGGATTTATGGAGTCCTTAAAACATCTGTTCCGTTCTGATTCCCCCGCTCAGTAC | 122 |
| 6395-R1-2 | 14q11.2 | GTTCCGAGGCAGGCTTTCCTCCTCTCTGCAGGGGAGAGGCTCCCTCACACAAGAGGAGGATTACACTGGCTCTGAGC | 123 |
| 6428-R1-1 | 2p24.1 | AAACTGGAACACATTCCTCAAGGGAGCAGGAAAGCATGAGAAGACAGTATGCTATTGCACCCTGTGATGAGAGTGGCAGTTT | 124 |
| 6433-L4-1 | 1q24.2 | AGAAGGCTGAGCAGCAGAGGCAGCAAGAGCTAGCTGCACATACCCAGCAACAGCCTTCCACTTCTGATCAGTCTTCT | 125 |
| 6511-R4-1 | 1q24.1 | AGCAAATTTACTATTGGGAATAAATATTTGATGCAGGTGAACACCTGCTAAATAGATATTATGTTTTAATATATTGTTAGCT | 126 |
| 6647-R2-1 | 1q23.3 | CTCAGTATCTTCAGCTTGGGAAACTGACCTCGTTAATTTTAATGAGGGGAAAAATTCTCCAGCTGGGGCTGAG | 127 |
| 6693-L3-2 | 11q24.1 | GACTGCAGGCATTTTCCTCTGCCTCTGTCAAGTGTAATTCTTTCTTGATGAATGACAAGGCAGGATAATAGGCTGTGGTC | 128 |
| 6998-L2-1 | 11p14.1 | AAAGACAGTTACTTTTCTCCACTGTGCTGCTACCACCAATTTGGTGGCTATTAATAGCTGGCAGATTAACTTCTTT | 129 |
| 7094-L3-1 | 2p23.2 | TTTTAATGTAATGTTATTATCCTGTCATTTAATTTAGCAATGACAAGTGATGATGAGATTTTGATTTGCATTAGAA | 130 |
| 7158-R3-1 | 3q13.31 | ATTCAACACAGATTCAGGTGCTCTCAACAGCCATGAAAATATATGGCTGAAGAGGGAATCTATAAATGTAATGAAT | 131 |
| 7271-L2-1 | 11p12 | AGGTGATGTTTTCAGAAATTGATGTCAAGAATAAAATAGCTGTTGGCAGTTACAACTGTTTGGATGTCATTTTACAAAACAATTGCCT | 132 |
| 7411-L3-2 | 18q22.3 | GAGTGTGAACTGGCTCCAGCTGTGACAATAAAACAGCAGGTGGCTGCTGTCATTAGGGGTGGCAGATGAGGCAGGGGACTAACATTC | 133 |
| 7824-R3-1 | 6q16.2 | CCTGGATGCTGTTTCATTATGTAGAGTCAGGCAAAAGACAGACGGATGTGTGTGTGAGGCGGCGATGAAGCTGGCACCAGG | 134 |
| 7828-R1-1 | 11q24.3 | GAGATTAGCGAAAGGGATTCTGGCCAAATCCCTGATCAAGTTGCTTGGCACAGAATTATTGATTGGCAAATCTT | 135 |
| 7997-L1-1 | 2q31.1 | TTGGACTAAATCATGGCAATTAGTGTAACGGAAATGTTTACAGCAATCTCTGATGGCAGTTCTACTAATGCAATGATTTAGCTCAA | 136 |
| 8012-L3-1 | 3q11.2 | AAATATTTATGTACTCAAATTATAAATCTAGTAAAGATGGCATTTCACCTTATACTAGTTATTTATTAATAATGAGAGCTGTATTT | 137 |
| 8016-R3-1 | 12q21.1 | AGAGGGGTGACTGCGGGGCTTGTTGCGCTGAAGATTTACAATGTACTTCTTGCAGGCGGCTCAGCAACCCCCTCT | 138 |
| 8075-L3-1 | 10q22.1 | CAGCTGGCCTGGTGCCCTGGTGCGTGGAGGTGTAGCTGGGCTCTGACCCAGCTCCTCAAACAGGTTCCATATGGCCCTCCCGGCTG | 139 |
| 8433_D-L4-1 | 17q25.3 | CCCGGCTCGGCCCCGCGTCTCTCCAGCTCCTCCGGCTCCTTTTAGTGCATAAATTAGTGATGGCATTTCCCGGAGAGCGGAGCACAACACAGGGCGCCGGGCTCGGG | 140 |
| 8468-L3-2 | 15q23 | GAGAGATTGTATCAGTGCTGATTTTCATTTAAATGGATGGCTATGAGATTTTTTAAAGCATGCCAAAAATCTGTTTGTACATCTCTC | 141 |
| 8505-L3-1 | 2p16.1 | CAGCAAATGTGAAAGAAAGGACACACGTAGGTACTGTCATTTAGGTAATGTCATCTATGATCAGTTTTTGTTTCATTTTTTGCTG | 142 |
| 9229-R3-1 | 11q25 | CTGACATTTACTTTCACTCATGAGCACAGGGGTGACCAGCCCCACCAGTCCTAGATGCTGAAGATAAATGTCAG | 143 |
| 9369-R3-2 | Xq26.3 | TCCCCTGATTTCCCTCTGTGGAAGAATGTGTGAATTCACATGCATCCTGTCCTAACTGTGCAGGGAAAATTCCAGTCAGGGGA | 144 |
| 9391-R3-1 | 2p14 | TAGCTGCCTCAGAGTAGAAAATAAAACTCAACAAGATTTATCTTGTTTTTAATTTCTATGTCTCCCTGGCAGCTG | 145 |

TABLE 3-continued

| Pre-microRNA Candidate | Chromosomal location | Pre-microRNA sequences | Pre-microRNA SEQ ID NO. |
|---|---|---|---|
| 9576-L3-2 | 1p21.2 | TTAAATTCTTCTACACTGATAAATATAATCAATCAACAGAGAACATGCTCTGAGGAATTAATTGTTGTCAGTTGATGTATTTAA | 146 |
| 9638-R3-1 | 8p21.3 | GCTATAATGGAAAACTGATGGCTTTTATCTCCCCAACTTTATGACTATTGATGGGATAGAGGCTGAGGTTTGATGACCATTTAATAGC | 147 |
| 9654-L4-1 | 3p25.3 | CCTGGAACTTTTAGTTTGCAGAGTCAAAGCTATGCTCACTCTCAACAATTGTAGAGAGGCTTTCTGGCTGGGCAATCTAAAAAACCGGG | 148 |
| 9688-L2-1 | Xq26.2 | TGCAGCAGAACAGTCTGGGGCCATTTAGCTTAGGGGCAAATAGTTCCTCATACTTCAAAGAGCCCTAAGGACATTGCTGCA | 149 |
| 9840-L3-2 | 5q14.1 | CTTGTATTTGTTGACATCCTGATTTATAAAAACCTGAACAAGTTCAGTTTCAATAATTCTTTTTGTTCAAGGAACACAAG | 150 |
| 9850-L3-1 | 5p15.2 | CCAGGAGAAATCAGGTATCTTGGCAGTGTGACCACCATGAATAAACAACAACTCTGGTGGCCTGTCTTCTGCATCTTCTGG | 151 |
| 9850-R3-1 | 5p15.2 | CCAGGAGAAATCAGGTATCTTGGCAGTGTGACCACCATGAATAAACAACAACTCTGGTGGCCTGTCTTCTGCATCTTCTGG | 152 |
| miR-1227 | 19p13.3 | GTGGGGCCAGGCGGTGGTGGGCACTGCTGGGGTGGGCACAGCAGCCATGCAGAGCGGGCATTTGACCCCGTGCCACCCTTTTCCCCAG | 153 |
| miR-125b | 21q21.1 | ACCAGACTTTTCCTAGTCCCTGAGACCCTAACTTGTGAGGTATTTTAGTAACATCACAAGTCAGGCTCTTGGGACCTAGGCGGAGGGGA | 154 |
| miR-125b | 11q24.1 | TGCGCTCCTCTCAGTCCCTGAGACCCTAACTTGTGATGTTTACCGTTTAAATCCACGGGTTAGGCTCTTGGGAGCTGCGAGTCGTGCT | 155 |
| miR-142-3p | 17q23.2 | GACAGTGCAGTCACCCATAAAGTAGAAAGCACTACTAACAGCACTGGAGGGTGTAGTGTTTCCTACTTTATGGATGAGTGTACTGTG | 156 |
| miR-155 | 21q21.3 | CTGTTAATGCTAATCGTGATAGGGGTTTTTGCCTCCAACTGACTCCTACATATTAGCATTAACAG | 157 |
| miR-16 | 13q14.2 | GTCAGCAGTGCCTTAGCAGCACGTAAATATTGGCGTTAAGATTCTAAAATTATCTCCAGTATTAACTGTGCTGCTGAAGTAAGGTTGAC | 158 |
| miR-16 | 3q25.33 | GTTCCACTCTAGCAGCACGTAAATATTGGCGTAGTGAAATATATATTAAACACCAATATTACTGTGCTGCTTTAGTGTGAC | 159 |
| miR-195* | 17p13.1 | AGCTTCCCTGGCTCTAGCAGCACAGAAATATTGGCACAGGGAAGCGAGTCTGCCAATATTGGCTGTGCTGCTCCAGGCAGGGTGGTG | 160 |
| miR-214 | 1q24.3 | GGCCTGGCTGGACAGAGTTGTCATGTGTCTGCCTGTCTACACTTGCTGTGCAGAACATCCGCTCACCTGTACAGCAGGCACAGACAGGCAGTCACATGACAACCCAGCCT | 161 |
| miR-29b | 7q32.3 | CTTCAGGAAGCTGGTTTCATATGGTGGTTTAGATTTAAATAGTGATTGTCTAGCACCATTTGAAATCAGTGTTCTTGGGGG | 162 |
| miR-29b | 1q32.2 | CTTCTGGAAGCTGGTTTCACATGGTGGCTTAGATTTTTCCATCTTTGTATCTAGCACCATTTGAAATCAGTGTTTTAGGAG | 163 |
| miR-326 | 11q13.4 | CTCATCTGTCTGTTGGGCTGGAGGCAGGGCCTTTGTGAAGGCGGGTGGTGCTCAGATCGCCTCTGGGCCCTTCCTCCAGCCCCGAGGCGGATTCA | 164 |
| miR-371-3p | 19q13.42 | GTGGCACTCAAACTGTGGGGGCACTTTCTGCTCTCTGGTGAAAGTGCCGCCATCTTTTGAGTGTTAC | 165 |
| miR-371-5p | 19q13.42 | GTGGCACTCAAACTGTGGGGGCACTTTCTGCTCTCTGGTGAAAGTGCCGCCATCTTTTGAGTGTTAC | 166 |
| miR-374b* | Xq13.2 | ACTCGGATGGATATAATACAACCTGCTAAGTGTCCTAGCACTTAGCAGGTTGTATTATCATTGTCCGTGTCT | 167 |
| miR-518d-5p | 19q13.42 | TCCCATGCTGTGACCCTCTAGAGGGAAGCACTTTCTGTTGTCTGAAAGAAACCAAAGCGCTTCCCTTGGAGCGTTACGGTTTGAGA | 168 |
| miR-520c-5p | 19q13.42 | TCTCAGGCTGTCGTCCTCTAGAGGGAAGCACTTTCTGTTGTCTGAAAGAAAAGAAAGTGCTTCCTTTTAGAGGGTTACCGTTTGAGA | 169 |
| miR-526a | 19q13.42 | GTGACCCTCTAGAGGGAAGCACTTTCTGTTGAAAGAAAAGAACATGCATCCTTTCAGAGGGTTAC | 170 |
| miR-526a | 19q13.42 | CTCAGGCTGTGACCCTCTAGAGGGAAGCACTTTCTGTTGCTTGAAAGAAGAAAGCGCTTCCTTTTAGAGGATTACTCTTTGAG | 171 |
| miR-524-5p | 19q13.42 | TCTCATGCTGTGACCCTACAAAGGGAAGCACTTTCTCTTGTCCAAAGGAAAAGAAGGCGCTTCCCTTTGGAGTGTTACGGTTTGAGA | 172 |

TABLE 3-continued

| Pre-microRNA Candidate | Chromosomal location | Pre-microRNA sequences | Pre-microRNA SEQ ID NO. |
|---|---|---|---|
| miR-525-3p | 19q13.42 | CTCAAGCTGTGACTCTCCAGAGGGATGCACTTTCTCTTATGTGAAAAAAAAGAAGGCGCTTCCCTTT AGAGCGTTACGGTTTGGG | 173 |
| miR-525-5p | 19q.13.42 | CTCAAGCTGTGACTCTCCAGAGGGATGCACTTTCTCTTATGTGAAAAAAAAGAAGGCGCTTCCCTTT AGAGCGTTACGGTTTGGG | 174 |
| miR-579 | 5p13.3 | CATATTAGGTTAATGCAAAAGTAATCGCGGTTTGTGCCAGATGACGATTTGAATTAATAAATTCATT TGGTATAAACCGCGATTATTTTTGCATCAAC | 175 |
| miR-885-3p | 3p25.3 | CCGCACTCTCTCCATTACACTACCCTGCCTCTTCTCCATGAGAGGCAGCGGGGTGTAGTGGATAGAG CACGGGT | 176 |
| miR-99b | 19q13.41 | GGCACCCACCCGTAGAACCGACCTTGCGGGGCCTTCGCCGCACACAAGCTCGTGTCTGTGGGTCCGT GTC | 177 |

TABLE 4

Mature microRNA Sequences (5' to 3')

| microRNA | sequence | SEQ ID NO |
|---|---|---|
| miR-1227 | CGUGCCACCCUUUUCCCCAG | 196 |
| miR-125b | UCCCUGAGACCCUAACUUGUGA | 197 |
| miR-142-3p | CAUAAAGUAGAAAGCACUACU | 198 |
| miR-155 | UUAAUGCUAAUCGUGAUAGGGGU | 199 |
| miR-16 | UAGCAGCACGUAAAUAUUGGCG | 200 |
| miR-195* | CCAAUAUUGGCUGUGCUGCUCC | 201 |
| miR-214 | ACAGCAGGCACAGACAGGCAGU | 202 |
| miR-29b | UAGCACCAUUUGAAAUCAGUGUU | 203 |
| miR-326 | CCUCUGGGCCCUUCCUCCAG | 204 |
| miR-371-3p | AAGUGCCGCCAUCUUUUGAGUGU | 205 |
| miR-371-5p | ACUCAAACUGUGGGGGCACU | 206 |
| miR-374b* | CUUAGCAGGUUGUAUUAUCAUU | 207 |
| miR-518d-5p miR-520c-5p miR-526a | CUCUAGAGGGAAGCACUUUCUG | 208 |
| miR-524-5p | CUACAAAGGGAAGCACUUUCUC | 209 |
| miR-525-3p | GAAGGCGCUUCCCUUUAGAGCG | 210 |
| miR-525-5p | CUCCAGAGGGAUGCACUUUCU | 211 |
| miR-579 | UUCAUUUGGUAUAAACCGCGAUU | 212 |
| miR-885-3p | AGGCAGCGGGGUGUAGUGGAUA | 213 |
| miR-99b | CACCCGUAGAACCGACCUUGCG | 214 |

In Table 2, the expression levels of target RNAs measured for stimulation of each of the identified TLRs are expressed as fold-changes in expression relative to expression levels measured in total RNA from human monocytes of healthy donors (see Example 1).

In some embodiments, target RNAs can be measured in samples collected at one or more times from a patient to monitor the status or progress of sepsis in the patient.

In some embodiments, the clinical sample to be tested is obtained from individuals who exhibit one or more symptoms of a systemic inflammatory response, including a body temperature greater than 38° C. or less than 36° C., a heart rate greater than 90 beats/minute, a respiratory rate greater than 20 breaths/min (or Paco2 less than 32 mm Hg), and a white blood cell count greater than 12,000 cells/μL or less than 4000 cells/μL, or with a content of greater than 10% immature forms. In some embodiments, the clinical sample to be tested is obtained from individuals who exhibit two or more of the above-described symptoms. In some embodiments, the clinical sample to be tested is obtained from asymptomatic individuals who are at risk for contracting sepsis, such as individuals who are elderly, immuno-compromised, critically ill, or are currently patients in, or have recently been discharged from, a hospital.

In some embodiments, the methods described herein are used for early detection of sepsis in a sample of human cells, such as those obtained by routine blood test. In some embodiments, the sample of human cells is a sample of human leukocytes. In some embodiments, the sample of human cells is a sample of human monocytes. Although for simplicity the discussion below refers to a sample of human monocytes, the skilled artisan will appreciate that the sample of human cells that can be used in the disclosed methods can include any human cells in which TLRs are expressed.

Thus, in some embodiments, methods of the present disclosure can be used for routine screening of individuals at risk for sepsis. In some embodiments, methods herein are used to (1) screen individuals who are elderly, (2) screen individuals who are immuno-compromised, (3) screen individuals who are critically ill or (4) screen individuals who are patients in, or have recently been discharged from, a hospital. In some embodiments, methods herein are used to screen neonates (less than 90 days old) with fever.

In some embodiments, the methods described herein can be used to determine the source of the underlying infection in a septic individual for targeted treatment of the underlying infection. In some embodiments, an increase in expression levels of one or more target RNAs associated with the stimulation of TLR2a, TLR2b, TLR4a, TLR4b or TLR5 indicates the presence of a bacterial infection in a septic individual. In some embodiments, an increase in expression levels of one or more target RNAs associated with the stimulation of TLR4a or TLR4b indicates the presence of an infection of gram-negative bacterial infection in the septic individual. In some embodiments, an increase in expression levels of one or more target RNAs associated with stimulation of TLR2a. TLR2b or TLR5 without concomitant stimulation of either TLR4a or TLR4b indicates the presence of a gram-positive bacterial infection in the septic individual. In some embodiments, an increase in expression levels of one or more target RNAs associated with stimulation of TLR2a without concomitant stimulation of TLR4a or TLR4b indicates the presence of either a gram-positive bacterial infection or a mycobacterial infection. In some embodiments, an increase in expression levels of one or more target RNAs associated with the stimulation of TLR3 or TLR7 indicates the presence of a viral infection. In some embodiments, an increase in expression levels of one or more target RNAs associated with the stimulation of TLR9 indicates the presence of a viral infection and/or a bacterial infection. In some embodiments, an increase in expression levels of: (i) one or more target RNAs associated with stimulation of TLR2a, TLR2b, TLR4a, TLR4b or TLR5; and (ii) one or more target RNAs associated with stimulation of TLR3 or TLR7 indicates the presence of both viral and bacterial infection.

In some embodiments, the methods described herein can be used to assess the effectiveness of a treatment for sepsis in a patient. In some embodiments, the target RNA expression levels are determined at various times during the treatment, and are compared to target RNA expression levels from an archival sample taken from the patient, e.g., by blood test, before the manifestation of any signs of sepsis or before beginning treatment. Ideally, target RNA expression levels in the normal blood sample evidence no aberrant changes in target RNA expression levels. Thus, in such embodiments, the progress of treatment of an individual with sepsis can be assessed by comparison to a sample from the same individual when he was healthy or prior to beginning treatment.

In some embodiments, the sample to be tested is a bodily fluid, such as blood, sputum, mucus, saliva, urine, semen, etc. In some embodiments, a sample to be tested is a blood sample. In some embodiments, the blood sample is whole blood, plasma, serum, or blood cells. In some embodiments, the blood sample is separated monocytes and/or lymphocytes. Monocytes and/or lymphocytes can be separated from whole blood by any method. In some embodiments, monocytes can be separated from whole blood or a fractionated or separated portion of whole blood using antibodies, e.g., to a cell surface receptor on the monocytes (such as CD14). In some such embodiments, the antibodies are coupled to beads, such as magnetic beads.

The clinical sample to be tested is, in some embodiments, freshly obtained. In other embodiments, the sample is a fresh frozen specimen.

In embodiments in which the method comprises detecting expression of more than one target RNA, the expression levels of the plurality of target RNAs may be detected concurrently or simultaneously in the same assay reaction. In some embodiments, expression levels are detected concurrently or simultaneously in separate assay reactions. In some embodiments, expression levels are detected at different times, e.g., in serial assay reactions.

In some embodiments, a method comprises detecting the level of at least one target RNA in a sample from a subject, wherein detection of a level of at least one target RNA that is greater than a normal level of the at least one target RNA indicates the presence of sepsis in the subject. In some embodiments, a method comprises detecting the level of at least one target RNA in a sample from a subject and comparing the level of the at least one target RNA in the sample to a normal level of the at least one target RNA, wherein a level of at least one target RNA in the sample that is greater than a normal level of the at least one target RNA indicates the presence of sepsis in the subject.

In some embodiments, a method of facilitating diagnosis of sepsis in a subject is provided. Such methods comprise detecting the level of at least one target RNA in a sample from the subject. In some embodiments, information concerning the level of at least one target RNA in the sample from the subject is communicated to a medical practitioner. A "medical practitioner," as used herein, refers to an individual or entity that diagnoses and/or treats patients, such as a hospital, a clinic, a physician's office, a physician, a nurse, or an agent of any of the aforementioned entities and individuals. In some embodiments, detecting the level of at least one target RNA is carried out at a laboratory that has received the subject's sample from the medical practitioner or agent of the medical practitioner. The laboratory carries out the detection by any method, including those described herein, and then communicates the results to the medical practitioner. A result is "communicated," as used herein, when it is provided by any means to the medical practitioner. In some embodiments, such communication may be oral or written, may be by telephone, in person, by e-mail, by mail or other courier, or may be made by directly depositing the information into, e.g., a database accessible by the medical practitioner, including databases not controlled by the medical practitioner. In some embodiments, the information is maintained in electronic form. In some embodiments, the information can be stored in a memory or other computer readable medium, such as RAM, ROM, EEPROM, flash memory, computer chips, digital video discs (DVD), compact discs (CDs), hard disk drives (HDD), magnetic tape, etc.

In some embodiments, methods of detecting the presence sepsis are provided. In some embodiments, methods of diagnosing sepsis are provided. In some embodiments, the method comprises obtaining a sample from a subject and providing the sample to a laboratory for detection of at least one target RNA level in the sample. In some embodiments, the method further comprises receiving a communication from the laboratory that indicates the at least one target RNA level in the sample. In some embodiments, sepsis is present if the level of at least one target RNA in the sample is greater than a normal level of the at least one target RNA. A "laboratory," as used herein, is any facility that detects the level of at least one target RNA in a sample by any method, including the methods described herein, and communicates the level to a medical practitioner. In some embodiments, a laboratory is under the control of a medical practitioner. In some embodiments, a laboratory is not under the control of the medical practitioner.

When a laboratory communicates the level of at least one target RNA to a medical practitioner, in some embodiments, the laboratory communicates a numerical value representing the level of at least one target RNA in the sample, with or without providing a numerical value for a normal level. In some embodiments, the laboratory communicates the level of at least one target RNA by providing a qualitative value, such as "high," "elevated." etc.

As used herein, when a method relates to detecting sepsis, determining the presence of sepsis, and/or diagnosing sepsis, the method includes activities in which the steps of the method are carried out, but the result is negative for the presence of sepsis. That is, detecting, determining, and diagnosing sepsis include instances of carrying out the methods that result in either positive or negative results (e.g., whether target RNA levels are normal or greater than normal).

As used herein, the term "subject" means a human. In some embodiments, the methods described herein may be used on samples from non-human animals.

The common, or coordinate, expression of target RNAs that are physically proximal to one another in the genome permits the informative use of such chromosome-proximal target RNAs in methods herein.

Table 3 identifies the chromosomal location of each of the 86 target RNAs capable of specifically hybridizing to a nucleic acid comprising a sequence selected from SEQ ID NOs: 1 to 86 in Table 2. Table 13 identifies the chromosomal location of the target RNAs capable of specifically hybridizing to a nucleic acid comprising a sequence selected from SEQ ID NOs: 226 to 399 and 950 in Table 12. Table 15 identifies the chromosomal location of the target RNAs capable of specifically hybridizing to a nucleic acid comprising a sequence selected from SEQ ID NOs: 565 to 707 in Table 14. Table 17 identifies the chromosomal location of the target RNAs capable of specifically hybridizing to a nucleic acid comprising a sequence selected from SEQ ID NOs: 863 to 897 in Table 16. Thus, in some embodiments, the level of expression of one or more target RNAs located within about 1 kilobase (kb), within about 2 kb, within about 5 kb, within about 10 kb, within about 20 kb, within about 30 kb, within about 40 kb, and even within about 50 kb of the chromosomal locations in Table 2 and Table 14 is detected in lieu of, or in addition to, measurement of expression of the respective tabulated target RNA in the methods described herein. See Baskerville, S. and Bartel D. P. (2005) RNA 11:241-247.

In some embodiments, in combination with detecting one or more target RNAs capable of specifically hybridizing to a nucleic acid comprising a sequence selected from SEQ ID NOs:1 to 67 and/or detecting one or more target RNAs comprising at least 15 contiguous nucleotides of a sequence selected from SEQ ID NOs: 196 to 399, 950, 565 to 707, and 863 to 897 and/or detecting one or more target RNAs that comprise a sequence that is complementary to at least 15 contiguous nucleotides of a sequence selected from SEQ ID NOs:1 to 67, methods herein further comprise detecting the level(s) of expression of at least one microRNA from the human miRNome.

In some embodiments, at least one target RNA is capable of specifically hybridizing to a nucleic acid comprising a sequence selected from SEQ ID NOs: 1 to 86. In some embodiments, at least one target RNA comprises at least 15 contiguous nucleotides that are complementary to at least a portion of a sequence selected from SEQ ID NOs: 1 to 86. In some embodiments, at least one target RNA comprises at least 15 contiguous nucleotides of a sequence selected from SEQ ID NOs: 196 to 399, 950, 565 to 707, and 863 to 897. In some embodiments, a target RNA, in its mature form, comprises fewer than 30 nucleotides. In some embodiments, a target RNA is a microRNA.

In some embodiments, more than one target RNA is detected simultaneously in a single reaction. In some embodiments, at least 2, at least 3, at least 5, or at least 10 target RNAs are detected simultaneously in a single reaction. In some embodiments, all target RNAs are detected simultaneously in a single reaction.

In some embodiments, an increase in expression of one or more target RNAs capable of specifically hybridizing to a nucleic acid comprising a sequence selected from SEQ ID NO: 1 to 86 in Table 2 in a sample is indicative of the presence of sepsis in an individual from whom the sample of blood or tissue has been taken. In some embodiments, an increase in expression of one or more target RNAs that comprise at least 15 contiguous nucleotides that are complementary to at least a portion of a sequence selected from SEQ ID NO: 1 to 86 in Table 2 in a sample is indicative of the presence of sepsis in an individual from whom the sample of blood or tissue has been taken. In some embodiments, an increase in expression of one or more target RNAs that comprise at least 15 contiguous nucleotides of a sequence selected from SEQ ID NOs: 196 to 399, 950, 565 to 707, and 863 to 897 in a sample is indicative of the presence of sepsis in an individual from whom the sample of blood or tissue has been taken.

In some embodiments, an increase in expression of one or more target RNAs capable of specifically hybridizing to a nucleic acid comprising a sequence selected from SEQ ID NO: 1, 2, 3, 4, 5, 7, 10, 12, 16, 18, 22, 24, 25, 26, 28, 30, 31, 32, 35, 36, 37, 41, 42, 43, 44, 53, 54, 55, 60, 61, 63, 65, 66, 68, 71, 77, 80, 81, 82, 83 or 85 in Table 2 is indicative of the presence of sepsis caused by viral infection.

In some embodiments, an increase in expression of one or more target RNAs capable of specifically hybridizing to a nucleic acid comprising a sequence selected from SEQ ID NO: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 or 86 in Table 2 in a sample of human monocytes is indicative of the presence of sepsis caused by a bacterial infection. In some embodiments, an increase in expression of one or more target RNAs capable of specifically hybridizing to a nucleic acid comprising a sequence selected from SEQ ID NO: 6, 11, 13, 15, 17, 19, 20, 21, 27, 29, 33, 34, 35, 38, 45, 46, 47, 48, 49, 56, 58, 69, 71, 73, 76, 84 or 86 in Table 2 in a sample of human monocytes is indicative of the presence of sepsis caused by an infection of gram-negative bacteria. In some embodiments, an increase in expression of one or more target RNAs capable of specifically hybridizing to a nucleic acid comprising a sequence selected from SEQ ID NO: 23, 30, 39, 52, 57, 60 65, 67 or 79 in Table 2 in a sample of human monocytes is indicative of the presence of sepsis caused by an infection of gram positive bacteria. In some embodiments, an increase in expression of one or more target RNAs capable of specifically hybridizing to a nucleic acid comprising a sequence selected from SEQ ID NO: 8, 14, 59, 62, 63, 64, 74 or 78 in Table 2 in a sample of human monocytes is indicative of the presence of sepsis caused by an infection of gram positive bacteria or mycobacteria.

In some embodiments, an increase in expression of one or more target RNAs capable of specifically hybridizing to a nucleic acid comprising a sequence selected from SEQ ID NO: SEQ ID NO: 9, 50, 51, 70, 72 or 75 in Table 2 in a sample of human monocytes is indicative of the presence of unmethylated CpG nucleic acids caused by a bacterial and/or a viral infection.

In some embodiments, an increase in expression of one or more target RNAs capable of specifically hybridizing to a nucleic acid comprising a sequence selected from SEQ ID NO: 1, 2, 3, 4, 5, 7, 10, 12, 16, 18, 22, 24, 25, 26, 28, 30, 31, 32, 35, 36, 37, 41, 42, 43, 44, 53, 54, 55, 60, 61, 63, 65, 66, 68, 71, 77, 80, 81, 82, 83 or 85 in Table 2 in a sample of human monocytes is indicative of stimulation of a toll-like receptor that recognizes virally-derived molecules. In some embodiments, these toll-like receptors are selected from TLR3 and TLR7.

In some embodiments, an increase in expression of one or more target RNAs capable of specifically hybridizing to a nucleic acid comprising a sequence selected from SEQ ID NO: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 or 86 in Table 2 in a sample of human monocytes is indicative of stimulation of a toll-like receptor that recognizes bacterially-derived molecules. In some embodiments, these toll-like receptors are selected from TLR2a, TLR2b, TLR4a, TLR4b and TLR5. In some embodiments, an increase in expression of one or more target RNAs capable of specifically hybridizing to a nucleic acid comprising a sequence selected from SEQ ID NO: 6, 11, 13, 15, 17, 19, 20, 21, 27, 29, 33, 34, 35, 38, 45, 46, 47, 48, 49, 56, 58, 69, 71, 73, 76, 84 or 86 in Table 2 in a sample of human monocytes is indicative of stimulation of a toll-like receptor that recognizes molecules derived from gram-negative bacteria. In some embodiments, these toll-like receptors are selected from TLR2a, TLR2b, TLR4a, TLR4b and TLR5. In some embodiments, an increase in expression of one or more target RNAs capable of specifically hybridizing to a nucleic acid comprising a sequence selected from SEQ ID NO: 23, 30, 39, 52, 57, 60 65, 67 or 79 in Table 2 in a sample of human monocytes is indicative of stimulation of a toll-like receptor that recognizes molecules derived from gram-positive bacteria. In some embodiments, these toll-like receptors are selected from TLR2a, TLR2b and TLR5. In some embodiments, an increase in expression of one or more target RNAs capable of specifically hybridizing to a nucleic acid comprising a sequence selected from SEQ ID NO: 8, 14, 59, 62, 63, 64, 74 or 78 in Table 2 in a sample of human monocytes is indicative of stimulation of a toll-like receptor that recognizes molecules derived from gram-positive bacteria or mycobacteria, such as TLR2a.

In some embodiments, an increase in expression of one or more target RNAs capable of specifically hybridizing to a nucleic acid comprising a sequence selected from SEQ ID NO: 9, 50, 51, 70, 72 or 75 in Table 2 in a sample of human monocytes is indicative of stimulation of TLR9, which recognizes unmethylated CpG nucleic acids caused by a bacterial and/or a viral infection.

In some embodiments, an increase in expression of one or more target RNAs comprising at least 15, at least 16, at least 17, at least 18, at least 19, at least 20, at least 21, at least 22, at least 23, or at least 24 contiguous nucleotides of a sequence selected from SEQ ID NOs: 226 to 289, 565 to 604, and 863 to 868 in a sample of human monocytes is indicative of sepsis. In some embodiments, an increase in expression of one or more target RNAs comprising at least 15, at least 16, at least 17, at least 18, at least 19, at least 20, at least 21, at least 22, at least 23, or at least 24 contiguous nucleotides of a sequence selected from SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, and 648 in a sample of human monocytes is indicative of sepsis. In some embodiments, an increase in expression of one or more target RNAs comprising at least 15, at least 16, at least 17, at least 18, at least 19, at least 20, at least 21, at least 22, at least 23, or at least 24 contiguous nucleotides of a sequence selected from SEQ ID NOs: 231, 236, 242, 260, 261, 266, 287, 566, 567, 568, 571, 570, 574, 580, 581, 588, 598, 601, 608, 624, 626, 629, and 632 in a sample of human monocytes is indicative of sepsis. In some embodiments, an increase in expression of one or more target RNAs comprising at least 15, at least 16, at least 17, at least 18, at least 19, at least 20, at least 21, at least 22, at least 23, or at least 24 contiguous nucleotides of a sequence selected from SEQ ID NOs: 231, 236, 237, 242, 245, 253, 260, 261, 262, 263, 266, 269, 275, 287, 303, 342, and 352 in a sample of human monocytes is indicative of sepsis. In some embodiments, an increase in expression of one or more target RNAs comprising at least 15, at least 16, at least 17, at least 18, at least 19, at least 20, at least 21, at least 22, at least 23, or at least 24 contiguous nucleotides of a sequence selected from SEQ ID NOs: 231, 236, 242, 260, 261, 266, and 287 in a sample of human monocytes is indicative of sepsis.

4.1.2. Exemplary Controls

In some embodiments, a normal level (a "control") for each target RNA can be determined as an average level or range that is characteristic of normal human monocytes or other reference material, against which the level measured in the sample can be compared. The determined average or range of target RNA in normal subjects can be used as a benchmark for detecting above-normal or below-normal levels of target RNA indicative of sepsis. In some embodiments, normal levels of target RNA can be determined using individual or pooled RNA-containing samples from one or more individuals, such as from healthy individuals or from intensive care patients with similar clinical severity of disease (e.g., having matched ICU clinical (APACHE II) scores) to those diagnosed with sepsis syndrome, but without diagnosis of sepsis syndrome.

In some embodiments, determining a normal level of expression of a target RNA comprises detecting a complex comprising a probe hybridized to a nucleic acid selected from a target RNA, a DNA amplicon of the target RNA, and a complement of the target RNA. That is, in some embodiments, a normal level of expression can be determined by detecting a DNA amplicon of the target RNA, or a complement of the target RNA rather than the target RNA itself. In some embodiments, a normal level of such a complex is determined and used as a control. The normal level of the complex, in some embodiments, correlates to the normal level of the target RNA. Thus, when a normal level of a target is discussed herein, that level can, in some embodiments, be determined by detecting such a complex.

In some embodiments, a control comprises RNA from cells of a single individual, e.g., a healthy individual or an intensive care patient with similar clinical severity of disease (e.g., having matched ICU clinical (APACHE II) scores) to a patient being tested for sepsis, but without diagnosis of sepsis syndrome. In some embodiments, a control comprises RNA from a pool of cells from multiple individuals. In some embodiments, a control comprises commercially-available human RNA, such as, for example, total RNA from CD14+ cells. In some embodiments, a normal level or normal range has already been predetermined prior to testing a sample for an elevated level.

In some embodiments, the normal level of target RNA can be determined from one or more continuous cell lines, typically cell lines previously shown to have expression levels of the at least one target RNA that approximate the level of expression in normal human monocytes.

In some embodiments, a method comprises detecting the level of expression of at least one target RNA. In some embodiments, a method further comprises comparing the level of expression of at least one target RNA to a normal level of expression of the at least one target RNA. In some embodiments, a method further comprises comparing the level of expression of at least one target RNA to a control level of expression of the at least one target RNA. A control level of expression of the at least one target RNA is, in some embodiments, the level of expression of the at least one target RNA in a normal cell. In some such embodiments, a control level may be referred to as a normal level. In some embodiments, a greater level of expression of the at least one target RNA relative to the level of expression of the at least one target RNA in a normal cell indicates sepsis. In some embodiments, a reduced level of expression of the at least one target RNA relative to the level of expression of the at least one target RNA in a normal cell indicates sepsis.

In some embodiments, the level of expression of the at least one target RNA is compared to a reference level of expression, e.g., from a patient with a confirmed case of sepsis syndrome. In some such embodiments, a similar level of expression of the at least one target RNA relative to the reference sample indicates sepsis.

In some embodiments, a level of expression of at least one target RNA that is at least about two-fold greater than a normal level of expression of the respective at least one target RNA indicates the presence of sepsis. In some embodiments, a level of expression of at least one target RNA that is at least about two-fold greater than the level of the respective at least one target RNA in a control sample comprised of normal cells indicates the presence of a sepsis. In various embodiments, a level of expression of at least one target RNA that is at least about 3-fold, at least about 4-fold, at least about 5-fold, at least about 6-fold, at least about 7-fold, at least about 8-fold, at least about 9-fold, or at least about 10-fold greater than the level of expression of the respective at least one target RNA in a control sample comprised of normal cells indicates the presence of sepsis. In various embodiments, a level of expression of at least one target RNA that is at least about 3-fold, at least about 4-fold, at least about 5-fold, at least about 6-fold, at least about 7-fold, at least about 8-fold, at least about 9-fold, or at least about 10-fold greater than a normal level of expression of the at least one target RNA indicates the presence of sepsis.

In some embodiments, a level of expression of at least one target RNA that is reduced by at least about two-fold relative to a normal level of expression of the respective at least one target RNA indicates the presence of sepsis. In some embodiments, a level of expression of at least one target RNA that is reduced by at least about two-fold as compared to the level of the respective at least one target RNA in a control sample comprised of normal cells indicates the presence of a sepsis. In various embodiments, a level of expression of at least one target RNA that is reduced by at least about 3-fold, at least about 4-fold, at least about 5-fold, at least about 6-fold, at least about 7-fold, at least about 8-fold, at least about 9-fold, or at least about 10-fold as compared to the level of expression of the respective at least one target RNA in a control sample comprised of normal cells indicates the presence of sepsis. In various embodiments, a level of expression of at least one target RNA that is reduced by at least about 3-fold, at least about 4-fold, at least about 5-fold, at least about 6-fold, at least about 7-fold, at least about 8-fold, at least about 9-fold, or at least about 10-fold as compared to a normal level of expression of the at least one target RNA indicates the presence of sepsis.

In some embodiments, a control level of expression of a target RNA is determined contemporaneously, such as in the same assay or batch of assays, as the level of expression of the target RNA in a sample. In some embodiments, a control level of expression of a target RNA is not determined contemporaneously as the level of expression of the target RNA in a sample. In some such embodiments, the control level of expression has been determined previously.

In some embodiments, the level of expression of a target RNA is not compared to a control level of expression, for example, when it is known that the target RNA is expressed at very low levels, or not at all, in normal cells. In such embodiments, detection of a high level of the target RNA in a sample is indicative of sepsis.

4.1.3. Exemplary Methods of Preparing RNAs

Target RNA can be prepared by any appropriate method. Total RNA can be isolated by any method, including, but not limited to, the protocols set forth in Wilkinson, M. (1988) Nucl. Acids Res. 16(22):10, 933; and Wilkinson, M. (1988) Nucl. Acids Res. 16(22): 10934, or by using commercially-available kits or reagents, such as the TRIzol® reagent (Invitrogen™), Total RNA Extraction Kit (iNtRON Biotechnology), Total RNA Purification Kit (Norgen Biotek Corp.), RNAqueous™ (Ambion), MagMAX™ (Ambion), RecoverAll™ (Ambion), RNeasy (Qiagen), etc.

In some embodiments, small RNAs are isolated or enriched. In some embodiments "small RNA" refers to RNA molecules smaller than about 200 nucleotides (nt) in length. In some embodiments, "small RNA" refers to RNA molecules smaller than about 100 nt, smaller than about 90 nt, smaller than about 80 nt, smaller than about 70 nt, smaller than about 60 nt, smaller than about 50 nt, or smaller than about 40 nt.

Enrichment of small RNAs can be accomplished by method. Such methods include, but are not limited to, methods involving organic extraction followed by adsorption of nucleic acid molecules on a glass fiber filter using specialized binding and wash solutions, and methods using spin column purification. Enrichment of small RNAs may be accomplished using commercially-available kits, such as mirVana™ Isolation Kit (Applied Biosystems), mirPremier™ microRNA Isolation Kit (Sigma-Aldrich), PureLink™ miRNA Isolation Kit (Invitrogen), miRCURY™ RNA isolation kit (Exiqon), microRNA Purification Kit (Norgen Biotek Corp.), miRNeasy kit (Qiagen), etc. In some embodiments, purification can be accomplished by the TRIzol® (Invitrogen) method, which employs a phenol/isothiocyanate solution to which chloroform is added to separate the RNA-containing aqueous phase. Small RNAs are subsequently recovered from the aqueous by precipitation with isopropyl alcohol. In some embodiments, small RNAs can be purified using chromatographic methods, such as gel electrophoresis using the flashPAGE™ Fractionator available from Applied Biosystems.

In some embodiments, small RNA is isolated from other RNA molecules to enrich for target RNAs, such that the small RNA fraction (e.g., containing RNA molecules that are 200 nucleotides or less in length, such as less than 100 nucleotides in length, such as less than 50 nucleotides in length, such as from about 10 to about 40 nucleotides in length) is substantially pure, meaning it is at least about 80%, 85%, 90%, 95% pure or more, but less than 100% pure, with respect to larger RNA molecules. Alternatively, enrichment of small RNA can be expressed in terms of fold-enrichment. In some embodiments, small RNA is enriched by about, at least about, or at most about 5×, 10×, 20×, 30×, 40×, 50×, 60×, 70×, 80×, 90×, 100×, 110×, 120×, 130×, 140×, 150×, 160×, 170×, 180×, 190×, 200×, 210×, 220×, 230×, 240×, 250×, 260×, 270×, 280×, 290×, 300×, 310×, 320×, 330×, 340×, 350×, 360×, 370×, 380×, 390×, 400×, 410×, 420×, 430×, 440×, 450×, 460×, 470×, 480×, 490×, 500×, 600×, 700×, 800×, 900×, 1000×, 1100×, 1200×, 1300×, 1400×, 1500×, 1600×, 1700×, 1800×, 1900×, 2000×, 3000×, 4000×, 5000×, 6000×, 7000×, 8000×, 9000×, 10,000× or more, or any range derivable therein, with respect to the concentration of larger RNAs in an RNA isolate or total RNA in a sample.

In yet other embodiments, expression is measured in a sample in which RNA has not first been purified from the cells.

In some embodiments, RNA is modified before target RNAs are detected. In some embodiments, the modified RNA is total RNA. In other embodiments, the modified RNA is small RNA that has been purified from total RNA or from cell lysates, such as RNA less than 200 nucleotides in length, such as less than 100 nucleotides in length, such as less than 50 nucleotides in length, such as from about 10 to about 40 nucleotides in length. RNA modifications that can be utilized in the methods described herein include, but are not limited to, the addition of a poly-dA or a poly-dT tail, which can be accomplished chemically or enzymatically, and/or the addition of a small molecule, such as biotin.

In some embodiments, one or more target RNAs are reverse transcribed. In some embodiments, where present, RNA is modified when it is reverse transcribed, such as when a poly-dA or a poly-dT tail is added to the cDNA during reverse transcription. In other embodiments, RNA is modified before it is reverse transcribed. In some embodiments, total RNA is reverse transcribed. In other embodiments, small RNAs are isolated or enriched before the RNA is reverse transcribed.

When a target RNA is reverse transcribed, a complement of the target RNA is formed. In some embodiments, the complement of the target RNA is detected rather than the target RNA itself (or a DNA copy thereof). Thus, when the methods discussed herein indicate that a target RNA is detected, or the level of a target RNA is determined, such detection or determination may be carried out on a complement of the target RNA instead of or in addition to, the target RNA itself. In some embodiments, when the complement of the target RNA is detected rather than the target RNA, a probe is used that is complementary to the complement of the target RNA. In such embodiments, the probe comprises at least a portion that is identical in sequence to the target RNA, although it may contain thymidine in place of uridine, and/or comprise other modified nucleotides.

In some embodiments, the method of detecting one or more target RNAs comprises amplifying cDNA complementary to said target RNA. Such amplification can be accomplished by any method. Exemplary methods include, but are not limited to, real time PCR, endpoint PCR, and amplification using T7 polymerase from a T7 promoter annealed to a cDNA, such as provided by the SenseAmp Plus™ Kit available at Implen, Germany.

When a target RNA or a cDNA complementary to a target RNA is amplified, in some embodiments, a DNA amplicon of a target RNA is formed. A DNA amplicon may be single stranded or double-stranded. In some embodiments, when a DNA amplicon is single-stranded, the sequence of the DNA amplicon is related to the target RNA in either the sense or antisense orientation. In some embodiments, the DNA amplicon of the target RNA is detected rather than the target RNA itself. Thus, when the methods discussed herein indicate that a target RNA is detected, or the level of a target RNA is determined, such detection or determination may be carried out on a DNA amplicon of the target RNA instead of, or in addition to, the target RNA itself. In some embodiments, when the DNA amplicon of the target RNA is detected rather than the target RNA, a probe is used that is complementary to the complement of the target RNA. In some embodiments, when the DNA amplicon of the target RNA is detected rather than the target RNA, a probe is used that is complementary to the target RNA. Further, I some embodiments, multiple probes may be used, and some probes may be complementary to the target RNA and some probes may be complementary to the complement of the target RNA.

In some embodiments, the method of detecting one or more target RNAs comprises RT-PCR, as described below. In some embodiments, detecting one or more target RNAs comprises real-time monitoring of an RT-PCR reaction, which can be accomplished by any method. Such methods include, but are not limited to, the use of TaqMan®, Molecular beacon, or Scorpion probes (i.e., FRET probes) and the use of intercalating dyes, such as SYBR green, EvaGreen, thiazole orange, YO-PRO, TO-PRO, etc.

4.1.4. Exemplary Analytical Methods

As described above, methods are presented for detecting sepsis in a sample from a patient. In some embodiments, the method comprises detecting a level of expression of at least one target RNA capable of specifically hybridizing to a nucleic acid comprising a sequence selected from SEQ ID NOs: 1 to 86 set forth in Table 2 that is greater in the sample than a normal level of expression of the at least one target RNA in a control sample, such as a sample from a patient that has not been diagnosed with sepsis syndrome, or a sample of normal human monocytes. In some embodiments, a method comprises detecting a level of one or more target RNAs that comprise a sequence that is complementary to at least 15 contiguous nucleotides of a sequence selected from SEQ ID NOs: 1 to 86 that is greater in the sample than a normal level of expression of the at least one target RNA in a control sample. In some embodiments, a method comprises detecting a level of one or more target RNAs that comprise at least 15 contiguous nucleotides of a sequence selected from SEQ ID NOs: 196 to 399, 950, 565 to 707, and 863 to 897 that is greater in the sample than a normal level of expression of the at least one target RNA in a control sample. In some embodiments, a target RNA, in its mature form, comprises fewer than 30 nucleotides. In some embodiments, a target RNA is a microRNA.

In some embodiments, such as those described above, the method further comprises detecting a level of expression of at least one target RNA of the human miRNome that does not specifically hybridize to a nucleic acid comprising a sequence selected from SEQ ID NOs: 1 to 86 and does not comprise at least 15 contiguous nucleotides of a sequence selected from SEQ ID NOs: 196 to 399, 950, 565 to 707, and 863 to 897, that is greater in the sample than a normal level of expression of the at least one target RNA in a control sample. As used herein, the term "human miRNome" refers to all microRNA genes in a human cell and the mature microRNAs produced therefrom.

Any analytical procedure capable of permitting specific and quantifiable (or semi-quantifiable) detection of the desired at least one target RNA may be used in the methods herein presented. Such analytical procedures include, but are not limited to, the microarray methods set forth in Example 1, the microbead methods set forth in Example 2, and methods known to those skilled in the art.

In some embodiments, detection of a target RNA comprises forming a complex comprising a polynucleotide that is complementary to a target RNA or to a complement thereof, and a nucleic acid selected from the target RNA, a DNA amplicon of the target RNA, and a complement of the target RNA. Thus, in some embodiments, the polynucleotide forms a complex with a target RNA. In some embodiments, the polynucleotide forms a complex with a complement of the target RNA, such as a cDNA that has been reverse transcribed from the target RNA. In some embodiments, the polynucleotide forms a complex with a DNA amplicon of the target RNA. When a double-stranded DNA amplicon is part of a complex, as used herein, the complex may comprise one or both strands of the DNA amplicon. Thus, in some embodiments, a complex comprises only one strand of the DNA amplicon. In some embodiments, a complex is a triplex and comprises the polynucleotide and both strands of the DNA amplicon. In some embodiments, the complex is formed by hybridization between the polynucleotide and the target RNA, complement of the target RNA, or DNA amplicon of the target RNA. The polynucleotide, in some embodiments, is a primer or probe.

In some embodiments, a method comprises detecting the complex. In some embodiments, the complex does not have to be associated at the time of detection. That is, in some embodiments, a complex is formed, the complex is then dissociated or destroyed in some manner, and components from the complex are detected. An example of such a system is a TaqMan® assay. In some embodiments, when the polynucleotide is a primer, detection of the complex may comprise amplification of the target RNA, a complement of the target RNA, or a DNA amplicon of a target RNA.

In some embodiments the analytical method used for detecting at least one target RNA in the methods set forth herein includes real-time quantitative RT-PCR. See Chen, C. et al. (2005) *Nucl. Acids Res.* 33:e179 and PCT Publication No. WO 2007/117256, which are incorporated herein by reference in its entirety. In some embodiments, the analytical method used for detecting at least one target RNA includes the method described in U.S. Publication No. US2009/0123912 A1, which is incorporated herein by reference in its entirety. In an exemplary method described in that publication, an extension primer comprising a first portion and second portion, wherein the first portion selectively hybridizes to the 3' end of a particular microRNA and the second portion comprises a sequence for universal primer, is used to reverse transcribe the microRNA to make a cDNA. A reverse primer that selectively hybridizes to the 5' end of the microRNA and a universal primer are then used to amplify the cDNA in a quantitative PCR reaction.

In some embodiments, the analytical method used for detecting at least one target RNA includes the use of a TaqMan® probe. In some embodiments, the analytical method used for detecting at least one target RNA includes a TaqMan® assay, such as the TaqMan® MicroRNA Assays sold by Applied Biosystems, Inc. In an exemplary TaqMan® assay, total RNA is isolated from the sample. In some embodiments, the assay can be used to analyze about 10 ng of total RNA input sample, such as about 9 ng of input sample, such as about 8 ng of input sample, such as about 7 ng of input sample, such as about 6 ng of input sample, such as about 5 ng of input sample, such as about 4 ng of input sample, such as about 3 ng of input sample, such as about 2 ng of input sample, and even as little as about 1 ng of input sample containing microRNAs.

The TaqMan® assay utilizes a stem-loop primer that is specifically complementary to the 3'-end of a target RNA. In an exemplary TaqMan® assay, hybridizing the stem-loop primer to the target RNA is followed by reverse transcription of the target RNA template, resulting in extension of the 3' end of the primer. The result of the reverse transcription is a chimeric (DNA) amplicon with the step-loop primer sequence at the 5' end of the amplicon and the cDNA of the target RNA at the 3' end. Quantitation of the target RNA is achieved by real time RT-PCR using a universal reverse primer having a sequence that is complementary to a sequence at the 5' end of all stem-loop target RNA primers, a target RNA-specific forward primer, and a target RNA sequence-specific TaqMan® probe.

The assay uses fluorescence resonance energy transfer ("FRET") to detect and quantitate the synthesized PCR product. Typically, the TaqMan® probe comprises a fluorescent dye molecule coupled to the 5'-end and a quencher molecule coupled to the 3'-end, such that the dye and the quencher are in close proximity, allowing the quencher to suppress the fluorescence signal of the dye via FRET. When the polymerase replicates the chimeric amplicon template to which the TaqMan® probe is bound, the 5'-nuclease of the polymerase cleaves the probe, decoupling the dye and the quencher so that FRET is abolished and a fluorescence signal is generated. Fluorescence increases with each RT-PCR cycle proportionally to the amount of probe that is cleaved.

Additional exemplary methods for RNA detection and/or quantification are described, e.g., in U.S. Publication No. US 2007/0077570 (Lao et al.), PCT Publication No. WO 2007/025281 (Tan et al.), U.S. Publication No. US2007/0054287 (Bloch), PCT Publication No. WO2006/0130761 (Bloch), and PCT Publication No. WO 2007/011903 (Lao et al.), which are incorporated by reference herein in their entireties for any purpose.

In some embodiments, quantitation of the results of real-time RT-PCR assays is done by constructing a standard curve from a nucleic acid of known concentration and then extrapolating quantitative information for target RNAs of unknown concentration. In some embodiments, the nucleic acid used for generating a standard curve is an RNA (e.g., microRNA) of known concentration. In some embodiments, the nucleic acid used for generating a standard curve is a purified double-stranded plasmid DNA or a single-stranded DNA generated in vitro.

In some embodiments, where the amplification efficiencies of the target nucleic acids and the endogenous reference are approximately equal, quantitation is accomplished by the comparative Ct (cycle threshold, e.g., the number of PCR cycles required for the fluorescence signal to rise above background) method. Ct values are inversely proportional to the amount of nucleic acid target in a sample. In some embodiments, Ct values of the target RNA of interest can be compared with a control or calibrator, such as RNA (e.g., microRNA) from normal tissue. In some embodiments, the Ct values of the calibrator and the target RNA samples of interest are normalized to an appropriate endogenous housekeeping gene.

In addition to the TaqMan® assays, other real-time RT-PCR chemistries useful for detecting and quantitating PCR products in the methods presented herein include, but are not limited to, Molecular Beacons, Scorpion probes and intercalating dyes, such as SYBR Green, EvaGreen, thiazole orange, YO-PRO, TO-PRO, etc., which are discussed below.

In some embodiments, real-time RT-PCR detection is performed specifically to detect and quantify the expression of a single target RNA. The target RNA, in some embodiments, is selected from a target RNA capable of specifically hybridizing to a nucleic acid comprising a sequence selected from SEQ ID NOs: 1 to 86. In some embodiments, the target RNA specifically hybridizes to a nucleic acid comprising a sequence selected from SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 and 86. In some embodiments, the target RNA specifically hybridizes to a nucleic acid comprising a sequence selected from SEQ ID NOs: 8, 14, 23, 30, 39, 52, 57, 59, 60, 62, 63, 64, 65, 67, 74, 76, 78 and 79. In some embodiments, the target RNA specifically hybridizes to a nucleic acid comprising a sequence selected from SEQ ID NOs: 6, 17, 19, 20, 21, 27, 29, 33, 34, 35, 38, 45, 46, 47, 48, 49, 69 and 84. In some embodiments, the target RNA specifically hybridizes to a nucleic acid comprising a sequence selected from SEQ ID NOs: 8, 14, 59, 62, 63, 64, 74, and 78. In some embodiments, the target RNA specifically hybridizes to a nucleic acid comprising a sequence selected from SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 and 85. In some embodiments, the target RNA specifically hybridizes to a nucleic acid comprising a sequence selected from SEQ ID NOs: 9, 50, 51, 70, 72 and 75. In some embodiments, the target RNA comprises at least 15 contiguous nucleotides of a sequence selected from SEQ ID NOs: 196 to 399, 950, 565 to 707, and 863 to 897. In some embodiments, the target RNA comprises at least 15 contiguous nucleotides of a sequence selected from SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, and 648. In some embodiments, the target RNA comprises at least 15 contiguous nucleotides of a sequence selected from SEQ ID NOs: 226 to 289, 565 to 604, or 863 to 868. In some embodiments, the target RNA comprises a sequence that is complementary to at least 15 contiguous nucleotides of a sequence selected from SEQ ID NOs: 1 to 86. In some embodiments, a target RNA, in its mature form, comprises fewer than 30 nucleotides. In some embodiments, a target RNA is a microRNA.

In various embodiments, real-time RT-PCR detection is utilized to detect, in a single multiplex reaction, at least 2, at least 3, at least 4, at least 5, at least 6, at least 7, or at least 8 target RNAs. At least one target RNA, in some embodiments, is capable of specifically hybridizing to a nucleic acid comprising a sequence selected from SEQ ID NOs: 1 to 86. In some embodiments, at least one target RNA comprises at least 15 contiguous nucleotides of a sequence selected from SEQ ID NOs: 196 to 399, 950, 565 to 707, and 863 to 897. In some embodiments, at least one target RNA comprises a sequence that is complementary to at least 15 contiguous nucleotides of a sequence selected from SEQ ID NOs: 1 to 86. In some embodiments, a target RNA, in its mature form, comprises fewer than 30 nucleotides. In some embodiments, a target RNA is a microRNA.

In some embodiments, the method comprises detecting expression in a multiplex RT-PCR reaction of at least 2, at least 3, at least 5, at least 10, at least 15, at least 20, at least 25, at least 30, at least 35, or at least 40 target RNAs, wherein each target RNA is capable of specifically hybridizing to a nucleic acid comprising a sequence selected from SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 and 86. In some embodiments, the method comprises detecting greater than normal expression, using a single multiplex RT-PCR reaction, of at least 2, at least 3, at least 4, at least 5, at least 6, at least 7, at least 8, at least 9, at least 10, at least 12, or at least 15 target RNAs, wherein each target RNA is capable of specifically hybridizing to a nucleic acid comprising a sequence selected from SEQ ID NOs: 8, 14, 23, 30, 39, 52, 57, 59, 60, 62, 63, 64, 65, 67, 74, 76, 78 and 79. In some embodiments, the method comprises detecting greater than normal expression, using a single multiplex RT-PCR reaction, of at least 2, at least 3, at least 4, at least 5, at least 6, at least 7, at least 8, at least 9, at least 10, at least 12, or at least 15 target RNAs, wherein each target RNA is capable of specifically hybridizing to a nucleic acid comprising a sequence selected from SEQ ID NOs: 6, 17, 19, 20, 21, 27, 29, 33, 34, 35, 38, 45, 46, 47, 48, 49, 69 and 84. In some embodiments, the method comprises detecting expression in a multiplex RT-PCR reaction of at least 2, at least 3, at least 4, at least 5, at least 6, at least 7, or at least 8 target RNAs, wherein each target RNA is capable of specifically hybridizing to a nucleic acid comprising a sequence selected from SEQ ID NOs: 8, 14, 59, 62, 63, 64, 74, and 78. In some embodiments, the method comprises detecting expression in a multiplex RT-PCR reaction of at least 2, at least 3, at least 5, at least 10, at least 15, at least 20, at least 25, or at least 30 target RNAs, wherein each target RNA is capable of specifically hybridizing to a nucleic acid comprising a sequence selected from SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 and 85. In some embodiments, the method comprises detecting expression in a multiplex RT-PCR reaction of at least 2, at least 3, at least 4, at least 5, or at least 6 target RNAs, wherein each target RNA is capable of specifically hybridizing to a nucleic acid comprising a sequence selected from SEQ ID NOs: 9, 50, 51, 70, 72 and 75. In some embodiments, the method comprises detecting expression in a multiplex RT-PCR reaction of at least two, at least five, at least 10, at least 15, at least 20, at least 25, or at least 30 target RNAs, wherein each target RNA is capable of specifically hybridizing to a nucleic acid comprising a sequence selected from SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, and 648. In some embodiments, the method comprises detecting expression in a multiplex RT-PCR reaction of at least two, at least five, at least 10, at least 15, or at least 20 target RNAs, wherein each target RNA is capable of specifically hybridizing to a nucleic acid comprising a sequence selected from SEQ ID NOs: 231, 236, 242, 260, 261, 266, 287, 566, 567, 568, 571, 570, 574, 580, 581, 588, 598, 601, 608, 624, 626, 629, and 632. In some embodiments, the method comprises detecting expression in a multiplex RT-PCR reaction of at least two, at least five, at least 10, at least 15, at least 20, at least 25, at least 30, at least 40, at least 50, at least 60, or at least 70 target RNAs, wherein each target RNA is capable of specifically hybridizing to a nucleic acid comprising a sequence selected from SEQ ID NOs: 226 to 289, 565 to 604, and 863 to 868.

In some multiplex embodiments, a plurality of probes, such as TaqMan®, probes, each specific for a different RNA target, is used. In some embodiments, each target RNA-specific probe is spectrally distinguishable from the other probes used in the same multiplex reaction.

In some embodiments, quantitation of real-time RT PCR products is accomplished using a dye that binds to double-stranded DNA products, such as SYBR Green, EvaGreen, thiazole orange, YO-PRO, TO-PRO, etc. In some embodiments, the assay is the QuantiTect SYBR Green PCR assay from Qiagen. In this assay, total RNA is first isolated from a sample. Total RNA is subsequently poly-adenylated at the 3'-end and reverse transcribed using a universal primer with poly-dT at the 5'-end. In some embodiments, a single reverse transcription reaction is sufficient to assay multiple target RNAs. Real-time RT-PCR is then accomplished using target RNA-specific primers and an miScript Universal Primer, which comprises a poly-dT sequence at the 5'-end. SYBR Green dye binds non-specifically to double-stranded DNA and upon excitation, emits light. In some embodiments, buffer conditions that promote highly-specific annealing of primers to the PCR template (e.g., available in the Quanti-Tect SYBR Green PCR Kit from Qiagen) can be used to avoid the formation of non-specific DNA duplexes and primer dimers that will bind SYBR Green and negatively affect quantitation. Thus, as PCR product accumulates, the signal from SYBR Green increases, allowing quantitation of specific products.

Real-time RT-PCR is performed using any RT-PCR instrumentation available in the art. Typically, instrumentation used in real-time RT-PCR data collection and analysis comprises a thermal cycler, optics for fluorescence excitation and emission collection, and optionally a computer and data acquisition and analysis software.

In some embodiments, the analytical method used in the methods described herein is a DASL® (cDNA-mediated Annealing, Selection, Extension, and Ligation) Assay, such as the MicroRNA Expression Profiling Assay available from Illumina, Inc. (See www.illumina.com/downloads/MicroR-NAAssayWorkflow.pdf). In some embodiments, total RNA is isolated from a sample to be analyzed by any method. Additionally, in some embodiments, small RNAs are isolated from a sample to be analyzed by any method. Total RNA or isolated small RNAs may then be polyadenylated (>18 A residues are added to the 3'-ends of the RNAs in the reaction mixture). The RNA is reverse transcribed using a biotin-labeled DNA primer that comprises from the 5' to the 3' end, a sequence that includes a PCR primer site and a poly-dT region that binds to the poly-dA tail of the sample RNA. The resulting biotinylated cDNA transcripts are then hybridized to a solid support via a biotin-streptavidin interaction and contacted with one or more target RNA-specific polynucleotides. The target RNA-specific polynucleotides comprise, from the 5'-end to the 3'-end, a region comprising a PCR primer site, region comprising an address sequence, and a target RNA-specific sequence.

In some DASL® embodiments, the target RNA-specific sequence comprises at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides having a sequence identically present in, or complementary to a region of, one of SEQ ID NOs: 1 to 86, 196 to 399, 950, 565 to 707, and 863 to 897. In some embodiments, the target RNA-specific sequence comprises a probe sequence that is complementary to at least a portion of a microRNA of the human miRNome.

After hybridization, the target RNA-specific polynucleotide is extended, and the extended products are then eluted from the immobilized cDNA array. A second PCR reaction using a fluorescently-labeled universal primer generates a fluorescently-labeled DNA comprising the target RNA-specific sequence. The labeled PCR products are then hybridized to a microbead array for detection and quantitation.

In some embodiments, the analytical method used for detecting and quantifying the expression of the at least one target RNA in the methods described herein is a bead-based flow cytometric assay. See Lu J. et al. (2005) Nature 435:834-838, which is incorporated herein by reference in its entirety. An example of a bead-based flow cytometric assay is the xMAP® technology of Luminex, Inc. (See www.luminexcorp.com/technology/index.html). In some embodiments, total RNA is isolated from a sample and is then labeled with biotin. The labeled RNA is then hybridized to target RNA-specific capture probes (e.g., FlexmiR™ products sold by Luminex, Inc. at www.luminexcorp.com/products/assays/index.html) that are covalently bound to microbeads, each of which is labeled with 2 dyes having different fluorescence intensities. A streptavidin-bound reporter molecule (e.g., streptavidin-phycoerythrin, also known as "SAPE") is attached to the captured target RNA and the unique signal of each bead is read using flow cytometry. In some embodiments, the RNA sample (total RNA or enriched small RNAs) is first polyadenylated, and is subsequently labeled with a biotinylated 3DNA™ dendrimer (i.e., a multiple-arm DNA with numerous biotin molecules bound thereto), such as those sold by Marligen Biosciences as the Vantage™ microRNA Labeling Kit, using a bridging polynucleotide that is complementary to the 3'-end of the poly-dA tail of the sample RNA and to the 5'-end of the polynucleotide attached to the biotinylated dendrimer. The streptavidin-bound reporter molecule is then attached to the biotinylated dendrimer before analysis by flow cytometry. See www.marligen.com/vantage-microrna-labeling-kit.html. In some embodiments, biotin-labeled RNA is first exposed to SAPE, and the RNA/SAPE complex is subsequently exposed to an anti-phycoerythrin antibody attached to a DNA dendrimer, which can be bound to as many as 900 biotin molecules. This allows multiple SAPE molecules to bind to the biotinylated dendrimer through the biotin-streptavidin interaction, thus increasing the signal from the assay.

In some embodiments, the analytical method used for detecting and quantifying the expression of the at least one target RNA in the methods described herein is by gel electrophoresis and detection with labeled probes (e.g., probes labeled with a radioactive or chemiluminescent label), such as by Northern blotting. In some embodiments, total RNA is isolated from the sample, and then is size-separated by SDS polyacrylamide gel electrophoresis. The separated RNA is then blotted onto a membrane and hybridized to radiolabeled complementary probes. In some embodiments, exemplary probes contain one or more affinity-enhancing nucleotide analogs as discussed below, such as locked nucleic acid ("LNA") analogs, which contain a bicyclic sugar moiety instead of deoxyribose or ribose sugars. See, e.g., Várallyay, E. et al. (2008) Nature Protocols 3(2):190-196, which is incorporated herein by reference in its entirety. In some embodiments, the total RNA sample can be further purified to enrich for small RNAs. In some embodiments, target RNAs can be amplified by, e.g., rolling circle amplification using a long probe that is complementary to both ends of a target RNA ("padlocked probes"), ligation to circularize the probe followed by rolling circle replication using the target RNA hybridized to the circularized probe as a primer. See, e.g., Jonstrup, S. P. et al. (2006) RNA 12:1-6, which is incorporated herein by reference in its entirety. The amplified product can then be detected and quantified using, e.g., gel electrophoresis and Northern blotting.

In alternative embodiments, labeled probes are hybridized to isolated total RNA in solution, after which the RNA is subjected to rapid ribonuclease digestion of single-stranded RNA, e g, unhybridized portions of the probes or unhybridized target RNAs. In these embodiments, the ribonuclease treated sample is then analyzed by SDS-PAGE and detection of the radiolabeled probes by, e.g., Northern blotting. See mirVana™ miRNA Detection Kit sold by Applied Biosystems, Inc. product literature at www.ambion.com/catalog/CatNum.php?1552.

In some embodiments, the analytical method used for detecting and quantifying the at least one target RNA in the methods described herein is by hybridization to a microarray. See, e.g., Liu, C. G. et al. (2004) Proc. Nat'l Acad. Sci. USA 101:9740-9744; Lim, L. P. et al. (2005) Nature 433: 769-773, each of which is incorporated herein by reference in its entirety, and Example 1.

In some embodiments, detection and quantification of a target RNA using a microarray is accomplished by surface plasmon resonance. See, e.g., Nanotech News (2006), available nano.cancer.gov/news_center/nanotech_news_2006-10-30b.asp. In these embodiments, total RNA is isolated from a sample being tested. Optionally, the RNA sample is further purified to enrich the population of small RNAs. After purification, the RNA sample is bound to an addressable microarray containing probes at defined locations on the microarray. Nonlimiting exemplary probes include probes comprising sequences set forth in SEQ ID NOs: 1 to 86. Exemplary probes also include, but are not limited to, probes comprising a region that is complementary to at least 15 contiguous nucleotides of a sequence selected from SEQ ID NOs: 196 to 399, 950, 565 to 707, and 868 to 897. Exemplary probes also include, but are not limited to, probes comprising at least 15 contiguous nucleotides of a sequence selected from SEQ ID NOs: 1 to 86. In some embodiments, the probes contain one or more affinity-enhancing nucleotide analogs as discussed below, such as locked nucleic acid ("LNA") nucleotide analogs. After hybridization to the microarray, the RNA that is hybridized to the array is first polyadenylated, and the array is then exposed to gold particles having poly-dT bound to them. The amount of bound target RNA is quantitated using surface plasmon resonance.

In some embodiments, microarrays are utilized in a RNA-primed, Array-based Klenow Enzyme ("RAKE") assay. See Nelson, P. T. et al. (2004) Nature Methods 1(2):1-7; Nelson, P. T. et al. (2006) RNA 12(2):1-5, each of which is incorporated herein by reference in its entirety. In some embodiments, total RNA is isolated from a sample. In some embodiments, small RNAs are isolated from a sample. The RNA sample is then hybridized to DNA probes immobilized at the 5'-end on an addressable array. The DNA probes comprise, in some embodiments, from the 5'-end to the 3'-end, a first region comprising a "spacer" sequence which is the same for all probes, a second region comprising three thymidine-containing nucleosides, and a third region comprising a sequence that is complementary to a target RNA of interest.

Exemplary target RNAs of interest include, but are not limited to, target RNAs capable of specifically hybridizing to a nucleic acid comprising a sequence selected from SEQ ID NOs: 1 to 86, target RNAs comprising a region that is identical to at least 15 contiguous nucleotides of a sequence selected from 196 to 399, 950, 565 to 707, and 863 to 897, and target RNAs comprising a region that is complementary to at least 15 contiguous nucleotides of a sequence selected from SEQ ID NOs: 1 to 86. Target RNAs also include target RNAs in the miRNome that do not specifically hybridize to a nucleic acid comprising a sequence selected from SEQ ID NOs: 1 to 86. In some embodiments, a target RNA, in its mature form, comprises fewer than 30 nucleotides. In some embodiments, a target RNA is a microRNA.

After the sample is hybridized to the array, it is exposed to exonuclease I to digest any unhybridized probes. The Klenow fragment of DNA polymerase I is then applied along with biotinylated dATP, allowing the hybridized target RNAs to act as primers for the enzyme with the DNA probe as template. The slide is then washed and a streptavidin-conjugated fluorophore is applied to detect and quantitate the spots on the array containing hybridized and Klenow-extended target RNAs from the sample.

In some embodiments, the RNA sample is reverse transcribed. In some embodiments, the RNA sample is reverse transcribed using a biotin/poly-dA random octamer primer. When than primer is used, the RNA template is digested and the biotin-containing cDNA is hybridized to an addressable microarray with bound probes that permit specific detection of target RNAs. In some embodiments, the microarray includes at least one probe comprising at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides identically present in, or complementary to a region of, a sequence selected from SEQ ID NOs: 1 to 86, 196 to 399, 950, 565 to 707, and 863 to 897. After hybridization of the cDNA to the microarray, the microarray is exposed to a streptavidin-bound detectable marker, such as a fluorescent dye, and the bound cDNA is detected. See Liu C. G. et al. (2008) Methods 44:22-30, which is incorporated herein by reference in its entirety.

In some embodiments, target RNAs are detected and quantified in an ELISA-like assay using probes bound in the wells of microtiter plates. See Mora J. R. and Getts R. C. (2006) BioTechniques 41:420-424 and supplementary material in BioTechniques 41(4):1-5; U.S. Patent Publication No. 2006/0094025 to Getts et al., each of which is incorporated by reference herein in its entirety. In these embodiments, a sample of RNA that is enriched in small RNAs is either polyadenylated, or is reverse transcribed and the cDNA is polyadenylated. The RNA or cDNA is hybridized to probes immobilized in the wells of a microtiter plates, wherein each of the probes comprises a sequence that is identically present in, or complementary to a region of, one of SEQ ID NOs: 1 to 86, 196 to 399, 950, 565 to 707, and 863 to 897, or a sequence such as one or more sequences of target RNAs (or the reverse complement thereof) of the human miRNome, depending on whether RNA or cDNA is hybridized to the array. In some embodiments, the hybridized RNAs are labeled using a capture sequence, such as a DNA dendrimer (such as those available from Genisphere, Inc., www.genisphere.com/about_3dna.html) that is labeled with a plurality of biotin molecules or with a plurality of horseradish peroxidase molecules, and a bridging polynucleotide that contains a poly-dT sequence at the 5'-end that binds to the poly-dA tail of the captured nucleic acid, and a sequence at the 3'-end that is complementary to a region of the capture sequence. If the capture sequence is biotinylated, the microarray is then exposed to streptavidin-bound horseradish peroxidase. Hybridization of target RNAs is detected by the addition of a horseradish peroxidase substrate such as tetramethylbenzidine (TMB) and measurement of the absorbance of the solution at 450 nM.

In still other embodiments, an addressable microarray is used to detect a target RNA using quantum dots. See Liang, R. Q. et al. (2005) Nucl. Acids Res. 33(2):e17, available at www.pubmedcentral.nih.gov/articlerender.fcgi?a-rtid=548377, which is incorporated herein by reference in its entirety. In some embodiments, total RNA is isolated from a sample. In some embodiments, small RNAs are isolated from the sample. The 3'-ends of the target RNAs are biotinylated using biotin-X-hydrazide. The biotinylated target RNAs are captured on a microarray comprising immobilized probes comprising sequences that are identically present in, or complementary to a region of, one or more of SEQ ID NOs: 1 to 86, 196 to 399, 950, 565 to 707, and 863 to 897 and/or probes comprising sequences other than those that are complementary to one or more microRNAs of the human miRNome. The hybridized target RNAs are then labeled with quantum dots via a biotin-streptavidin binding. A confocal laser causes the quantum dots to fluoresce and the signal can be quantified. In alternative embodiments, small RNAs can be detected using a colorimetric assay. In these embodiments, small RNAs are labeled with streptavidin-conjugated gold followed by silver enhancement. The gold nanoparticles bound to the hybridized target RNAs catalyze the reduction of silver ions to metallic silver, which can then be detected colorimetrically with a CCD camera.

In some embodiments, detection and quantification of one or more target RNAs is accomplished using microfluidic devices and single-molecule detection. In some embodiments, target RNAs in a sample of isolated total RNA are hybridized to two probes, one which is complementary to nucleic acids at the 5'-end of the target RNA and the second which is complementary to the 3'-end of the target RNA. Each probe comprises, in some embodiments, one or more affinity-enhancing nucleotide analogs, such as LNA nucleotide analogs and each is labeled with a different fluorescent dye having different fluorescence emission spectra. The sample is then flowed through a microfluidic capillary in which multiple lasers excite the fluorescent probes, such that a unique coincident burst of photons identifies a particular target RNA, and the number of particular unique coincident bursts of photons can be counted to quantify the amount of the target RNA in the sample. See U.S. Patent Publication No. 2006/0292616 to Neely et al., which is hereby incorporated by reference in its entirety. In some alternative embodiments, a target RNA-specific probe can be labeled with 3 or more distinct labels selected from, e.g., fluorophores, electron spin labels, etc., and then hybridized to an RNA sample, such as total RNA, or a sample that is enriched in small RNAs. Nonlimiting exemplary target RNA-specific probes include probes comprising sequences selected from of SEQ ID NOs: 1 to 86. Nonlimiting exemplary target RNA-specific probes include probes comprising sequences that are complementary to sequences selected from of SEQ ID NOs: 1 to 86. Nonlimiting exemplary target RNA-specific probes also include probes comprising at least 15 contiguous nucleotides of, or the complement of at least 15 contiguous nucleotides of, a sequence selected from SEQ ID NOs: 1 to 86, 196 to 399, 950, 565 to 707, and 863 to 897.

Optionally, the sample RNA is modified before hybridization. The target RNA/probe duplex is then passed through channels in a microfluidic device and that comprise detectors that record the unique signal of the 3 labels. In this way, individual molecules are detected by their unique signal and counted. See U.S. Pat. Nos. 7,402,422 and 7,351,538 to Fuchs et al., U.S. Genomics, Inc., each of which is incorporated herein by reference in its entirety.

In some embodiments, the detection and quantification of one or more target RNAs is accomplished by a solution-based assay, such as a modified Invader assay. See Allawi H. T. et al. (2004) RNA 10:1153-1161, which is incorporated herein by reference in its entirety. In some embodiments, the modified invader assay can be performed on unfractionated detergent lysates of cells. In other embodiments, the modified invader assay can be performed on total RNA isolated from cells or on a sample enriched in small RNAs. The target RNAs in a sample are annealed to two probes which form hairpin structures. A first probe has a hairpin structure at the 5' end and a region at the 3'-end that has a sequence that is complementary to the sequence of a region at the 5'-end of a target RNA. The 3'-end of the first probe is the "invasive polynucleotide". A second probe has, from the 5' end to the 3'-end a first "flap" region that is not complementary to the target RNA, a second region that has a sequence that is complementary to the 3'-end of the target RNA, and a third region that forms a hairpin structure. When the two probes are bound to a target RNA target, they create an overlapping configuration of the probes on the target RNA template, which is recognized by the Cleavase enzyme, which releases the flap of the second probe into solution. The flap region then binds to a complementary region at the 3'-end of a secondary reaction template ("SRT"). A FRET polynucleotide (having a fluorescent dye bound to the 5'-end and a quencher that quenches the dye bound closer to the 3' end) binds to a complementary region at the 5'-end of the SRT, with the result that an overlapping configuration of the 3'-end of the flap and the 5'-end of the FRET polynucleotide is created. Cleavase recognizes the overlapping configuration and cleaves the 5'-end of the FRET polynucleotide, generates a fluorescent signal when the dye is released into solution.

4.1.5. Exemplary Polynucleotides

In some embodiments, polynucleotides are provided. In some embodiments, synthetic polynucleotides are provided. Synthetic polynucleotides, as used herein, refer to polynucleotides that have been synthesized in vitro either chemically or enzymatically. Chemical synthesis of polynucleotides includes, but is not limited to, synthesis using polynucleotide synthesizers, such as OligoPilot (GE Healthcare), ABI 3900 DNA Synthesizer (Applied Biosystems), and the like. Enzymatic synthesis includes, but is not limited to, producing polynucleotides by enzymatic amplification, e.g., PCR.

In some embodiments, a polynucleotide is provided that comprises at least 8, at least 9, at least 10, at least 11, at least 12, at least 13, at least 14, or at least 15 contiguous nucleotides of a sequence selected from SEQ ID NOs: 1 to 86, 196 to 399, 950, 565 to 707, and 863 to 897 and sequences complementary to SEQ ID NOs: 1 to 86, 196 to 399, 950, 565 to 707, and 863 to 897. In some embodiments, the polynucleotide further comprises a region having a sequence that is not found in, or complementary to, any of SEQ ID NOs: 1 to 86, 196 to 399, 950, 565 to 707, and 863 to 897. In some embodiments, a polynucleotide is provided that comprises at least 8, at least 9, at least 10, at least 11, at least 12, at least 13, at least 14, or at least 15 contiguous nucleotides of a sequence selected from SEQ ID NOs: 1 to 67, 215 to 399, 950, and 863 to 897, and sequences complementary to SEQ ID NOs: 1 to 67, 215 to 399, 950, and 863 to 897. In some embodiments, the polynucleotide further comprises a region having a sequence that is not found in, or complementary to, any of SEQ ID NOs: 1 to 67, 215 to 399, 950, or 863 to 897.

A "region" can comprise the full-length sequence, or the complement of the full-length sequence, of a particular sequence, such as any of SEQ ID NOs: 1 to 86, 196 to 399, 950, 565 to 707, and 863 to 897, or it can comprise a subsequence, or the complement of a subsequence, of a particular sequence, such as any of SEQ ID NOs: 1 to 86, 196 to 399, 950, 565 to 707, and 863 to 897. Such subsequences may comprise, in some embodiments, 8, 9, 10, 11, 12, 13, 14, 15, 16, 17, 18, 19, 20, 21, 22, 23, 24, 25, 26, 27, 28, 29, or more contiguous nucleotides from a particular SEQ ID NO or its complement.

In various embodiments, a polynucleotide comprises fewer than 500, fewer than 300, fewer than 200, fewer than 150, fewer than 100, fewer than 75, fewer than 50, fewer than 40, or fewer than 30 nucleotides. In various embodiments, a polynucleotide is between 8 and 200, between 8 and 150, between 8 and 100, between 8 and 75, between 8 and 50, between 8 and 40, or between 8 and 30 nucleotides long.

In some embodiments, the polynucleotide is a primer. In some embodiments, the primer is labeled with a detectable moiety. In some embodiments, a primer is not labeled. A primer, as used herein, is a polynucleotide that is capable of specifically hybridizing to a target RNA or to a cDNA reverse transcribed from the target RNA or to an amplicon that has been amplified from a target RNA or a cDNA (collectively referred to as "template"), and, in the presence of the template, a polymerase and suitable buffers and reagents, can be extended to form a primer extension product.

In some embodiments, the polynucleotide is a probe. In some embodiments, the probe is labeled with a detectable moiety. A detectable moiety, as used herein, includes both directly detectable moieties, such as fluorescent dyes, and indirectly detectable moieties, such as members of binding pairs. When the detectable moiety is a member of a binding pair, in some embodiments, the probe can be detectable by incubating the probe with a detectable label bound to the second member of the binding pair. In some embodiments, a probe is not labeled, such as when a probe is a capture probe, e.g., on a microarray or bead. In some embodiments, a probe is not extendable, e.g., by a polymerase. In other embodiments, a probe is extendable.

In some embodiments, the polynucleotide is a FRET probe that in some embodiments is labeled at the 5'-end with a fluorescent dye (donor) and at the 3'-end with a quencher (acceptor), a chemical group that absorbs (i.e., suppresses) fluorescence emission from the dye when the groups are in close proximity (i.e., attached to the same probe). In other embodiments, the donor and acceptor are not at the ends of the FRET probe. Thus, in some embodiments, the emission spectrum of the donor moiety should overlap considerably with the absorption spectrum of the acceptor moiety.

4.1.5.1. Exemplary Polynucleotide Modifications

In some embodiments, the methods of detecting at least one target RNA described herein employ one or more polynucleotides that have been modified, such as polynucleotides comprising one or more affinity-enhancing nucleotide analogs. Modified polynucleotides useful in the methods described herein include primers for reverse transcription, PCR amplification primers, and probes. In some embodiments, the incorporation of affinity-enhancing nucleotides increases the binding affinity and specificity of a polynucleotide for its target nucleic acid as compared to polynucleotides that contain only deoxyribonucleotides, and allows for the use of shorter polynucleotides or for shorter regions of complementarity between the polynucleotide and the target nucleic acid.

In some embodiments, affinity-enhancing nucleotide analogs include nucleotides comprising one or more base modifications, sugar modifications and/or backbone modifications.

In some embodiments, modified bases for use in affinity-enhancing nucleotide analogs include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In some embodiments, affinity-enhancing nucleotide analogs include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In some embodiments, affinity-enhancing nucleotide analogs include backbone modifications such as the use of peptide nucleic acids (PNA; e.g., an oligomer including nucleobases linked together by an amino acid backbone). Other backbone modifications include phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, a polynucleotide includes at least one affinity-enhancing nucleotide analog that has a modified base, at least nucleotide (which may be the same nucleotide) that has a modified sugar, and/or at least one internucleotide linkage that is non-naturally occurring.

In some embodiments, an affinity-enhancing nucleotide analog contains a locked nucleic acid ("LNA") sugar, which is a bicyclic sugar. In some embodiments, a polynucleotide for use in the methods described herein comprises one or more nucleotides having an LNA sugar. In some embodiments, a polynucleotide contains one or more regions consisting of nucleotides with LNA sugars. In other embodiments, a polynucleotide contains nucleotides with LNA sugars interspersed with deoxyribonucleotides. See, e.g., Frieden, M. et al. (2008) Curr. Pham. Des. 14(11):1138-1142.

4.1.5.2. Exemplary Primers

In some embodiments, a primer is provided. In some embodiments, a primer is identical or complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of a target RNA. In some embodiments, a primer may also comprise portions or regions that are not identical or complementary to the target RNA. In some embodiments, a region of a primer that is identical or complementary to a target RNA is contiguous, such that any region of a primer that is not identical or complementary to the target RNA does not disrupt the identical or complementary region.

In some embodiments, a primer comprises a portion that is identically present in a target RNA. In some such embodiments, a primer that comprises a region that is identically present in the target RNA is capable of selectively hybridizing to a cDNA that has been reverse transcribed from the RNA, or to an amplicon that has been produced by amplification of the target RNA or cDNA. In some embodiments, the primer is complementary to a sufficient portion of the cDNA or amplicon such that it selectively hybridizes to the cDNA or amplicon under the conditions of the particular assay being used.

As used herein, "selectively hybridize" means that a polynucleotide, such as a primer or probe, will hybridize to a particular nucleic acid in a sample with at least 5-fold greater affinity than it will hybridize to another nucleic acid present in the same sample that has a different nucleotide sequence in the hybridizing region. Exemplary hybridization conditions are discussed in Example 1. In some embodiments, a polynucleotide will hybridize to a particular nucleic acid in a sample with at least 10-fold greater affinity than it will hybridize to another nucleic acid present in the same sample that has a different nucleotide sequence in the hybridizing region.

Nonlimiting exemplary primers include primers comprising sequences that are identically present in, or complementary to a region of sequences selected from SEQ ID NOs: 1 to 86. Exemplary primers also include, but are not limited to, primers comprising regions that are identical or complementary to at least 15 contiguous nucleotides of sequences selected from SEQ ID NOs: 1 to 86, 196 to 399, 950, 565 to 707, and 863 to 897.

In some embodiments, a primer is used to reverse transcribe a target RNA, for example, as discussed herein. In some embodiments, a primer is used to amplify a target RNA or a cDNA reverse transcribed therefrom. Such amplification, in some embodiments, is quantitative PCR, for example, as discussed herein. In some embodiments, a primer comprises a detectable moiety.

4.1.5.3. Exemplary Probes

In various embodiments, methods of detecting the presence of a sepsis comprise hybridizing nucleic acids of a human sample with a probe. In some embodiments, the probe comprises a portion that is complementary to a target RNA. In some embodiments, the probe comprises a portion that is identically present in the target RNA. In some such embodiments, a probe that is complementary to a target RNA is complementary to a sufficient portion of the target RNA such that it selectively hybridizes to the target RNA under the conditions of the particular assay being used. In some embodiments, a probe that is complementary to a target RNA is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the target RNA. In some embodiments, a probe that is complementary to a target RNA comprises a region that is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the target RNA. That is, a probe that is complementary to a target RNA may also comprise portions or regions that are not complementary to the target RNA. In some embodiments, a region of a probe that is complementary to a target RNA is contiguous, such that any region of a probe that is not complementary to the target RNA does not disrupt the complementary region.

In some embodiments, the probe comprises a portion that is identically present in the target RNA. In some such embodiments, a probe that comprises a region that is identically present in the target RNA is capable of selectively hybridizing to a cDNA that has been reverse transcribed from the RNA, or to an amplicon that has been produced by amplification of the target RNA or cDNA. In some embodiments, the probe is complementary to a sufficient portion of the cDNA or amplicon such that it selectively hybridizes to the cDNA or amplicon under the conditions of the particular assay being used. In some embodiments, a probe that is complementary to a cDNA or amplicon is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the cDNA or amplicon. In some embodiments, a probe that is complementary to a target RNA comprises a region that is complementary to at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides of the cDNA or amplicon. That is, a probe that is complementary to a cDNA or amplicon may also comprise portions or regions that are not complementary to the cDNA or amplicon. In some embodiments, a region of a probe that is complementary to a cDNA or amplicon is contiguous, such that any region of a probe that is not complementary to the cDNA or amplicon does not disrupt the complementary region.

Nonlimiting exemplary probes include probes comprising sequences set forth in SEQ ID NOs: 1 to 86. Nonlimiting exemplary probes include probes comprising sequences that are identically present in, or complementary to a region of, sequences selected from SEQ ID NOs: 1 to 86, 196 to 399, 950, 565 to 707, and 863 to 897. Exemplary probes also include, but are not limited to, probes comprising regions that are identical or complementary to at least 15 contiguous nucleotides of sequences selected from SEQ ID NOs: 1 to 86, 196 to 399, 950, 565 to 707, and 863 to 897.

In some embodiments, the method of detectably quantifying one or more target RNAs comprises: (a) isolating total RNA; (b) reverse transcribing a target RNA to produce a cDNA that is complementary to the target RNA; (c) amplifying the cDNA from (b); and (d) detecting the amount of a target RNA using real time RT-PCR and a detection probe.

As described above, in some embodiments, the real time RT-PCR detection is performed using a FRET probe, which includes, but is not limited to, a TaqMan® probe, a Molecular beacon probe and a Scorpion probe. In some embodiments, the real time RT-PCR detection and quantification is performed with a TaqMan® probe, i.e., a linear probe that typically has a fluorescent dye covalently bound at one end of the DNA and a quencher molecule covalently bound at the other end of the DNA. The FRET probe comprises a sequence that is complementary to a region of the cDNA such that, when the FRET probe is hybridized to the cDNA, the dye fluorescence is quenched, and when the probe is digested during amplification of the cDNA, the dye is released from the probe and produces a fluorescence signal. In such embodiments, the amount of target RNA in the sample is proportional to the amount of fluorescence measured during cDNA amplification.

The TaqMan® probe typically comprises a region of contiguous nucleotides having a sequence that is complementary to a region of a target RNA or its complementary cDNA that is reverse transcribed from the target RNA template (i.e., the sequence of the probe region is complementary to or identically present in the target RNA to be detected) such that the probe is specifically hybridizable to the resulting PCR amplicon. In some embodiments, the probe comprises a region of at least 6 contiguous nucleotides having a sequence that is fully complementary to or identically present in a region of a cDNA that has been reverse transcribed from a target RNA template, such as comprising a region of at least 8 contiguous nucleotides, at least 10 contiguous nucleotides, at least 12 contiguous nucleotides, at least 14 contiguous nucleotides, or at least 16 contiguous nucleotides having a sequence that is complementary to or identically present in a region of a cDNA reverse transcribed from a target RNA to be detected.

In some embodiments, the region of the cDNA that has a sequence that is complementary to the TaqMan® probe sequence is at or near the center of the cDNA molecule. In some embodiments, there are independently at least 2 nucleotides, at least 3 nucleotides, at least 4 nucleotides, at least 5 nucleotides of the cDNA at the 5'-end and at the 3'-end of the region of complementarity.

In some embodiments, Molecular Beacons can be used to detect and quantitate PCR products. Like TaqMan® probes, Molecular Beacons use FRET to detect and quantitate a PCR product via a probe having a fluorescent dye and a quencher attached at the ends of the probe. Unlike TaqMan® probes, Molecular Beacons remain intact during the PCR cycles. Molecular Beacon probes form a stem-loop structure when free in solution, thereby allowing the dye and quencher to be in close enough proximity to cause fluorescence quenching. When the Molecular Beacon hybridizes to a target, the stem-loop structure is abolished so that the dye and the quencher become separated in space and the dye fluoresces. Molecular Beacons are available, e.g., from Gene Link™ (see www.genelink.com/newsite/products/mbintro.asp).

In some embodiments, Scorpion probes can be used as both sequence-specific primers and for PCR product detection and quantitation. Like Molecular Beacons, Scorpion probes form a stem-loop structure when not hybridized to a target nucleic acid. However, unlike Molecular Beacons, a Scorpion probe achieves both sequence-specific priming and PCR product detection. A fluorescent dye molecule is attached to the 5'-end of the Scorpion probe, and a quencher is attached to the 3'-end. The 3' portion of the probe is complementary to the extension product of the PCR primer, and this complementary portion is linked to the 5'-end of the probe by a non-amplifiable moiety. After the Scorpion primer is extended, the target-specific sequence of the probe binds to its complement within the extended amplicon, thus opening up the stem-loop structure and allowing the dye on the 5'-end to fluoresce and generate a signal. Scorpion probes are available from, e.g, Premier Biosoft International (see www.premierbiosoft.com/tech_notes/Scorpion.html).

In some embodiments, labels that can be used on the FRET probes include colorimetric and fluorescent labels such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2', 4',5',7'-Tetrabromosulfonefluorescein, and TET.

Specific examples of fluorescently labeled ribonucleotides useful in the preparation of RT-PCR probes for use in some embodiments of the methods described herein are available from Molecular Probes (Invitrogen), and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences (GE Healthcare), such as Cy3-UTP and Cy5-UTP.

Examples of fluorescently labeled deoxyribonucleotides useful in the preparation of RT-PCR probes for use in the methods described herein include Dinitrophenyl (DNP)-1'-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. Fluorescently labeled nucleotides are commercially available and can be purchased from, e.g., Invitrogen.

In some embodiments, dyes and other moieties, such as quenchers, are introduced into polynucleotide used in the methods described herein, such as FRET probes, via modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into a polynucleotide, for example, by way of solid phase synthesis of the polynucleotide. In other embodiments, the modified nucleotide includes one or more reactive groups that can react with a dye or quencher before, during, or after incorporation of the modified nucleotide into the nucleic acid. In specific embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In specific embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink.

Exemplary detectable moieties also include, but are not limited to, members of binding pairs. In some such embodiments, a first member of a binding pair is linked to a polynucleotide. The second member of the binding pair is linked to a detectable label, such as a fluorescent label. When the polynucleotide linked to the first member of the binding pair is incubated with the second member of the binding pair linked to the detectable label, the first and second members of the binding pair associate and the polynucleotide can be detected. Exemplary binding pairs include, but are not limited to, biotin and streptavidin, antibodies and antigens, etc.

In some embodiments, multiple target RNAs are detected in a single multiplex reaction. In some such embodiments, each probe that is targeted to a unique cDNA is spectrally distinguishable when released from the probe. Thus, each target RNA is detected by a unique fluorescence signal.

One skilled in the art can select a suitable detection method for a selected assay, e.g., a real-time RT-PCR assay. The selected detection method need not be a method described above, and may be any method.

4.2. Exemplary Compositions and Kits

In another aspect, compositions are provided. In some embodiments, compositions are provided for use in the methods described herein.

In some embodiments, a composition comprises at least one polynucleotide. In some embodiments, a composition comprises at least one primer. In some embodiments, a composition comprises at least one probe. In some embodiments, a composition comprises at least one primer and at least one probe.

In some embodiments, compositions are provided that comprise at least one target RNA-specific primer. The term "target RNA-specific primer" encompasses primers that have a region of contiguous nucleotides having a sequence that is (i) identically present in one of SEQ ID NOs: 1 to 86, 196 to 399, 950, 565 to 707, or 863 to 897, or (ii) complementary to the sequence of a region of contiguous nucleotides found in one of SEQ ID NOs: 1 to 86, 196 to 399, 950, 565 to 707, or 863 to 897.

In some embodiments, compositions are provided that comprise at least one target RNA-specific probe. The term "target RNA-specific probe" encompasses probes that have a region of contiguous nucleotides having a sequence that is (i) identically present in one of SEQ ID NOs: 1 to 86, 196 to 399, 950, 565 to 707, or 863 to 897, or (ii) complementary to the sequence of a region of contiguous nucleotides found in one of SEQ ID NOs: 1 to 86, 196 to 399, 950, 565 to 707, or 863 to 897.

In some embodiments, target RNA-specific primers and probes comprise deoxyribonucleotides. In other embodiments, target RNA-specific primers and probes comprise at least one nucleotide analog. Nonlimiting exemplary nucleotide analogs include, but are not limited to, analogs described herein, including LNA analogs and peptide nucleic acid (PNA) analogs. In some embodiments, target RNA-specific primers and probes comprise at least one nucleotide analog which increases the hybridization binding energy (e.g., an affinity-enhancing nucleotide analog, discussed above). In some embodiments, a target RNA-specific primer or probe in the compositions described herein binds to one target RNA in the sample. In some embodiments, a single primer or probe binds to multiple target RNAs, such as multiple isomirs.

In some embodiments, more than one primer or probe specific for a single target RNA is present in the compositions, the primers or probes capable of binding to overlapping or spatially separated regions of the target RNA.

It will be understood, even if not explicitly stated hereinafter, that in some embodiments in which the compositions described herein are designed to hybridize to cDNAs reverse transcribed from target RNAs, the composition comprises at least one target RNA-specific primer or probe (or region thereof) having a sequence that is identically present in a target RNA (or region thereof).

In some embodiments, a target RNA is capable of specifically hybridizing to at least one probe comprising a sequence selected from SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 and 86. In some embodiments, a target RNA is capable of specifically hybridizing to at least one nucleic acid probe comprising a sequence selected from SEQ ID NOs: 8, 14, 23, 30, 39, 52, 57, 59, 60, 62, 63, 64, 65, 67, 74, 76, 78 and 79. In some embodiments, a target RNA is capable of specifically hybridizing to at least one nucleic acid probe comprising a sequence selected from SEQ ID NOs: 6, 17, 19, 20, 21, 27, 29, 33, 34, 35, 38, 45, 46, 47, 48, 49, 69 and 84. In some embodiments, a target RNA is capable of specifically hybridizing to at least one nucleic acid probe comprising a sequence selected from SEQ ID NOs: 8, 14, 59, 62, 63, 64, 74, and 78. In some embodiments, a target RNA is capable of specifically hybridizing to at least one nucleic acid probe comprising a sequence selected from SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 and 85. In some embodiments, a target RNA is capable of specifically hybridizing to at least one nucleic acid probe comprising a sequence selected from SEQ ID NOs: 9, 50, 51, 70, 72 and 75. In some embodiments, a target RNA is capable of specifically hybridizing to at least one probe comprising a sequence selected from SEQ ID NOs: 1 to 86. In some embodiments, a target RNA comprises at least 15 contiguous nucleotides of a sequence selected from SEQ ID NOs: 196 to 399, 950, 565 to 707, and 863 to 897. In some embodiments, a target RNA comprises at least 15 contiguous nucleotides of a sequence selected from SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, and 648. In some embodiments, a target RNA comprises at least 15 contiguous nucleotides of a sequence selected from SEQ ID NOs: 231, 236, 242, 260, 261, 266, 287, 566, 567, 568, 571, 570, 574, 580, 581, 588, 598, 601, 608, 624, 626, 629, and 632. In some embodiments, a target RNA comprises at least 15 contiguous nucleotides of a sequence selected from SEQ ID NOs: 226 to 289, 565 to 604, and 863 to 868. In some embodiments, a target RNA comprises a sequence that is complementary to at least 15 contiguous nucleotides of a sequence selected from SEQ ID NOs: 1 to 86. In some embodiments, a target RNA, in its mature form, comprises fewer than 30 nucleotides. In some embodiments, a target RNA is a microRNA.

In some embodiments, the composition comprises a plurality of target RNA-specific primers and/or probes for each of at least 2, at least 3, at least 4, at least 5, at least 6, at least 7, or at least 8 target RNAs, the target RNAs comprising a region of contiguous nucleotides having a sequence that is identically present in one of SEQ ID NOs: 87 to 177, 948, 400 to 564, 949, 708 to 862, and 898 to 932. In some embodiments, the plurality includes a target RNA-specific primer and/or probe specific for each of at least 2, at least 3, at least 4, at least 5, at least 6, at least 7, at least 8, at least 9, at least 10, at least 11, or at least 12 target RNAs, the target RNAs comprising a region of contiguous nucleotides having a sequence that is identically present in one of SEQ ID NOs: 87 to 177, 948, 400 to 564, 949, 708 to 862, and 898 to 932. In some embodiments, the plurality includes a target RNA-specific primer and/or probe specific for each of at least 2, at least 3, at least 4, at least 5, at least 6, at least 7, at least 8, at least 9, at least 10, at least 15, at least 20, at least 25, at least 30, at least 40, at least 50, at least 75, or at least 100 target RNAs comprising a region of contiguous nucleotides having a sequence that is identically present in one of SEQ ID NOs: 87 to 177, 948, 400 to 564, 949, 708 to 862, and 898 to 932. It will be understood that, in some embodiments, target RNAs described herein comprise a sequence identically present in a sequence set forth in Table 3, 13, 15, or 17, except that thymine (T) bases in the sequences shown in Table 3, 13, 15, or 17 are replaced by uracil (U) bases in the target RNAs.

In some embodiments, a composition is an aqueous composition. In some embodiments, the aqueous composition comprises a buffering component, such as phosphate, tris, HEPES, etc., and/or additional components, as discussed below. In some embodiments, a composition is dry, for example, lyophilized, and suitable for reconstitution by addition of fluid. A dry composition may include a buffering component and/or additional components.

In some embodiments, a composition comprises one or more additional components. Additional components include, but are not limited to, salts, such as NaCl, KCl, and $MgCl_2$; polymerases, including thermostable polymerases; dNTPs; RNase inhibitors; bovine serum albumin (BSA) and the like; reducing agents, such as β-mercaptoethanol; EDTA and the like; etc. One skilled in the art can select suitable composition components depending on the intended use of the composition.

In some embodiments, an addressable microarray component is provided that comprises target RNA-specific probes attached to a substrate.

Microarrays for use in the methods described herein comprise a solid substrate onto which the probes are covalently or non-covalently attached. In some embodiments, probes capable of hybridizing to one or more target RNAs or cDNAs are attached to the substrate at a defined location ("addressable array"). Probes can be attached to the substrate in a wide variety of ways, as will be appreciated by those in the art. In some embodiments, the probes are synthesized first and subsequently attached to the substrate. In other embodiments, the probes are synthesized on the substrate. In some embodiments, probes are synthesized on the substrate surface using techniques such as photopolymerization and photolithography.

In some embodiments, the solid substrate is a material that is modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. In some embodiments, the substrates allow optical detection without appreciably fluorescing.

In some embodiments, the substrate is planar. In other embodiments, probes are placed on the inside surface of a tube, such as for flow-through sample analysis to minimize sample volume. In other embodiments, probes can be in the wells of multi-well plates. In still other embodiments, probes can be attached to an addressable microbead array. In yet other embodiments, the probes can be attached to a flexible substrate, such as a flexible foam, including closed cell foams made of particular plastics.

The substrate and the probe can each be derivatized with functional groups for subsequent attachment of the two. For example, in some embodiments, the substrate is derivatized with one or more chemical functional groups including, but not limited to, amino groups, carboxyl groups, oxo groups and thiol groups. In some embodiments, probes are attached directly to the substrate through one or more functional groups. In some embodiments, probes are attached to the substrate indirectly through a linker (i.e., a region of contiguous nucleotides that space the probe regions involved in hybridization and detection away from the substrate surface). In some embodiments, probes are attached to the solid support through the 5' terminus. In other embodiments, probes are attached through the 3' terminus. In still other embodiments, probes are attached to the substrate through an internal nucleotide. In some embodiments the probe is attached to the solid support non-covalently, e.g., via a biotin-streptavidin interaction, wherein the probe biotinylated and the substrate surface is covalently coated with streptavidin.

In some embodiments, the compositions comprise a microarray having probes attached to a substrate, wherein at least one of the probes (or a region thereof) comprises a sequence that is identically present in, or complementary to a region of, one of SEQ ID NOs: 1 to 86, 196 to 399, 950, 565 to 707, or 863 to 897. In some embodiments, at least 2, at least 5, at least 10, at least 15, at least 20, at least 25, at least 30, at least 40, at least 50, or at least 100 of the probes comprise a sequence that is identically present in, or complementary to a region of one of SEQ ID NOs: 1 to 86, 196 to 399, 950, 565 to 707, or 863 to 897. In some embodiments, the microarray comprises at least one target RNA-specific probe comprising a sequence that is identically present in, or complementary to a region of, one of SEQ ID NOs: 1 to 86, 196 to 399, 950, 565 to 707, or 863 to 897 and at least one target RNA-specific probe comprising a sequence that is identically present in, or complementary to a region of a target RNA of the human miRNome. In some embodiments, the microarray comprises each target RNA-specific probe at only one location on the microarray. In some embodiments, the microarray comprises at least one target RNA-specific probe at multiple locations on the microarray.

As used herein, the terms "complementary" or "partially complementary" to a target RNA (or target region thereof), and the percentage of "complementarity" of the probe sequence to that of the target RNA sequence is the percentage "identity" to the reverse complement of the sequence of the target RNA. In determining the degree of "complementarity" between probes used in the compositions described herein (or regions thereof) and a target RNA, such as those disclosed herein, the degree of "complementarity" is expressed as the percentage identity between the sequence of the probe (or region thereof) and the reverse complement of the sequence of the target RNA that best aligns therewith. The percentage is calculated by counting the number of aligned bases that are identical as between the 2 sequences, dividing by the total number of contiguous nucleotides in the probe, and multiplying by 100.

In some embodiments, the microarray comprises at least one probe having a region with a sequence that is fully complementary to a target region of a target RNA. In other embodiments, the microarray comprises at least one probe having a region with a sequence that comprises one or more base mismatches when compared to the sequence of the best-aligned target region of a target RNA.

As noted above, a "region" of a probe or target RNA, as used herein, may comprise or consist of 8, 9, 10, 11, 12, 13, 14, 15, 16, 17, 18, 19, 20, 21, 22, 23, 24, 25, 26, 27, 28, 29 or more contiguous nucleotides from a particular SEQ ID NO or the complement thereof. In some embodiments, the region is of the same length as the probe or the target RNA. In other embodiments, the region is shorter than the length of the probe or the target RNA.

In some embodiments, the microarray comprises at least one probe having a region of at least 10, at least 11, at least 13, at least 14, at least 15, at least 16, at least 17, at least 18, at least 19, at least 20, at least 21, at least 22, at least 23, at least 24, or at least 25 contiguous nucleotides with a sequence that is identically present in, or complementary to a region of, one of SEQ ID NOs: 1 to 68, 196 to 399, 950, 565 to 707, or 863 to 897.

In some embodiments, the microarray comprises at least one probe having a region with a sequence that is identically present in, or complementary to a region of, one of SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 or 86. In some embodiments, the microarray comprises at least one, at least two, at least three, at least five, at least 10, at least 15, at least 20, at least 25, at least 30, at least 35, or at lest 40 probes that each comprise a region with a sequence that is identically present in, or complementary to a region of, one of SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 and 86. In some embodiments, the microarray further comprises additional probes that do not have a region with a sequence that is identically present in, or complementary to a region of, one of SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 or 86.

In some embodiments, the microarray comprises at least one probe having a region with a sequence that is identically present in, or complementary to a region of, one of SEQ ID NOs: 8, 14, 23, 30, 39, 52, 57, 59, 60, 62, 63, 64, 65, 67, 74, 76, 78 or 79. In some embodiments, the microarray comprises at least one, at least two, at least three, at least five, at least eight, at least 10, at least 12, or at least 15 probes that each comprise a region with a sequence that is identically present in, or complementary to a region of, one of SEQ ID NOs: 8, 14, 23, 30, 39, 52, 57, 59, 60, 62, 63, 64, 65, 67, 74, 76, 78 and 79. In some embodiments, the microarray further comprises additional probes that do not have a region with a sequence that is identically present in, or complementary to a region of, one of SEQ ID NOs: 8, 14, 23, 30, 39, 52, 57, 59, 60, 62, 63, 64, 65, 67, 74, 76, 78 and 79.

In some embodiments, the microarray comprises at least one probe having a region with a sequence that is identically present in, or complementary to a region of, one of SEQ ID NOs: 6, 17, 19, 20, 21, 27, 29, 33, 34, 35, 38, 45, 46, 47, 48, 49, 69 or 84. In some embodiments, the microarray comprises at least one, at least two, at least three, at least five, at least eight, at least 10, at least 12, or at least 15 probes that each comprise a region with a sequence that is identically present in, or complementary to a region of, one of SEQ ID NOs: 6, 17, 19, 20, 21, 27, 29, 33, 34, 35, 38, 45, 46, 47, 48, 49, 69 or 84. In some embodiments, the microarray further comprises additional probes that do not have a region with a sequence that is identically present in, or complementary to a region of, one of SEQ ID NOs: 6, 17, 19, 20, 21, 27, 29, 33, 34, 35, 38, 45, 46, 47, 48, 49, 69 or 84.

In some embodiments, the microarray comprises at least one probe having a region with a sequence that is identically present in, or complementary to a region of, one of SEQ ID NOs: 8, 14, 59, 62, 63, 64, 74, or 78. In some embodiments, the microarray comprises at least one, at least two, at least three, at least four, at least five, at least six, at least seven, or at least eight probes that each comprise a region with a sequence that is identically present in, or complementary to a region of, one of SEQ ID NOs: 8, 14, 59, 62, 63, 64, 74, or 78. In some embodiments, the microarray further comprises additional probes that do not have a region with a sequence that is identically present in, or complementary to a region of, one of SEQ ID NOs: 8, 14, 59, 62, 63, 64, 74, or 78.

In some embodiments, the microarray comprises at least one probe having a region with a sequence that is identically present in, or complementary to a region of, one of SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 or 85. In some embodiments, the microarray comprises at least one, at least two, at least three, at least four, at least five, at least ten, at least 15, at least 20, at least 25, or at least 30 probes that each comprise a region with a sequence that is identically present in, or complementary to a region of, one of SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 or 85. In some embodiments, the microarray further comprises additional probes that do not have a region with a sequence that is identically present in, or complementary to a region of, one of SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 or 85.

In some embodiments, the microarray comprises at least one probe having a region with a sequence that is identically present in, or complementary to a region of, one of SEQ ID NOs: 9, 50, 51, 70, 72 or 75. In some embodiments, the microarray comprises at least one, at least two, at least three, at least four, at least five, or at least six probes that each comprise a region with a sequence that is identically present in, or complementary to a region of, one of SEQ ID NOs: 9, 50, 51, 70, 72 or 75. In some embodiments, the microarray further comprises additional probes that do not have a region with a sequence that is identically present in, or complementary to a region of, one of SEQ ID NOs: 9, 50, 51, 70, 72 or 75.

In some embodiments, the microarray comprises at least one probe having a region with a sequence that is identically present in, or complementary to a region of, one of SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, or 648. In some embodiments, the microarray comprises at least two, at least five, at least 10, at least 15, at least 20, at least 25, or at least 30 probes that each comprise a region with a sequence that is identically present in, or complementary to a region of, one of SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, or 648. In some embodiments, the microarray further comprises additional probes that do not have a region with a sequence that is identically present in, or complementary to a region of, one of SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, or 648.

In some embodiments, the microarray comprises at least one probe having a region with a sequence that is identically present in, or complementary to a region of, one of SEQ ID NOs: 231, 236, 242, 260, 261, 266, 287, 566, 567, 568, 571, 570, 574, 580, 581, 588, 598, 601, 608, 624, 626, 629, or 632. In some embodiments, the microarray comprises at least two, at least five, at least 10, at least 15, or at least 20 probes that each comprise a region with a sequence that is identically present in, or complementary to a region of, one of SEQ ID NOs: 231, 236, 242, 260, 261, 266, 287, 566, 567, 568, 571, 570, 574, 580, 581, 588, 598, 601, 608, 624, 626, 629, or 632. In some embodiments, the microarray further comprises additional probes that do not have a region with a sequence that is identically present in, or complementary to a region of, one of SEQ ID NOs: 231, 236, 242, 260, 261, 266, 287, 566, 567, 568, 571, 570, 574, 580, 581, 588, 598, 601, 608, 624, 626, 629, or 632.

In some embodiments, the microarray comprises at least one probe having a region with a sequence that is identically present in, or complementary to a region of, one of SEQ ID NOs: 226 to 289, 565 to 604, or 863 to 868. In some embodiments, the microarray comprises at least two, at least five, at least 10, at least 15, at least 20, at least 25, at least 30, at least 40, at least 50, at least 60, or at least 70 probes that each comprise a region with a sequence that is identically present in, or complementary to a region of, one of SEQ ID NOs: 226 to 289, 565 to 604, or 863 to 868. In some embodiments, the microarray further comprises additional probes that do not have a region with a sequence that is identically present in, or complementary to a region of, one of SEQ ID NOs: 226 to 289, 565 to 604, or 863 to 868.

In some embodiments, the microarrays comprise probes having a region with a sequence that is complementary to target RNAs that comprise a substantial portion of the human miRNome (i.e., the publicly known microRNAs that have been accessioned by others into miRBase (microma.sanger.ac.uk/ at the time the microarray is fabricated), such as at least about 60%, at least about 70%, at least about 80%, at least about 90%, or at least about 95% of the human miRNome. In some embodiments, the microarrays comprise probes that have a region with a sequence that is identically present in target RNAs that comprise a substantial portion of the human miRNome, such as at least about 60%, at least about 70%, at least about 80%, at least about 90%, or at least about 95% of the human miRNome.

In some embodiments, components are provided that comprise probes attached to microbeads, such as those sold by Luminex, each of which is internally dyed with red and infrared fluorophores at different intensities to create a unique signal for each bead. In some embodiments, the compositions useful for carrying out the methods described herein include a plurality of microbeads, each with a unique spectral signature. Each uniquely labeled microbead is attached to a unique target RNA-specific probe such that the unique spectral signature from the dyes in the bead is associated with a particular probe sequence. Nonlimiting exemplary probe sequences include SEQ ID NOs: 1 to 86. Nonlimiting exemplary probe sequences also include probes comprising a region that is identically present in, or complementary to, a sequence selected from SEQ ID NOs: 1 to 86, 196 to 399, 950, 565 to 707, and 863 to 897. In some embodiments, a probe sequence comprises at least 8, at least 9, at least 10, at least 11, at least 12, at least 13, at least 14, at least 15, at least 16, at least 17, at least 18, at least 19, at least 20, at least 21, at least 22, at least 23, or at least 24 contiguous nucleotides that are identically present in, or complementary to a region of, one of SEQ ID NOs: 1 to 86, 196 to 399, 950, 565 to 707, or 863 to 897.

In some embodiments, a uniquely labeled microbead has attached thereto a probe having a region with a sequence that is identically present in, or complementary to a region of one of SEQ ID NOs: 1 to 86, 196 to 399, 950, 565 to 707, or 863 to 897. In other embodiments, the uniquely labeled microbead has attached thereto a probe having a region with a sequence that comprises one or more base mismatches when compared to the most similar sequence selected from SEQ ID NOs: 1 to 86, 196 to 399, 950, 565 to 707, and 863 to 897, and sequences complementary to SEQ ID NOs: 1 to 86, 196 to 399, 950, 565 to 707, and 863 to 897.

In some embodiments, a composition is provided that comprises a plurality of uniquely labeled microbeads, wherein at least one microbead has attached thereto a probe having a region of at least 10, at least 11, at least 13, at least 14, at least 15, at least 16, at least 17, at least 18, at least 19, at least 20, at least 21, at least 22, at least 23, at least 24, or at least 25 contiguous nucleotides with a sequence that is identically present in, or complementary to a region of, one of SEQ ID NOs: 1 to 86, 196 to 399, 950, 565 to 707, or 863 to 897.

In some embodiments, the compositions comprise a plurality of uniquely labeled microbeads, at least one of which has attached thereto a target RNA-specific probe having a region with a sequence that is identically present in, or complementary to a region of, one of SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 or 86. In some embodiments, the compositions comprise at least two, at least three, at least five, at least 8, at least ten, at least 15, at least 20, at least 25, at least 30, at least 35, or at least 40 uniquely labeled microbeads that each have attached thereto a unique target RNA-specific probe having a region with a sequence that is identically present in, or complementary to a region of, a different one of SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 or 86. In some embodiments, the composition comprises at least one uniquely labeled microbead having attached thereto a target RNA-specific probe having a region with a sequence that is not present in, or complementary to a region of, any of SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 or 86

In some embodiments, the compositions comprise a plurality of uniquely labeled microbeads, wherein at least one microbead has attached thereto a probe having a region with a sequence that is identically present in, or complementary to a region of, one of SEQ ID NOs: 8, 14, 23, 30, 39, 52, 57, 59, 60, 62, 63, 64, 65, 67, 74, 76, 78 or 79. In some embodiments, the compositions comprise at least two, at least three, at least five, at least eight, at least 10, at least 12, at least 15, or at least 18 uniquely labeled microbeads that each have attached thereto a unique target RNA-specific probe having a region with a sequence that is identically present in, or complementary to a region of, a different one of SEQ ID NOs: 8, 14, 23, 30, 39, 52, 57, 59, 60, 62, 63, 64, 65, 67, 74, 76, 78 or 79. In some embodiments, the composition comprises at least one uniquely labeled microbead having attached thereto a target RNA-specific probe having a region with a sequence that is not present in, or complementary to a region of, any of SEQ ID NOs: 8, 14, 23, 30, 39, 52, 57, 59, 60, 62, 63, 64, 65, 67, 74, 76, 78 or 79.

In some embodiments, the compositions comprise a plurality of uniquely labeled microbeads, wherein at least one microbead has attached thereto a probe having a region with a sequence that is identically present in, or complementary to a region of, one of SEQ ID NOs: 6, 17, 19, 20, 21, 27, 29, 33, 34, 35, 38, 45, 46, 47, 48, 49, 69 or 84. In some embodiments, the compositions comprise at least two, at least three, at least five, at least eight, at least 10, at least 12, at least 15, or at least 18 uniquely labeled microbeads that each have attached thereto a unique target RNA-specific probe having a region with a sequence that is identically present in, or complementary to a region of, a different one of SEQ ID NOs: 6, 17, 19, 20, 21, 27, 29, 33, 34, 35, 38, 45, 46, 47, 48, 49, 69 or 84. In some embodiments, the composition comprises at least one uniquely labeled microbead having attached thereto a target RNA-specific probe having a region with a sequence that is not present in, or complementary to a region of, any of SEQ ID NOs: 6, 17, 19, 20, 21, 27, 29, 33, 34, 35, 38, 45, 46, 47, 48, 49, 69 or 84.

In some embodiments, the compositions comprise a plurality of uniquely labeled microbeads, wherein at least one microbead has attached thereto a probe having a region with a sequence that is identically present in, or complementary to a region of, one of SEQ ID NOs: 8, 14, 59, 62, 63, 64, 74, or 78. In some embodiments, the compositions comprise at least two, at least three, at least four, at least five, at least six, at least seven, or at least eight uniquely labeled microbeads that each have attached thereto a unique target RNA-specific probe having a region with a sequence that is identically present in, or complementary to a region of, a different one of SEQ ID NOs: 8, 14, 59, 62, 63, 64, 74, or 78. In some embodiments, the composition comprises at least one uniquely labeled microbead having attached thereto a target RNA-specific probe having a region with a sequence that is not present in, or complementary to a region of, any of SEQ ID NOs: 8, 14, 59, 62, 63, 64, 74, or 78.

In some embodiments, the compositions comprise a plurality of uniquely labeled microbeads, wherein at least one microbead has attached thereto a probe having a region with a sequence that is identically present in, or complementary to a region of, one of SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 or 85. In some embodiments, the compositions comprise at least two, at least three, at least five, at least 8, at least ten, at least 15, at least 20, at least 25, at least 30, or at least 35 uniquely labeled microbeads that each have attached thereto a unique target RNA-specific probe having a region with a sequence that is identically present in, or complementary to a region of, a different one of SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 or 85. In some embodiments, the composition comprises at least one uniquely labeled microbead having attached thereto a target RNA-specific probe having a region with a sequence that is not present in, or complementary to a region of, any of SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 or 85.

In some embodiments, the compositions comprise a plurality of uniquely labeled microbeads, wherein at least one microbead has attached thereto a probe having a region with a sequence that is identically present in, or complementary to a region of, one of SEQ ID NOs: 9, 50, 51, 70, 72 or 75. In some embodiments, the compositions comprise at least two, at least three, at least four, at least five, or at least six uniquely labeled microbeads that each have attached thereto a unique target RNA-specific probe having a region with a sequence that is identically present in, or complementary to a region of, a different one of SEQ ID NOs: 9, 50, 51, 70, 72 or 75. In some embodiments, the composition comprises at least one uniquely labeled microbead having attached thereto a target RNA-specific probe having a region with a sequence that is not present in, or complementary to a region of, any of SEQ ID NOs: 9, 50, 51, 70, 72 or 75.

In some embodiments, the compositions comprise a plurality of uniquely labeled microbeads, wherein at least one microbead has attached thereto a probe having a region with a sequence that is identically present in, or complementary to a region of one of SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, or 648. In some embodiments, the compositions comprise at least two, at least five, at least 10, at least 15, at least 20, at least 25, or at least 30 uniquely labeled microbeads that each have attached thereto a unique target RNA-specific probe having a region with a sequence that is identically present in, or complementary to a region of, a different one of SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, or 648. In some embodiments, the composition comprises at least one uniquely labeled microbead having attached thereto a target RNA-specific probe having a region with a sequence that is not present in, or complementary to a region of, any of SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, or 648.

In some embodiments, the compositions comprise a plurality of uniquely labeled microbeads, wherein at least one microbead has attached thereto a probe having a region with a sequence that is identically present in, or complementary to a region of, one of SEQ ID NOs: 231, 236, 242, 260, 261, 266, 287, 566, 567, 568, 571, 570, 574, 580, 581, 588, 598, 601, 608, 624, 626, 629, or 632. In some embodiments, the compositions comprise at least two, at least five, at least 10, at least 15, or at least 20 uniquely labeled microbeads that each have attached thereto a unique target RNA-specific probe having a region with a sequence that is identically present in, or complementary to a region of, a different one of SEQ ID NOs: 231, 236, 242, 260, 261, 266, 287, 566, 567, 568, 571, 570, 574, 580, 581, 588, 598, 601, 608, 624, 626, 629, or 632. In some embodiments, the composition comprises at least one uniquely labeled microbead having attached thereto a target RNA-specific probe having a region with a sequence that is not present in, or complementary to a region of, any of SEQ ID NOs: 231, 236, 242, 260, 261, 266, 287, 566, 567, 568, 571, 570, 574, 580, 581, 588, 598, 601, 608, 624, 626, 629, or 632.

In some embodiments, the compositions comprise a plurality of uniquely labeled microbeads, wherein at least one microbead has attached thereto a probe having a region with a sequence that is identically present in, or complementary to a region of, one of SEQ ID NOs: 226 to 289, 565 to 604, or 863 to 868. In some embodiments, the compositions comprise at least two, at least five, at least 10, at least 15, at least 20, at least 25, at least 30, at least 40, at least 50, at least 60, or at least 70 uniquely labeled microbeads that each have attached thereto a unique target RNA-specific probe having a region with a sequence that is identically present in, or complementary to a region of, a different one of SEQ ID NOs: 226 to 289, 565 to 604, or 863 to 868. In some embodiments, the composition comprises at least one uniquely labeled microbead having attached thereto a target RNA-specific probe having a region with a sequence that is not present in, or complementary to a region of, any of SEQ ID NOs: 226 to 289, 565 to 604, or 863 to 868.

In some embodiments, the compositions comprise a plurality of uniquely labeled microbeads, wherein the plurality comprises at least one microbead having attached thereto a probe having a region with a sequence that is identically present in, or complementary to a region of, one of SEQ ID NOs: 1 to 86, 196 to 399, 950, 565 to 707, or 863 to 897. In some embodiments, the plurality comprises at least two, at least five, at least 10, at least 15, at least 20, at least 25, at least 30, at least 40, at least 50, at least 60, at least 75, or at least 100 microbeads each of which having attached thereto a probe having a region with a sequence that is identically present in, or complementary to a region of, one of SEQ ID NOs: 1 to 86, 196 to 399, 950, 565 to 707, or 863 to 897. In some embodiments, a composition comprises at least one uniquely labeled microbead having attached thereto a target RNA-specific probe having a region with a sequence that is not present in, or complementary to a region of, any of SEQ ID NOs: 1 to 86, 196 to 399, 950, 565 to 707, or 863 to 897.

In some embodiments, the compositions comprise a plurality of uniquely labeled microbeads, at least one of which has attached thereto a probe having a region with a sequence that identically present in, or complementary to a region of, one of SEQ ID NOs: 1 to 86, 196 to 399, 950, 565 to 707, or 863 to 897 and at least a second bead that has attached thereto a probe having a region with a sequence that is identically present in, or complementary to a region of, a target RNA from the human miRNome.

In some embodiments, the compositions comprise a plurality of uniquely labeled microbeads, each of which has attached thereto a unique probe having a region that is complementary to target RNAs that comprise a substantial portion of the human miRNome, such as at least about 60%, at least about 70%, at least about 80%, at least about 90%, or at least about 95% of the human miRNome. In some embodiments, the compositions comprise a plurality of uniquely labeled microbeads having attached thereto a unique probe having a region with a sequence that is identically present in target RNAs that comprise a substantial portion of the human miRNome, such as at least about 60%, at least about 70%, at least about 80%, at least about 90%, or at least about 95% of the human miRNome.

In some embodiments, compositions are provided that comprise at least one polynucleotide for detecting at least one target RNA. In some embodiments, the polynucleotide is used as a primer for a reverse transcriptase reaction. In some embodiments, the polynucleotide is used as a primer for amplification. In some embodiments, the polynucleotide is used as a primer for RT-PCR. In some embodiments, the polynucleotide is used as a probe for detecting at least one target RNA. In some embodiments, the polynucleotide is detectably labeled. In some embodiments, the polynucleotide is a FRET probe. In some embodiments, the polynucleotide is a TaqMan® probe, a Molecular Beacon, or a Scorpion probe.

In some embodiments, a composition comprises at least one FRET probe having a sequence that is identically present in, or complementary to a region of, one of SEQ ID NOs: 1 to 86, 196 to 399, 950, 565 to 707, or 863 to 897. In some embodiments, a composition comprises at least two, at least five, at least 10, at least 15, at least 20, at least 25, at least 30, at least 40, at least 50, at least 60, at least 75, or at least 100 FRET probes, each of which has a sequence that is identically present in, or complementary to a region of, a different one of SEQ ID NOs: 1 to 86, 196 to 399, 950, 565 to 707, or 863 to 897. In some embodiments, a FRET probe is labeled with a donor/acceptor pair such that when the probe is digested during the PCR reaction, it produces a unique fluorescence emission that is associated with a specific target RNA. In some embodiments, when a composition comprises multiple FRET probes, each probe is labeled with a different donor/acceptor pair such that when the probe is digested during the PCR reaction, each one produces a unique fluorescence emission that is associated with a specific probe sequence and/or target RNA. In some embodiments, the sequence of the FRET probe is complementary to a target region of a target RNA. In other embodiments, the FRET probe has a sequence that comprises one or more base mismatches when compared to the sequence of the best-aligned target region of a target RNA.

In some embodiments, a composition comprises a FRET probe consisting of at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides, wherein at least a portion of the sequence is identically present in, or complementary to a region of one of SEQ ID NOs: 1 to 86, 196 to 399, 950, 565 to 707, or 863 to 897. In some embodiments, at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides of the FRET probe are identically present in, or complementary to a region of one of SEQ ID NOs: 1 to 86, 196 to 399, 950, 565 to 707, or 863 to 897. In some embodiments, the FRET probe has a sequence with one, two or three base mismatches when compared to the sequence or complement of one of SEQ ID NOs: 1 to 86, 196 to 399, 950, 565 to 707, or 863 to 897.

In some embodiments, the compositions comprise at least one target RNA-specific FRET probe comprising a sequence that is identically present in, or complementary to a region of, one of SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 or 86. In some embodiments, the compositions comprise at least two, at least three, at least five, at least 8, at least ten, at least 15, at least 20, at least 25, at least 30, at least 35, or at least 40 uniquely labeled target RNA-specific FRET probes, each comprising a sequence that is identically present in, or complementary to a region of, a different one of 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 or 86.

In some embodiments, the compositions comprise at least one target RNA-specific FRET probe comprising a sequence that is identically present in, or complementary to a region of, one of SEQ ID NOs: 8, 14, 23, 30, 39, 52, 57, 59, 60, 62, 63, 64, 65, 67, 74, 76, 78 or 79. In some embodiments, the compositions comprise at least two, at least three, at least five, at least eight, at least 10, at least 12, at least 15, or at least 18 uniquely labeled target RNA-specific FRET probes, each of which comprises a sequence that is identically present in, or complementary to a region of a different one of SEQ ID NOs: 8, 14, 23, 30, 39, 52, 57, 59, 60, 62, 63, 64, 65, 67, 74, 76, 78 or 79.

In some embodiments, the compositions comprise at least one target RNA-specific FRET probe comprising a sequence that is identically present in, or complementary to a region of one of SEQ ID NOs: 6, 17, 19, 20, 21, 27, 29, 33, 34, 35, 38, 45, 46, 47, 48, 49, 69 or 84. In some embodiments, the compositions comprise at least two, at least three, at least five, at least eight, at least 10, at least 12, at least 15, or at least 18 uniquely labeled target RNA-specific FRET probes, each of which comprises a sequence that is identically present in, or complementary to a region of a different one of SEQ ID NOs: 6, 17, 19, 20, 21, 27, 29, 33, 34, 35, 38, 45, 46, 47, 48, 49, 69 or 84.

In some embodiments, the compositions comprise at least one target RNA-specific FRET probe comprising a sequence that is identically present in, or complementary to a region of, one of SEQ ID NOs: 8, 14, 59, 62, 63, 64, 74, or 78. In some embodiments, the compositions comprise at least two, at least three, at least four, at least five, at least six, at least seven, or at least eight uniquely labeled target RNA-specific FRET probes, each of which comprises a sequence that is identically present in, or complementary to a region of, a different one of SEQ ID NOs: 8, 14, 59, 62, 63, 64, 74, or 78.

In some embodiments, the compositions comprise at least one target RNA-specific FRET probe comprising a sequence that is identically present in, or complementary to a region of, one of SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 or 85. In some embodiments, the compositions comprise at least two, at least three, at least five, at least 8, at least ten, at least 15, at least 20, at least 25, at least 30, or at least 35 uniquely labeled target RNA-specific FRET probes, each of which comprises a sequence that is identically present in, or complementary to a region of, a different one of SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 or 85.

In some embodiments, the compositions comprise at least one target RNA-specific FRET probe comprising a sequence that is identically present in, or complementary to a region of, one of SEQ ID NOs: 9, 50, 51, 70, 72 or 75. In some embodiments, the compositions comprise at least two, at least three, at least four, at least five, or at least six uniquely labeled target RNA-specific FRET probes, each of which comprises a sequence that is identically present in, or complementary to a region of, a different one of SEQ ID NOs: 9, 50, 51, 70, 72 or 75.

In some embodiments, the compositions comprise at least one target RNA-specific FRET probe comprising a sequence that is identically present in, or complementary to a region of, one of SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, or 648. In some embodiments, the compositions comprise at least two, at least five, at least 10, at least 15, at least 20, at least 25, or at least 30 uniquely labeled target RNA-specific FRET probes, each of which comprises a sequence that is identically present in, or complementary to a region of, a different one of SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, or 648.

In some embodiments, the compositions comprise at least one target RNA-specific FRET probe comprising a sequence that is identically present in, or complementary to a region of, one of SEQ ID NOs: 231, 236, 242, 260, 261, 266, 287, 566, 567, 568, 571, 570, 574, 580, 581, 588, 598, 601, 608, 624, 626, 629, or 632. In some embodiments, the compositions comprise at least two, at least five, at least 10, at least 15, or at least 20 uniquely labeled target RNA-specific FRET probes, each of which comprises a sequence that is identically present in, or complementary to a region of, a different one of SEQ ID NOs: 231, 236, 242, 260, 261, 266, 287, 566, 567, 568, 571, 570, 574, 580, 581, 588, 598, 601, 608, 624, 626, 629, or 632.

In some embodiments, the compositions comprise at least one target RNA-specific FRET probe comprising a sequence that is identically present in, or complementary to a region of, one of SEQ ID NOs: 226 to 289, 565 to 604, or 863 to 868. In some embodiments, the compositions comprise at least two, at least five, at least 10, at least 15, at least 20, at least 25, at least 30, at least 40, at least 50, at least 60, or at least 70 uniquely labeled target RNA-specific FRET probes, each of which comprises a sequence that is identically present in, or complementary to a region of a different one of SEQ ID NOs: 226 to 289, 565 to 604, or 863 to 868.

In some embodiments, a kit comprises a polynucleotide discussed above. In some embodiments, a kit comprises at least one primer and/or probe discussed above. In some embodiments, a kit comprises at least one polymerase, such as a thermostable polymerase. In some embodiments, a kit comprises dNTPs. In some embodiments, kits for use in the real time RT-PCR methods described herein comprise one or more target RNA-specific FRET probes and/or one or more primers for reverse transcription of target RNAs and/or one or more primers for amplification of target RNAs or cDNAs reverse transcribed therefrom.

In some embodiments, one or more of the primers and/or probes is "linear". A "linear" primer refers to a polynucleotide that is a single stranded molecule, and typically does not comprise a short region of, for example, at least 3, 4 or 5 contiguous nucleotides, which are complementary to another region within the same polynucleotide such that the primer forms an internal duplex. In some embodiments, the primers for use in reverse transcription comprise a region of at least 4, at least 5, at least 6, at least 7 or more contiguous nucleotides at the 3'-end that has a sequence that is complementary to region of at least 4, at least 5, at least 6, at least 7 or more contiguous nucleotides at the 5'-end of a target RNA.

In some embodiments, a kit comprises one or more pairs of linear primers (a "forward primer" and a "reverse primer") for amplification of a cDNA reverse transcribed from a target RNA. Accordingly, in some embodiments, a first primer comprises a region of at least 4, at least 5, at least 6, at least 7, at least 8, at least 9, or at least 10 contiguous nucleotides having a sequence that is identical to the sequence of a region of at least 4, at least 5, at least 6, at least 7, at least 8, at least 9, or at least 10 contiguous nucleotides at the 5'-end of a target RNA. Furthermore, in some embodiments, a second primer comprises a region of at least 4, at least 5, at least 6, at least 7, at least 8, at least 9, or at least 10 contiguous nucleotides having a sequence that is complementary to the sequence of a region of at least 4, at least 5, at least 6, at least 7, at least 8, at least 9, or at least 10 contiguous nucleotides at the 3'-end of a target RNA. In some embodiments, the kit comprises at least a first set of primers for amplification of a cDNA that is reverse transcribed from a target RNA capable of specifically hybridizing to a nucleic acid comprising a sequence identically present in one of SEQ ID NOs: 1 to 86 and/or a cDNA that is reverse transcribed from a target RNA that comprises at least 15 contiguous nucleotides of a sequence selected from SEQ ID NOs: 196 to 399, 950, 565 to 707, and 863 to 897.

In some embodiments, the kit comprises at least two, at least five, at least 10, at least 15, at least 20, at least 25, at least 30, at least 40, at least 50, at least 60, at least 75, or at least 100 sets of primers, each of which is for amplification of a cDNA that is reverse transcribed from a different target RNA capable of specifically hybridizing to a sequence selected from SEQ ID NOs: 1 to 86 and/or a cDNA that is reverse transcribed from a target RNA that comprises at least 15 contiguous nucleotides of a sequence selected from SEQ ID NOs: 196 to 399, 950, 565 to 707 and 863 to 897. In some embodiments, the kit comprises at least one set of primers that is capable of amplifying more than one cDNA reverse transcribed from a target RNA in a sample.

In some embodiments, probes and/or primers for use in the compositions described herein comprise deoxyribonucleotides. In some embodiments, probes and/or primers for use in the compositions described herein comprise deoxyribonucleotides and one or more nucleotide analogs, such as LNA analogs or other duplex-stabilizing nucleotide analogs described above. In some embodiments, probes and/or primers for use in the compositions described herein comprise all nucleotide analogs. In some embodiments, the probes and/or primers comprise one or more duplex-stabilizing nucleotide analogs, such as LNA analogs, in the region of complementarity.

In some embodiments, the compositions described herein also comprise probes, and in the case of RT-PCR, primers, that are specific to one or more housekeeping genes for use in normalizing the quantities of target RNAs. Such probes (and primers) include those that are specific for one or more products of housekeeping genes selected from U6 snRNA, RNU44, RNU48, U47, 7SL scRNA, U1 snRNA, 5.8S rRNA, and U87 scaRNA.

In some embodiments, the kits for use in real time RT-PCR methods described herein further comprise reagents for use in the reverse transcription and amplification reactions. In some embodiments, the kits comprise enzymes such as reverse transcriptase, and a heat stable DNA polymerase, such as Taq polymerase. In some embodiments, the kits further comprise deoxyribonucleotide triphosphates (dNTPs) for use in reverse transcription and amplification. In further embodiments, the kits comprise buffers optimized for specific hybridization of the probes and primers.

4.2.1. Exemplary Normalization of RNA Levels

In some embodiments, quantitation of target RNA expression levels requires assumptions to be made about the total RNA per cell and the extent of sample loss during sample preparation. In order to correct for differences between different samples or between samples that are prepared under different conditions, the quantities of target RNAs in some embodiments are normalized to the expression of at least one endogenous housekeeping gene.

Appropriate genes for use as reference genes in the methods described herein include those as to which the quantity of the product does not vary between normal samples and samples from sepsis patients, or between different cell lines or under different growth and sample preparation conditions. In some embodiments, endogenous housekeeping genes useful as normalization controls in the methods described herein include, but are not limited to, U6 snRNA, RNU44, RNU48, U47, 7SL scRNA, U1 snRNA, 5.8S rRNA, and U87 scaRNA. In typical embodiments, the at least one endogenous housekeeping gene for use in normalizing the measured quantity of microRNAs is selected from U6 snRNA, RNU44, RNU48, U47, 7SL scRNA, U1 snRNA, 5.8S rRNA, and U87 scaRNA. In some embodiments, one housekeeping gene is used for normalization. In some embodiments, more than one housekeeping gene is used for normalization.

4.2.2. Exemplary Qualitative Methods

In some embodiments, methods comprise detecting a qualitative change in a target RNA profile generated from a human sample as compared to a normal target RNA profile (in some exemplary embodiments, a target RNA profile of a control sample). Some qualitative changes in the expression profile are indicative of the presence of sepsis in a sample from a subject. The term "target RNA profile" refers to a set of data regarding the concurrent expression of a plurality of target RNAs in the same sample.

In some embodiments, at least one, at least two, at least three, at least four, at least five, at least six, at least seven, at least eight, at least 10, at least 12, at least 15, at least 20, at least 25, at least 30, at least 35, or at least 40 of the target RNAs of the plurality of target RNAs are capable of specifically hybridizing to a nucleic acid comprising a sequence selected from SEQ ID NOs: 6, 8, 11, 13, 14, 15, 17, 19, 20, 21, 23, 27, 29, 30, 33, 34, 35, 38, 39, 45, 46, 47, 48, 49, 52, 56, 57, 58, 59, 60, 62, 63, 64, 65, 67, 69, 71, 73, 74, 76, 78, 79, 84 and 86. In some embodiments, at least one, at least two, at least three, at least four, at least five, at least six, at least seven, at least eight, at least nine, at least 10, at least 11, at least 12, at least 15, or at least 18 of the target RNAs of the plurality of target RNAs is capable of specifically hybridizing to a nucleic acid comprising a sequence selected from SEQ ID NOs: 8, 14, 23, 30, 39, 52, 57, 59, 60, 62, 63, 64, 65, 67, 74, 76, 78 and 79. In some embodiments, at least one, at least two, at least three, at least four, at least five, at least six, at least seven, at least eight, at least nine, at least 10, at least 11, at least 12, at least 15, or at least 18 of the target RNAs of the plurality of target RNAs is capable of specifically hybridizing to a nucleic acid comprising a sequence selected from SEQ ID NOs: 6, 17, 19, 20, 21, 27, 29, 33, 34, 35, 38, 45, 46, 47, 48, 49, 69 and 84. In some embodiments, at least one, at least two, at least three, at least four, at least five, at least six, at least seven, or at least eight of the target RNAs of the plurality of target RNAs is capable of specifically hybridizing to a nucleic acid comprising a sequence selected from SEQ ID NOs: 8, 14, 59, 62, 63, 64, 74, and 78. In some embodiments, at least one, at least two, at least three, at least four, at least five, at least six, at least seven, at least eight, at least 10, at least 12, at least 15, at least 20, at least 25, at least 30, or at least 35 of the target RNAs of the plurality of target RNAs is capable of specifically hybridizing to a nucleic acid comprising a sequence selected from SEQ ID NOs: 1, 2, 3, 4, 5, 7, 10, 12, 16, 18, 22, 24, 25, 26, 28, 30, 31, 32, 37, 41, 42, 43, 44, 53, 54, 55, 61, 66, 68, 77, 80, 81, 82, 83 and 85. In some embodiments, at least one, at least two, at least three, at least four, at least five, or at least six of the target RNAs of the plurality of target RNAs is capable of specifically hybridizing to a nucleic acid comprising a sequence selected from SEQ ID NOs: 9, 50, 51, 70, 72 and 75.

In some embodiments, at least one, at least two, at least five, at least 10, at least 15, at least 20, at least 25, at least 30, at least 40, at least 50, at least 60, or at least 75 of the plurality of target RNAs is capable of specifically hybridizing to a nucleic acid comprising a sequence selected from SEQ ID NOs: 1 to 86. In some embodiments, at least one, at least two, at least five, at least 10, at least 15, at least 20, at least 25, at least 30, at least 40, at least 50, at least 75, or at least 100 of the plurality of target RNAs comprises at least 15 contiguous nucleotides of a sequence selected from SEQ ID NOs: 196 to 399, 950, 565 to 707, and 863 to 897. In some embodiments, at least one, at least two, at least five, at least 10, at least 15, at least 20, or at least 25 of the plurality of target RNAs comprises at least 15 contiguous nucleotides of a sequence selected from SEQ ID NOs: 231, 236, 237, 242, 245, 253, 260, 261, 262, 263, 266, 269, 275, 287, 303, 342, 352, 566, 567, 568, 571, 570, 573, 574, 575, 577, 579, 580, 581, 588, 591, 598, 601, 608, 612, 613, 624, 626, 629, 632, 635, 637, 641, 642, 644, and 648. In some embodiments, at least one, at least two, at least five, at least 10, at least 15, at least 20, or at least 25 of the plurality of target RNAs comprises at least 15 contiguous nucleotides of a sequence selected from SEQ ID NOs: 231, 236, 242, 260, 261, 266, 287, 566, 567, 568, 571, 570, 574, 580, 581, 588, 598, 601, 608, 624, 626, 629, and 632. In some embodiments, at least one, at least two, at least five, at least 10, at least 15, at least 20, at least 25, at least 30, at least 40, at least 50, at least 60, or at least 70 of the plurality of target RNAs comprises at least 15 contiguous nucleotides of a sequence selected from SEQ ID NOs: 226 to 289, 565 to 604, and 863 to 868. In some embodiments, at least one, at least two, at least five, at least 10, at least 15, at least 20, at least 25, at least 30, at least 40, at least 50, at least 60, or at least 75 of the plurality of target RNAs comprises a sequence that is complementary to at least 15 contiguous nucleotides of a sequence selected from SEQ ID NOs: 1 to 86. In some embodiments, a target RNA, in its mature form, comprises fewer than 30 nucleotides. In some embodiments, a target RNA is a microRNA.

Qualitative expression data for use in preparing target RNA expression profiles is obtained using any suitable analytical method, including the analytical methods presented herein.

In some embodiments, for example, concurrent expression data are obtained using, e.g., a microarray, as described above. Thus, in addition to use for quantitative expression level assays of specific target RNAs as described above, a microarray comprising probes having sequences that are complementary to a substantial portion of the miRNome may be employed to cam/out target RNA gene expression profiling, for analysis of target RNA expression patterns.

In some embodiments, distinct target RNA signatures are associated with established markers for sepsis. In some embodiments, distinct target RNA signatures are associated with established markers for sepsis caused by bacterial infection, such as for sepsis caused by gram-positive bacterial infection, sepsis caused by gram-negative bacterial infection or sepsis caused by mycobacterial infection. In some embodiments, distinct target RNA signatures are associated with established markers for sepsis caused by viral infection. In some embodiments, distinct target RNA signatures are associated with established markers for sepsis caused by multiple infection, such as by co-infection with bacteria and viruses, or by co-infection with more than one viral or more than one bacterial strain. In some embodiments, distinct target RNA signatures are associated directly with the level of severity of the sepsis.

According to the expression profiling method, in some embodiments, total RNA from a sample from a subject suspected of having sepsis is quantitatively reverse transcribed to provide a set of labeled oligonucleotides complementary to the RNA in the sample. The oligonucleotides are then hybridized to a microarray comprising target RNA-specific probes to provide a hybridization profile for the sample. The result is a hybridization profile for the sample representing the expression pattern of target RNAs in the sample. The hybridization profile comprises the signal from the binding of the oligonucleotides reverse transcribed from the sample to the target RNA-specific probes in the microarray. In some embodiments, the profile is recorded as the presence or absence of binding (signal vs. zero signal). In some embodiments, the profile recorded includes the intensity of the signal from each hybridization. The profile is compared to the hybridization profile generated from a normal, i.e., nonseptic sample, or in some embodiments, a control sample. An alteration in the signal is indicative of the presence of sepsis in the subject.

4.3. Exemplary Additional Target RNAs

In some embodiments, in combination with detecting one or more target RNAs that are capable of specifically hybridizing to a nucleic acid comprising a sequence selected from SEQ ID NOs:1 to 86 and/or detecting one or more target RNAs comprising at least 15 contiguous nucleotides of a sequence selected from SEQ ID NOs: 196 to 399, 950, 565 to 707, and 863 to 897 and/or detecting one or more target RNAs that comprise a sequence that is complementary to at least 15 contiguous nucleotides of a sequence selected from SEQ ID NOs:1 to 86, methods herein further comprise detecting the level(s) of expression of at least one other marker associated with sepsis.

In some embodiments, the methods described herein further comprise detecting altered expression of sepsis-associated small RNAs with non-canonical hairpins.

In alternative embodiments, the methods described herein further comprise detecting chromosomal codependents, i.e., target RNAs clustered near each other in the human genome which tend to be regulated together. Accordingly, in further embodiments, the methods comprise detecting the expression of one or more target microRNAs, each situated within the chromosome no more than 50,000 bp from the chromosomal location of the pre-microRNA sequences in Table 2.

The following examples are for illustration purposes only, and are not meant to be limiting in any way.

5. EXAMPLES 5.1 Example 1

MicroRNAs from Monocytes

Using microarray analysis, distinct microRNAs were demonstrated to be overexpressed in monocytes in response to stimulation with pathogen mimics (agonists).

Cell Lines

Total RNA was prepared from the monocyte cell line THP-1 (ATCC No. TIB-202), which is an acute monocytic leukemia cell line of human peripheral blood origin.

Stimulation of Monocytes

Both THP-1 cells and pooled human monocytes from healthy donors were stimulated with different Toll-Like Receptors (TLR) agonists set forth in Table 5 below.

TABLE 5

| TLR Stimulated | Agonist |
|---|---|
| TLR2a | 1 µg/ml Pam3CSK4 (Invitrogen) |
| TLR2b | 10 µg/ml peptidoglycan (Invitrogen) |
| TLR3 | 25 µg/ml poly(I:C) (Invitrogen) |
| TLR4a | 10 µg/ml ultrapure LPS (from E. coli strain K12, Invitrogen) |
| TLR4b | 1 µg/ml LPS (E. coli O55:B5, Sigma) |
| TLR5 | 100 ng/ml Flagellin (S. typhimurium, Invitrogen) |
| TLR7 | 5 µg/ml imiquimod-R837(Invitrogen) |
| TLR9 | 5 µM CpG oligonucleotide (Invitrogen) |
| | 50 ng/ml phorbol myristyl acetate in combination with 1 uM ionomycin |
| | RPMI medium alone |

THP-1 cells were obtained from American Type Culture Collection (Manassas, Va.). THP-1 cells were grown to a concentration of 2.5 million per milliliter in RPMI medium 1640 supplemented with 10% FBS, 1× nonessential amino acids, 100 units/ml penicillin, 100 units/ml streptomycin, and 2 mM glutamine in a humidified incubator containing 5% $CO_2$ at 37° C. Human monocytes were isolated from whole blood of healthy donors (St Guy's hospital, UK), using CD14 positive magnetic microbead positive selection (according to manufacturer's protocol, Miltenyi Biotec). Isolated monocytes were then cultured with RPMI 1640 medium to a concentration of 2.5 million per milliliter in 6-well plates and cultured in a humidified incubator containing 5% $CO_2$ at 37° C.

To analyze miRNA expression, cells were treated for 8 h or 24 h with the stimuli shown above in Table 5. Concentrations were chosen according to manufactory recommendations and publication: Taganov, K. et al. PNAS, 103(33), p. 12481-6.

Total RNA was isolated by using standard TRIzol® protocol (Invitrogen). Cells from two confluent 75 cm² flasks were harvested (=approx 10⁷ cells). Total RNA was prepared using TRIzol® Reagent, Invitrogen (Carlsbad, Calif.) according to the manufacturer's protocol. All RNA samples were diluted in RNase-free water and stored in −80° C. (−112° F.).

RNA quality was assessed by calculating OD 260/280 ratios. The quality of all RNA samples was high as assessed using an Agilent Bioanalyser 2100, as exemplified by the electropherogram shown in FIG. 1 obtained for total RNA from human monocyte cell line THP-1 after stimulation for 8 h with agonist Pam3CSK4. Similar electropherograms were obtained for total RNA from the other cell samples as well.

MicroRNA Purification

MicroRNA purification was performed using a Flash PAGE Fractionator (Ambion). The Ambion gel purification protocol enriches for small RNAs less than 40 nucleotides (nt) long, including microRNAs. Briefly, a total RNA sample was loaded onto a pre-cast gel using the Flash PAGE Fractionator. The total RNA fraction smaller than 40 nt (the "microRNA fraction") was recovered after gel migration and resuspended into nuclease free water.

Microarray Analysis

Probe Design and Spotting

The oligonucleotide probes used for microarray preparation had the configuration 5'-NH$_2$—(C)$_6$-(spacer)-(oligomer probe sequence)-3'. The 5'-amino group allowed chemical bonding onto the array support. Each also included an identical spacer sequence of 15 nt, as shown below, to prevent non-specific interactions of the oligonucleotide probes with the array support:

(SEQ ID NO: 933)
5'AminoC6-TTGTAATACGACTCA-Oligo probe sequence.

Probe sequences given in Table 2 omit the linker.

The probes were synthesized according to standard protocols by Eurofins MWG Operon (Ebersberg, Germany). Nexterion (Schott) microarray glass slides were used as the solid support for the microarray.

The oligonucleotide probe concentration used for the spotting was 25 μmol. The probes were spotted in duplicate using the Nexterion spotting buffer provided with the array glass support by Schott with 1 SDS (sodium dodecyl sulfate) added to allow larger spat sizes (e.g., 100-150 microns compared to 70-100 microns without SDS). The spotter used was the QArray mini (Genetix) equipped with Stealth SMP3 pins (Telechem). After deposition of one series of spots, the spotting needle was washed 5 times with 60 mM NaOH before spotting the next series of probes. Each slide is designed with 32 blocks of spotted probes, with each block being a 20×20 square of spotted probes. Each probe was spotted in duplicate. Spotted glass slides were stored at 4° C. until use.

MicroRNA Labelling

The labelling of the microRNA fraction was adapted from a published protocol developed at EMBL (Heidelburg, Germany) by the European Molecular Biology Group (Castoldi et al., "A sensitive array for microRNA expression profiling (miChip) based on locked nucleic acids (LNA)," *RNA* 2006 May; 12(5):913-20. Epub 2006 Mar. 15, incorporated herein by reference in its entirety). Briefly, the microRNA fraction was incubated for 6 hours at 4° C. with a mixture containing 10 μM of dye-labelled tetra-nucleotide (5'-rUrUrUrU-Cy5-3') (or alternatively, 5'-rUrUrUrU-Cy3-3') (Biospring, Germany) in Ambion buffer diluted to 1× with RNase free water, 8% polyethylene glycol (PEG), 2 mM adenosine triphosphate (ATP), and T4 RNA ligase (0.7 U/μl). The labelling reaction was run by heating the mixture for 15 minutes at 65° C. This procedure ligated the poly-U dye-labelled tail to the 3' end of all the microRNAs. Labelled samples were stored at 4° C. before hybridization.

Array Hybridization

The labelled microRNA fraction was hybridized to the spotted arrays using a Discovery hybridization station (Ventana, Tucson, Ariz.). Briefly, 2 mL of a mixture of 1% BSA, 2×SSC, and 0.2% SDS was incubated with the chips for 30 min at 42° C. Then the chips were washed once using EZ Prep buffer (Ventana) and then three more times with Ribowash (Ventana). Next, 20 μl of the labelled microRNA mixture and 180 μl of ChipHybe Reagent (Ventana) were added to the array. The arrays were heated for 6 minutes at 37° C., then were incubated at 42° C. for 8 hours, after which the heating was stopped. The chips were washed once with Ribowash (Ventana) and then heated for 2 minutes at 37° C. The chips were washed again with Ribowash (Ventana) with one drop of CheapClean (Ventana) added, and incubated for 2 minutes at 37° C. The chips were washed two more times using Ribowash (Ventana). The chips were stored dry overnight. On the following day, the final washes were done according to Ventana's instructions for the Discovery hybridization station. The slides were washed twice with 2×SSC+0.2×SDS buffer and then one more time with 0.1× SSC. All the slides were dried using a speed centrifuge from Arrayit (TeleChem International, Sunnyvale, Calif.) at room temperature and kept in the dark before scanning.

As an alternative to the ChipHybe Reagent solution (solution 1), the following solution may be used for array hybridization (solution 2) to form probe:target RNA hybrids by mixing 2 parts of the 1.5×TMAC Hybridization Solution to 1 part (v:v) sample, so that the final component concentrations are 3M TMAC, 0.10% Sarkosyl, 50 nM Tris, and 4 mM EDTA, and incubating on the array at 42° C. for 8 h:

TABLE 6

1.5X TMAC Hybridization Solution

| Reagent | Catalog Number | Final Conc | Amount/ 250 mL |
|---|---|---|---|
| 5 M TMAC* | Sigma T3411 | 4.5 M | 225 mL |
| 20% Sarkosyl | — | 0.15% | 1.88 mL |
| 1 M Tris-HCl, pH 8.0 | Sigma T3038 | 75 mM | 18.75 mL |
| 0.5 M EDTA, pH 8.0 | Invitrogen 15575-020 | 6 mM | 3.0 mL |
| H$_2$O | — | — | 1.37 mL |

*TMAC is tetramethyl ammonium chloride

Array Image Acquisition

The arrays were scanned using an Axon™ scanner (Molecular Devices, Sunnyvale, Calif.) and their Genepix™ software. The image was formatted in tif format, defined by an image color depth of 16 bits/pixel (1600*1600). At such setting, pixels can assume intensity values ranging from 0 to 65,535. Pixels exhibiting the maximum intensity value are "saturated" and were assigned the value of 65,535. The resolution of the array scan was set at 10 μnl/pixel. For hybridization experiments using different fluorescent dyes (e.g., Cy5 and Cy3) the photomultiplier tube (PMT) was adjusted to the higher intensity spot (Cy3 is scanned at lower PMT settings than Cy5).

Array Image Analysis

The PMT of the laser scanner digitized the captured fluorescence intensity for each given "point" of a slide and stored the numerical value as a pixel corresponding to that point. A picture composed of such pixels was then analyzed.

The first task for image analysis was to detect the spot position, using a process called segmentation. Spots were segmented by circles of adaptable or fixed radius. To be reliably segmented and quantified, the spot diameter was required to be more than 5-6 pixels. Before segmentation an indexing grid was provided giving the approximate positions of the spots. The segmentation itself detected the limits of spots near the grid circles. Briefly, the Genepix software assigns a circle to each spot on the array (segmentation). The segmentation had to be conducted in a somewhat flexible way due to spotting imperfections and/or support deformation, as the spots were almost never on a perfectly rectangular grid.

After segmentation by the software, the circles were modified manually and adjusted onto the spots until all the spots on the array were clearly identified. At this stage, if the array presented high background noise preventing real spots from being distinguished from the background, the array was rejected for further analysis.

The second task of image analysis was to quantify spots and export the data into a result file. This was a relatively easy and well-defined task once the spots were located on the image. The statistical approach used most frequently to quantify spot intensity was the mean or median of pixels belonging to a spot. The median approach was more robust than the mean value in the presence of outlier pixels. In practice, however, there was little difference in the results obtained using mean or median.

Array Data Analysis

All the array data were analysed using the R bioconductor package ("Bioconductor: open software development for computational biology and bioinformatics," *Genome Biol.* 2004; 5(10):R80. Epub 2004 Sep. 15, which is incorporated herein by reference in its entirety).

Array data were first tested for quality by comparing the spot intensities for the internal controls. (Tables 7 and 8) One internal control (SEQ ID NO: 178) was used as a labelling control (this synthetic RNA is added to the purified microRNA fraction before labelling), and 7 other internal controls (SEQ ID NOs: 179-185) were used for the normalization of the data (these synthetic RNA controls are added to the total RNA fraction before hybridization at 520 fmol each/array).

TABLE 7

Internal controls added to total RNA or microRNA fraction

| Sequence | Identifier |
|---|---|
| CGCGCGUCGCUUUAUCUACUGU | SEQ ID NO: 178; CTL30_COMP |
| UUAUCGUUCGAUAAGUCGCGUU | SEQ ID NO: 179; CTL11_COMP |
| GAAGUUACUAUGUAGGCAACCU | SEQ ID NO: 180; CTL23_COMP |
| CGCGGGACUAAUUGUUACCGGG | SEQ ID NO: 181; CTL26_COMP |
| UCGCGUCGAACUCCGCAACCGA | SEQ ID NO: 182; CTL29_COMP |
| ACCGAACGCCGUACCCAUCGGG | SEQ ID NO: 183; CTL31_COMP |

TABLE 7-continued

Internal controls added to total RNA or microRNA fraction

| Sequence | Identifier |
|---|---|
| CGAGGGUAACGACUCUCGUGUC | SEQ ID NO: 184; CTL36_COMP |
| GCGUACCGACGCGUAGACGGAC | SEQ ID NO: 185; CTL13_COMP |

TABLE 8

Probes for hybridization of control sequences in microarray experiments

| Sequence (5'-3') | Sequence identification number |
|---|---|
| TTGTAATACGACTCAACAGTAGATAAAGCGACGCGCG | SEQ ID NO: 186; CTL30 |
| TTGTAATACGACTCAAACGCGACTTATCGAACGATAA | SEQ ID NO: 187; CTL11 |
| TTGTAATACGACTCAAGGTTGCCTACATAGTAACTTC | SEQ ID NO: 188; CTL23 |
| TTGTAATACGACTCACCCGGTAACAATTAGTCCCGCG | SEQ ID NO: 189; CTL26 |
| TTGTAATACGACTCATCGGTTGCGGAGTTCGACGCGA | SEQ ID NO: 190; CTL29 |
| TTGTAATACGACTCACCCGATGGGTACGGCGTTCGGT | SEQ ID NO: 191; CTL31 |
| TTGTAATACGACTCAGACACGAGAGTCGTTACCCTCG | SEQ ID NO: 192; CTL36 |
| TTGTAATACGACTCACCCGGTAACAATTAGACCCGCG | SEQ ID NO: 193; CTL26_MUT |
| TTGTAATACGACTCAGTCCGTCTACGCGTCGGTACGC | SEQ ID NO: 194; CTL13 |
| TTGTAATACGACTCAGGCCGTCTACGCGTCGGTACGC | SEQ ID NO: 195; CTL13_MUT |

All sequences for which the intensity of the spot was higher than the mean local background intensity plus 1.5 times its standard deviation were categorized as expressed microRNAs. The following criteria were required to be met in order consider the array intensity data valid for further analysis:

1. Specificity of the hybridization controls had to be within acceptance criteria (e.g. CTL26 vs. its corresponding single base mutant, CTL26 MUT, or CTL13 vs. its corresponding single base mutant, CTL13 MUT.
2. Approximate equality of the signal intensity of the replicates of the positive controls
3. Approximate equality between median block signal intensities based on the positive controls for each block
4. Approximate equality between median array signals based on all sequences detected
5. Signal intensity for the purification and labelling control (CTL30).

Statistical normalization of the data was done by computing the Log 2ratio where the Log 2ratio equals average intensity signal of the duplicated spots/median intensity of all positives controls for the block. The normalization was done per block to avoid non-homogenous labelling of all blocks of the array. This block-by-block normalization has been shown to be more efficient then using overall normalization of the slide. The obtained values are Log 2 values.

The intensities of the spots for each oligonucleotide probe were compared in the sample from the THP-1 cell line versus normal human monocytes, resulting in an evaluation of the relative expression for each microRNA.

The expression fold-change corresponds to $2^{(Log\ 2ratio)}$. The Log 2ratio is the ratio between the two conditions compared, or log 2(Xcell-line/Xnormal), which is the same as (log 2Xcell-line–log 2Xnormal), where X is the measured intensity value. In cases where there was no signal from the "normal" condition, the lowest measured intensity value in the experiment was used as the baseline from which a fold-change expression value was calculated. A fold-change value of less than zero corresponds to a down-regulation of (1/fold-change) times.

Data are tabulated in Table 2, and include all microRNAs over-expressed in monocytes in response to stimulation with one or more TLR agonists.

5.2 Example 2

Analysis of MicroRNAs from Stimulated Monocytes on Luminex Platform

The Luminex technology (Luminex Corp., Austin, Tex.) is based on liquid phase hybridization to probe-labelled beads, followed by flow cytometry detection of beads with differing ratios of fluorescent dyes. Beads with up to 100 different dye ratios are available, making it possible to interrogate a single sample for up to 100 analytes simultaneously.

Monocyte Samples

Human monocytes are isolated form whole blood of healthy donors using CD14 positive magnetic microbead positive selection (according to manufacturer's protocol, Miltenyi Biotec). Isolated monocytes are then cultured with RPMI 1640 medium to a concentration of 2.5 million per milliliter in 6-well plates, in a humidified incubator containing 5% $CO_2$ at 37° C.

Stimulation of Monocytes

To analyze miRNA expression, cells are treated for 8 h or 24 h with the stimuli shown above in Table 5 (Example 1).

Isolation of Total RNA from Monocyte Samples

Cells from two confluent 75 $cm^2$ flasks are harvested (=approx $10^7$ cells) for each agonist used to stimulate the monocytes. Total RNA is prepared using TRIzol® Reagent, Invitrogen (Carlsbad, Calif.) according to the manufacturer's protocol. All RNA samples are diluted in RNase-free water and stored in −80° C. (−112° F.).

Coupling of Probes to Luminex Beads

Aliquots of each 5'-amino-modified probe (having the structure 5'AminoC6-probe sequence, i.e., similar to the structure in Example 1, but without the linker sequence) are prepared at a concentration of 0.1 mmol/μL in molecular biology grade water. The probes are coupled to the beads using carbodiimide chemistry according to the manufacturer's protocol (Luminex bead coupling protocol). The probe-coupled beads are stored at 4° C.

Total RNA Preparation for Luminex Analysis

Eight fmoles of each of 7 internal controls (the same synthetic RNAs used for the array controls) are added to the total RNA fraction isolated from the patient samples. For each sample, three replicates are assayed in parallel. For each replicate, 250 ng of total RNA is used. Prior to hybridization with Luminex beads, the total RNA preparation is treated with calf intestinal phosphatase (CIP; Invitrogen) to prevent the formation of dendrimers, which result from the circularization of a single RNA molecule, or concatenation to another RNA molecule. Pre-treatment with CIP is according to the manufacturer's protocol, and removes 5'-phosphate groups.

Bead Labelling and Hybridization

After CIP treatment, the total RNA fraction is labelled with biotin using the Vantage microRNA Labelling Kit (Marligen). The labelled fraction is hybridized to the Luminex beads using the Marligen protocol. Briefly, the polynucleotide beads are mixed with the Marligen hybridization solution (1.5×TMAC) and the labelled total RNA. The hybridization is performed at 60° C. for an hour in the dark. After hybridization, the beads are washed using the Luminex standard 6×SSPET wash buffer (sodium phosphate, sodium chloride, EDTA, Triton X-100, pH 7.4).

Detection of Bead Hybridization

The detection of the Luminex beads is done using streptavidin phycoerythrin (SAPE) (Europa Bioproducts, Cambridge, UK). The SAPE is added to the washed beads according to the Luminex protocol. The beads are then read using the Luminex IS-200 instrument on the high gain setting for better resolution.

Data Acquisition and Analysis

The Luminex IS-200 reads at least 25 beads of each dye-ratio in the reaction mix. Each dye-ratio bead corresponds to a particular probe sequence, and the intensity value is returned as an average value of all read beads. The mean fluorescence intensity (MFI) data is normalized using synthetic RNA controls or alternatively using the mean of expressed oligonucleotides, and fold changes between normal and stimulated or diseased samples are computed using the Bioplex software (Bio-Rad, Hercules, Calif.) and the R bioconductor package (Bioconductor: open software development for computational biology and bioinformatics, Genome Biol. 2004; 5(10):R80. Epub 2004 Sep. 15).

Table 9 lists exemplary internal controls RNAs that can be added to total RNA prior to hybridization to the beads. Table 10 shows the corresponding probe sequences that are coupled to control beads.

TABLE 9

| Internal controls added to total RNA fraction | | |
|---|---|---|
| CGCGCGUCGCUUUAUCUACUGU | SEQ ID NO: 178; | CTL30_COMP |
| UUAUCGUUCGAUAAGUCGCGUU | SEQ ID NO: 179; | CTL11_COMP |
| GAAGUUACUAUGUAGGCAACCU | SEQ ID NO: 180; | CTL23_COMP |
| CGCGGGACUAAUUGUUACCGGG | SEQ ID NO: 181; | CTL26_COMP |
| UCGCGUCGAACUCCGCAACCGA | SEQ ID NO: 182; | CTL29_COMP |
| ACCGAACGCCGUACCCAUCGGG | SEQ ID NO: 183; | CTL31_COMP |
| CGAGGGUAACGACUCUCGUGUC | SEQ ID NO: 184; | CTL36_COMP |
| GCGUACCGACGCGUAGACGGAC | SEQ ID NO: 185; | CTL13_COMP |
| CGCGAUAAACGCCGGAUGGACC | SEQ ID NO: 944; | CTL28_COMP |
| UCGAGCGACUCCCGUAAUUUAA | SEQ ID NO: 945; | CTL35_COMP |

TABLE 10

Probes for hybridization of control sequences in Luminex experiments

| Sequence (5'-3') | Sequence identification number |
|---|---|
| ACAGTAGATAAAGCGACGCGCG | SEQ ID NO: 934; CTL30b |
| AACGCGACTTATCGAACGATAA | SEQ ID NO: 935; CTL11b |
| AGGTTGCCTACATAGTAACTTC | SEQ ID NO: 936; CTL23b |
| CCCGGTAACAATTAGTCCCGCG | SEQ ID NO: 937; CTL26b |
| TCGGTTGCGGAGTTCGACGCGA | SEQ ID NO: 938; CTL29b |
| CCCGATGGGTACGGCGTTCGGT | SEQ ID NO: 939; CTL31b |
| GACACGAGAGTCGTTACCCTCG | SEQ ID NO: 940; CTL36b |
| CCCGGTAACAATTAGACCCGCG | SEQ ID NO: 941; CTL26b_MUT |
| GTCCGTCTACGCGTCGGTACGC | SEQ ID NO: 942; CTL13b |
| GGCCGTCTACGCGTCGGTACGC | SEQ ID NO: 943; CTL13b_MUT |
| GGTCCATCCGGCGTTTATCGCG | SEQ ID NO: 946; CTL28 |
| TTAAATTACGGGAGTCGCTCGA | SEQ ID NO: 947; CTL35 |

Analysis

All sequences for which the intensity of the coupled bead is higher than 50 MFI are categorized as expressed microRNAs. The following criteria must be met in order consider the coupled bead intensity data valid for further analysis:

1. Approximate equality of the signal intensity of the replicates of the positive controls;
2. Approximate equality between median well signal intensities based on the positive controls for each well;
3. Approximate equality between median wells signals based on all sequences detected.

Statistical normalization of the data is done by computing the Log 2ratio where the Log 2ratio equals average intensity signal of 50 replicates of the same bead (each coupled to the same oligo sequence) divided by the median intensity of all of the positive controls in one well. The normalization is done per well to avoid non-homogenous labelling of all wells of the plate. This well-by-well normalization has been shown to be more efficient then using overall normalization of the plate. The obtained values are Log 2 values.

The intensities of the beads for each coupled bead are compared in the sample from monocytes from healthy donors grown in PMI medium, which does not activate the cells, versus monocytes stimulated in vitro (stimulated with a TLR agonist or grown in PMA medium, which activates the cells), resulting in an evaluation of the relative expression for each microRNA.

The expression fold-change corresponds to $2^{(Log\ 2ratio)}$. The Log 2ratio is the ratio between the two conditions compared, or log 2(Xcell-line/Xnormal), which is the same as (log 2Xcell-line−log 2Xnormal), where X is the measured intensity value. In cases where there is no signal from the "normal" condition, the lowest measured intensity value in the experiment is used as the baseline from which a fold-change expression value was calculated. A fold-change value of less than zero corresponds to a down-regulation of (1/fold-change) times. A two-fold change, either upregulated or downregulated, is considered significant.

5.3 Example 3

Bioinformatic Analysis to Identify microRNAs

In order to identify the microRNAs detected with the probes shown, e.g., in Table 2, small RNA sequencing (smRNASeq) datasets were analysed using the probe sequences to identify expressed microRNAs detected by those sequences. The analysis identified 11 sequences with precise ends, corresponding to 11 arms. Those 11 candidate microRNA sequences are show in Table 11.

TABLE 11 microRNA candidate sequences corresponding to probes

| Arm name | microRNA candidate sequence 5' -> 3' | SEQ ID |
|---|---|---|
| 4214-R | CCCCTGCAGAGCTCACA | 215 |
| 6511-R | AATAGATATTATGTTTTA | 216 |
| 7997-L | TAGTGTAACGGAAATGTTTACA | 217 |
| 6433-L | AAGGCTGAGCAGCAGAGGCAGCAAGAGC | 218 |
| 3995-L | TGGCCTGACGTGAGGAGG | 219 |
| 6192-L | TGGGTGGGTGGTTTTTT | 220 |
| 6998-L | TTCTCCACTGTGCTGCTACC | 221 |
| 9654-L | AGCTATGCTCACTCTCAA | 222 |
| 4504-L | AAATCAATAAATAATCAG | 223 |
| 5230-L | TGTGTTGGGTGACCCTGG | 224 |
| 4440-L | GCCCAGTGCTCTGAATGTCAAA | 225 |

5.4 Example 5

Sequencing Analysis to Identify microRNAs Associated with Sepsis

Total RNA from a sepsis patient was used for preparing a smRNASeq dataset. Briefly, 5 μg of total RNA was used for small RNA sequencing on a Solexa GA 11 (Illumina) using a standard library and sequencing protocol provided by the manufacturer.

The number of times a microRNA appeared in the sepsis smRNASeq dataset was then compared to the number of times the same microRNA appeared in each of 77 non-sepsis patient smRNASeq datasets. When the sepsis smRNASeq dataset contained the highest number of counts for a particular microRNA, it was assigned a rank of 1. When the sepsis smRNASeq dataset contained the second highest number of counts for a particular microRNA, it was assigned a rank of 2, and so on. All candidates having a rank between 1 and 5 were retained. A total of 175 candidate microRNA sequences, corresponding to 165 different aims, are shown in Table 12, along with the rank assigned to each sequence. When a microRNA has multiple isomirs, the sum of all of the counts for all of the isomirs was used for the comparison. Furthermore, when a precursor gene for a particular microRNA sequence is present at multiple locations in the genome, both candidate names are shown, with the same ranking and same sequence. Either or both of those candidates may be present at increased levels in the sepsis patient sample.

TABLE 12

Novel microRNAs found at higher numbers in a sepsis smRNASeq dataset

| microRNA Candidate Name | MicroRNA Candidate Sequence 5' -> 3' | Rank | SEQ ID NO |
|---|---|---|---|
| 11253-L | CTGTAATTAGTCAGTTTTCTGT | 1 | 226 |
| 11312-L | GTGGACTCCAGCAGTAG | 1 | 227 |
| 13196-R | AGAGCTCTCTGGCTTTGCCTAAA | 1 | 228 |
| 13339-L | ACCCTCAGTCCGTATTGGTCTCT | 1 | 229 |
| 13367-L | TGCTGTATTGTCAGGTAGTGA | 1 | 230 |
| 13446-R | AGCTTTTGGGAATTCAGGTAG | 1 | 231 |
| 13448-L | TATGTATGTATGTATGT | 1 | 232 |
| 13452-L | TATGGAGGTTCTAGACCATGT | 1 | 233 |
| 13627-L | ATCCTAGCTTGCCTGAGACTGT | 1 | 234 |
| 13629-L | TCTGATCAGGCAAAATTGCAGA | 1 | 235 |
| 13642-R | AAAAACTGTGATTACTTTTGCA | 1 | 236 |
| 13661-R | GAGACAGTAGTTCTTGCCTGGT | 1 | 237 |
| 13665-R | TCTCTTTATATGTACTGGAGC | 1 | 238 |
| 13667-R | TAAAAACCGTGACTACTTCTG | 1 | 239 |
| 13670-L | ATAGGACTTTTGAAGGAAGAG | 1 | 240 |
| 13672-R | AAATGTTGAGATACACTGAA | 1 | 241 |
| 13677-L | AATTACAGATTGTCTCAGAGAA | 1 | 242 |
| 13691-R | AAAATCCTTTTTGTTTTTCCAG | 1 | 243 |
| 13692-R | ATTTAACTGGACATCTTGCATT | 1 | 244 |
| 13694-L | ACCTGGACCCAGCGTAGACAAAGA | 1 | 245 |
| 13694-R | CATATCTACCTGGACCCAGTG | 1 | 246 |
| 13694-R | CATATCTACCTGGACCCAGTGTA | 1 | 247 |
| 13696-L | ATCCTAGCTTGCCTGAGACTGT | 1 | 248 |
| 13716-L | AAGAGTTACTAGAACTATT | 1 | 249 |
| 13716-R | GAATAGTTTTAGTAACTCTTGA | 1 | 250 |
| 13717-L | AATTTATTCTTGGTAGGTTGTA | 1 | 251 |
| 13717-R | CAACGTACTAAGAATAAATTTC | 1 | 252 |
| 13719-L | AGCTCTAGAAAGATTGTTGACCA | 1 | 253 |
| 13721-R | ATTGTTTAGTACCTATAATG | 1 | 254 |
| 13727-L | CGGAGTTGTAAGTGTTGACAA | 1 | 255 |
| 13727-R | ACTTACAACTCTGGAAAAGCAGA | 1 | 256 |
| 13729-L | AGCAATACTGTTACCTGAAATA | 1 | 257 |
| 13731-L | GAAGAACTGTTGCATTTGCCCTG | 1 | 258 |
| 13755-L | TAGTGGTCAGAGGGCTTATGA | 1 | 259 |
| 14086-L | GGTGTAATGGTTAGCACTCTGGA | 1 | 260 |
| 14093-L | AGTGGTAGAGCATTTGA | 1 | 261 |
| 14111-L | GTAGTGTTTCTTACTTTA | 1 | 262 |

TABLE 12-continued

Novel microRNAs found at higher numbers in a sepsis smRNASeq dataset

| microRNA Candidate Name | MicroRNA Candidate Sequence 5' -> 3' | Rank | SEQ ID NO |
|---|---|---|---|
| 14113-L | AGATCGCCGAAGCGTCGGA | 1 | 263 |
| 14117-R | TTAAAACTTTAAGTGTGCCTA | 1 | 264 |
| 14154-L | AGTTTCTAAGGATCATGTCTG | 1 | 265 |
| 14177-L | TAGTGGTTAGTACTCTG | 1 | 266 |
| 14226-R | AGTTTCTAAGGATCATGTCTG | 1 | 267 |
| 14229-R | ACCTTCACTGTGACTCTGCTG | 1 | 268 |
| 14371-R | GTTTCCGTAGCGTAGTGGTTATCA | 1 | 269 |
| 14375-R | AGTCCTTAACAAGCATTGAGA | 1 | 270 |
| 14390-L | GTTAAGTGCTCCAAGGAGGTGG | 1 | 271 |
| 14390-L | GTTGCTATCGGGGACTAC | 1 | 272 |
| 14399-L | GCTGTGCTACGTCGCCCTGGA | 1 | 273 |
| 14479-R | ATTTTTCTTATAGGCTTCTAAG | 1 | 274 |
| 14482-R | GAATATGGGTATATTAGTTTGG | 1 | 275 |
| 14499-L | GGCCAGCCACCAGGAGGGCTGC | 1 | 276 |
| 14570-R | ACTAATAGAGGTAATAGTTGAA | 1 | 277 |
| 14596-R | TAGGAGGGAATAGTAAAAGCAG | 1 | 278 |
| 182-R | GACGTCAGAGGGAATCC | 1 | 279 |
| 2851-R | CAGAAGGGGAGTTGGGAGCAGA | 1 | 280 |
| 4215-L | TATGAACAGTGGATAGATTAAAGG | 1 | 281 |
| 4417-L | ATCGGAGAAACTCCCTGCGATGAG | 1 | 282 |
| 4784-L | CATCTTTTATTTGGTAAATTATGA | 1 | 283 |
| 4784-R | ATTGATTGTGGCAAAGTT | 1 | 284 |
| 4784-R | TATATTGATTGTGGCAAAGTT | 1 | 285 |
| 5392-R | ATGAGATACTGTCGGAGA | 1 | 286 |
| 6415-R | ATTGTCCTTGCTGTTTGGAGATA | 1 | 287 |
| 7038-R | ATTTTCTGAACTGTACAT | 1 | 288 |
| 7491-R | GTGGATTTTGTTTGCTGT | 1 | 289 |
| 11626-R | ACTGGCCTGGGACTACCGGGGG | 2 | 290 |
| 13270-L | TTGTTCTTTGGTCTTTCAGC | 2 | 291 |
| 13322-R | CATTACTGATTTTCTTTTCTTAGA | 2 | 292 |
| 13375-L | AGGGGCTGGGGTTTCAGGTTCT | 2 | 293 |
| 13375-L | CAGGGGCTGGGGTTTCAGGTT | 2 | 294 |
| 13400-R | TTGTCTCTTGTTCCTCACACAG | 2 | 295 |
| 13437-R | ATATTATTAGCCACTTCTGGAT | 2 | 296 |
| 13446-L | ACCTGAATTACCAAAAGCTTT | 2 | 297 |
| 13447-R | TATGGAAAGACTTTGCCACTCT | 2 | 298 |

TABLE 12-continued

Novel microRNAs found at higher numbers in a sepsis smRNASeq dataset

| microRNA Candidate Name | MicroRNA Candidate Sequence 5' -> 3' | Rank | SEQ ID NO |
|---|---|---|---|
| 13448-R | TATGGAAAGACTTTGCCACTCT | 2 | 299 |
| 13465-R | TAACGCATAATATGGACATGT | 2 | 300 |
| 13531-R | AGACTGACCTTCAACCCCACAG | 2 | 301 |
| 13629-R | CCTGCAACTTTGCCTGATCAGA | 2 | 302 |
| 13640-L | TGGATATGATGACTGAA | 2 | 303 |
| 13686-L | ACTTGTAATGGAGAACACTAAGC | 2 | 304 |
| 13687-R | ATTAAGGACATTTGTGATTGAT | 2 | 305 |
| 13704-R | TTTTTGTCAGTACATGTTAATG | 2 | 306 |
| 13710-R | ATTTGCTGTTAAGATATGGGAT | 2 | 307 |
| 14113-R | ACTACCGTTGGTTTCCGC | 2 | 308 |
| 14151-R | AGAGTTTGGATTAGTGGG | 2 | 309 |
| 14170-L | AACTAGCTCTGTGGATCCTGAC | 2 | 310 |
| 14220-L | TACGGATAATTGTAGCACTTC | 2 | 311 |
| 14327-R | AATGTTGGAATCCTCGCTAGAGC | 2 | 312 |
| 14328-R | TGTGGGACTTCTGGCCTTGACT | 2 | 313 |
| 14347-R | ACCTGGGTTGTCCCCTCTAG | 2 | 314 |
| 14361-L | GCCTGGACTGCCTGGAGAAAGCG | 2 | 315 |
| 14385-L | GTGGCCGAGGACTTTGA | 2 | 316 |
| 14385-L | GTGGCCGAGGACTTTGATT | 2 | 317 |
| 14385-L | GTGGCCGAGGACTTTGATTG | 2 | 318 |
| 14415-R | TTAAGATTTGGTGCAATAT | 2 | 319 |
| 14483-R | ACTCTTTAAGGATAGGGCTGAA | 2 | 320 |
| 14508-L | TAGGGGAAAAGTCCTGATCCGG | 2 | 321 |
| 14527-R | TAGACAATCTGTGTAGAGTGC | 2 | 322 |
| 14532-L | TGAGACCAGGACTGGATGCACCA | 2 | 323 |
| 14539-R | AAGTTTCTCTGAAGGTGTAG | 2 | 324 |
| 14539-R | AGTTTCTCTGAAGGTGTAG | 2 | 325 |
| 14541-R | ATTAAGGACATTTGTGATT | 2 | 326 |
| 14549-R | TTGTAACATTCTGGTGTGTTG | 2 | 327 |
| 14578-R | TTGTAACATTCTGGTGTGTTG | 2 | 328 |
| 62-L | GAATTAATGGCTGGCTGGGAG | 2 | 329 |
| 6520-R | ATATTGGAATCCCCGCTAGAGC | 2 | 330 |
| 7578-L | GGGGCTGTAGCTCAGGG | 2 | 331 |
| 11607-R | GGAGGAACCTTGGAGCTTCGGC | 3 | 332 |
| 12625-R | GCAGCCCAGCTGAGGCCTCTG | 3 | 333 |
| 13005-R | AACAACTTAGACACGTGACTGTA | 3 | 334 |
| 13214-L | TTCCTTAACTAAAGTACTCAGA | 3 | 335 |
| 13244-R | CAGGCAGCTGTTAACAG | 3 | 336 |
| 13340-L | GAAGCAGCGCCTGTCGCAACTCG | 3 | 337 |
| 13452-R | TACATGGATGGAAACCTTCAAGCA | 3 | 338 |
| 13628-L | AGACCCATTGAGGAGAAGGTTC | 3 | 339 |
| 13655-L | CAAAAGTGATCGTGGTTTTTG | 3 | 340 |
| 13677-R | TCTCTCGGACAAGCTGTAGGT | 3 | 341 |
| 14085-L | CTAAGCCAGGGATTGTGGGT | 3 | 342 |
| 14156-R | CTTACACTCTTGTCCATCTAGA | 3 | 343 |
| 14161-R | TGAACAGCCTCTGGCAATC | 3 | 344 |
| 14244-R | TCACAATGCTGACACTCAAACTGCTGACA | 3 | 345 |
| 14289-R | ATGTAGTCTCCCCTACCTAG | 3 | 346 |
| 14380-R | CATGAGATCCAACTCTGAGC | 3 | 347 |
| 14409-R | TGAGTTTAGAGCTGTCTGCT | 3 | 348 |
| 14469-R | GACACCTCTGCACTCAAGGCGG | 3 | 349 |
| 14469-R | GACACCTCTGCACTCAAGGCGGC | 3 | 350 |
| 14485-L | GCAAGAAAGTGAGACTCTGCCT | 3 | 351 |
| 14556-R | AAGTTTCTCTGAACGTGTA | 3 | 352 |
| 14567-R | CATGCTAGGATAGAAAGAATGGG | 3 | 353 |
| 14581-L | TATCCAGCTTGTTACTATATGC | 3 | 354 |
| 2970-L | CCTCCCAAAGTGCTGGGATTA | 3 | 355 |
| 607-R | AATGATGATGCAAGAACTGAGA | 3 | 356 |
| 6493-L | TAGGAGCTATCAGAACTTAGTG | 3 | 357 |
| 11549-L | GTTCCTGCTGAACTGAGCCAGT | 4 | 358 |
| 11667-L | GTTCCTGCTGAACTGAGCCAGT | 4 | 359 |
| 12627-R | CCAACTAACCTCTGTATTCCAG | 4 | 360 |
| 13374-L | TGTTCCTCTGTCTCCCAGACTCTG | 4 | 361 |
| 13681-R | TGAGGAGATCGTCGAGGTTGGC | 4 | 362 |
| 13705-L | CCTCCCACTGCAGAGCCTGGG | 4 | 363 |
| 14069-R | GCCGGGTACTTTCGTATT | 4 | 364 |
| 14137-R | TTGGCTGGTCTCTGCTCCGCAG | 4 | 365 |
| 14200-L | CCTCCCAAAGTGCTGGGATTACAGG | 4 | 366 |
| 14244-L | GTTGGAGGATGAAAGTA | 4 | 367 |
| 14275-L | TGCCTTAGGAGAAAGTTTCTGG | 4 | 368 |
| 14288-R | GCCCGGAGAGCTGGGAGCCAGA | 4 | 369 |
| 14303-R | ACCGGATGGAGCTCTAGGGA | 4 | 370 |
| 14332-L | TGCCTTAGGAGAAAGTTTCTGG | 4 | 371 |

TABLE 12-continued

Novel microRNAs found at higher numbers in a sepsis smRNASeq dataset

| microRNA Candidate Name | MicroRNA Candidate Sequence 5' -> 3' | Rank | SEQ ID NO |
|---|---|---|---|
| 14367-R | ATGGATGATGATATCTGAGT | 4 | 372 |
| 14452-L | TTCCTTAACTAAAGTACTC | 4 | 373 |
| 14543-L | GAGCCAGTGGTGAGACAGTGAG | 4 | 374 |
| 14601-L | CGGGGCTGCCCTGAACGGGCCC | 4 | 375 |
| 2999-R | GTTCGAGACCAGCCTGGCC | 4 | 376 |
| 373-R | GTCGAACTTGACTATCTAG | 4 | 377 |
| 6216-L | GTGCTCTGAATGTCAAAGTGAAGA | 4 | 378 |
| 13413-R | CAGTTCAATGGTGTTCAGCAGA | 5 | 379 |
| 13630-L | AAAAGTAGTTGTGGTTTT | 5 | 380 |
| 13679-L | AAAAGTAGTTGTGGTTTT | 5 | 381 |
| 13709-R | AAGGGCTTCCTCTCTGCAGGAC | 5 | 382 |
| 13734-L | TGGACTTTTTCAGATTTGGGGAT | 5 | 383 |
| 13745-L | GACTCACTCACAGGATTGTGCA | 5 | 384 |
| 13748-L | GACTCACTCACAGGATTGTGCA | 5 | 385 |
| 13753-L | CCACTTGGATCTGAAGGCTGCC | 5 | 386 |
| 13761-L | TGAGGAGGATCTGAAGGATTGGA | 5 | 387 |
| 14121-R | TCATGTTGCTCTGCTGTTGCC | 5 | 388 |
| 14336-R | AGGAGAATCACTTGAACCC | 5 | 389 |
| 14338-R | ATGAAGTGTGACGTGGAC | 5 | 390 |
| 14338-R | TGGACATCCGCAAAGACCTGTACGCC | 5 | 391 |
| 14442-R | GCCTTTTTAACCGCGAGCGACA | 5 | 392 |
| 14454-R | ATGAAGTGTGACGTGGAC | 5 | 393 |
| 14454-R | TGGACATCCGCAAAGACCTGTACGCCAA | 5 | 394 |
| 14494-L | AGGACTGGACTCCCGGCAGCC | 5 | 395 |
| 14575-R | AAGGGCTTCCTCTCTGCAGGAC | 5 | 396 |
| 14583-L | ATGGCCAGAGCTCACACAGAGG | 5 | 950 |
| 14584-L | ATGGCCAGAGCTCACACAGAGG | 5 | 397 |
| 2850-L | AAAGTGCTGGGATTACAGG | 5 | 398 |
| 4135-R | GATGCCTGGGAGTTGCGATCTG | 5 | 399 |

Predicted microRNA precursor sequences for the microRNAs listed in Table 12 are shown in Table 13.

TABLE 13

Precursor sequences and chromosomal locations (from human genome NCBI36) of the microRNAs in Table 17

| microRNA Candidate | microRNA precursor Sequence 5'->3' | chrom | start | end | strand | SEQ ID NO |
|---|---|---|---|---|---|---|
| 62-L | GCAAAAGACATTTCCTTAGAATTAATGGCTGGCTGGGAGGCAGAGCCAAGGGCCACTGGTTCCTCCCAGCTGGTCATTAATCCTCAGGAAATGCCTGC | 12 | 64538072 | 64538169 | -1 | 400 |
| 182-R | GGAGTTCCTGTGACGCAATTAGCCATATAAGGAGCTCGGCCGGCGCGGCGGAGTGTTTGTTTGGTATCCTAGCAATGACGTCAGAGGGAATCC | 19 | 50662759 | 50662851 | -1 | 401 |
| 373-R | TTGGATGGTTTAGTGAGGCCCTCGGATCAGCCCGCTGGGTCAGCCCACTGCCCTGGCGGAACGCTGAGAAGACAGTCGAACTTGACTATCTAG | 2 | 132728445 | 132728537 | -1 | 402 |
| 607-R | GGGGGCTCATTAGGTGGAGATTGGTTTTTAATCAGCACCATGGCAATGATGATGCAAGAACTGAGATGCCACCTGATCCCCTGCCCCC | 1 | 158601772 | 158601859 | 1 | 403 |
| 2850-L | CAAAGTGCTGGGATTACAGGCGTGAGCCCCCGTGCCCGGCCTGTGTGTTTTTATAAAAAAGTTTTGGCTGGGCACAGTGGCTCACGCCTGTAATCCCAACACTTTG | 19 | 10794434 | 10794541 | -1 | 404 |
| 2851-R | CCCTTCCTGCCGGCCGGCCCCCTCCTCAGGCCCCTCCTTCTCAGCCCCAGCTCCCGCTCACCCCTGCCACGTCAAAGGAGGCAGAAGGGGAGTTGGGAGCAGAGAGGGGACCACGGGCTGGCTGGTCTGGGG | 9 | 130047027 | 130047158 | -1 | 405 |
| 2970-L | GCCTCCCAAAGTGCTGGGATTATAGGCGTGAGCCACTACGCCCAGCCTCTGAAACATTTTAAAAAATTATCTGGGTTAGGCCGGGCGTGGTGGCTCACGCCTGTAATTCCAGCACTTTGGGAGGC | 19 | 58991703 | 58991827 | 1 | 406 |
| 2999-R | GCCCAGGCTGCTGTCAAACTCCTGAGCTCACCCAGGCGCAATGGCTCATGCTTGTAATCCCAGCACTGGGAGGCCAAGGTGGGCAGATCACCTGAGGTCAGGAGTTCGAGACCAGCCTGGCC | 11 | 74716486 | 74716607 | -1 | 407 |
| 4135-R | CGGGTAAAGGTCGCCCTCAAGGTGACCCGCCTACTTTGCGGGATGCCTGGGAGTTGCGATCTGCCCG | 22 | 41341277 | 41341343 | 1 | 408 |

TABLE 13-continued

Precursor sequences and chromosomal locations (from human genome NCBI36) of the microRNAs in Table 17

| microRNA Candidate | microRNA precursor Sequence 5'->3' | chrom | start | end | strand | SEQ ID NO |
|---|---|---|---|---|---|---|
| 4215-L | GGCTTACAGAATTATGAACAGTGGATAGATTAAAGGCATTTAATATTTGTAAT TCATAATAACTGTAGAAATGGCC | 12 | 104086228 | 104086303 | 1 | 409 |
| 4417-L | GCTGGGGTTCATCGGAGAAACTCCCTGCGATGAGCCACTAGGGTCACGGACAG GGAACTTTTTGATGAGCGCCGAGT | 14 | 34943859 | 34943935 | 1 | 410 |
| 4784-R | AACTTTGTTAATCATCTTTTATTTGGTAAATTATGAATGGGTATACATTTGTA CAGTTCGTGTATATTGATTGTGGCAAAGTT | 12 | 9180205 | 9180287 | 1 | 411 |
| 4784-L | AACTTTGTTAATCATCTTTTATTTGGTAAATTATGAATGGGTATACATTTGTA CAGTTCGTGTATATTGATTGTGGCAAAGTT | 12 | 9180205 | 9180287 | 1 | 412 |
| 4784-R | AACTTTGTTAATCATCTTTTATTTGGTAAATTATGAATGGGTATACATTTGTA CAGTTCGTGTATATTGATTGTGGCAAAGTT | 12 | 9180205 | 9180287 | 1 | 413 |
| 5392-R | CTCTCTCTCTCAGTTACTCACAAAACATGGCTGTCTTATTCAGAGATTAGCAA TTATTGTAATGAGATACTGTCGGAGAGGG | 2 | 160081288 | 160081369 | 1 | 414 |
| 6216-L | CATGTGATTTCTGCCCACTGCTCTGAATGTCAAAGTGAAGAAATTCAATGAAG CACGGGTAAACGGCGGGAGTAACTATG | 11 | 77275152 | 77275231 | 1 | 415 |
| 6415-R | AGAAAATAACATTGTCAGACGTGTCATCCCCAGATACAATGGACAATATGCTA TTATAATCGTATGGCATTGTCCTTGCTGTTTGGAGATAATAGTGCTGACTTTA TTCCTCT | 2 | 207682945 | 207683057 | -1 | 416 |
| 6493-L | TTATTTACCAGCTCAGAATGTGGTAGGAGCTATCAGAACTTAGTGATCAAGTG AAGTCGTAGTTACTAATTTCTGATGCTCTTCCCCTGCAGAAGAGAGCTGTGGG AAG | 1 | 169826822 | 169826930 | 1 | 417 |
| 6520-R | GCTTCCAGAAGTGCACGCTCTAGCGAGGATTCCAACATTGGGGGAATTGGCCC AATATTGGAATCCCCGCTAGAGCGTGCACCTAAGC | 1 | 54292336 | 54292423 | -1 | 418 |
| 7038-R | ATTTAAAGAGAATTTTATTTACAGTTATTTCAAATGTAGAGAATGTAATTTTC TGAACTGTACATAAGTGCTCAATTTAAAT | 18 | 28363735 | 28363816 | 1 | 419 |
| 7491-R | TCATTAATTTATGCAAGGTAGCAGCCAGCATATTAGTTCACACCATTTGTGGA TTTTGTTTGCTGTCTCACATGCAAGGTGAAATGG | 5 | 115808968 | 115809054 | 1 | 420 |
| 7578-L | GAGGGGCTGTAGCTCAGGGTGTGCACTGCGAGGCTGGACCTGTTGAGTCTGCA GTGGACATCCATTTAGCTTCAGGTTGTC | 2 | 104755260 | 104755340 | 1 | 421 |
| 11253-L | GGCGTGCCTGGGAGTTGGCACTAAGTACAGCTGTAATTAGTCAGTTTTCTGTC CTGTCCACACAGAAAACCGTCTAGTTACAGTTGTAAGTTGTGCCAGACCTAAT CGCT | 1 | 234082900 | 234083009 | -1 | 422 |
| 11312-L | CCACCAACCTGTGGGAAGGCAGGTGGACTCCAGCAGTAGGTAGGTAACATCCA AGGTAGCCATACACAGCTGGTGTTTGTGAATCTGCACTTCCCCTGGGCAATGG | 6 | 90036688 | 90036793 | -1 | 423 |
| 11549-L | GGGCTTGACCCCTGTTCCTGCTGAACTGAGCCAGTGTACACAAACCAACTGTG TTTCAGCTCAGTAGGCACGGGAGGCAGAGCCC | 19 | 13808092 | 13808176 | 1 | 424 |
| 11607-R | GCTGAAGCTCTAAGGTTCCGCCTGCGGGCAGGAAGCGGAGGAACCTTGGAGCT TCGGC | 22 | 29886048 | 29886105 | -1 | 425 |
| 11626-R | ATGGCCTCTCCAGTCTGCAGCTCCCGGCAGCCTCGGGCCACACTCCCGGGATC CCCAGGGACTGGCCTGGGACTACCGGGGGTGGCGGCCGTGGCTCTGGCTAT | 16 | 533277 | 533300 | 1 | 426 |
| 11667-L | GGCTTTTTGCTCAAGGGCTCGACTCCTGTTCCTGCTGAACTGAGCCAGTGTGT AAAATGAGAACTGATATCAGCTCAGTAGGCACCGGAGGGCGGGTCCAATCGAC AGCC | 9 | 96888104 | 96888213 | -1 | 427 |
| 12625-R | CCACACCTGAGAACACGGCAGGTGAGCAGGACGAGGCTGGGCTGAACCCGTGG GTGAGGAGTGCAGCCCAGCTGAGGCCTCTGCTGTCTTATCTGTCTCCTACAGG CAATGG | 11 | 65160334 | 65160444 | 1 | 428 |
| 12627-R | CCACCTGGTTCCTGTACCCGTTCAGACGGTTCTTTGCAAGACATTCCTCCCAT TGTTCACCCCCAACTAACCTCTGTATTCCAGGGGC | 17 | 75962769 | 75962856 | 1 | 429 |
| 13005-R | TACAGTTCTGTCTAGGCAGTGGCTTGGGTTTTTATCGAGCAACAACTTAGACA CGTGACTGTAATATGCTGCAACTGTGTGTACTGAAAATATGTGAAAATGGTTG AATGTGGACTGTGTATATATGTATGTAAAAATTTCTGTGAGATGCTGCTGTC | 12 | 66342382 | 66342539 | 1 | 430 |

TABLE 13-continued

Precursor sequences and chromosomal locations (from human genome NCBI36) of the microRNAs in Table 17

| microRNA Candidate | microRNA precursor Sequence 5'->3' | chrom | start | end | strand | SEQ ID NO |
|---|---|---|---|---|---|---|
| 13196-R | AGGTGCTCCACCGTTCCTGCTGTGGAGAAGGAGGCGAAGTCAGAGAGCTCTTC CAAGCTTTCCCCAGGAAGAGCTCTCTGGCTTTGCCTTAAAGCTCCCCAGAGGT TTTGGAGGCTG | 10 | 103976793 | 103976909 | 1 | 431 |
| 13214-L | ATTTCTTTCCTTAACTAAAGTACTCAGATATTTATCCAAACATTATTGCTATG GGATTTCCTGCAGAAAGACTTGAAGGCGTATACAGGACAATATTGATGATGTA GTAAGGTAAGAA | 10 | 89643735 | 89643853 | 1 | 432 |
| 13244-R | GCTGTGCTGTGTGCCAATGTTTCGTTTGCCTCAGACAGGTATCTCTTCGTTAT CAGAAGAGTTGCTTCATTTCATCTGGGAGCAGAAAACAGCAGGCAGCTGTTAA CAG | 11 | 65027130 | 65027238 | 1 | 433 |
| 13270-L | TGGATGATTTGGAGTAGCAAAGCAGCAATTGTTCTTTGGTCTTTCAGCCATGA CCTGACCTTCTGTCTGTGAGACCAAAGAACTACTTTGCTTGGCCACCATCT | 1 | 241576085 | 241576188 | 1 | 949 |
| 13322-R | TTCTAGAACCGTAAAAAAGGAAGTAAGTACTGGTACATTACATTTTACACTTC ATATTCTGTGGCCTGTTTAAAAGAGTCACCATTACTGATTTTCTTTTCTTAGA TATCACCTGGAG | 16 | 51818856 | 51818973 | 1 | 434 |
| 13339-L | GCGGCGGACACCATCTTCTTTAAACCCTCAGTCCGTATTGGTCTCTATGGCAT CCATAGAGGCCATTCGGCTCTGAGGTCCTCAGTAAAGAAACTTAGATGGTATT ACTGTGT | 17 | 7150842 | 7150954 | -1 | 435 |
| 13340-L | CTCGTGGGAAGCAGCGCCTGTCGCAACTCGCCACTTGTTCTCCTCACAGCAGG TTCAGGAGAAGTGGCACCTGGTGGAGGACCTGTCGCGA | 17 | 73648461 | 73648551 | 1 | 436 |
| 13367-L | TATAAAAATAGGTAATATAGAAAATAAAACACATACTGCTGTATTGTCAGGTA GTGATAGGATTTATCACTACCTGACAATACAGTATGTGTTTGTTTTATATATT TAGGGTGTACA | 19 | 8360164 | 8360280 | -1 | 437 |
| 13374-L | TGGCGCTGCTCTGCTGTTCCTCTGTCTCCCAGACTCTGGGTGGATGGAGCAGG TCGGGGGCCAGGGGACAGGAAGGCTAGGGCC | 20 | 61388601 | 61388684 | 1 | 438 |
| 13375-L | ACCCTCTCAGGACCCCTCCTAAGGGGTAGGCAGGGGCTGGGGTTTCAGGTTCT CAGTCAGAACCTTGGCCCCTCTCCCCAGACCCCCAGGCTGTGGTGAGGGTCTG AGAGCTGGTAC | 20 | 62178716 | 62178832 | -1 | 439 |
| 13400-R | ATCTATTTTGTGTGAGTACAGAGAGCATCTGAATGGGTACAGTTGTTGTCTCT TGTTCCTCACACAGGCACCAGA | 22 | 28733036 | 28733110 | 1 | 440 |
| 13413-R | GGATTGACATCGCTAGATTTCCCATTACTGTTGCTGAATCCAGAGAGCAGCAT GAGTTCCTGAAATGCAGTTCAATGGTGTTCAGCAGACGGTGGATGCGGAAAAT CTTCATTTTTCCC | 2 | 74619921 | 74620039 | -1 | 441 |
| 13437-R | ATCTCTGATATGGAAGAAATCCAGAAGTGGCTAATAATATTGACACTATAACA ATAATGTCAATATTATTAGCCACTTCTGGATTTATGAATCATGTCTCAAGG ATT | 3 | 87358016 | 87358122 | -1 | 442 |
| 13446-L | TGGAAGCCTACCATTTATGTCCTCTTGAGGTACCTGAATTACCAAAAGCTTTAT GTATTCTGAAGTTATTGAAAATAAGAGCTTTTGGGAATTCAGGTAGTTCAGGAG TGACTTTTCTAAA | 4 | 153629918 | 153630038 | -1 | 443 |
| 13446-R | TGGAAGCCTACCATTTATGTCCTCTTGAGGTACCTGAATTACCAAAAGCTTTAT GTATTCTGAAGTTATTGAAAATAAGAGCTTTTGGGAATTCAGGTAGTTCAGGAG TGACTTTTCTAAA | 4 | 153629918 | 153630038 | -1 | 444 |
| 13447-R | CCAAAGTTCTTCACTTTAAAGAGTGGCAAAGTCTTTCCATATGTGTAACAGACA TACATACATACATATGGAAAGACTTTGCCACTCTTGAAAGTGAAGAGTGTGTGT | 4 | 160269396 | 160269504 | 1 | 445 |
| 13448-R | TCTTCACTTTCAAGAGTGGCAAAGTCTTTCCATATGTATGTATGTATGTCTGTT ACACATATGGAAAGACTTTGCCACTCTTTAAAGTGAAGAAC | 4 | 160269402 | 160269496 | -1 | 446 |
| 13448-L | TCTTCACTTTCAAGAGTGGCAAAGTCTTTCCATATGTATGTATGTATGTCTGTT ACACATATGGAAAGACTTTGCCACTCTTTAAAGTGAAGAAC | 4 | 160269402 | 160269496 | -1 | 447 |
| 13452-R | TTCATTCTATTGAGCTGACTGGCTTGTATGGAGGTTCTAGACCATGTTAGTGTT CAAGTCTACATGGATGGAAACCTTCAAGCAGGCCAAGCAGGAGACAGGTGGAAG AAG | 4 | 40198797 | 40198907 | -1 | 448 |
| 13452-L | TTCATTCTATTGAGCTGACTGGCTTGTATGGAGGTTCTAGACCATGTTAGTGTT CAACTCTACATGGATGGAAACCTTCAAGCAGGCCAAGCAGGAGACAGGTGGAAG AAG | 4 | 40198797 | 40198907 | -1 | 449 |

TABLE 13-continued

Precursor sequences and chromosomal locations (from human genome NCBI36) of the microRNAs in Table 17

| microRNA Candidate | microRNA precursor Sequence 5'->3' | chrom | start | end | strand | SEQ ID NO |
|---|---|---|---|---|---|---|
| 13465-R | GTCTATCAAGAGAGGAATGAACAGTTAAATTATAACATGTCCATATTATGGGTTAGTTGTGGACACATACTAACGCATAATATGGACATGTTATAATTTAACTGTTCCTTTCTGAGAG | 5 | 170746260 | 170746377 | -1 | 450 |
| 13531-R | TCCCTCTGCCCCTCACCTGCTGCTTGGGGTTTGGGGTGCAGACATTGCCAGAGGATGGGCAGCAGACTGACCTTCAACCCCACAGGTATCCACCACAGTGG | 9 | 131671687 | 131671787 | 1 | 451 |
| 13627-L | CCCACCATCCTAGCTTGCCTGAGACTGTCCTGGTTTTAGCACTGAAAGTGCCTGTTCCAGGAAACCCTGCAGTCTCCAGCAAACTGGGACAGTGGG | 2 | 71607460 | 71607555 | 1 | 452 |
| 13628-L | GCTTCTCTGAGGATGAAAGACCCATTGAGGAGAAGGTTCTGCTGGCTGAGAACCTTCCTCTCCATGGGTCTTTCATCCTCAAAGAAC | 22 | 48323039 | 48323125 | -1 | 453 |
| 13629-R | GCTCTGTGATTGCCTCTGATCAGGCAAAATTGCAGACTGTCTTCCCAAATAGCCTGCAACTTTGCCTGATCAGAGGCAGTCACAGAGC | 2 | 102415176 | 102415263 | 1 | 454 |
| 13629-L | GCTCTGTGATTGCCTCTGATCAGGCAAAATTGCAGACTGTCTTCCCAAATAGCCTGCAACTTTGCCTGATCAGAGGCAGTCACAGAGC | 2 | 102415176 | 102415263 | 1 | 455 |
| 13630-L | ATTCTCTTAGGTTGGTGCAAAAGTAGTTGTGGTTTTGCCATTCATTTCAGTGATAAAAACCGCAATTACTTTTGCACCAACCTAATCGAAT | 2 | 126329376 | 126329466 | 1 | 456 |
| 13640-L | TTTAAGAACTGGATATGATGACTGAAATAAGCTCCATATCAATGAGAATTTCAATGGGATTATGTGCAGTCAATGTCCAGTAATTAGA | 3 | 19331342 | 19331429 | -1 | 457 |
| 13642-R | TTAGTTTGGTGCAAAAGTAATCACGGTTTTTGCTATTGAAAGTAATAGCAAAAACTTTCAATAGCAAAAACTGTGATTACTTTTGCATCAATCTAA | 3 | 38039376 | 38039471 | 1 | 458 |
| 13655-L | AGAAAATGTTAGGGTGGTGCAAAAGTGATCGTGGTTTTTGCAATTTTTTAATGACAAAAACCACAATTACTTTTGCACCAACCTAACCTTGTTTT | 4 | 174425875 | 174425970 | 1 | 459 |
| 13661-R | AGTTTCCATGATAGGGAAACCAGGCAAGAAATATTGTCTCCTCAAGTTGCGACGAGACAGTAGTTCTTGCCTGGTTTCTCTATCATGGAGTCT | 6 | 2799256 | 2799348 | -1 | 460 |
| 13665-R | TGTGCTCCAGTACATATAAAGAGACTTATTAAGATGATCTTTTCTTAATAAGTCTCTTTATATGTACTGGAGCCCG | 6 | 82532186 | 82532261 | -1 | 461 |
| 13667-R | TATTGGGTGGGTGCAAAAGTAATTGCGGTTTTTGCTATTAGTTTCAATGGTAAAAACCGTGACTACTTCTGCACCAACCTAGTA | 6 | 108204187 | 108204270 | -1 | 462 |
| 13670-L | AAAATAGGACTTTTGAAGGAAGAGTTTTTTTTCACATTTTCACACTTTTCCTTCAAAAGTCATATTTT | 6 | 135559044 | 135559111 | 1 | 463 |
| 13672-R | AGAGAAGTTTTCAGTGTAACTCAACATTTGAAGTGTACTTGCCCTTGGACCAAGCAATTCTTCAAATGTTGAGATACACTGAAAACTTTCTCT | 6 | 154546929 | 154547022 | -1 | 464 |
| 13677-L | GGATAATAGGACAAGACAAATTACAGATTGTCTCAGAGAAAACAAATGAGTTACTCTCTCGGACAAGCTGTAGGTCCTACCTAAATGTCC | 7 | 138379372 | 138379461 | -1 | 465 |
| 13677-R | GGATAATAGGACAAGACAAATTACAGATTGTCTCAGAGAAAACAAATGAGTTACTCTCTCGGACAAGCTGTAGGTCCTACCTAAATGTCC | 7 | 138379372 | 138379461 | -1 | 466 |
| 13679-L | TAGGTTCATGCAAAAGTAGTTGTGGTTTTGCCATTACTTTCAATGGATGGCAAAAACAGCAATTACTTTTGCACCAACCTA | 8 | 69201988 | 69202068 | -1 | 467 |
| 13681-R | GAGGGAAAGCAGGCCAACCTCGAGGATCTCCCCAGCCTTGGCGTTCAGGTGCTGAGGAGATCGTCGAGGTTGGCCTGCTTCCCCTC | 8 | 96154315 | 96154400 | -1 | 468 |
| 13686-L | AAGGAACAGGGGACACTTGTAATGGAGAACACTAAGCTATGGACTGCTATGGACTGCTAGTGCTCTCCGTTACAAGTATCCCTGTTACCTT | 9 | 20401145 | 20401236 | -1 | 469 |
| 13687-R | GATATTTGAACCTCCTCCCGTGAATCACAAATGTCCTTAATAGCAATCCTTAAATGCCATTAAGGACATTTGTGATTGATGGGAGGAGGATGAAATATT | 9 | 67905119 | 67905217 | 1 | 470 |
| 13691-R | GGGAAAAAAAAAGGATTTGTCTTGTAGCCAGGATATTGTTTAAAGAAAATCCTTTTTGTTTTCCAGGTGGACC | 9 | 113734202 | 113734277 | 1 | 471 |
| 13692-R | AGGGCTGCTAGATTTAATGGATCAAATCACAAGATGCCTAGTTAAATTTGAATTTTAAATTTAACTGGACATCTTGCATTTTATCTGGTAATCCT | 9 | 122531275 | 122531369 | -1 | 472 |
| 13694-L | CTCTGCCCCATCTCCACCTGGACCCAGCGTAGACAAAGAGGTGTTTCTACTCCATATCTACCTGGACCCAGTGTAGATGGGAGGAG | X | 1372805 | 1372890 | 1 | 473 |

TABLE 13-continued

Precursor sequences and chromosomal locations (from human genome NCBI36) of the microRNAs in Table 17

| microRNA Candidate | microRNA precursor Sequence 5'->3' | chrom | start | end | strand | SEQ ID NO |
|---|---|---|---|---|---|---|
| 13694-R | CTCTGCCCCATCTCCACCTGGACCCAGCGTAGACAAAGAGGTGTTTCTACTCCA TATCTACCTGGACCCAGTGTAGATGGGAGGAG | X | 1372805 | 1372890 | 1 | 474 |
| 13696-L | GTAGGATAAATGACTCATCCTAGCTTGCCTGAGACTGTCCCAGTTTGAAAACTG GACCTCATCAGTCCTAGACACACTGGGATGTGGTTCACCCTAT | X | 7115401 | 7115497 | 1 | 475 |
| 13704-R | TTTATTGTGAAATATGTCATTAATATGTACTGACAAAGCGTATCTGTGTAATAA ATATGCTTTTTGTCAGTACATGTTAATGGTATATTTCATAACAAA | 10 | 5769057 | 5769155 | 1 | 476 |
| 13705-L | CTGTTCCGGGCATCACCTCCCACTGCAGAGCCTGGGGAGCCGGACAGCTCCCTT CCCAGGCTCTGCAGTGGGAACTGATGCCTGGAACAG | 10 | 6234161 | 6234250 | 1 | 477 |
| 13709-R | GATCATTATTCAGGCCGGTCCTGCAGAGAGGAAGCCCTTCTGCTTACAGGTATT GGAAGGGCTTCCTCTCTGCAGCACCGGCCTGAATAATGTAATC | 10 | 103351157 | 103351253 | 1 | 478 |
| 13710-R | CAGTTTCTCTTCCATCCCATATCTTAACAGCTAATCTAGTAAATTCTATCTTCA GAAGATTTGCTGTTAAGATATGGGATGGAGGAGAAATCTG | 11 | 33155668 | 33155761 | 1 | 479 |
| 13716-L | TTTTTCTCCCAGTCAAGAGTTACTAGAACTATTCAACCTTCAGCTGTGTTGAAT AGTTTTAGTAACTCTTGACTGGGAGAAAAG | 12 | 21562856 | 21562939 | 1 | 480 |
| 13716-R | TTTTTCTCCCAGTCAACAGTTACTAGAACTATTCAACCTTCAGCTGTGTTGAAT AGTTTTAGTAACTCTTGACTGGGAGAAAAG | 12 | 21562856 | 21562939 | 1 | 481 |
| 13717-L | AGCTGGACTGAGAGAAATTTATTCTTGGTAGGTTGTACATTCCTAAACATGTAC AACGTACTAAGAATAAATTTCTCTCAGTCCAGCT | 12 | 29307836 | 29307923 | 1 | 482 |
| 13717-R | AGCTGGACTGAGAGAAATTTATTCTTGGTAGGTTGTACATTCCCAAACATGTAC AACGTACTAAGAATAAATTTCTCTCAGTCCAGCT | 12 | 29307836 | 29307923 | 1 | 483 |
| 13719-L | GGTTAGCACAGAGTGGGAGCTCTAGAAAGATTGTTGACCAATCATCTTATTGAC TAGACCATCTTTCTAGAGTATAACTATTTTGGACACC | 12 | 64931121 | 64931211 | 1 | 484 |
| 13721-R | GCTGCGTTTGCACTGCTTCTCCAAAACCACATTATAGGTACTAAACAACATTGT TTAGTACCTATAATGTGCTAGACTCCTGGCTGCTAGCGAGGT | 12 | 70365967 | 70366062 | -1 | 485 |
| 13727-R | GGTATGTATCTGCTTTTCCGGAGTTGTAAGTGTTGACAATATCCAGAATGACAT TGTCTTTGTCAACACTTACAACTCTGGAAAAGCAGATACATACC | 14 | 90236780 | 90236877 | -1 | 486 |
| 13727-L | GGTATGTATCTGCTTTTCCGGAGTTGTAAGTGTTGACAATATCCAGAATGACAT TGTCTTTGTCAACACTTACAACTCTGGAAAAGCAGATACATACC | 14 | 90236780 | 90236877 | -1 | 487 |
| 13729-L | AGTATGACACCTCAAAGAAGCAATACTGTTACCTGAAATAGGCTGCGAAGATAA CAGTATTTCAGATAACAGTATTACATCTTTGAAGTGTCATATT | 15 | 33451756 | 33451852 | -1 | 488 |
| 13731-L | AAAAAAAGGGAAAGAAGAACTGTTGCATTTGCCCTGCACTCAGTTTGCACAGGG TAAATGCAATAGTTCTTCTTTCCCTTTTTTT | 15 | 63798639 | 63799723 | -1 | 489 |
| 13734-L | GTTTTGGATTTTGGACTTTTTCAGATTTGGGGATATTTGCATTATACTTATCCT AAATCTGAAAGTCCAAAACCTGAAAT | 15 | 88228177 | 88228256 | -1 | 490 |
| 13745-L | GCCTCAAATTTAAGGAGGGACTCACTCACAGGATTGTGCAAATGCAAAGTTGGC TTTTGCATGACCCTGGGAGTAGGTGCCTCCTTAAATTTTGC | 16 | 29517998 | 29518092 | -1 | 491 |
| 13748-L | GCCTCAAATTTAAGGAGGGACTCACTCACAGGATTGTGCAAATGCAAAGTTGGC TTTTGCATGACCCTGGGAGTAGGTGCCTCCTTAAATTTTGC | 16 | 21424868 | 21424962 | -1 | 492 |
| 13753-L | CTGTAGGTTCTGTCTTGGGCCACTTGGATCTGAAGGCTGCCCCTTTGCTCTCTG GGGTAGCCTTCAGATCTTGGTGTTTTGAATTCTTACTATAG | 17 | 52323626 | 52323720 | -1 | 493 |
| 13755-L | TGCCTACAGTGAATCCCTAGTGGTCAGAGGGCTTATGATATATTGTGAGAGCCA TGTCATAAGCCTTTTGGCCACTAGGGATTCAATGTATGCA | 18 | 3875346 | 3875439 | 1 | 494 |
| 13761-L | TTGAGGAAGGGTCAGGCATGAGGAGGATCTGAAGGATTGGACTCAGGTTCGAAA CCTCCACTTCCTCCTCATCTCCTACCCTCTCCACTCAG | 19 | 60428648 | 60428739 | -1 | 495 |
| 14069-R | AGTATAGTGGTGAGTATCCCCGCCTGTCACGCGGGAGACCGGGGTTCGATTCCC CGACGGGGAGGCCGGGTACTTTCGTATTTTAAATACAGAGGGGAGACTTTGTT GGCGATGCTT | 12 | 123990092 | 123990209 | -1 | 496 |
| 14085-L | GGCCTAATGGATAAGGCATTGGCCTCCTAAGCCAGGGATTGTGGGTTCGAGTCC CACCCGGGGTAAAGAAAGGCCGAATTTTAGTGTTCCTTATCGGGC | 16 | 3142910 | 3143008 | 1 | 497 |

TABLE 13-continued

Precursor sequences and chromosomal locations (from human genome NCBI36) of the microRNAs in Table 17

| microRNA Candidate | microRNA precursor Sequence 5'->3' | chrom | start | end | strand | SEQ ID NO |
|---|---|---|---|---|---|---|
| 14086-L | GAAGGCAGCTACACATGCGTGGCGGTTCCATGTGTAATGGTTAGCACTCTGGACTCTGAATCCAGCGATCCGAGTTCAAATCTCGGTGGAACCTGCATTGGTTTTTGTTTTTT | 15 | 63948435 | 63948548 | -1 | 498 |
| 14093-L | TCAGTGGTAGAGCATTTGACTGCAGATCAAGAGGTCCCCGGTTCAAATCCGGGTGCCCCCTCTGTGCTCCGGAGTTACCTCGTTTTGTTGGT | 17 | 34564239 | 34564330 | -1 | 499 |
| 14111-L | TGTAGTGTTTCTTACTTTAAATATGTAAAATGTGTAACATGCAGAGCGAAAGGGGCAGTGA | Y | 8054989 | 8055049 | -1 | 500 |
| 14113-R | AAAGTCGGTGCCGGAGGCTCCCAGCTCAGATCGCCGAAGCGTCGGACTACCGTTGGTTTCCGCAACTTCCTGGATTATCCTCGCCAAGGACTTTG | 19 | 2427098 | 2427192 | 1 | 501 |
| 14113-L | AAAGTCGGTGCCGGAGGCTCCCAGCTCAGATCGCCGAAGCGTCGGACTACCGTTGGTTTCCGCAACTTCCTGGATTATCCTCGCCAAGGACTTTG | 19 | 2427098 | 2427192 | 1 | 502 |
| 14117-R | AATCAACTTCCTAGGCACACTTAAAGTTATAGCTACATCAGTTATAACTATATCAGTTAAAACTTTAAGTGTGCCTAGGAAGTTGATT | 11 | 46731242 | 46731329 | -1 | 503 |
| 14121-R | ACATATTGGTCTGTTGTCAGGCTCAGCAGCATGGCTGACTAAAGACATTGACATCATGACATTGTCATGTTGCTCTGCTGTTGCCCCTGGCTCTAGCTGGCCTACTTGT | 1 | 229467154 | 229467262 | 1 | 504 |
| 14137-R | AGCCCTGGGGTGGTCTCTAGCCAAGGCTCTGGGGTCTCACCCTTGGCTGGTCTCTGCTCCGCAGGCCT | 8 | 27346804 | 27346872 | 1 | 505 |
| 14151-R | AGTGGAGAAGGCCACGATTTTTTGATGTCATTTTGTGTAAGGGCGCAGACTGCTGCGAACAGAGTGGTGATAGCGCCTAGGCATAGTGTGAGAGTTTGGATTAGTGGGTTATTCTCTGC | 5 | 134289131 | 134289250 | 1 | 506 |
| 14154-L | ATAGTTTTAGAGTTTCTAAGGATCATGTCTGTGAGTCAGGATTCCAGAGACCATGGTCCTGATGGGATGGAGCCTGGAGACGTCATTGAGAGTA | 13 | 60110163 | 60110256 | -1 | 507 |
| 14156-R | ATGATGGCTATGGATTTGGGTCAGATAGATTTGGAAGAGGTAAGGTAAGAATTGAATTTCTCAGTTGAAGGATGCTTACACTCTTGTCCATCTAGACCTCAATTACTGTTTTTCA | 5 | 178977520 | 178977634 | -1 | 508 |
| 14161-R | ATTCTAGATTAAATGGTCAAGGAAGACAGTCTGTGGCAAAGGCCCAGTTCAAGTTTAGAACTGAACAGCCTCTGGCAATCTATCTTCCACAAATAGGCAGCATTTTAAAGGTCTCAGAGA | 10 | 122640045 | 122640164 | -1 | 509 |
| 14170-L | CACGTCACCTGATATCAGGTATTTACTCTGAACTAGCTCTGTGGATCCTGACAGACAGCCTGATAGACAGGATCCACAGAGCTAGTCCAGAGTAAAAGACCTAAATCAGCTGTGG | 8 | 92286868 | 92286982 | 1 | 510 |
| 14177-L | CAGTAGTGGTTAGTACTCTGAATTAACTTATCTAAATCAATGAAAATAATAGTGAACCTCTGCT | 1 | 69384134 | 69384197 | -1 | 511 |
| 14200-L | CCTGCCTCGGCCTCCCAAAGTGCTGGGATTACAGGCAGGAGCCCCCGTTGCCACTGCTGCTGCTGCTGCCCCTGCTGCCACTGTGGCTGGGCCTGGCAGGG | 22 | 29111449 | 29111549 | -1 | 512 |
| 14220-L | CGGATAATTGTAGCACTTCCTGGTTCATACGGATAATTGTAGCACTTCCTGGTTTGCAGGGACATTGCAATACTTCCTGGTTCATATGGATAATTGTAGCACTTCT | X | 2557830 | 2557935 | 1 | 513 |
| 14226-R | CTCAAACAACTCAATAGGAAAAAAAACTAATAATCTGATTTAAAAACGGGCAAAAGAGAGTTTCTAAGGATCATGTCTGAGA | 10 | 93886209 | 93886290 | 1 | 514 |
| 14229-R | CTCGGCCTCCCTTCATGGTGGGACCAGGCCCAGCAGGGAATGTCAGGGCCACCCCTGACCTTCACTGTGACTCTGCTGCAGAGGGTGGCCTGGAG | 7 | 44057873 | 44057967 | 1 | 515 |
| 14244-L | CTGTGCTTTGTGTGTTGGAGGATGAAAGTACGGAGTGATCCATCGGCTAAGTGTCTTGTCACAATGCTGACACTCAAACTGCTGACAGCACACGTTTTTCACAG | 16 | 70349796 | 70349899 | -1 | 516 |
| 14244-R | CTGTGCTTTGTGTGTTGGAGGATGAAAGTACGGAGTGATCCATCGGCTAAGTGTCTTGTCACAATGCTGACACTCAAACTGCTGACAGCACACGTTTTTCACAG | 16 | 70349796 | 70349899 | -1 | 517 |
| 14275-L | GAAACTCGGTGACTCCAGGGACTGCCTTAGGAGAAAGTTTCTGGAAGTTCTGACATTCCAGAAACTTTCTCCTAAGGCAGTCCCTGGGAGTCACTGAGTCAGTCC | 22 | 26646503 | 26646607 | -1 | 518 |
| 14288-R | GCAACTCGCCTGGCTCCCTTCTCTCCGTCTGCCTCCTGGCCGCGGGGCCCGGAGAGCTGGGAGCCAGAGGGTGT | 6 | 41809263 | 41809336 | -1 | 519 |

TABLE 13-continued

Precursor sequences and chromosomal locations (from human genome NCBI36) of the microRNAs in Table 17

| microRNA Candidate | microRNA precursor Sequence 5'->3' | chrom | start | end | strand | SEQ ID NO |
|---|---|---|---|---|---|---|
| 14289-R CCCTAC- CTAGGT | GCAAGGGTTGAGGAGGGACTTAACATCAATGAATTCATGAGGTGATGTAGTCTC | 20 | 33683569 | 33683634 | -1 | 520 |
| 14303-R | GCCCTTCGGTAGCTGGTCCCTTAACTCAGTGGTGAATGGCGACCGGATGGAGCT CTAGGGAAGCGACAGCAGCGGCGGGT | 16 | 74108610 | 74108689 | -1 | 521 |
| 14327-R | GGAAGAGGGCTTAGGTGCACGCTCTAGCGGGGATTCCATATTGGGCCAATTCCC CCAATGTTGGAATCCTCGCTAGAGCGTGCACTTCTGGAAGCTAGGAACCTCC | 1 | 54292328 | 54292434 | 1 | 522 |
| 14328-R | GGAAGAGTCAAGTCAAGGCCAGAGGTCCCACAGCAGGGCTGGAAAGCACACCTG TGGGACTTCTGGCCTTGACTTGACTCTTTC | 12 | 103509541 | 103509624 | 1 | 523 |
| 14332-L | GGACTGACTCAGTGACTCCCAGGGACTGCCTTAGGAGAAAGTTTCTGGAATGTC AGAACTTCCAGAAACTTTCTCCTAAGGCAGTCCCTGGAGTCACCGAGTTTCT CTT | 22 | 26646503 | 26646611 | 1 | 524 |
| 14336-R | GGCACAGACTCATCCCTGATCAAAGCCTCCACCCCCCCCCCAAAAAAAGATCT GGGCACCTACTTGGGAAGCTGAGGCAGGAGAATCACTTGAACCC | 19 | 57737967 | 57738064 | -1 | 525 |
| 14338-R | GGCATGGAGTCCTGTGGCATCCACGAAACTACCTTCAACTCCATCATGAAGTGT GACGTGGACATCCGCAAAGACCTGTACGCC | 7 | 5534260 | 5534343 | -1 | 526 |
| 14347-R | GGGCAGGAGGGAGTGGGGTGGGACCCAGCTGTTGGCCATGGCGACAACACCTGG GTTGTCCCCTCTAGGGTCCA | 1 | 226651366 | 226651439 | -1 | 527 |
| 14361-L | GGGGCTAATCGCCTGGACTGCCTGGAGAAAGCGAAGCTAGTACCCCCTTTCTCC AACAGTCCTTAGTTTCCAGGCCCT | 17 | 53514138 | 53514215 | -1 | 528 |
| 14367-R | GGTAATCTCATCAGAAAGATAGGCAGCTTCCAAGTCCCAGGGCCTCGTAAGCAG AGGCACAGTTATGGATGATGATATCTGAGTGATATTGTGCTT | 2 | 135573962 | 135574057 | 1 | 529 |
| 14371-R | GGTTAACTTACAATAAATGAAGCTTTTATGCAGGTTTCCGTAGCGTAGTGGTTA TCA | 9 | 103368541 | 103368597 | -1 | 530 |
| 14375-R | GTAAGGTGGAGAGATTACCGTGTTATAAAGAACTTTGGGATATTTTTCAAATT AACCTGACCATTCTTTTGAAACCAGAGTCCTTAACAAGCATTGAGATATATTTC TCCATGAAGGCT | 3 | 12602278 | 12602397 | -1 | 531 |
| 14380-R | GTGAGAAATGATGAGGGTCAACATTCTTCATACCAAAGTGAAGACATGAGATCC AACTCTGAGCTCACC | 3 | 52697944 | 52698012 | 1 | 532 |
| 14385-L | GTGGCCGAGGACTTTGATTGTACATTGTTCTTTTTTTAATAGTCATTCCAAATA TCATGAGATGCATTGTTACAGGAAGTCCCTTGCCCTCCTAAAAGCCAC | 6 | 146967008 | 146967109 | 1 | 533 |
| 14390-L | GTTGCTATCGGGGACTACAATGGCCACGTCGGTCTGGGTGTTAAGTGCTCCAAG GAGGTGGCCACCGCCATCCATGGGGCCATCATCCTGGCCAAGCTCTCCATTGTC CCCGTGCGCAGA | 1 | 51489239 | 51489358 | -1 | 534 |
| 14399-L | TCAAGGAAAAGCTGTGCTACGTCGCCCTGGACTTCGAGCAGGAGATGGCCACGG CAGCCTCCAGCTCCTCCCTGG | 9 | 102533969 | 102534043 | 1 | 535 |
| 14409-R | TCCATCCGTATTGAGGATGAGGACACCTCTGAACTCACAGAGCAGGCTGTGAGT TTAGAGCTGTCTGCTCTAAACTCAGGTGGA | X | 47580920 | 47581003 | -1 | 536 |
| 14415-R | TCTATTGCTATGCCTCCAAGTTCATTAATATTTTCTTCTCATTGTAAAGACTGG GGGACCTCTTTCTTAAGTGATCTTTGTCTTAAGATTTGGTGCAATATATCAGT AGA | 11 | 32063048 | 32063157 | 1 | 537 |
| 14442-R | TGTGCTTGCGCATAACTGGGGCCGCCTGGCCTCCCGCGGGCGGCCTTTTTAACC GCGAGCGACA | 17 | 59577497 | 59577560 | 1 | 538 |
| 14452-L | TTCCTTAACTAAAGTACTCCCTCTCAAATCAAAGTGGTTATGGTTCTAAAAACT CCGATTGGAGAATTTACAGGATAGGAGG | 4 | 128346613 | 128346694 | 1 | 539 |
| 14454-R | TTGGGCATGGAATCCTGCGGCATCCACAAGACCACCTTCAACTCCATCATGAAG TGTGACGTGGACATCCGCAAAGACCTGTACGCCAA | X | 53188939 | 53189027 | -1 | 540 |
| 14469-R | CTGGTGGCTGGGCCGACGACTCGGGGCGCGGCCGTGAGCGCAGAGGCCATGGAG CCGGAGCTCGCGGACACCTCTGCACTCAAGGCGGCGCCCTACGGCCACTCGCG GAG | 7 | 101730795 | 101730904 | 1 | 541 |
| 14479-R | GAGAAATTTGTATATTTTCTATTTAGAAGCCTATAGATAGAATATAGGAAAAAA GCTATATTTTCTTATAGGCTTCTAAGTAGAAAATGTATTTGCAAGGAT | 2 | 69512355 | 69512457 | -1 | 542 |

TABLE 13-continued

Precursor sequences and chromosomal locations (from human genome NCBI36) of the microRNAs in Table 17

| microRNA Candidate | microRNA precursor Sequence 5'->3' | chrom | start | end | strand | SEQ ID NO |
|---|---|---|---|---|---|---|
| 14482-R | GATCTATGACGTGGAGCTAACCAAACTAATATACCCATATTCTGGCTAGGTGATCATCAGAATATGGGTATATTAGTTTGGTTAGCTCTACATTGTAGATCTAT | 18 | 35510661 | 35510764 | 1 | 543 |
| 14483-R | GATGGCTTTTATCATTGGGCCAGTGACGACCCATTCAGCCGTATCAGTGAAGAGTGAAGCACTGCACTCTTTAAGGATAGGGCTGAATGGTTTATCACCCATTCAGCGGT | 16 | 76971867 | 76971976 | 1 | 544 |
| 14485-L | GCACCACTAGACTCCAGCCTGGGCAAGAAAGTGAGACTCTGCCTCTTTTTGTTTCTGAGCCAGAGTCTTGCTCTGTTGCTCAGGCTGGAGTGCAATGGCGTGA | 7 | 74097020 | 74097123 | -1 | 545 |
| 14494-L | GCGCGGCCGCGGGAGGTGTAACAGGACTGGACTCCCGGCAGCCCCAGGGCAGGGGCGTGGGGAGCTGGTCCTAGCTCAGCGCTCCCG | 15 | 81527083 | 81527169 | 1 | 546 |
| 14499-L | GGACGTAGTGGTGTAGAGAGGCATTAAGAACGCAGGTGGCAGGGCCAGCCACCAGGAGGGCTGCGTGCCACCCGGGCAGCTCTGCTGCTCACTGGCAGTGTCACCTGCGGAAACTCTCCATC | 20 | 49502833 | 49502954 | -1 | 547 |
| 14508-L | GTAGCAGTGGTGGTGGTAGCAAGGGGGTGATGTAGATTCTGAAGAGCAGCCCTTCCTGTTAGGGGAAAAGTCCTGATCCGGGAACCCACAGCCCCGTTCCTGGGCTTCTCCTCTGTAGCCAGCCTCAGCCGAGCAGCTGC | 17 | 40367490 | 40367629 | -1 | 548 |
| 14527-R | TCCCAATACGAGGCACTGAGTTAAGTGTTCTACACAGATAATCTGTTATTAATGAGAGAATAGAATAGACAATCTGTGTAGAGTGCTTAACCTGGTGCCCAGTGTTTTCA | 11 | 17982809 | 17982918 | -1 | 549 |
| 14532-L | TGCGTTGGCCTGTGGGCATGGCCTGAGACCAGGACTGGATGCACCACTCTCCCTGTGATGAGGTGAAGCCAGCTCTGGTCTGGGCCATTTCACAGGATTCCAGAAGC | 2 | 240531091 | 240531197 | -1 | 550 |
| 14539-R | TTAAAGACCTTAAGAGGCAACAAAGACTATACTTTCAGGGATCATTTCTCTAGTTCAATACTACAGAAGTTTCTCTGAAGGTGTAGCAAGCACCAGAAACCACGAGGA | 4 | 159841271 | 159841378 | 1 | 551 |
| 14541-R | TTAATATTTCATCCTCCTCCCATCAATCACAAATGTCCTTAATGGCATTTAAGGATTGCTATTAAGGACATTTGTGATTCACGGGAGGAGGTTCAAATATCATGAA | 9 | 67905114 | 67905219 | -1 | 552 |
| 14543-L | TTATATCCAGAGCCTGAATGAAAGAGCCAGTGGTGAGACAGTGAGTTGATTACTTCTCACTGTTTCACCACTGGCTCTTTGGTTCATGCTAACAATGTATCT | 10 | 74150779 | 74150880 | 1 | 553 |
| 14549-R | TTGTAACATCCGGTGTGTTGTAACATTCCAGTGTGTTGTAACATTTGGTGTTACATGCTGTGTTGTAACATTCTGGTGTGTTGTAACATTCCCGGTGTGTTGTAAC | 12 | 131953101 | 131953206 | -1 | 554 |
| 14556-R | AAATACAAAATAATTCGAGAATAAAGACTATGCTTTCAGGGATCATTTCTATAGTTCGTTACTCGGGAAGTTTCTCTGAACGTGTAAAGCACCGAACAAAAAAAAAAAAAC | 10 | 88799960 | 88800071 | 1 | 555 |
| 14567-R | ACACATTTTCTTTGCTAAGTCCCTTCTTTCTATCCTAGTATAACTTGAAGAATTCAAATAGTCATGCTAGGATAGAAAGAATGGGACTTGGCCAGGGAAGAAGAGTTG | 7 | 19711490 | 19711597 | -1 | 556 |
| 14570-R | AGAAATTATGCCACTTTTAATTTCAGCTACTACCTCTATTAGGATTTGGGAGTTATACTAATAGAGGTAATAGTTGAAATTAAGAGTGGATGAGTTCTGGT | 6 | 35740457 | 35740557 | -1 | 557 |
| 14575-R | AGCTGATTACATTATTCAGGCCGGTCCTGCAGAGAGGAAGCCCTTCCAATACCTGTAAGCAGAAGGGCTTCCTCTCTGCAGGACCGGCCTGAATAATGATCCTAACGC | 10 | 103351150 | 103351257 | -1 | 558 |
| 14578-R | AGTAACATCCAGATGTGTTGTAACATTCCAGTGTGTTGTAACATTCCTGTAACATTCCAATGTGTTGTAACATTCTGGTGTGTTGTAACATTCCTGTAACATTCTGGT | 12 | 131953328 | 131953435 | -1 | 559 |
| 14581-L | ATACCATTGGGCCTTGCTTCTTTATCCAGCTTGTTACTATATGCTTTTTAAATGGGGCACAGAGTGACAAGCTGGTTAAAGAAGCAAGACCCCTTCAAGATTA | 14 | 59183411 | 59183513 | -1 | 560 |
| 14583-L | ATGGGGGAACCACAGGCAGCAAATGGCCAGAGCTCACACAGAGGGATGAGTGCACTTCACCTGCAGTGTGACTCAGCAGGCCAACAGATGCTATCAGGGAAGAGCACT | 2 | 111795045 | 111795152 | -1 | 561 |
| 14584-L | ATGGGGGAACCACAGGCAGCAAATGGCCAGAGCTCACACAGAGGGATGAGTGCACTTCACCTGCAGTGTGACTCAGCAGGCCAACAGATGCTATCAGGGAAGAGCACT | 2 | 87710376 | 87710483 | 1 | 562 |
| 14596-R | CCAACCCCATCTTCTTAAATGTCTTACTGCTTTTACTGTTCCCTCCTAGAGTCCATTCTTTACTCTAGGAGGGAATAGTAAAAGCAGTAAGACATTTAGTAAAAGGCTTT | 2 | 86273648 | 86273757 | -1 | 563 |
| 14601-L | CCCAGGTAAAGGGCCCAGGTGACCCGGGGCTGCCCTGAACGGGCCCGGCTCTGGTGCGCTTGCTCAGCCAGGCCCGCTCCCCGCTGCCCCCTAGGCTTCTCATCGCTGTCGCTGTC | 11 | 63838955 | 63839070 | 1 | 564 |

A similar analysis was carried out to identify microRNAs in miRBase (human version 14.0) that are at increased levels in the sepsis patient sample as compared to the 77 non-sepsis patient smRNASeq datasets. Again, the microRNAs were ranked from 1 to 5, depending on whether the sepsis patient smRNASeq dataset contained the highest number of counts of the particular microRNA, the second highest, etc. The results are shown in Table 14.

TABLE 14 microRNAs from miRBase found at higher numbers in a sepsis smRNASeq dataset

| microRNA name | microRNA RANK | Sequence 5'->3' | SEQ ID NO |
|---|---|---|---|
| miR-101 | 1 | TACAGTACTGTGATAACTGAA | 565 |
| miR-140-5p | 1 | CAGTGGTTTTACCCTATGGTAG | 566 |
| miR-142-3p | 1 | TGTAGTGTTTCCTACTTTATGGA | 567 |
| miR-142-5p | 1 | CATAAAGTAGAAAGCACTACT | 568 |
| miR-143* | 1 | GGTGCAGTGCTGCATCTCTGGT | 569 |
| miR-144 | 1 | TACAGTATAGATGATGTACT | 570 |
| miR-144* | 1 | GGATATCATCATATACTGTAAG | 571 |
| miR-148a | 1 | TCAGTGCACTACAGAACTTTGT | 572 |
| miR-1537 | 1 | AAAACCGTCTAGTTACAGTTGT | 573 |
| miR-15a | 1 | TAGCAGCACATAATGGTTTGTG | 574 |
| miR-16-1* | 1 | CCAGTATTAACTGTGCTGCTGA | 575 |
| miR-16-2* | 1 | CCAATATTACTGTGCTGCTTTA | 576 |
| miR-185* | 1 | AGGGGCTGGCTTTCCTCTGGTC | 577 |
| miR-2115 | 1 | AGCTTCCATGACTCCTGATGGA | 578 |
| miR-2115* | 1 | CATCAGAATTCATGGAGGCTAG | 579 |
| miR-223 | 1 | TGTCAGTTTGTCAAATACCCCA | 580 |
| miR-223* | 1 | CGTGTATTTGACAAGCTGAGTT | 581 |
| miR-27a* | 1 | AGGGCTTAGCTGCTTGTGAGCA | 582 |
| miR-30e | 1 | TGTAAACATCCTTGACTGGAAG | 583 |
| miR-30e* | 1 | CTTTCAGTCGGATGTTTACAGC | 584 |
| miR-338-3p | 1 | TCCAGCATCAGTGATTTTGTTG | 585 |
| miR-338-5p | 1 | AACAATATCCTGGTGCTGAGTG | 586 |
| miR-374a* | 1 | CTTATCAGATTGTATTGTAATT | 587 |
| miR-451 | 1 | AAACCGTTACCATTACTGAGTT | 588 |
| miR-486-5p | 1 | TCCTGTACTGAGCTGCCCCGAG | 589 |
| miR-548e | 1 | AAAAACTGAGACTACTTTTGCA | 590 |
| miR-548f | 1 | AAAAACTGTAATTACTTTT | 591 |
| miR-548j | 1 | AAAAGTAATTGCGGTCTTTGGT | 592 |
| miR-548n | 1 | CAAAAGTAATTGTGGATTTTGT | 593 |
| miR-548q | 1 | GCTGGTGCAAAAGTAATGGCGG | 594 |
| miR-576-3p | 1 | AAGATGTGGAAAAATTGGAATC | 595 |
| miR-582-3p | 1 | TAACTGGTTGAACAACTGAACC | 596 |

TABLE 14-continued microRNAs from miRBase found at higher numbers in a sepsis smRNASeq dataset

| microRNA name | microRNA RANK | Sequence 5'->3' | SEQ ID NO |
|---|---|---|---|
| miR-617 | 1 | AGACTTCCCATTTGAAGGTGGC | 597 |
| miR-618 | 1 | AAACTCTACTTGTCCTTCTGAGT | 598 |
| miR-624* | 1 | TAGTACCAGTACCTTGTGTTCA | 599 |
| miR-625* | 1 | GACTATAGAACTTTCCCCCTCA | 600 |
| miR-627 | 1 | GTGAGTCTCTAAGAAAAGAGGA | 601 |
| miR-628-5p | 1 | ATGCTGACATATTTACTAGAGG | 602 |
| miR-629* | 1 | GTTCTCCCAACGTAAGCCCAGC | 603 |
| miR-640 | 1 | ATGATCCAGGAACCTGCCTCT | 604 |
| miR-1225-5p | 2 | GTGGGTACGGCCCAGTGGGGGG | 605 |
| miR-1255a | 2 | AGGATGAGCAAAGAAAGTAGATT | 606 |
| miR-126* | 2 | CATTATTACTTTTGGTACGCG | 607 |
| miR-148a* | 2 | AAAGTTCTGAGACACTCCGACT | 608 |
| miR-26b* | 2 | CCTGTTCTCCATTACTTGGCTC | 609 |
| miR-30a* | 2 | CTTTCAGTCGGATGTTTGCAGC | 610 |
| miR-425 | 2 | AATGACACGATCACTCCCGTTGA | 611 |
| miR-450b-5p | 2 | TTTTGCAATATGTTCCTGAATA | 612 |
| miR-503 | 2 | TAGCAGCGGGAACAGTTCTGCAG | 613 |
| miR-514 | 2 | ATTGACACTTCTGTGAGTAGA | 614 |
| miR-548b-5p | 2 | AAAAGTAATTGTGGTTTTGGCC | 615 |
| miR-548d-3p | 2 | CAAAAACCACAGTTTCTTTTGC | 616 |
| miR-548d-5p | 2 | AAAAGTAATTGTGGTTTTTGCC | 617 |
| miR-580 | 2 | TTGAGAATGATGAATCATTAGG | 618 |
| miR-616* | 2 | ACTCAAAACCCTTCAGTGACTT | 619 |
| miR-1179 | 3 | AAGCATTCTTTCATTGGTTGG | 620 |
| miR-1244 | 3 | AAGTAGTTGGTTTGTATGAGATGGTT | 621 |
| miR-126 | 3 | TCGTACCGTGAGTAATAATGCG | 622 |
| miR-1291 | 3 | TGGCCCTGACTGAAGACCAGCAGT | 623 |
| miR-140-3p | 3 | TACCACAGGGTAGAACCACGG | 624 |
| miR-145* | 3 | GGATTCCTGGAAATACTGTTCT | 625 |
| miR-146a | 3 | TGAGAACTGAATTCCATGGGTT | 626 |
| miR-146a* | 3 | CCTCTGAAATTCAGTTCTTCAG | 627 |
| miR-146b-3p | 3 | TGCCCTGTGGACTCAGTTCTGG | 628 |
| miR-146b-5p | 3 | TGAGAACTGAATTCCATAGGCT | 629 |
| miR-148b* | 3 | AAGTTCTGTTATACACTCAGGC | 630 |
| miR-150* | 3 | CTGGTACAGGCCTGGGGACAG | 631 |
| miR-17* | 3 | ACTGCAGTGAAGGCACTTGTAG | 632 |
| miR-181a* | 3 | ACCATCGACCGTTGATTGTACC | 633 |

TABLE 14-continued microRNAs from miRBase found at higher numbers in a sepsis smRNASeq dataset

| microRNA name | microRNA RANK | Sequence 5'->3' | SEQ ID NO |
|---|---|---|---|
| miR-191* | 3 | GCTGCGCTTGGATTTCGTCCCC | 634 |
| miR-199b-5p | 3 | CCCAGTGTTTAGACTATCTGTTC | 635 |
| miR-26a-1* | 3 | CCTATTCTTGGTTACTTGCACG | 636 |
| miR-29b-2* | 3 | CTGGTTTCACATGGTGGCTTAG | 637 |
| miR-340* | 3 | TCCGTCTCAGTTACTTTATAGC | 638 |
| miR-361-3p | 3 | TCCCCCAGGTGTGATTCTGATTT | 639 |
| miR-422a | 3 | ACTGGACTTAGGGTCAGAAGGC | 640 |
| miR-425* | 3 | ATCGGGAATGTCGTGTCCGCCC | 641 |
| miR-454* | 3 | ACCCTATCAATATTGTCTCTGC | 642 |
| miR-502-5p | 3 | ATCCTTGCTATCTGGGTGCTA | 643 |
| miR-542-3p | 3 | TGTGACAGATTGATAACTGAAA | 644 |
| miR-550 | 3 | AGTGCCTGAGGGAGTAAGAGCCC | 645 |
| miR-551a | 3 | GCGACCCACTCTTGGTTTCCA | 646 |
| miR-573 | 3 | CTGAAGTGATGTGTAACTGATCAG | 647 |
| miR-598 | 3 | TACGTCATCGTTGTCATCGTCA | 648 |
| miR-643 | 3 | ACTTGTATGCTAGCTCAGGTAG | 649 |
| miR-671-5p | 3 | AGGAAGCCCTGGAGGGGCTGGAG | 650 |
| let-7f | 4 | TGAGGTAGTAGATTGTATAGTT | 651 |
| let-7g | 4 | TGAGGTAGTAGTTTGTACAGTT | 652 |
| miR-103 | 4 | AGCAGCATTGTACAGGGCTATGA | 653 |
| miR-103-2* | 4 | AGCTTCTTTACAGTGCTGCCTTG | 654 |
| miR-107 | 4 | AGCAGCATTGTACAGGGCTATCA | 655 |
| miR-1197 | 4 | TAGGACACATGGTCTACTTCT | 656 |
| miR-1250 | 4 | ACGGTGCTGGATGTGGCCTTT | 657 |
| miR-1277 | 4 | TACGTAGATATATATGTATTTT | 658 |
| miR-1278 | 4 | TAGTACTGTGCATATCATCTAT | 659 |
| miR-1299 | 4 | TTCTGGAATTCTGTGTGAGGGA | 660 |
| miR-143 | 4 | TGAGATGAAGCACTGTAGCTC | 661 |
| miR-150 | 4 | TCTCCCAACCCTTGTACCAGTG | 662 |
| miR-155* | 4 | CTCCTACATATTAGCATTAACA | 663 |
| miR-181a | 4 | AACATTCAACGCTGTCGGTGAGT | 664 |
| miR-181b | 4 | AACATTCATTGCTGTCGGTGGGT | 665 |
| miR-186 | 4 | CAAAGAATTCTCCTTTTGGGCT | 666 |
| miR-196b | 4 | TAGGTAGTTTCCTGTTGTTGGG | 667 |
| miR-1976 | 4 | CCTCCTGCCCTCCTTGCTGT | 668 |
| miR-21 | 4 | TAGCTTATCAGACTGATGTTGA | 669 |
| miR-219-1-3p | 4 | AGAGTTGAGTCTGGACGTCCCG | 670 |
| miR-221* | 4 | ACCTGGCATACAATGTAGATTT | 671 |
| miR-378 | 4 | ACTGGACTTGGAGTCAGAAGG | 672 |
| miR-423-3p | 4 | AGCTCGGTCTGAGGCCCCTCAGT | 673 |
| miR-500* | 4 | ATGCACCTGGGCAAGGATTCTG | 674 |
| miR-502-3p | 4 | AATGCACCTGGGCAAGGATTCA | 675 |
| miR-532-5p | 4 | CATGCCTTGAGTGTAGGACCGT | 676 |
| miR-548k | 4 | AAAAGTACTTGCGGATTTTGCT | 677 |
| miR-556-5p | 4 | GATGAGCTCATTGTAATATGAG | 678 |
| miR-581 | 4 | TCTTGTGTTCTCTAGATCAGT | 679 |
| miR-584 | 4 | TTATGGTTTGCCTGGGACTGAG | 680 |
| miR-590-3p | 4 | TAATTTTATGTATAAGCTAGT | 681 |
| miR-616 | 4 | AGTCATTGGAGGGTTTGAGCAG | 682 |
| miR-629 | 4 | TGGGTTTACGTTGGGAGAACT | 683 |
| miR-92a | 4 | TATTGCACTTGTCCCGGCCTGT | 684 |
| miR-941 | 4 | CACCCGGCTGTGTGCACATGTGC | 685 |
| miR-942 | 4 | TCTTCTCTGTTTTGGCCATGTG | 686 |
| miR-944 | 4 | AAATTATTGTACATCGGATGAG | 687 |
| miR-1255b | 5 | CGGATGAGCAAAGAAAGTGGTT | 688 |
| miR-1257 | 5 | AGTGAATGATGGGTTCTGACC | 689 |
| miR-1285 | 5 | TCTGGGCAACAAAGTGAGACCT | 690 |
| miR-130b* | 5 | ACTCTTTCCCTGTTGCACTAC | 691 |
| miR-181c* | 5 | AACCATCGACCGTTGAGTGGAC | 692 |
| miR-186* | 5 | GCCCAAAGGTGAATTTTTTGGG | 693 |
| miR-18a | 5 | TAAGGTGCATCTAGTGCAGATAG | 694 |
| miR-18b | 5 | TAAGGTGCATCTAGTGCAGTTAG | 695 |
| miR-190b | 5 | TGATATGTTTGATATTGGGTT | 696 |
| miR-20b* | 5 | ACTGTAGTATGGGCACTTCCAG | 697 |
| miR-24-2* | 5 | TGCCTACTGAGCTGAAACACAG | 698 |
| miR-28-3p | 5 | CACTAGATTGTGAGCTCCTGGA | 699 |
| miR-30c-1* | 5 | CTGGGAGAGGGTTGTTTACTCC | 700 |
| miR-363 | 5 | AATTGCACGGTATCCATCTGTA | 701 |
| miR-450a | 5 | TTTTGCGATGTGTTCCTAATAT | 702 |
| miR-548g | 5 | AAAACTGTAATTACTTTTGTAC | 703 |
| miR-548o | 5 | CCAAAACTGCAGTTACTTTTGC | 704 |
| miR-582-5p | 5 | TTACAGTTGTTCAACCAGTTACT | 705 |
| miR-664* | 5 | ACTGGCTAGGGAAAATGATTGGAT | 706 |
| miR-93 | 5 | CAAAGTGCTGTTCGTGCAGGTAG | 707 |

The microRNA precursor sequences for the microRNAs listed in Table 14 are shown in Table 15.

TABLE 15

Precursor sequences and chromosomal locations (from human genome NCBI36) of the microRNAs in Table 19

| Gene name | Precursor Sequence 5'->3' | chrom | start | end | strand | SEQ ID NO |
|---|---|---|---|---|---|---|
| hsa-mir-101-1 | TGCCCTGGCTCAGTTATCACAGTGCTGATGCTGTCTATTCTAAAGGTACAGTACTGTGATAACTGAAGGATGGCA | 1 | 65296705 | 65296779 | -1 | 708 |
| hsa-mir-101-2 | ACTGTCCTTTTTCGGTTATCATGGTACCGATGCTGTATATCTGAAAGGTACAGTACTGTGATAACTGAAGAATGGTGGT | 9 | 4840297 | 4840375 | 1 | 709 |
| hsa-mir-140 | TGTGTCTCTCTCTGTGTCCTGCCAGTGGTTTTACCCTATGGTAGGTTACGTCATGCTGTTCTACCACAGGGTAGAACCACGGACAGGATACCGGGGCACC | 16 | 68524485 | 68524584 | 1 | 710 |
| hsa-mir-142 | GACAGTGCAGTCACCCATAAAGTAGAAAGCACTACTAACAGCACTGGAGGGTGTAGTGTTTCCTACTTTATGGATGAGTGTACTGTG | 17 | 53763592 | 53763678 | -1 | 711 |
| hsa-mir-143 | GCGCAGCGCCCTGTCTCCCAGCCTGAGGTGCAGTGCTGCATCTCTGGTCAGTTGGGAGTCTGAGATGAAGCACTGTAGCTCAGGAAGAGAGAAGTTGTTCTGCAGC | 5 | 148788674 | 148788779 | 1 | 712 |
| hsa-mir-144 | TGGGGCCCTGGCTGGGATATCATCATATACTGTAAGTTTGCGATGAGACACTACAGTATAGATGATGTACTAGTCCGGGCACCCCC | 17 | 24212677 | 24212762 | -1 | 713 |
| hsa-mir-148a | GAGGCAAAGTTCTGAGACACTCCGACTCTGAGTATGATAGAAGTCAGTGCACTACAGAACTTTGTCTC | 7 | 25956064 | 25956131 | -1 | 714 |
| hsa-mir-1537 | ACAGCTGTAATTAGTCAGTTTTCTGTCCTGTCCACACAGAAAACCGTCTAGTTACAGTTGT | 1 | 234082923 | 234082983 | -1 | 715 |
| hsa-mir-15a | CCTTGGAGTAAAGTAGCAGCACATAATGGTTTGTGGATTTTGAAAAGGTGCAGGCCATATTGTGCTGCCTCAAAAATACAAGG | 13 | 49521256 | 49521338 | -1 | 716 |
| hsa-mir-16-1 | GTCAGCAGTGCCTTAGCAGCACGTAAATATTGGCGTTAAGATTCTAAAATTATCTCCAGTATTAACTGTGCTGCTGAAGTAAGGTTGAC | 13 | 49521110 | 49521198 | -1 | 717 |
| hsa-mir-16-2 | GTTCCACTCTAGCAGCACGTAAATATTGGCGTAGTGAAATATATATTAAACACCAATATTACTGTGCTGCTTTAGTGTGAC | 3 | 161605227 | 161605307 | 1 | 718 |
| hsa-mi-185 | AGGGGGCGAGGGATTGGAGAGAAAGGCAGTTCCTGATGGTCCCCTCCCCAGGGGCTGGCTTTCCTCTGGTCCTTCCCTCCCA | 22 | 18400662 | 18400743 | 1 | 719 |
| hsa-mir-2115 | ACTGTCATCCCACTGCTTCCAGCTTCCATGACTCCTGATGGAGGAATCACATGAATTCATCAGAATTCATGGAGGCTAGAAGCAGTATGAGGATCATTTA | 3 | 48332854 | 48332953 | -1 | 720 |
| hsa-mir-223 | CCTGGCCTCCTGCAGTGCCACGCTCCGTGTATTTGACAAGCTGAGTTGGACACTCCATGTGGTAGAGTGTCAGTTTGTCAAATACCCCAAGTGCGGCACATGCTTACCAG | X | 65155437 | 65155546 | 1 | 721 |
| hsa-mir-27a | CTGAGGAGCAGGGCTTAGCTGCTTGTGAGCAGGGTCCACACCAAGTCGTGTTCACAGTGGCTAAGTTCCGCCCCCAG | 19 | 13808254 | 13808331 | -1 | 722 |
| hsa-mir-30e | GGGCAGTCTTTGCTACTGTAAACATCCTTGACTGGAAGCTGTAAGGTGTTCAGAGGAGCTTTCAGTCGGATGTTTACAGCGGCAGGCTGCCA | 1 | 40992614 | 40992705 | 1 | 723 |
| hsa-mir-338 | TCTCCAACAATATCCTGGTGCTGAGTGATGACTCAGGCGACTCCAGCATCAGTGATTTTGTTGAAGA | 17 | 76714278 | 76714344 | -1 | 724 |
| hsa-mir-374a | TACATCGGCCATTATAATACAACCTGATAAGTGTTATAGCACTTATCAGATTGTATTGTAATTGTCTGTGTA | X | 73423846 | 73423917 | -1 | 725 |
| hsa-mir-451 | CTTGGGAATGGCAAGGAAACCGTTACCATTACTGAGTTTAGTAATGGTAATGGTTCTCTTGCTATACCCAGA | 17 | 24212513 | 24212584 | -1 | 726 |
| hsa-mir-486 | GCATCCTGTACTGAGCTGCCCCGAGGCCCTTCATGCTGCCCAGCTCGGGGCAGCTCAGTACAGGATAC | 8 | 41637116 | 41637183 | -1 | 727 |
| hsa-mir-548e | TTATTAGGTTGGTACAAAAGCAATCGCGGTTTTTGCTATTACTTTTAAAGGCAAAAACTGAGACTACTTTTGCACCAACCTGATAGAA | 10 | 112738674 | 112738761 | 1 | 728 |
| hsa-mir-548f-1 | ATTAGGTTGGTGCAAAAGTAATCACAGTTTTTGACATTACTTTCAAAGACAAAAACTGTAATTACTTTTGGACCAACCTAATAG | 10 | 56037640 | 56037723 | -1 | 729 |

TABLE 15-continued

Precursor sequences and chromosomal locations
(from human genome NCBI36) of the microRNAs in Table 19

| Gene name | Precursor Sequence 5'->3' | chrom | start | end | strand | SEQ ID NO |
|---|---|---|---|---|---|---|
| hsa-mir-548f-2 | TAATAACTATTAGGTTGGTGCGAACATAATTGCAGTTTTTATCATTA CTTTTAATGGCAAAAACTGTAATTACTTTTGCACCAACCTAATATTT TAGT | 2 | 212999232 | 212999329 | -1 | 730 |
| hsa-mir-548f-3 | ATTAGGTTGGTGCAAACCTAATTGCAATTTTTGCAGTTTTTTTAAGT AATTGCAAAAACTGTAATTACTTTTGCACCAACCTAATAC | 5 | 109877429 | 109877515 | -1 | 731 |
| hsa-mir-548l-4 | GAGTTCTAACGTATTAGGTTGGTGCAAAAGTAATAGTGGTTTTTGCC ATTAAAAGTAATGACAAAAACTGTAATTACTTTTGGAACAATATTAA TAGAATTTCAG | 7 | 146706042 | 146706146 | -1 | 732 |
| hsa-mir-548f-5 | TATTAGGTTGCTGCAAAAGTAATCATGTTTTTTTCCATTGTAAGTAA TGGGAAAAACTGTAATTACTTTTGTACCAACCTAATAGC | X | 32569512 | 32569597 | -1 | 733 |
| hsa-mir-548j | GGGCAGCCAGTGAATAGTTAGCTGGTGCAAAAGTAATTGCGGTCTTT GGTATTACTTTCAGTGGCAAAAACTGCATTACTTTTGCACCAGCCTA CTAGAACGCTGAGTTCAG | 22 | 25281178 | 25281289 | -1 | 734 |
| hsa-mir-548n | AGGTTGGTGCAAAAGTAATTGTGGATTTTGTCGTTAAAAATAGCAAA ACCCGCAATTACTTTTGCACCAACCTAA | 7 | 34946897 | 34946971 | -1 | 735 |
| hsa-mir-548q | ATATTAGGCTGGTGCAAAAGTAATGGCGGTTTTTGCCATTACTTTTC ATTTTTACCATTAAAAGTAATGGCAAAAAGCATGATTACTTTTTCAC CAACCT | 10 | 12807259 | 12807358 | -1 | 736 |
| hsa-mir-576 | TACAATCCAACGAGGATTCTAATTTCTCCACGTCTTTGGTAATAAGG TTTGGCAAAGATGTGGAAAAATTGGAATCCTCATTCGATTGGTTATA ACCA | 4 | 110629303 | 110629400 | 1 | 737 |
| hsa-mir-582 | ATCTGTGCTCTTTGATTACAGTTGTTCAACCAGTTACTAATCTAACT AATTGTAACTGGTTGAACAACTGAACCCAAAGGGTGCAAAGTAGAAA CATT | 5 | 59035189 | 59035286 | -1 | 738 |
| hsa-mir-617 | CATCATAAGGAGCCTAGACTTCCCATTTGAAGGTGGCCATTTCCTAC CACCTTCAAATGGTAAGTCCAGGCTCCTTCTGATTCAATAAATGAGG AGC | 12 | 79750443 | 79750539 | -1 | 739 |
| hsa-mir-618 | CTCTTGTTCACAGCCAAACTCTACTTGTCCTTCTGAGTGTAATTACG TACATGCAGTAGCTCAGGAGACAAGCAGGTTTACCCTGTGGATGAGT CTGA | 12 | 79853646 | 79853743 | -1 | 740 |
| hsa-mir-624 | AATGCTGTTTCAAGGTAGTACCAGTACCTTGTGTTCAGTGGAACCAA GGTAAACACAAGGTATTGGTATTACCTTGAGATAGCATTACACCTAA GTG | 14 | 30553603 | 30553699 | -1 | 741 |
| hsa-mir-625 | AGGGTAGAGGGATGAGGGGGAAAGTTCTATAGTCCTGTAATTAGATC TCAGGACTATAGAACTTTCCCCCTCATCCCTCTGCCCT | 14 | 65007573 | 65007657 | 1 | 742 |
| hsa-mir-627 | TACTTATTACTGGTAGTGAGTCTCTAAGAAAAGAGGAGGTGGTTGTT TTCCTCCTCTTTTCTTTGAGACTCACTACCAATAATAAGAAATACTA CTA | 15 | 40279060 | 40279156 | -1 | 743 |
| hsa-mir-628 | ATAGCTGTTGTGTCACTTCCTCATGCTGACATATTTACTAGAGGGTA AAATTAATAACCTTCTAGTAAGAGTGGCAGTCGAAGGGAAGGGCTCA T | 15 | 53452430 | 53452524 | -1 | 744 |
| hsa-mir-629 | TCCCTTTCCCAGGGGAGGGGCTGGGTTTACGTTGGGAGAACTTTTAC GGTGAACCAGGAGGTTCTCCCAACGTAAGCCCAGCCCCTCCCCTCTG CCT | 15 | 68158765 | 68158861 | -1 | 745 |
| hsa-mir-640 | GTGACCCTGGGCAAGTTCCTGAAGATCAGACACATCAGATCCCTTAT CTGTAAAATGGGCATGATCCAGGAACCTGCCTCTACGGTTGCCTTGG GG | 19 | 19406872 | 19406967 | 1 | 746 |
| hsa-mir-1225 | GTGGGTACGGCCCAGTGGGGGGGAGAGGGACACGCCCTGGGCTCTGC CCAGGGTGCAGCCGGACTGACTGAGCCCCTGTGCCGCCCCAG | 16 | 2080197 | 2080286 | -1 | 747 |
| hsa-mir-1255a | ATTGGAAATCCTTTGAGTTGCTTCTCAAGGATGAGCAAAGAAAGTAG ATTTTTTAGATTCTAAAGAAACTATCTTCTTTGCTCATCCTTGAGAA GCAACTCCTTATCCATTAA | 4 | 102470482 | 102470594 | -1 | 748 |
| hsa-mir-126 | CGCTGGCGACGGGACATTATTACTTTTGGTACGCGCTGTGACACTTC AAACTCGTACCGTGAGTAATAATGCGCCGTCCACGGCA | 9 | 138684875 | 138684959 | 1 | 749 |

TABLE 15-continued

Precursor sequences and chromosomal locations
(from human genome NCBI36) of the microRNAs in Table 19

| Gene name | Precursor Sequence 5'->3' | chrom | start | end | strand | SEQ ID NO |
|---|---|---|---|---|---|---|
| hsa-mir-148a | GAGGCAAAGTTCTGAGACACTCCGACTCTGAGTATGATAGAAGTCAGTGCACTACAGAACTTTGTCTC | 7 | 25956064 | 25956131 | -1 | 750 |
| hsa-mir-26b | CCGGGACCCAGTTCAAGTAATTCAGGATAGGTTGTGTGCTGTCCAGCCTGTTCTCCATTACTTGGCTCGGGGACCGG | 2 | 218975613 | 218975689 | 1 | 751 |
| hsa-mir-30a | GCGACTGTAAACATCCTCGACTGGAAGCTGTGAAGCCACAGATGGGCTTTCAGTCGGATGTTTGCAGCTGC | 6 | 72169975 | 72170045 | -1 | 752 |
| hsa-mir-425 | GAAAGCGCTTTGGAATGACACGATCACTCCCGTTGAGTGGGCACCCGAGAAGCCATCGGGAATGTCGTGTCCGCCCAGTGCTCTTTC | 3 | 49032585 | 49032671 | -1 | 753 |
| hsa-mir-450b | GCAGAATTATTTTTGCAATATGTTCCTGAATATGTAATATAAGTGTATTGGGATCATTTTGCATCCATAGTTTTGTAT | X | 133501881 | 133501958 | -1 | 754 |
| hsa-mir-503 | TGCCCTAGCAGCGGGAACAGTTCTGCAGTGAGCGATCGGTGCTCTGGGGTATTGTTTCCGCTGCCAGGGTA | X | 133508024 | 133508094 | -1 | 755 |
| hsa-mir-514-1 | AACATGTTGTCTGTGGTACCCTACTCTGGAGAGTGACAATCATGTATAATTAAATTTGATTGACACTTCTGTGAGTAGAGTAACGCATGACACGTACG | X | 146168457 | 146168554 | -1 | 756 |
| hsa-mir-514-2 | GTTGTCTGTGGTACCCTACTCTGGAGAGTGACAATCATGTATAACTAAATTTGATTGACACTTCTGTGAGTAGAGTAACGCATGACAC | X | 146171153 | 146171240 | -1 | 757 |
| hsa-mir-514-3 | GTTGTCTGTGGTACCCTACTCTGGAGAGTGACAATCATGTATAACTAAATTTGATTGACACTTCTGTGAGTAGAGTAACGCATGACAC | X | 146173851 | 146173938 | -1 | 758 |
| hsa-mir-548b | CAGACTATATATTTAGGTTGGCGCAAAAGTAATTGTGGTTTTGGCCTTTATTTTCAATGGCAAGAACCTCAGTTGCTTTTGTGCCAACCTAATACTT | 6 | 11943191 | 119432007 | -1 | 759 |
| hsa-mir-548d-1 | AAACAAGTTATATTAGGTTGGTGCAAAAGTAATTGTGGTTTTTGCCTGTAAAGTAATGGCAAAAACCACAGTTTCTTTTGCACCAGACTAATAAAG | 8 | 124429455 | 124429551 | -1 | 760 |
| hsa-mir-548d-2 | GAGAGGGAAGATTTAGGTTGGTGCAAAAGTAATTGTGGTTTTTGCCATTGAAAGTAATGGCAAAAACCACAGTTTCTTTTGCACCAACCTAATAAAA | 17 | 62898067 | 62898163 | -1 | 761 |
| hsa-mir-580 | ATAAAATTTCCAATTGGAACCTAATGATTCATCAGACTCAGATATTTAAGTTAACAGTATTTGAGAATGATGAATCATTAGGTTCCGGTCAGAAATT | 5 | 36183751 | 36183847 | -1 | 762 |
| hsa-mir-616 | TTAGGTAATTCCTCCACTCAAAACCCTTCAGTGACTTCCATGACATGAAATAGGAAGTCATTGGAGGGTTTGAGCAGAGGAATGACCTGTTTTAAAA | 12 | 56199213 | 56199309 | -1 | 763 |
| hsa-mir-1179 | GGCTGGAAAGGAAGAAGCATTCTTTCATTGGTTGGTGTGTATTGCCTTGTCAACCAATAAGAGGATGCCATTTATCCTTTTCTGACTAGCT | 15 | 86952342 | 86952432 | 1 | 764 |
| hsa-mir-1244 | ATCTTATTCCGAGCATTCCAGTAACTTTTTTGTGTATGTACTTAGCTGTACTATAAGTAGTTGGTTTGTATGAGATGGTTAAAAA | 12 | 12156153 | 12156237 | 1 | 765 |
| hsa-mir-1244 | ATCTTATTCCGAGCATTCCAGTAACTTTTTTGTGTATGTACTTAGCTGTACTATAAGTAGTTGGTTTGTATGAGATGGTTAAAAA | 12 | 9283330 | 9283414 | -1 | 766 |
| hsa-mir-1244 | ATCTTATTCCGAGCATTCCAGTAACTTTTTTGTGTATGTACTTAGCTGTACTATAAGTAGTTGGTTTGTATGAGATGGTTAAAAA | 2 | 232286268 | 232286352 | 1 | 767 |
| hsa-mir-1244 | ATCTTATTCCGAGCATTCCAGTAACTTTTTTGTGTATGTACTTAGCTGTACTATAAGTAGTTGGTTTGTATGAGATGGTTAAAAA | 5 | 118338180 | 118338264 | 1 | 768 |
| hsa-mir-12 | CGCTGGCGACGGGACATTATTACTTTTGGTACGCGCTGTGACACTTCAAACTCGTACCGTGAGTAATAATGCGCCGTCCACGGCA | 9 | 138684875 | 138684959 | 1 | 769 |
| hsa-mir-1291 | GGTAGAATTCCAGTGGCCCTGACTGAAGACCAGCAGTTGTACTGTGGCTGTTGGTTTCAAGCAGAGGCCTAAAGGACTGTCTTCCTG | 12 | 47334494 | 47334580 | -1 | 770 |
| hsa-miR-140 | TGTGTCTCTCTGTGTCCTGCCAGTGGTTTTACCCTATGGTAGGTTACGTCATGCTGTTCTACCACAGGGTAGAACCACGGACAGGATACCGGGGCACC | 16 | 68524485 | 68524584 | 1 | 771 |

TABLE 15-continued

Precursor sequences and chromosomal locations
(from human genome NCBI36) of the microRNAs in Table 19

| Gene name | Precursor Sequence 5'->3' | chrom | start | end | strand | SEQ ID NO |
|---|---|---|---|---|---|---|
| hsa-mir-145 | CACCTTGTCCTCACGGTCCAGTTTTCCCAGGAATCCCTTAGATGCTA AGATGGGGATTCCTGGAAATACTGTTCTTGAGGTCATGGTT | 5 | 148790402 | 148790489 | 1 | 772 |
| hsa-mir-146a | CCGATGTGTATCCTCAGCTTTGAGAACTGAATTCCATGGGTTGTGTC AGTGTCAGACCTCTGAAATTCAGTTCTTCAGCTGGGATATCTCTGTC ATCGT | 5 | 159844937 | 159845035 | 1 | 773 |
| hsa-mir-146b | CCTGGCACTGAGAACTGAATTCCATAGGCTGTGAGCTCTAGCAATGC CCTGTGGACTCAGTTCTGGTGCCCGG | 10 | 104186259 | 104186331 | 1 | 774 |
| hsa-mir-148b | CAAGCACGATTAGCATTTGAGGTGAAGTTCTGTTATACACTCAGGCT GTGGCTCTCTGAAAGTCAGTGCATCACAGAACTTTGTCTCGAAAGCT TTCTA | 12 | 53017267 | 53017365 | 1 | 775 |
| hsa-mir-150 | CTCCCCATGGCCCTGTCTCCCAACCCTTGTACCAGTGCTGGGCTCAG ACCCTGGTACAGGCCTGGGGGACAGGGACCTGGGGAC | 19 | 54695854 | 54695937 | -1 | 776 |
| hsa-mir-17 | GTCAGAATAATGTCAAAGTGCTTACAGTGCAGGTAGTGATATGTGCA TCTACTGCAGTGAAGGCACTTGTAGCATTATGGTGAC | 13 | 90800860 | 90800943 | 1 | 777 |
| hsa-mir-181a-1 | TGAGTTTTGAGGTTGCTTCAGTGAACATTCAACGCTGTCGGTGAGTT TGGAATTAAAATCAAAACCATCGACCGTTGATTGTACCCTATGGCTA ACCATCATCTACTCCA | 1 | 197094796 | 197094905 | -1 | 778 |
| hsa-mir-191 | CGGCTGGACAGCGGGCAACGGAATCCCAAAAGCAGCTGTTGTCTCCA GAGCATTCCAGCTGCGCTTGGATTTCGTCCCCTGCTCTCCTGCCT | 3 | 49033055 | 49033146 | -1 | 779 |
| hsa-mir-199b | CCAGAGGACACCTCCACTCCGTCTACCCAGTGTTTAGACTATCTGTT CAGGACTCCCAAATTGTACAGTAGTCTGCACATTGGTTAGGCTGGGC TGGGTTAGACCCTCGG | 9 | 130046821 | 130046930 | -1 | 780 |
| hsa-mir-26a-1 | GTGGCCTCGTTCAAGTAATCCAGGATAGGCTGTGCAGGTCCCAATGG GCCTATTCTTGGTTACTTGCACGGGGACGC | 3 | 37985899 | 37985975 | 1 | 781 |
| hsa-mir-29b-2 | CTTCTGGAAGCTGGTTTCACATGGTGGCTTAGATTTTTCCATCTTTG TATCTAGCACCATTTGAAATCAGTGTTTTAGGAG | 1 | 206042411 | 206042491 | -1 | 782 |
| hsa-mir-340 | TTGTACCTGGTGTGATTATAAAGCAATGAGACTGATTGTCATATGTC GTTTGTGGGATCCGTCTCAGTTACTTTATAGCCATACCTGGTATCTT A | 5 | 179374909 | 179375003 | -1 | 783 |
| hsa-mir-361 | GGAGCTTATCAGAATCTCCAGGGGTACTTTATAATTTCAAAAAGTCC CCCAGGTGTGATTCTGATTTGCTTC | X | 85045297 | 85045368 | -1 | 784 |
| hsa-mir-422a | GAGAGAAGCACTGGACTTAGGGTCAGAAGGCCTGAGTCTCTCTGCTG CAGATGGGCTCTCTGTCCCTGAGCCAAGCTTTGTCCTCCCTGG | 15 | 61950182 | 61950271 | -1 | 785 |
| hsa-mir-425 | GAAAGCGCTTTGGAATGACACGATCACTCCCGTTGAGTGGGCACCCG AGAAGCCATCGGGAATGTCGTGTCCGCCCAGTGCTCTTTC | 3 | 49032585 | 49032671 | -1 | 786 |
| hsa-mir-454 | TCTGTTTATCACCAGATCCTAGAACCCTATCAATATTGTCTCTGCTG TGTAAATAGTTCTGAGTAGTGCAATATTGCTTATAGGGTTTTGGTGT TTGGAAAGAACAATGGGCAGG | 17 | 54569901 | 54570015 | -1 | 787 |
| hsa-mir-502 | TGCTCCCCCTCTCTAATCCTTGCTATCTGGGTGCTAGTGCTGGCTCA ATGCAATGCACCTGGGCAAGGATTCAGAGAGGGGGAGCT | X | 49665946 | 49666031 | 1 | 788 |
| hsa-mir-542 | CAGATCTCAGACATCTCGGGGATCATCATGTCACGAGATACCAGTGT GCACTTGTGACAGATTGATAACTGAAAGGTCTGGGAGCCACTCATCT TCA | X | 133503037 | 133503133 | -1 | 789 |
| hsa-mir-550-1 | TGATGCTTTGCTGGCTGGTGCAGTGCCTGAGGGAGTAAGAGCCCTGT TGTTGTAAGATAGTGTCTTACTCCCTCAGGCACATCTCCAACAAGTC TCT | 7 | 30295935 | 30296031 | 1 | 790 |
| hsa-mir-550-2 | TGATGCTTTGCTGGCTGGTGCAGTGCCTGAGGGAGTAAGAGCCCTGT TGTTGTCAGATAGTGTCTTACTCCCTCAGGCACATCTCCAGCGAGTC TCT | 7 | 32739118 | 32739214 | 1 | 791 |
| hsa-mir-551a | GGGGACTGCCGGGTGACCCTGGAAATCCAGAGTGGGTGGGGCCAGTC TGACCGTTTCTAGGCGACCCACTCTTGGTTTCCAGGGTTGCCCTGGA AA | 1 | 3467119 | 3467214 | -1 | 792 |

TABLE 15-continued

Precursor sequences and chromosomal locations
(from human genome NCBI36) of the microRNAs in Table 19

| Gene name | Precursor Sequence 5'->3' | chrom | start | end | strand | SEQ ID NO |
|---|---|---|---|---|---|---|
| hsa-mir-573 | TTTAGCGGTTTCTCCCTGAAGTGATGTGTAACTGATCAGGATCTACTCATGTCGTCTTTGGTAAAGTTATGTCGCTTGTCAGGGTGAGGAGAGTTTTTG | 4 | 24130913 | 24131011 | -1 | 793 |
| hsa-mir-598 | GCTTGATGATGCTGCTGATGCTGGCGGTGATCCCGATGGTGTGAGCTGGAAATGGGGTGCTACGTCATCGTTGTCATCGTCATCATCATCATCCGAG | 8 | 10930126 | 10930222 | -1 | 794 |
| hsa-mir-643 | ACCAAGTGATATTCATTGTCTACCTGAGCTAGAATACAAGTAGTTGGCGTCTTCAGAGACACTTGTATGCTAGCTCAGGTAGATATTGAATGAAAAA | 19 | 57476862 | 57476958 | 1 | 795 |
| hsa-mir-671 | GCAGGTGAACTGGCAGGCCAGGAAGAGGAGGAAGCCCTGGAGGGGCTGGAGGTGATGGATGTTTTCCTCCGGTTCTCAGGGCTCCACCTCTTTCGGGCCGTAGAGCCAGGGCTGGTGC | 7 | 150566440 | 150566557 | 1 | 796 |
| hsa-let-7f-1 | TCAGAGTGAGGTAGTAGATTGTATAGTTGTGGGGTAGTGATTTTACCCTGTTCAGGAGATAACTATACAATCTATTGCCTTCCCTGA | 9 | 95978450 | 95978536 | 1 | 797 |
| hsa-let-7f-2 | TGTGGGATGAGGTAGTAGATTGTATAGTTTTAGGGTCATACCCCATCTTGGAGATAACTATACAGTCTACTGTCTTTCCCACG | X | 53600878 | 53600960 | -1 | 798 |
| hsa-let-7g | AGGCTGAGGTAGTAGTTTGTACAGTTTGAGGGTCTATGATACCACCCGGTACAGGAGATAACTGTACAGGCCACTGCCTTGCCA | 3 | 52277334 | 52277417 | -1 | 799 |
| hsa-mir-103-1 | TACTGCCCTCGGCTTCTTTACAGTGCTGCCTTGTTGCATATGGATCAAGCAGCATTGTACAGGGCTATGAAGGCATTG | 5 | 167920479 | 167920556 | -1 | 800 |
| hsa-mir-103-2 | TTGTGCTTTCAGCTTCTTTACAGTGCTGCCTTGTAGCATTCAGGTCAAGCAGCATTGTACAGGGCTATGAAAGAACCA | 20 | 3846141 | 3846218 | 1 | 801 |
| hsa-mir-107 | CTCTCTGCTTTCAGCTTCTTTACAGTGTTGCCTTGTGGCATGGAGTTCAAGCAGCATTGTACAGGGCTATCAAAGCACAGA | 10 | 91342484 | 91342564 | -1 | 802 |
| hsa-mir-1197 | ACTTCCTGGTATTTGAAGATGCGGTTGACCATGGTGTGTACGCTTTATTTGTGACGTAGGACACATGGTCTACTTCTTCTCAATATCA | 14 | 100561654 | 100561741 | 1 | 803 |
| hsa-mir-1250 | CTGTCCCGCTGGCCTGGCAGGTGACGGTGCTGGATGTGGCCTTTTTGCCTTTTCTAAAGGCCACATTTTCCAGCCCATTCAACCTTCCAGAGCCCTCTGAAGTGGCCACAGGC | 17 | 76721591 | 76721703 | -1 | 804 |
| hsa-mir-1277 | ACCTCCCAAATATATATATATATGTACGTATGTGTATATAAATGTATACGTAGATATATATGTATTTTTGGTGGGTTT | X | 117404385 | 117404462 | 1 | 805 |
| hsa-mir-1278 | ATTTGCTCATAGATGATATGCATAGTACTCCCAGAACTCATTAAGTTGGTAGTACTGTGCATATCATCTATGAGCGAATAG | -1 | 1913722576 | 191372336 | 1 | 806 |
| hsa-mir-1299 | CCTCATGGCAGTGTTCTGGAATCCTACGTGAGGGACAATCATTCAGACCCACGTAGCAGTGTTCTGGAATTCTGTGTGAGGGA | 9 | 68292059 | 68292141 | -1 | 807 |
| hsa-mir-143 | GCGCAGCGCCCTGTCTCCCAGCCTGAGGTGCAGTGCTGCATCTCTGGTCAGTTGGGAGTCTGAGATGAAGCACTGTAGCTCAGGAAGAGAGAAGTTGTTCTGCAGC | 5 | 148788674 | 148788779 | 1 | 808 |
| hsa-mir-150 | CTCCCCATGGCCCTGTCTCCCAACCCTTGTACCAGTGCTGGGCTCAGACCCTGGTACAGGCCTGGGGACAGGGACCTGGGGAC | 19 | 54695854 | 54695937 | -1 | 809 |
| hsa-mir-155 | CTGTTAATGCTAATCGTGATAGGGGTTTTTGCCTCCAACTGACTCCTACATATTAGCATTAACAG | 21 | 25868163 | 25868227 | 1 | 810 |
| hsa-mir-181a-1 | TGAGTTTTGAGGTTGCTTCAGTGAACATTCAACGCTGTCGGTGAGTTTGGAATTAAAATCAAAACCATCGACCGTTGATTGTACCCTATGGCTAACCATCATCTACTCCA | 1 | 197094796 | 197094905 | -1 | 811 |
| hsa-mir-181a-2 | AGAAGGGCTATCAGGCCAGCCTTCAGAGGACTCCAAGGAACATTCAACGCTGTCGGTGAGTTTGGGATTTGAAAAAACCACTGACCGTTGACTGTACCTTGGGGTCCTTA | 9 | 126494542 | 126494651 | 1 | 812 |
| hsa-mir-181b-1 | CCTGTGCAGAGATTATTTTTTAAAAGGTCACAATCAACATTCATTGCTGTCGGTGGGTTGAACTGTGTGGACAAGCTCACTGAACAATGAATGCAACTGTGGCCCCGCTT | 1 | 197094625 | 197094734 | -1 | 813 |
| hsa-mir-181b-2 | CTGATGGCTGCACTCAACATTCATTGCTGTCGGTGGGTTTGAGTCTGAATCAACTCACTGATCAATGAATGCAAACTGCGGACCAAACA | 9 | 126495810 | 126495898 | 1 | 814 |

TABLE 15-continued

Precursor sequences and chromosomal locations
(from human genome NCBI36) of the microRNAs in Table 19

| Gene name | Precursor Sequence 5'->3' | chrom | start | end | strand | SEQ ID NO |
|---|---|---|---|---|---|---|
| hsa-mir-186 | TGCTTGTAACTTTCCAAAGAATTCTCCTTTTGGGCTTTCTGGTTTTA TTTTAAGCCCAAAGGTGAATTTTTTGGGAAGTTTGAGCT | 1 | 71305902 | 71305987 | -1 | 815 |
| hsa-mir-196b | ACTGGTCGGTGATTTAGGTAGTTTCCTGTTGTTGGGATCCACCTTTC TCTCGACAGCACGACACTGCCTTCATTACTTCAGTTG | 7 | 27175624 | 27175707 | -1 | 816 |
| hsa-mir-1976 | GCAGCAAGGAAGGCAGGGGTCCTAAGGTGTGTCCTCCTGCCCTCCTT GCTGT | 1 | 26753620 | 26753671 | 1 | 817 |
| hsa-mir-21 | TGTCGGGTAGCTTATCAGACTGATGTTGACTGTTGAATCTCATGGCA ACACCAGTCGATGGGCTGTCTGACA | 17 | 55273409 | 55273480 | 1 | 818 |
| hsa-mir-219-1 | CCGCCCCGGGCCGCGGCTCCTGATTGTCCAAACGCAATTCTCGAGTC TATGGCTCCGGCCGAGAGTTGAGTCTGGACGTCCCGAGCCGCCGCCC CCAAACCTCGAGCGGG | 6 | 33283590 | 33283699 | 1 | 819 |
| hsa-mir-221 | TGAACATCCAGGTCTGGGGCATGAACCTGGCATACAATGTAGATTTC TGTGTTCGTTAGGCAACAGCTACATTGTCTGCTGGGTTTCAGGCTAC CTGGAAACATGTTCTC | X | 45490529 | 45490638 | -1 | 820 |
| hsa-mir-378 | AGGGCTCCTGACTCCAGGTCCTGTGTGTTACCTAGAAATAGCACTGG ACTTGGAGTCAGAAGGCCT | 5 | 149092581 | 149092646 | 1 | 821 |
| hsa-mir-423 | ATAAAGGAAGTTAGGCTGAGGGGCAGAGAGCGAGACTTTTCTATTTT CCAAAAGCTCGGTCTGAGGCCCCTCAGTCTTGCTTCCTAACCCGCGC | 17 | 25468223 | 25468316 | 1 | 822 |
| hsa-mir-500 | GCTCCCCCTCTCTAATCCTTGCTACCTGGGTGAGAGTGCTGTCTGAA TGCAATGCACCTGGGCAAGGATTCTGAGAGCGAGAGC | X | 49659779 | 49659862 | 1 | 823 |
| hsa-mir-502 | TGCTCCCCCTCTCTAATCCTTGCTATCTGGGTGCTAGTGCTGGCTCA ATGCAATGCACCTGGGCAAGGATTCAGAGAGGGGGAGCT | X | 49665946 | 49666031 | 1 | 824 |
| hsa-mir-532 | CGACTTGCTTTCTCTCCTCCATGCCTTGAGTGTAGGACCGTTGGCAT CTTAATTACCCTCCCACACCCAAGGCTTGCAAAAAAGCGAGCCT | X | 49654494 | 49654584 | 1 | 825 |
| hsa-mir-548k | CTTTTCTCAAGTATTGCTGTTAGGTTGGTGCAAAAGTACTTGCGGAT TTTGCTTTACTTTTAATGGCAAAAACCGCAATTATTTTTGCTTCAAC CTAATATGATGCAAAATTGGCT | 11 | 69807709 | 69807824 | 1 | 826 |
| hsa-mir-556 | GATAGTAATAAGAAAGATGAGCTCATTGTAATATGAGCTTCATTTAT ACATTTCATATTACCATTAGCTCATCTTTTTTATTACTACCTTCAAC A | 1 | 160578960 | 160579054 | 1 | 827 |
| hsa-mir-581 | GTTATGTGAAGGTATTCTTGTGTTCTCTAGATCAGTGCTTTTAGAAA ATTTGTGTGATCTAAAGAACACAAAGAATACCTACACAGAACCACCT GC | 5 | 53283091 | 53283186 | -1 | 828 |
| hsa-mir-584 | TAGGGTGACCAGCCATTATGGTTTGCCTGGGACTGAGGAATTTGCTG GGATATGTCAGTTCCAGGCCAACCAGGCTGGTTGGTCTCCCTGAAGC AAC | 5 | 148422069 | 148422165 | -1 | 829 |
| hsa-mir-590 | TAGCCAGTCAGAAATGAGCTTATTCATAAAAGTGCAGTATGGTGAAG TCAATCTGTAATTTTATGTATAAGCTAGTCTCTGATTGAAACATGCA GCA | 7 | 73243464 | 73243560 | 1 | 830 |
| hsa-mir-616 | TTAGGTAATTCCTCCACTCAAAACCCTTCAGTGACTTCCATGACATG AAATAGGAAGTCATTGGAGGGTTTGAGCAGAGGAATGACCTGTTTTA AAA | 12 | 56199213 | 56199309 | -1 | 831 |
| hsa-mir-629 | TCCCTTTCCCAGGGGAGGGGCTGGGTTTACGTTGGGAGAACTTTTAC GGTGAACCAGGAGGTTCTCCCAACGTAAGCCCAGCCCCTCCCCTCTG CCT | 15 | 68158765 | 68158861 | -1 | 832 |
| hsa-mir-92a-1 | CTTTCTACACAGGTTGGGATCGGTTGCAATGCTGTGTTTCTGTATGG TATTGCACTTGTCCCGGCCTGTTGAGTTTGG | 13 | 90801569 | 90801646 | 1 | 833 |
| hsa-mir-92a-2 | TCATCCCTGGGTGGGGATTTGTTGCATTACTTGTGTTCTATATAAAG TATTGCACTTGTCCCGGCCTGTGGAAGA | X | 133131234 | 133131308 | -1 | 834 |
| hsa-mir-941-1 | CCCGGCTGTGTGGACATGTGCCCAGGGCCCGGGACAGCGCCACGGAA GAGGACGCACCCGGCTGTGTGCACATGTGCCCAGGGCCCGGG | 20 | 62021238 | 62021326 | 1 | 835 |
| hsa-mir-941-2 | CCCGGCTGTGTGCACATGTGCCCAGGGCCCGGGACAGCGCCACGGAA GAGGACGCACCCGGCTGTGTGCACATGTGCCCAGGGCCCGGG | 20 | 62021545 | 62021633 | 1 | 836 |

TABLE 15-continued

Precursor sequences and chromosomal locations
(from human genome NCBI36) of the microRNAs in Table 19

| Gene name | Precursor Sequence 5'->3' | chrom | start | end | strand | SEQ ID NO |
|---|---|---|---|---|---|---|
| hsa-mir-941-3 | CCCGGCTGTGTGCACATGTGCCCAGGGCCCGGGACAGCGCCACGGAA GAGGACGCACCCGGCTGTGTGCACATGTGCCCAGGGCCCGGG | 20 | 62021657 | 62021745 | 1 | 837 |
| hsa-mir-942 | ATTAGGAGAGTATCTTCTCTGTTTTGGCCATGTGTGTACTCACAGCC CCTCACACATGGCCGAAACAGAGAAGTTACTTTCCTAAT | 1 | 117438788 | 117438873 | 1 | 838 |
| hsa-mir-944 | GTTCCAGACACATCTCATCTGATATACAATATTTTCTTAAATTGTAT AAAGAGAAATTATTGTACATCGGATGAGCTGTGTCTGGGAT | 3 | 191030405 | 191030492 | 1 | 839 |
| hsa-mir-1255b-1 | TACGGATGAGCAAAGAAAGTGGTTTCTTAAAATGGAATCTACTCTTT GTGAAGATGCTGTGAA | 4 | 36104383 | 36104445 | -1 | 840 |
| hsa-mir-1255b-2 | TCTTACGGATGAGCAAAGAAAGTGGTTTGCGCCTCAAGAAACCACTT TCTTTGCTCATCCATAAGGA | 1 | 166234522 | 166234588 | 1 | 841 |
| hsa-mir-1257 | GCCCTGGGCTTGTGCTTGGGGAGTGAATGATGGGTTCTGACCCCCAT GCACCCCTGTGGGCCCCTGGCATCACTGGCCCCATCCTTCACCCCTG CCAACCACGCTTGCCCTGTGCCT | 20 | 59961997 | 59962113 | -1 | 842 |
| hsa-mir-1285-1 | TGTAGAGATAGGATCTCACTTTGTTGCCCAGGCTGGTCTCAAACTCC TGGTCTGGGCAACAAAGTGAGACCTTATCTCTACAAG | 7 | 91671265 | 91671348 | -1 | 843 |
| hsa-mir-1285-2 | TTTGGGAGGCCGAGGCTGGTGCATCACTTGAGCCCAGCAATTTGAGA CCAATCTGGGCAACAAAGTGAGACCTCCGTCTCTACAAAGA | 2 | 70333554 | 70333641 | -1 | 844 |
| hsa-mir-130b | GGCCTGCCCGACACTCTTTCCCTGTTGCACTACTATAGGCCGCTGGG AAGCAGTGCAATGATGAAAGGGCATCGGTCAGGTC | 22 | 20337593 | 20337674 | 1 | 845 |
| hsa-mir-181c | CGGAAAATTTGCCAAGGGTTTGGGGAACATTCAACCTGTCGGTGAG TTTGGGCAGCTCAGGCAAACCATCGACCGTTGAGTGGACCCTGAGGC CTGGAATTGCCATCCT | 19 | 13846513 | 13846622 | 1 | 846 |
| hsa-mir-186 | TGCTTGTAACTTTCCAAAGAATTCTCCTTTTGGGCTTTCTGGTTTTA TTTTAAGCCCAAAGGTGAATTTTTTGGGAAGTTTGAGCT | 1 | 71305902 | 71305987 | -1 | 847 |
| hsa-mir-18a | TGTTCTAAGGTGCATCTAGTGCAGATAGTGAAGTAGATTAGCATCTA CTGCCCTAAGTGCTCCTTCTGGCA | 13 | 90801006 | 90801076 | 1 | 848 |
| hsa-mir-18b | TGTGTTAAGGTGCATCTAGTGCAGTTAGTGAAGCAGCTTAGAATCTA CTGCCCTAAATGCCCCTTCTGGCA | X | 133131737 | 133131807 | -1 | 849 |
| hsa-mir-190b | TGCTTCTGTGTGATATGTTTGATATTGGGTTGTTTAATTAGGAACCA ACTAAATGTCAAACATATTCTTACAGCAGCAG | 1 | 152432765 | 152432843 | -1 | 850 |
| hsa-mir-20b | AGTACCAAAGTGCTCATAGTGCAGGTAGTTTTGGCATGACTCTACTG TAGTATGGGCACTTCCAGTACT | X | 133131505 | 133131573 | -1 | 851 |
| hsa-mir-24-2 | CTCTGCCTCCCGTGCCTACTGAGCTGAAACACAGTTGGTTTGTGTAC ACTGGCTCAGTTCAGCAGGAACAGGG | 19 | 13808101 | 13808173 | -1 | 852 |
| hsa-mir-28 | GGTCCTTGCCCTCAAGGAGCTCACAGTCTATTGAGTTACCTTTCTGA CTTTCCCACTAGATTGTGAGCTCCTGGAGGGCAGGCACT | 3 | 189889263 | 189889348 | 1 | 853 |
| hsa-mir-30c-1 | ACCATGCTGTAGTGTGTGTAAACATCCTACACTCTCAGCTGTGAGCT CAAGGTGGCTGGGAGAGGGTTGTTTACTCCTTCTGCCATGGA | 1 | 40995543 | 40995631 | 1 | 854 |
| hsa-mir-363 | TGTTGTCGGGTGGATCACGATGCAATTTTGATGAGTATCATAGGAGA AAAATTGCACGGTATCCATCTGTAAACC | X | 133131074 | 133131148 | -1 | 855 |
| hsa-mir-450a-1 | AAACGATACTAAACTGTTTTTGCGATGTGTTCCTAATATGCACTATA AATATATTGGGAACATTTTGCATGTATAGTTTTGTATCAATATA | X | 133502037 | 133502127 | -1 | 856 |
| hsa-mir-450a-2 | CCAAAGAAAGATGCTAAACTATTTTTGCGATGTGTTCCTAATATGTA ATATAAATGTATTGGGGACATTTTGCATTCATAGTTTTGTATCAATA ATATGG | X | 133502204 | 133502303 | -1 | 857 |
| hsa-mir-548g | AGTTATTAGATTAGTGCAAAAGTAATTGCAGTTTTTGCATTACGTTC TATGGCAAAACTGTAATTACTTTTGTACCAACATAATACTTC | 4 | 148485231 | 148485319 | -1 | 858 |
| hsa-mir-548o | TGGTGAAAATGTGTTGATTGTAATGGTTCCTATTCTGATCAATAAAC ATGGTTTGAGCCTAGTTACAATGATCTAAAATTCACGGTCCAAAACT GCAGTTACTTTTGCACCAAC | 7 | 101833194 | 101833307 | -1 | 859 |

TABLE 15-continued

Precursor sequences and chromosomal locations
(from human genome NCBI36) of the microRNAs in Table 19

| Gene name | Precusor Sequence 5'->3' | chrom | start | end | strand | SEQ ID NO |
|---|---|---|---|---|---|---|
| hsa-mir-582 | ATCTGTGCTCTTTGATTACAGTTGTTCAACCAGTTACTAATCTAACTAATTGTAACTGGTTGAACAACTGAACCCAAAGGGTGCAAAGTAGAAACATT | 5 | 59035189 | 59035286 | -1 | 860 |
| hsa-mir-664 | GAACATTGAAACTGGCTAGGGAAAATGATTGGATAGAAACTATTATTCTATTCATTTATCCCCAGCCTACAAAATGAAAAAA | 1 | 218440503 | 218440584 | -1 | 861 |
| hsa-mir-93 | CTGGGGGCTCCAAAGTGCTGTTCGTGCAGGTAGTGTGATTACCCAACCTACTGCTGAGCTAGCACTTCCCGAGCCCCGG | 7 | 99529327 | 99529406 | -1 | 862 |

Finally, a similar analysis identified novel star forms of microRNAs in miRBase (human version 14.0) that are present at increased levels in the sepsis smRNASeq dataset. While the precursor and mature microRNA are in miRBase, the novel star forms identified in this analysis are not. Again, the microRNAs were ranked from 1 to 5, depending on whether the sepsis patient smRNASeq dataset contained the highest number of counts of the particular microRNA, the second highest, etc. The results are shown in Table 16.

TABLE 16

Novel star-form microRNAs upregulated
in a sepsis smRNASeq dataset

| microRNA name | RANK | microRNA Sequence 5'->3' | SEQ ID NO |
|---|---|---|---|
| mir-1537-STAR-5P | 1 | CTGTAATTAGTCAGTTTTCTGT | 863 |
| mir-451-STAR-3P | 1 | TAATGGTAATGGTTCTCTTG | 864 |
| mir-580-STAR-5P | 1 | TAATGATTCATCAGACTCAGA | 865 |
| mir-606-STAR-5P | 1 | TTAGTAGTTTTACTATGATGAGG | 866 |
| mir-643-STAR-5P | 1 | ACCTGAGCTAGAATACAAGTAGT | 867 |
| mir-659-STAR-5P | 1 | AGGACCTTCCCTGAACCAAGGA | 868 |
| mir-1284-STAR-3P | 2 | GAAAGCCCATGTTTGTATTGGA | 869 |
| mir-215-STAR-3P | 2 | TCTGTCATTTCTTTAGGCCAATA | 870 |
| mir-345-STAR-3P | 2 | CCCTGAACGAGGGGTCTGGAG | 871 |
| mir-548j-STAR-3P | 2 | CAAAAACTGCATTACTTTTGCA | 872 |
| mir-642-STAR-3P | 2 | AGACACATTTGGAGAGGGAAC | 873 |
| mir-1277-STAR-5P | 3 | TATATATATATATGTACGTATG | 874 |
| mir-548a-1-STAR-5P | 3 | GTTGGTGCAAAAGTAATTG | 875 |
| mir-548f-1-STAR-5P | 3 | GTTGGTGCAAAAGTAAT | 876 |
| mir-548h-1-STAR-3P | 3 | AAACTGGAATTACTTTTG | 877 |
| mir-597-STAR-3P | 3 | AGTGGTTCTCTTGTGGCTCAAG | 878 |

TABLE 16-continued

Novel star-form microRNAs upregulated
in a sepsis smRNASeq dataset

| microRNA name | RANK | microRNA Sequence 5'->3' | SEQ ID NO |
|---|---|---|---|
| mir-939-STAR-3P | 3 | CTGGGCCTCTGCTCCCCAG | 879 |
| mir-1285-1-STAR-5P | 4 | TCTCACTTTGTTGCCCAG | 880 |
| mir-1975-STAR-5P | 4 | TGTGGGTTATTGTTAAGT | 881 |
| mir-2277-STAR-5P | 4 | AGCGCGGGCTGAGCGCTGCCAGTC | 882 |
| mir-376a-2-STAR-5P | 4 | GTAGATTTTCCTTCTATGGTT | 883 |
| mir-421-STAR-5P | 4 | CTCATTAAATGTTTGTTGAATGA | 884 |
| mir-548e-STAR-5P | 4 | CAAAAGCAATCGCGGTTTTTGC | 885 |
| mir-548f-4-STAR-5P | 4 | GTTGGTGCAAAAGTAAT | 886 |
| mir-941-1-STAR-5P | 4 | ACATGTGCCCAGGGCCCGGGACAGCG | 887 |
| mir-941-2-STAR-5P | 4 | ACATGTGCCCAGGGCCCGGGACAGCG | 888 |
| mir-941-3-STAR-5P | 4 | ACATGTGCCCAGGGCCCGGGACAGCG | 889 |
| mir-1234-STAR-5P | 5 | GGGGGGGGGGGGGGGGG | 890 |
| mir-1273-STAR-5P | 5 | AGGAGAATTGCTTGAACCC | 891 |
| mir-1307-STAR-5P | 5 | TCGACCGGACCTCGACCGGCT | 892 |
| mir-153-2-STAR-5P | 5 | GTCATTTTGTGATGTTGCAGCT | 893 |
| mir-181b-1-STAR-3P | 5 | CTCACTGAACAATGAATGCA | 894 |
| mir-548h-3-STAR-3P | 5 | CAAAAACTGCAATTACTTTTG | 895 |
| mir-548h-4-STAR-3P | 5 | CAAAAACCGCAATTACTTTTG | 896 |
| mir-548l-STAR-3P | 5 | CAAAAACTGCAGTTACTT | 897 |

The microRNA precursor sequences for the microRNAs listed in Table 16 are shown in Table 17.

TABLE 17

Precursor sequences and chromosomal locations
(from human genome NCBI36) of the microRNAs in Table 16

| Gene name | Precusor Sequence 5'->3' | chrom | start | end | strand | SEQ ID NO |
|---|---|---|---|---|---|---|
| hsa-mir-1537 | ACAGCTGTAATTAGTCAGTTTTCTGTCCTGTCCACACAGAAAACCGTCTAGTTACAGTTGT | 1 | 234082923 | 234082983 | -1 | 898 |
| hsa-mir-451 | CTTGGGAATGGCAAGGAAACCGTTACCATTACTGAGTTTAGTAATGGTAATGGTTCTCTTGCTATACCCAGA | 17 | 24212513 | 24212584 | -1 | 899 |
| hsa-mir-580 | ATAAAATTTCCAATTGGAACCTAATGATTCATCAGACTCAGATATTTAAGTTAACAGTATTTGAGAATGATGAATCATTAGGTTCCGGTCAGAAATT | 5 | 36183751 | 36183847 | -1 | 900 |
| hsa-mir-606 | TGTATCCTTGGTTTTTAGTAGTTTTACTATGATGAGGTGTGCCATCCACCCCATCATAGTAAACTACTGAAAATCAAAGATACAAGTGCCTGACCA | 10 | 76982222 | 76982317 | 1 | 901 |
| hsa-mir-643 | ACCAAGTGATATTCATTGTCTACCTGAGCTAGAATACAAGTAGTTGGCGTCTTCAGAGACACTTGTATGCTAGCTCAGGTAGATATTGAATGAAAAA | 19 | 57476862 | 57476958 | 1 | 902 |
| hsa-mir-659 | TACCGACCCTCGATTTGGTTCAGGACCTTCCCTGAACCAAGGAAGAGTCACAGTCTCTTCCTTGGTTCAGGGAGGGTCCCCAACAATGTCCTCATGG | 22 | 36573631 | 36573727 | -1 | 903 |
| hsa-mir-1284 | ATTTTGATATATAAGCCAGTTTAATGTTTTCTATACAGACCCTGGCTTTTCTTAAATTTTATATATTGGAAAGCCCATGTTTGTATTGGAAACTGCTGGTTTCTTTCATACTGAAAATCT | 3 | 71673811 | 71673930 | -1 | 904 |
| hsa-mir-215 | ATCATTCAGAAATGGTATACAGGAAAATGACCTATGAATTGACAGACAATATAGCTGAGTTTGTCTGTCATTTCTTTAGGCCAATATTCTGTATGACTGTGCTACTTCAA | 1 | 218357818 | 218357927 | -1 | 905 |
| hsa-mir-345 | ACCCAAACCCTAGGTCTGCTGACTCCTAGTCCAGGGCTCGTGATGGCTGGTGGGCCCTGAACGAGGGGTCTGGAGGCCTGGGTTTGAATATCGACAGC | 14 | 99843949 | 99844046 | 1 | 906 |
| hsa-mir-548j | GGGCAGCCAGTGAATAGTTAGCTGGTGCAAAAGTAATTGCGGTCTTTGGTATTACTTTCAGTGGCAAAAACTGCATTACTTTTGCACCAGCCTACTAGAACGCTGAGTTCAG | 22 | 25281178 | 25281289 | -1 | 907 |
| hsa-mir-642 | ATCTGAGTTGGGAGGGTCCCTCTCCAAATGTGTCTTGGGGTGGGGATCAAGACACATTTGGAGAGGGAACCTCCCAACTCGGCCTCTGCCATCATT | 19 | 50870026 | 50870122 | 1 | 908 |
| hsa-mir-1277 | ACCTCCCAAATATATATATATATGTACGTATGTGTATATAAATGTATACGTAGATATATATGTATTTTTGGTGGGTTT | X | 117404385 | 117404462 | 1 | 909 |
| hsa-mir-548a-1 | TGCAGGGAGGTATTAAGTTGGTGCAAAAGTAATTGTGATTTTTGCCATTAAAAGTAACGACAAAACTGGCAATTACTTTTGCACCAAACCTGGTATT | 6 | 18679994 | 18680090 | 1 | 910 |
| hsa-mir-548f-1 | ATTAGGTTGGTGCAAAAGTAATCACAGTTTTTGACATTACTTTCAAAGACAAAAACTGTAATTACTTTTGGACCAACCTAATAG | 10 | 56037640 | 56037723 | -1 | 911 |
| hsa-mir-548h-1 | TCTGTCCATTAGGTGGGTGCAAAAGTAATCGCGGTTTTTGTCATTACTTTTAATGGTAAAAACTGGAATTACTTTTGCACTGACCTAATATTAAGCCAGATA | 14 | 63631495 | 63631596 | -1 | 912 |
| hsa-mir-597 | TACTTACTCTACGTGTGTGTCACTCGATGACCACTGTGAAGACAGTAAAATGTACAGTGGTTCTCTTGTGGCTCAAGCGTAATGTAGAGTACTGGTC | 8 | 9636592 | 9636688 | 1 | 913 |
| hsa-mir-939 | TGTGGGCAGGGCCCTGGGGAGCTGAGGCTCTGGGGGTGGCCGGGGCTGACCCTGGGCCTCTGCTCCCCAGTGTCTGACCGCG | 8 | 145590172 | 145590253 | -1 | 914 |
| hsa-mir-1285-1 | TGTAGAGATAGGATCTCACTTTGTTGCCCAGGCTGGTCTCAAACTCCTGGTCTGGGCAACAAAGTGAGACCTTATCTCTACAAG | 7 | 91671265 | 91671348 | -1 | 915 |
| hsa-mir-1975 | AGTTGGTCCGAGTGTTGTGGGTTATTGTTAAGTTGATTTAACATTGTCTCCCCCCACAACCGCGCTTGACTAGCT | 7 | 148269513 | 148269587 | 1 | 916 |
| hsa-mir-2277 | GTGCTTCCTGCGGGCTGAGCGCGGGCTGAGCGCTGCCAGTCAGCGCTCACATTAAGGCTGACAGCGCCCTGCCTGGCTCGGCCGGCGAAGCTC | 5 | 92982158 | 92982250 | -1 | 917 |
| hsa-mir-376a-2 | GGTATTTAAAAGGTAGATTTTCCTTCTATGGTTACGTGTTTGATGGTTAATCATAGAGGAAAATCCACGTTTTCAGTATC | 14 | 100576159 | 100576238 | 1 | 913 |

TABLE 17-continued

Precursor sequences and chromosomal locations
(from human genome NCBI36) of the microRNAs in Table 16

| Gene name | Precusor Sequence 5'->3' | chrom | start | end | strand | SEQ ID NO |
|---|---|---|---|---|---|---|
| hsa-mir-421 | GCACATTGTAGGCCTCATTAAATGTTTGTTGAATGAAAAAATGAATCATCAACAGACATTAATTGGGCGCCTGCTCTGTGATCTC | X | 73354937 | 73355021 | -1 | 919 |
| hsa-mir-548e | TTATTAGGTTGGTACAAAAGCAATCGCGGTTTTTGCTATTACTTTTAAAGGCAAAAACTGAGACTACTTTTGCACCAACCTGATAGAA | 10 | 112738674 | 112738761 | 1 | 920 |
| hsa-mir-548f-4 | GAGTTCTAACGTATTAGGTTGGTGCAAAAGTAATAGTGGTTTTTGCCATTAAAAGTAATGACAAAAACTGTAATTACTTTTGGAACAATATTAATAGAATTTCAG | 7 | 146706042 | 146706146 | -1 | 921 |
| hsa-mir-941-1 | CCCGGCTGTGTGGACATGTGCCCAGGGCCCGGGACAGCGCCACGGAAGAGGACGCACCCGGCTGTGTGCACATGTGCCCAGGGCCCGGG | 20 | 62021238 | 62021326 | 1 | 922 |
| hsa-mir-941-2 | CCCGGCTGTGTGCACATGTGCCCAGGGCCCGGGACAGCGCCACGGAAGAGGACGCACCCGGCTGTGTGCACATGTGCCCAGGGCCCGGG | 20 | 62021545 | 62021633 | 1 | 923 |
| hsa-mir-941-3 | CCCGGCTGTGTGCACATGTGCCCAGGGCCCGGGACAGCGCCACGGAAGAGGACGCACCCGGCTGTGTGCACATGTGCCCAGGGCCCGGG | 20 | 62021657 | 62021745 | 1 | 924 |
| hsa-mir-1234 | GTGAGTGTGGGGTGGCTGGGGGGGGGGGGGGGGCCGGGGACGGCTTGGGCCTGCCTAGTCGGCCTGACCACCCACCCCACAG | 8 | 145596284 | 145596367 | -1 | 925 |
| hsa-mir-1273 | TGAGGCAGGAGAATTGCTTGAACCCGGGTGGTGGAGGTTGCAGTGAGCCAAGATTGCGCCACTGCACTCCAGCCTGGGCGACAAAGCAAGACTCTTTCTTGGA | 8 | 101105386 | 101105488 | -1 | 926 |
| hsa-mir-1307 | CATCAAGACCCAGCTGAGTCACTGTCACTGCCTACCAATCTCGACCGGACCTCGACCGGCTCGTCTGTGTTGCCAATCGACTCGGCGTGGCGTCGGTCGTGGTAGATAGGCGGTCATGCATACGAATTTTCAGCTCTTGTTCTGGTGAC | 10 | 105144000 | 105144148 | -1 | 927 |
| hsa-mir-153-2 | AGCGGTGGCCAGTGTCATTTTTGTGATGTTGCAGCTAGTAATATGAGCCCAGTTGCATAGTCACAAAAGTGATCATTGGAAACTGTG | 7 | 157059789 | 157059875 | -1 | 928 |
| hsa-mir-181b-1 | CCTGTGCAGAGATTATTTTTTAAAAGGTCACAATCAACATTCATTGCTGTCGGTGGGTTGAACTGTGTGGACAAGCTCACTGAACAATGAATGCAACTGTGGCCCCGCTT | 1 | 197094625 | 197094734 | -1 | 929 |
| hsa-mir-548h-3 | TCTGATTCTGCATGTATTAGGTTGGTGCAAAAGTAATCGCGGTTTTTGTCATTGAAAGTAATAGCAAAAACTGCAATTACTTTTGCACCAACCTAAAAGTAGTCACTGTCTTCAGATA | 17 | 13387571 | 13387688 | -1 | 930 |
| hsa-mir-548h-4 | GCTATTAGGTTGGTGCAAAAGTAATCGCGGTTTTTGTCATTACTTTAATTACTTTACGTTTCATTAATGACAAAAACCGCAATTACTTTTGCACCAACCTAATACTTGCTA | 8 | 26962287 | 26962397 | -1 | 931 |
| hsa-mir-5481 | TATTAGGTTGGTGCAAAAGTATTTGCGGGTTTTGTCGTAGAAAGTAATGGCAAAAACTGCAGTTACTTGTGCACCAACCAAATGCT | 11 | 93839309 | 93839394 | -1 | 932 |

5.6 Example 6

Analysis of MicroRNA Count Ratio from smRNASeq Datasets

Table 18 shows the ratio of the number of counts in the sepsis smRNASeq dataset versus the average number of counts from all of the other smRNASeq datasets for each novel microRNA for which the ratio was 2 or higher.

TABLE 18

Novel microRNAs with counts at least 2-fold higher than average count in other datasets

| microRNA | Rank | Counts sepsis/ average count other datasets | Ratio counts sepsis/ average count other datasets | SEQ ID NO |
|---|---|---|---|---|
| 13446-R | 1 | 140/12.81 | 11 | 231 |
| 13629-L | 1 | 860/256.28 | 3 | 235 |
| 13642-R | 1 | 768/55.16 | 14 | 236 |
| 13661-R | 1 | 47/7.12 | 7 | 237 |
| 13667-R | 1 | 17/7.4 | 2 | 239 |
| 13677-L | 1 | 817/60.33 | 14 | 242 |
| 13694-L | 1 | 96/13.75 | 7 | 245 |
| 13719-L | 1 | 141/29.33 | 5 | 253 |
| 13729-L | 1 | 143/22.58 | 6 | 257 |
| 13731-L | 1 | 32/8.36 | 4 | 258 |
| 14086-L | 1 | 18789/900.97 | 21 | 260 |
| 14093-L | 1 | 3327/276.54 | 12 | 261 |
| 14111-L | 1 | 394/46.66 | 8 | 262 |
| 14113-L | 1 | 26/4.15 | 6 | 263 |
| 14177-L | 1 | 4202/280.34 | 15 | 266 |
| 14371-R | 1 | 67/12.30 | 5 | 269 |
| 14482-R | 1 | 16/3.31 | 5 | 275 |

TABLE 18-continued

Novel microRNAs with counts at least 2-fold higher than average count in other datasets

| microRNA | Rank | Counts sepsis/ average count other datasets | Ratio counts sepsis/ average count other datasets | SEQ ID NO |
|---|---|---|---|---|
| 2851-R | 1 | 20/6.33 | 3 | 280 |
| 6415-R | 1 | 572/43.61 | 13 | 287 |
| 11626-R | 2 | 140/45.26 | 3 | 290 |
| 13447-R | 2 | 25/9.8 | 3 | 298 |
| 13448-R | 2 | 25/9.8 | 3 | 299 |
| 13465-R | 2 | 137/30.62 | 4 | 300 |
| 13629-R | 2 | 146/51.71 | 3 | 302 |
| 13640-L | 2 | 225/43.28 | 5 | 303 |
| 13686-L | 2 | 16/6.88 | 2 | 304 |
| 13710-R | 2 | 18/6.33 | 3 | 307 |
| 14327-R | 2 | 39/16.4 | 2 | 312 |
| 14347-R | 2 | 17/5.1 | 3 | 314 |
| 11607-R | 3 | 232/64.96 | 4 | 332 |
| 13214-L | 3 | 29/9.79 | 3 | 335 |
| 13244-R | 3 | 35/10.57 | 3 | 336 |
| 13452-R | 3 | 37/17.92 | 2 | 338 |
| 13677-R | 3 | 116/51.03 | 2 | 341 |
| 14085-L | 3 | 1777/287.46 | 6 | 342 |
| 14556-R | 3 | 3397/566.68 | 6 | 352 |
| 607-R | 3 | 41/19.70 | 2 | 356 |
| 14244-L | 4 | 708/211.84 | 3 | 367 |
| 373-R | 4 | 443/130.5 | 3 | 377 |
| 6216-L | 4 | 101/36.51 | 3 | 378 |
| 4135-R | 5 | 117/35.45 | 3 | 399 |

MicroRNAs 13446-R, 13642-R, 13661-R, 13677-L, 13694-L, 13719-L, 13729-L, 14086-L, 14093-L, 14111-L, 14113-L, 14177-L, 14371-R, 14482-R, 6415-R, 13640-L, 14085-L, and 14556-R (SEQ ID NOs: 231, 236, 237, 242, 245, 253, 260, 261, 262, 263, 266, 269, 275, 287, 303, 342, and 352 respectively) had counts in the sepsis smRNASeq dataset of at least 5-fold greater than the average counts in the other datasets. Of those, microRNAs 13446-R, 13642-R, 13677-L, 14086-L, 14093-L, 14177-L, and 6415-R (SEQ ID NOs: 231, 236, 242, 260, 261, 266, and 287, respectively) had counts in the sepsis smRNASeq dataset of at least 10-fold greater than the average counts in the other datasets.

Table 19 shows the ratio of the number of counts in the sepsis smRNASeq dataset versus the average number of counts from all of the other smRNASeq datasets for each microRNA from miRBase for which the ratio was 2 or higher.

TABLE 19

MicroRNAs with counts at least 2-fold higher than average count in other datasets

| microRNA | Rank | Counts sepsis/ average count other datasets | Ratio counts sepsis/ average count other datasets | SEQ ID NO |
|---|---|---|---|---|
| miR-140-5p | 1 | 13151/840.48 | 16 | 566 |
| miR-142-3p | 1 | 609070/16023.27 | 38 | 567 |
| miR-142-5p | 1 | 8409/369.84 | 23 | 568 |
| miR-144* | 1 | 47480/3056.12 | 16 | 571 |
| miR-144 | 1 | 736/38.88 | 19 | 570 |
| miR-1537 | 1 | 48/6.58 | 7 | 573 |
| miR-15a | 1 | 31217/2471.38 | 13 | 574 |
| miR-16-1* | 1 | 237/35.03 | 7 | 575 |
| miR-185* | 1 | 290/40.12 | 7 | 577 |
| miR-2115* | 1 | 199/34.66 | 6 | 579 |
| miR-2115 | 1 | 57/15.5 | 4 | 578 |
| miR-223 | 1 | 54934/2708.04 | 20 | 580 |
| miR-223* | 1 | 7766/722.27 | 11 | 581 |
| miR-451 | 1 | 40796/2026.45 | 20 | 588 |
| miR-548f | 1 | 848/106.8 | 8 | 591 |
| miR-618 | 1 | 1830/172.7 | 11 | 598 |
| miR-627 | 1 | 3189/209.91 | 15 | 601 |
| miR-148a* | 2 | 11446/970.839 | 12 | 608 |
| miR-450b-5p | 2 | 1137/131.39 | 9 | 612 |
| miR-503 | 2 | 2319/271.67 | 9 | 613 |
| miR-126 | 3 | 10982/5020.08 | 2 | 622 |
| miR-140-3p | 3 | 99511/7917.09 | 13 | 624 |
| miR-146a | 3 | 114148/11930.10 | 10 | 626 |
| miR-146b-5p | 3 | 114217/11737.09 | 10 | 629 |
| miR-17* | 3 | 4530/457.59 | 10 | 632 |
| miR-199b-5p | 3 | 1879/255.69 | 7 | 635 |
| miR-29b-2* | 3 | 143/27.83 | 5 | 637 |
| miR-425* | 3 | 1267/226.26 | 6 | 641 |
| miR-454* | 3 | 170/30.93 | 5 | 642 |
| miR-542-3p | 3 | 3998/545.18 | 7 | 644 |
| miR-598 | 3 | 2832/491.33 | 6 | 648 |
| miR-181a | 4 | 31615/9973.87 | 3 | 664 |
| miR-28-3p | 5 | 3873/1254.94 | 3 | 699 |

MicroRNAs miR-140-5p, miR-142-3p, miR-142-5p, miR-144*, miR-144, miR-1537, miR-15a, miR-16-1*, miR-185*, miR-2115*, miR-223, miR-223*, miR-451, miR-548f, miR-618, miR-627, miR-148a*, miR-450b-5p, miR-503, miR-140-3p, miR-146a, miR-146b-5p, miR-17*, miR-199b-5p, miR-29b-2*, miR-425*, miR-454*, miR-542-3p, and miR-598 (SEQ ID NOs: 566, 567, 568, 571, 570, 573, 574, 575, 577, 579, 580, 581, 588, 591, 598, 601, 608, 612, 613, 624, 626, 629, 632, 635, 637, 641, 642, 644, and 648, respectively) had counts in the sepsis smRNASeq dataset of at least 5-fold greater than the average counts in the other datasets. Of those, microRNAs miR-140-5p, miR-142-3p, miR-142-5p, miR-144*, miR-144, miR-15a, miR-223, miR-223*, miR-451, miR-618, miR-627, miR-148a*, miR-140-3p, miR-146b-5p, and miR-17* (SEQ ID NOs: 566, 567, 568, 571, 570, 574, 580, 581, 588, 598, 601, 608, 624, 626, 629, and 632, respectively) had counts in the sepsis smRNASeq dataset of at least 10-fold greater than the average counts in the other datasets.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that changes can be made without departing from the spirit and scope of the invention(s).

What is claimed is:

1. A polynucleotide comprising a sequence of at least 17 contiguous nucleotides that is identical or fully complementary to a sequence of at least 17 contiguous nucleotides of SEQ ID NO: 235, wherein the polynucleotide is fewer than 100 nucleotides long, and wherein the polynucleotide comprises a fluorescent dye.

2. The polynucleotide of claim 1, wherein the polynucleotide comprises a sequence of at least 18 contiguous nucleotides that is identical or fully complementary to a sequence of at least 18 contiguous nucleotides of SEQ ID NO: 235.

3. The polynucleotide of claim 1, wherein the polynucleotide comprises a sequence of at least 19 contiguous nucleotides that is identical or fully complementary to a sequence of at least 19 contiguous nucleotides of SEQ ID NO: 235.

4. The polynucleotide of claim 1, wherein the polynucleotide comprises a sequence of at least 20 contiguous nucleotides that is identical or fully complementary to a sequence of at least 20 contiguous nucleotides of SEQ ID NO: 235.

5. The polynucleotide of claim 1, wherein the polynucleotide further comprises a quencher molecule.

6. The polynucleotide of claim 1, wherein the polynucleotide further comprises a sequence that is not identical or complementary to SEQ ID NO: 235.

7. A composition comprising a plurality of uniquely labeled fluorescence resonance energy transfer (FRET) probes, wherein at least one uniquely labeled FRET probe comprises a sequence of at least 8 contiguous nucleotides that is identical or fully complementary to a sequence of at least 8 contiguous nucleotides of SEQ ID NO: 235, and wherein at least one uniquely labeled FRET probe of the plurality of uniquely labeled FRET probes comprises a sequence of at least 8 contiguous nucleotides that is identical or fully complementary to a sequence of at least 8 contiguous nucleotides of SEQ ID NO: 662, wherein each uniquely labeled FRET probe is between 8 and 100 nucleotides long, and wherein each uniquely labeled FRET probe comprises a fluorescent dye and a quencher molecule.

8. A kit comprising a polynucleotide of claim 1.

9. A kit comprising a composition of claim 7.

10. The kit of claim 8, wherein the kit further comprises at least one polymerase.

11. The kit of claim 8, wherein the kit further comprises dNTPs.

\* \* \* \* \*

UNITED STATES PATENT AND TRADEMARK OFFICE
CERTIFICATE OF CORRECTION

PATENT NO. : 9,493,832 B2
APPLICATION NO. : 12/698715
DATED : November 15, 2016
INVENTOR(S) : Vilanova et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 803 days.

Signed and Sealed this
Sixth Day of February, 2018

Joseph Matal
*Performing the Functions and Duties of the
Under Secretary of Commerce for Intellectual Property and
Director of the United States Patent and Trademark Office*